US010829789B2

(12) United States Patent
Luo et al.

(10) Patent No.: US 10,829,789 B2
(45) Date of Patent: Nov. 10, 2020

(54) METHODS AND ORGANISM WITH INCREASED XYLOSE UPTAKE

(71) Applicant: Creatus Biosciences Inc., Vancouver (CA)

(72) Inventors: Zongli Luo, Vancouver (CA); Hendrik Jurgens Jansen van Vuuren, Lions Bay (CA); Allan George DeBono, Vancouver (CA); Andrew Taplin Ferguson, Vancouver (CA)

(73) Assignee: Creatus Biosciences Inc., West Vancouver (CA)

( * ) Notice: Subject to any disclaimer, the term of this patent is extended or adjusted under 35 U.S.C. 154(b) by 145 days.

(21) Appl. No.: 15/849,191

(22) Filed: Dec. 20, 2017

(65) Prior Publication Data

US 2018/0195092 A1 Jul. 12, 2018

Related U.S. Application Data

(60) Provisional application No. 62/437,600, filed on Dec. 21, 2016.

(51) Int. Cl.
| | | |
|---|---|---|
| *C12P 7/18* | (2006.01) | |
| *C12P 7/62* | (2006.01) | |
| *C12P 7/16* | (2006.01) | |
| *C12R 1/865* | (2006.01) | |
| *C12P 7/04* | (2006.01) | |
| *C12P 7/22* | (2006.01) | |
| *C12P 7/06* | (2006.01) | |
| *C07K 14/39* | (2006.01) | |
| *C12N 15/52* | (2006.01) | |

(52) U.S. Cl.
CPC ................ *C12P 7/18* (2013.01); *C07K 14/39* (2013.01); *C12N 15/52* (2013.01); *C12P 7/04* (2013.01); *C12P 7/06* (2013.01); *C12P 7/16* (2013.01); *C12P 7/22* (2013.01); *C12P 7/62* (2013.01); *C12R 1/865* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| | | |
|---|---|---|
| 4,368,268 A | 1/1983 | Gong |
| 5,514,583 A | 5/1996 | Picataggio et al. |
| 5,712,133 A | 1/1998 | Picataggio et al. |
| 5,965,408 A | 10/1999 | Short |
| 6,582,944 B1 | 6/2003 | Hallborn et al. |
| 7,127,379 B2 | 10/2006 | Palsson et al. |
| 7,226,735 B2 | 6/2007 | Jeffries et al. |
| 7,985,567 B2 | 7/2011 | Chou et al. |
| 8,071,298 B2 | 12/2011 | Abbas et al. |
| 8,114,641 B2 | 2/2012 | Picataggio et al. |
| 8,530,226 B2 | 9/2013 | Festel et al. |
| 8,900,841 B2 | 12/2014 | Medoff et al. |
| 8,975,049 B2 | 3/2015 | Liao et al. |
| 2002/0012939 A1 | 1/2002 | Palsson |
| 2002/0168654 A1 | 11/2002 | Maranas et al. |
| 2003/0059792 A1 | 3/2003 | Palsson et al. |
| 2003/0224363 A1 | 12/2003 | Park et al. |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2004/0142456 A1 | 7/2004 | Jeffries et al. |
| 2004/0231661 A1 | 11/2004 | Griffin et al. |
| 2005/0153411 A1 | 7/2005 | Wahlbom et al. |
| 2006/0234364 A1 | 10/2006 | Rajgarhia et al. |
| 2008/0187973 A1 | 8/2008 | Viitanen et al. |
| 2009/0047719 A1 | 2/2009 | Burgard et al. |
| 2010/0129885 A1 | 5/2010 | Khramtsov et al. |
| 2010/0261241 A1 | 10/2010 | Khramtsov et al. |
| 2013/0035515 A1 | 2/2013 | Dobson et al. |
| 2018/0171366 A1 | 6/2018 | Luo et al. |
| 2018/0195051 A1 | 7/2018 | Luo et al. |
| 2018/0195093 A1 | 7/2018 | Van Vuuren et al. |

FOREIGN PATENT DOCUMENTS

| | | |
|---|---|---|
| KR | 100199819 B1 | 6/1999 |
| KR | 100259470 B1 | 6/2000 |
| WO | WO 1990/008193 A1 | 7/1990 |
| WO | WO 1995/028476 A1 | 10/1995 |
| WO | WO 1999/031241 A1 | 6/1999 |
| WO | WO 2007/050671 A2 | 5/2007 |
| WO | WO 2008/098227 A2 | 8/2008 |
| WO | WO 2009/049274 A2 | 4/2009 |
| WO | WO 2009/103026 A1 | 8/2009 |
| WO | WO 2009/103533 A1 | 8/2009 |
| WO | WO 2009/116066 A2 | 9/2009 |
| WO | WO 2009/131286 A1 | 10/2009 |
| WO | WO 2010/071697 A1 | 6/2010 |
| WO | WO 2011/022651 A1 | 2/2011 |
| WO | WO 2011/029166 A1 | 3/2011 |
| WO | WO 2011/031897 A1 | 3/2011 |
| WO | WO 2011/153144 A1 | 12/2011 |
| WO | WO 2012/011962 A2 | 1/2012 |
| WO | WO 2012/058603 A1 | 5/2012 |
| WO | WO 2012/173659 A2 | 12/2012 |

(Continued)

OTHER PUBLICATIONS

Goncalves DL et al. Xylose and xylose/glucose co-fermentation by recombinant *Saccharomyces cerevisiae* strains expressing individual hexose transporters. 2014. Enzyme and Microbial Technology. 63:13-20 (Year: 2014).*

(Continued)

Primary Examiner — Paul J Holland
(74) Attorney, Agent, or Firm — Jones Day

(57) ABSTRACT

Provided herein are novel xylose transporters and their variants, as well as nucleic acid encoding the novel xylose transporters and their variants. Provided herein are also non-naturally occurring microbial organisms having increased xylose uptake and increased production of bio-derived compounds using xylose as a substrate, as well as methods to make and use these microbial organisms.

21 Claims, 5 Drawing Sheets

Specification includes a Sequence Listing.

(56) References Cited

FOREIGN PATENT DOCUMENTS

| WO | WO 2013/178699 A1 | 12/2013 |
| --- | --- | --- |
| WO | WO 2014/045297 A2 | 3/2014 |
| WO | WO 2015/179701 A1 | 11/2015 |
| WO | WO 2018/112634 A1 | 6/2018 |
| WO | WO 2018/112636 A1 | 6/2018 |
| WO | WO 2018/112638 A1 | 6/2018 |
| WO | WO 2018/112639 A1 | 6/2018 |

OTHER PUBLICATIONS

Jeon WY et al. Xylitol production is increased by expression of codon-optimized Neurospora crassa xylose reductase gene in Candida tropicalis. 2012. Bioprocess Biosystem Engineering. 35:191-198 (Year: 2012).*
Lloyd D et al. Snf2 controls pulcherriminic acid biosynthesis and antifungal activity of the biocontrol yeast *Metschnikowia pulcherrima*. 2019. Molecular Microbiology. 112(1), 317-332. (Year: 2019).*
Santamauro F et al. Low-cost lipid production by an oleaginous yeast cultured in a non-sterile conditions using model waste resources. 2014. Biotechnology for Biofuels. 7:34. p. 1-11 (Year: 2014).*
XP_018714886. GenBank. p. 1-2. 2016 (Year: 2016).*
XP_018710985. GenBank. p. 1-2. 2016 (Year: 2016).*
XP_018714073. GenBank. p. 1-2. 2016 (Year: 2016).*
XP_018713575. GenBank. p. 1-2. 2016 (Year: 2016).*
Kizer L et al. Application of Functional Genomics to Pathway Optimization for Increased Isoprenoid Production. 2008. Applied and Environmental Microbiology. vol. 74, No. 10. p. 3229-3241. (Year: 2008).*
Prather KLJ et al. De novo biosynthetic pathways: rational design of microbial chemical factories. 2008. Current Opinion in Biotechnology. 19:468-474. (Year: 2008).*
Abbas, "Lignocellulosics to ethanol: meeting ethanol demand in the future," *The Alcohol Textbook*, 4th Edition, Jacques et al. (ed.), Nottingham University Press, Nottingham, UK, pp. 41-57 (2003).
Abbas, "Emerging biorefineries and biotechnological applications of nonconventional yeast: now and in the future," *The Alcohol Textbook*, 4th Edition, Jacques et al. (ed.), Nottingham University Press, Nottingham, UK, pp. 171-191 (2003).
Ahmad et al., "Enhancement of xylitol production in Candida tropicalis by co-expression of two genes involved in pentose phosphate pathway," *Bioprocess Biosyst. Eng.*, 35:199-204 (2012).
Ahmad et al "Enhancement of xylitol production in glycerol kinase disrupted Candida tropicalis by co-expression of three genes involved in glycerol metabolic pathway," *Bioprocess Biosyst. Eng.*, 36:1279-1284 (2013).
Aldermann et al., "The active transport of monosaccharides by the yeast*Metschnikowia reukaufii*: Evidence for an electrochemical gradient of H+ across the cell membrane," *Exp. Mycol.*, 5:120-132 (1981).
Apel et al., "Evolved hexose transporter enhances xylose uptake and glucose/xylose co-utilization in *Saccharomyces cerevisiae*," *Scientific Reports*, 6:19512 (2016).
Atsumi et al., "Non-fermentative pathways for synthesis of branched-chain higher alcohols as biofuels," *Nature*, 451:86-89 (2008).
Avalos et al., "Compartmentalization of metabolic pathways in yeast mitochondria improves the production of branched-chain alcohols," *Nat. Biotechnol.*, 31(4):355-341 (2013).
Azarpazhooh et al., "Xylitol for preventing acute otitis media in children up to 12 years of age," *Cochrane Database Syst. Rev.*, 11:CD007095 (2016).
Barbosa et al., "Screening of yeasts for production of xylitol fromd-xylose and some factors which affect xylitol yield inCandida guilliermondii," *J. Ind. Microbiol.*, 3:241-251 (1988).
Beall et al., "Parametric studies of ethanol production form xylose and other sugars by recombinant *Escherichia coli*," *Biotechnol. Bioeng.*, 38(3):296-303 (1991).

Berezina et al., "Reconstructing the clostridial n-butanol metabolic pathway in Lactobacillus brevis," *Appl. Microbiol. Biotechnol.*, 87(2):635-646 (2010).
Bergquist et al., "Degenerate oligonucleotide gene shuffling (DOGS) and random drift mutagenesis (RNDM): two complementary techniques for enzyme evolution" *Biomol. Eng.*, 22:63-72 (2005).
Bergquist et al., "Degenerate oligonucleotide gene shuffling," *Methods Mol. Biol.*, 352:191-204 (2007).
Bhandiwad et al., "Metabolic engineering of Thermoanaerobacterium saccharolyticum for n-butanol production," *Metab. Eng.*, 21:17-25 (2014).
Bowie et al., "Deciphering the message in protein sequences: tolerance to amino acid substitutions," *Science*, 247:1306-1310 (1990).
Brat et al., "Isobutanol production from D-xylose by recombinant *Saccharomyces cerevisiae*," *FEMS Yeast Res.*, 13(2):241-244 (2013).
Bura et al., "Novel endophytic yeast *Rhodotorula mucilaginosa* strain PTD3 I: production of xylitol and ethanol" *J. Ind. Microbiol. Biotechnol.*, 39:1003-1011 (2012).
Cadete et al., "*Cyberlindnera xylosilytica* sp. nov., a xylitol-producing yeast species isolated from lignocellulosic materials," *Int. J. Syst. Evol. Microbiol.*, 65(9):2968-2974 (2015).
Cheng et al., "Genetically engineered *Pichia pastoris* yeast for conversion of glucose to xylitol by a single-fermentation process," *Appl. Microbiol. Biotechnol.*, 98(8):3539-3552 (2014).
Cheng et al., "Xylitol production from xylose mother liquor: a novel strategy that combines the use of recombinant Bacillus subtilis and Candida maltose," *Microb. Cell Fact.*, 10:5 (2011).
Chiang et al., "A new pathway of pentose metabolism," *Biochem. Biophys. Res. Commun.*, 3(5):554-559 (1960).
Chiang et al., "Metabolism of d-xylose by moulds," *Nature*, 188:79-81 (1960).
Chiang et al., "The conversion of D-xylose to xylitol by Penicillum chrysogenum," *Biochim. Biophys. Acta*, 29:664-665 (1958).
Chin et al., "Analysis of NADPH supply during xylitol production by engineered *Escherichia coli*," *Biotechnol. Bioeng.*, 102(1):209-220 (2009).
Chin et al., "Codon Optimization OnLine (COOL): a web-based multi-objective optimization platform for synthetic gene design," *Bioinformatics*, 30(15):2210-2212 (2014).
Chin et al., "Improved NADPH supply for xylitol production by engineered *Escherichia coli* with glycolytic mutations," *Biotechnol. Prog.*, 27:333-341 (2011).
Chung et al., "Computational codon optimization of synthetic gene for protein expression," *BMC Syst Biol.*, 6:134 (2012).
Chung et al., "Stable expression of xylose reductase gene enhances xylitol production in recombinant *Saccharomyces cerevisiae*," *Enzyme Microb. Technol.*, 30:809-816 (2002).
Cirino et al., Engineering *Escherichia coli* for xylitol production from glucose-xylose mixtures *Biotechnol. Bioeng.*, 95(6):1167-1176 (2006).
Coco et al., "DNA shuffling method for generating highly recombined genes and evolved enzymes" *Nat. Biotechnol.*, 19:354-359 (2001).
Colonna et al., "Synthesis and radiocarbon evidence of terephthalate polyesters completely prepared from renewable resources," *Green Chem.*, 13:2543-2548 (2011).
Cosman et al., "ULBPs, novel MHC class I-related molecules, bind to CMV glycoprotein UL16 and stimulate NK cytotoxicity through the NKG2D receptor," *Immunity*, 14:123-133 (2001).
Crameri et al., "DNA shuffling of a family of genes from diverse species accelerates directed evolution," *Nature*, 391:288-291 (1998).
Currie et al., "Authentication and dating of biomass components of industrial materials; links to sustainable technology," *Nucl. Instr. Methods Phys. Res. B*, 172:281-287 (2000).
Dahiya et al., "Xylitol production from sugar cane bagasse by fermentation," *Modernisation of Indian Sugar Industry*, Gehlawat ed., Arnold Publishers, New Dehli, pp. 292-303 (1990).
Dahiya, "Xylitol production by Petromyces albertensis grown on medium containing D-xylose," *Can. J. Microbiol.*, 37:14-18 (1991).
Dashtban et al., "Xylitol Production by Genetically Engineered Trichoderma reesei Strains Using Barley Straw as Feedstock," *Appl. Biochem. Biotechnol.*, 169:554-569 (2013).

(56) References Cited

OTHER PUBLICATIONS

Dellomonaco et al., "Engineered reversal of the (β-oxidation cycle for the synthesis of fuels and chemicals," *Nature*, 476(7360):355-359 (2011).
Dhar et al., "Engineering of Corynebacterium glutamicum for xylitol production from lignocellulosic pentose sugars." *J. Biotechnol.*, 230:63-71 (2016).
Drucker et al., "Comparative effects of the substance-sweeteners glucose, sorbitol, sucrose, xylitol and trichlorosucrose on lowering of pH by two oral *Streptococcus mutans* strains in vitro," *Arch Oral Biol.*, 24(12):965-970 (1979).
Feldmann et al., "Pentose metabolism in Zymomonas mobilis wild-type and recombinant strains," *Appl. Microbiol. Biotechnol.*, 38(3):354-361 (1992).
Felpeto-Santero et al., "Engineering alternative isobutanol production platforms," *AMB Express*, 5(1):32 (2015).
Fuglsang, "Codon optimizer: a freeware tool for codon optimization," *Protein Expr. Purif.*, 31(2):247-249 (2003).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Gao et al., "UpGene: Application of a web-based DNA codon optimization algorithm," *Biotechnol. Prog.*, 20(2):443-448 (2004).
Gibbs et al., "Degenerate oligonucleotide gene shuffling (DOGS): a method for enhancing the frequency of recombination with family shuffling," *Gene*, 271:13-20 (2001).
Gong et al., "Conversion of pentoses by yeasts," *Biotechnol. Bioeng.*, 25:85-102 (1983).
Gong et al., "Quantitative production of xylitol from D-xylose by a high-xylitol producing yeast mutant *Candida tropicalis* HXP2," *Biotechnol. Lett.*, 3:125-130 (1981).
Govinden et al., "Xylitol production by recombinant *Saccharomyces cerevisiae* expressing the Pichia stipitis and Candida shehatae XYL1 genes," *Appl. Microbiol. Biotechnol.*, 55:76-80 (2001).
Grillaud et al., "The polyols in pediatric dentistry: advantages of xylitol," *Arch. Pediatr.*, 12(7):1180-1186 (2005). (English abstract attached).
Guamán-Burneo et al., "Xylitol production by yeasts isolated from rotting wood in the Galápagos Islands, Ecuador, and description of *Cyberlindnera galapagoensis* f.A., sp. Nov," *Antonie Van Leeuwenhoek*, 108(4):919-931 (2015).
Guirimand et al., "Cell surface engineering of *Saccharomyces cerevisiae* combined with membrane separation technology for xylitol production from rice straw hydrolysate," *Appl. Microbiol. Biotechnol.*, 100(8):3477-3487 (2016).
Hallborn et al., "The influence of cosubstrate and aeration on xylitol formation by recombinant*Saccharomyces cerevisiae* expressing theXYL1 gene," *Appl. Microbiol. Biotechnol.*, 42:326-333 (1994).
Hallborn et al., "Xylitol production by recombinant *Saccharomyces cerevisiae*," *Bio/Technology*, 9:1090-1095 (1991).
Hanai et al., "Engineered synthetic pathway for isopropanol production in *Escherichia coli*," *Appl. Environ. Microbiol.*, 73(24):7814-7818 (2007).
Haresaku et al., "Long-term effect of xylitol gum use on mutans streptococci in adults," *Caries Res.*, 41(3):198-203 (2007).
Hayes et al., "Combining computational and experimental screening for rapid optimization of protein properties," *Proc. Natl. Acad. Sci. USA*, 99(25):15926-15931 (2002).
Hector et al., "Expression of a heterologous xylose transporter in a *Saccharomyces cerevisiae* strain engineered to utilize xylose improves aerobic xylose consumption," *Appl. Microbiol. Biotechnol.*, 80(4):675-684 (2008).
Hellinga, "Computational protein engineering," *Nat. Struct. Biol.*, 5(7):525-527 (1998).
Hibbert et al., "Directed evolution of biocatalytic processes," *Biomol. Eng.*, 22:11-19 (2005).
Higashide et al., "Metabolic engineering of Clostridium cellulolyticum for production of isobutanol from cellulose," *Appl. Environ. Microbiol.*, 77(8):2727-2733 (2011).
Hirabayashi et al., "Improving xylitol production through recombinant expression of xylose reductase in the white-rot fungus *Phanerochaete sordida* YK-624," *J. Biosci. Bioeng.*, 120:6-8 (2015).
Hoffmeister et al., "Mitochondrial trans-2-enoyl-CoA reductase of wax ester fermentation from Euglena gracilis defines a new family of enzymes involved in lipid synthesis," *J. Biol. Chem.*, 280(6):4329-4338 (2005).
Hong et al., "Overexpression of D-xylose reductase (xyl1) gene and antisense inhibition of D-xylulokinase (xyiH) gene increase xylitol production in Trichoderma reesei," *Biomed. Res. Int.*, 2014:169705 (2014).
Huisman et al., "Enzyme Evolution for Chemical Process Applications," *Biocatalysis in the Pharmaceutical and Biotechnology Industries*, Patel Ed., CRC Press, Boca Raton, Florida, pp. 717-742 (2007).
Iverson et al., "Engineering a synthetic anaerobic respiration for reduction of xylose to xylitol using NADH output of glucose catabolism by *Escherichia coli* AI21," *BMC Syst. Biol.*, 10:31 (2016).
Iverson et al., "Increasing reducing power output (NADH) of glucose catabolism for reduction of xylose to xylitol by genetically engineered *Escherichia coli* AI05," *World I Microbiol. Biotechnol.*, 29:1225-1232 (2013).
Izumori et al., "Production of xylitol from D-xylose by *Mycobacterium smegmatis*" *J. Ferment. Technol.*, 66(1):33-36 (1988).
Jeffries et al., "Metabolic engineering for improved fermentation of pentoses by yeasts," *Appl. Microbiol. Biotechnol.*, 63:495-509 (2004).
Jeon et al., "Effect of heterologous xylose transporter expression in Candida tropicalis on xylitol production rate," *Bioprocess Biosyst. Eng.*, 36:809-817 (2013).
Jeon et al., "Xylitol production is increased by expression of codon-optimized Neurospora crassa xylose reductase gene in Candida tropicalis," *Bioprocess Biosyst. Eng.*, 35:191-198 (2012).
Jin et al., "*Saccharomyces cerevisiae* engineered for xylose metabolism exhibits a respiratory response," *Appl. Environ. Microbiol.*, 70(11):6816-6825 (2004).
Jin et al., "Stoichiometric network constraints on xylose metabolism by recombinant *Saccharomyces cerevisiae*," *Metab. Eng.*, 6:229-238 (2004).
Jo et al., "Dual utilization of NADPH and NADH cofactors enhances xylitol production in engineered *Saccharomyces cerevisiae*," *Biotechnol. J.*, 10:1935-1943 (2015).
Junyapate et al., "*Yamadazyma ubonensis* f.a., sp. nov., a novel xylitol-producing yeast species isolated in Thailand," *Antonie Van Leeuwenhoek*, 105:471-480 (2014).
Kamat et al., "Xylitol production by Cyberlindnera (Williopsis) saturnus, a tropical mangrove yeast from xylose and corn cob hydrolysate," *J. Appl. Microbiol.*, 115(6):1357-1367 (2013).
Karlen et al., "Absolute determination of the activity of two C-14 dating standards," *Arkiv Geofysik*, 4:465-471 (1964).
Khankal et al., "Role of xylose transporters in xylitol production from engineered *Escherichia coli*.," *J. Biotechnol.*, 134:246-252 (2008).
Kim et al., "Metabolic engineering of *Saccharomyces cerevisiae* for the production of 2-phenylethanol via Ehrlich pathway," *Biotechnol. Bioeng.*, 111(1):115-124 (2014).
Kim et al., "Production of xylitol from D-xylose and glucose with recombinant Corynebacterium glutamicum," *Enzyme Microb. Technol.*, 46:366-371 (2010).
Ko et al "Enhancement of xylitol productivity and yield using a xylitol dehydrogenase gene-disrupted mutant of Candida tropicalis under fully aerobic conditions," *Biotechnol. Lett.*, 28(15):1159-1162 (2006).
Ko et al., "Production of xylitol from D-xylose by a xylitol dehydrogenase gene-disrupted mutant of Candida tropicalis," *Appl. Environ. Microbiol.*, 72(6):4207-4213 (2006).
Kordowska-Wiater, "Production of arabitol by yeasts: current status and future prospects," *J. Appl. Microbiol.*, 119(2):303-314 (2015).
Kretz et al., "Gene site saturation mutagenesis: a comprehensive mutagenesis approach," *Methods Enzymol.*, 388:3-11 (2004).

(56) References Cited

OTHER PUBLICATIONS

Kudahettige-Nilsson et al., "Biobutanol production by Clostridium acetobutylicum using xylose recovered from birch Kraft black liquor," *Bioresour. Technol.*, 176:71-79 (2015).
Landschulz et al., "The leucine zipper: a hypothetical structure common to a new class of DNA binding proteins," *Science*, 240:1759-1764 (1988).
Lee et al., "A new approach to directed gene evolution by recombined extension on truncated templates (RETT)," *J. Molec. Catalysis B:Enzym.*, 26:119-129 (2003).
Lee et al., "Characterization of two-substrate fermentation processes for xylitol production using recombinant *Saccharomyces cerevisiae* containing xylose reductase gene," *Process Biochem.*, 35:1199-1203 (2000).
Lee et al., "Cloning and characterization of the xyl1 gene, encoding an NADH-preferring xylose reductase from Candida parapsilosis, and its functional expression in Candida tropicalis," *Appl. Environ. Microbiol.*, 69:6179-6188 (2003).
Lee et al., "Isobutanol production in engineered *Saccharomyces cerevisiae* by overexpression of 2-ketoisovalerate decarboxylase and valine biosynthetic enzymes," *Bioprocess. Biosyst. Eng.*, 35(9):1467-1475 (2012).
Lin et al., "Consolidated bioprocessing of cellulose to isobutanol using Clostridium thermocellum," *Metab. Eng.*, 31:44-52 (2015).
Lin et al., "Isobutanol production at elevated temperatures in thermophilic Geobacillus thermoglucosidasius," *Metab. Eng.*, 24:1-8 (2014).
Loser et al., "Perspectives for the biotechnological production of ethyl acetate by yeasts," *Appl. Microbiol. Biotechnol.*, 98(12):5397-5415 (2014).
Low et al., "Mimicking somatic hypermutation: affinity maturation of antibodies displayed on bacteriophage using a bacterial mutator strain," *J. Mol. Biol.*, 260(3):359-368 (1996).
Lutz et al., "Creating multiple-crossover DNA libraries independent of sequence identity," *Proc. Natl. Acad. Sci. USA*, 98(20):11248-11253 (2001).
Lutz et al., "Rapid generation of incremental truncation libraries for protein engineering using α-phosphothioate nucleotides," *Nucleic Acids Res.*, 29(4):e16 (2001).
Maguire et al., "Xylitol and caries prevention—is it a magic bullet?," *Br. Dent. J.*, 194(8):429-436 (2003).
Mann, "An International Reference Material for Radiocarbon Dating," *Radiocarbon*, 25(2):519-527 (1983).
Matsushika et al., "Ethanol production from xylose in engineered *Saccharomyces cerevisiae* strains: current state and perspectives," *Appl. Microbiol. Biotechnol.*, 84(1):37-53 (2009).
Morissey et al., "Cell factory applications of the yeast *Kluyveromyces marxianus* for the biotechnological production of natural flavour and fragrance molecules," *Yeast*, 32(1):3-16 (2015).
Muller et al., "Nucleotide exchange and excision technology (NExT) DNA shuffling: a robust method for DNA fragmentation and directed evolution," *Nucleic Acids Res.*, 33(13):e117 (2005).
Nair et al., "Evolution in Reverse: Engineering a D-Xylose-Specific Xylose Reductase," *ChemBioChem*, 9(8):1213-1215 (2008).
Ness et al., "Synthetic shuffling expands functional protein diversity by allowing amino acids to recombine independently" *Nat. Biotechnol.*, 20(12):1251-1255 (2002).
Nielsen et al., "Engineering alternative butanol production platforms in heterologous bacteria," *Metab. Eng.*, 11(4-5):262-273 (2009).
Nijland et al., "Improving pentose fermentation by preventing ubiquitination of hexose transporters in *Saccharomyces cerevisiae*," *Biotechnol. Biofuels*, 9:158 (2016).
Nozaki et al., "Production of D-arabitol by Metschnikowia reukaufii AJ14787," *Biosci. Biotechnol. Biochem.*, 67(9):1923-1929 (2003).
Nyyssölä et al., "Production of xylitol from D-xylose by recombinant Lactococcus lactis," *J. Biotechnol.*, 118:55-66 (2005).
Oh et al., "Enhanced xylitol production through simultaneous co-utilization of cellobiose and xylose by engineered *Saccharomyces cerevisiae*," *Metab. Eng.*, 15:226-234 (2013).
Onishi et al., "Microbial production of xylitol from glucose.," *Appl. Microbiol.*, 18(6):1031-1035 (1969).
Onishi et al., "The production of xylitol, L-arabinitol and ribitol by yeasts," *Agr. Biol. Chem.*, 30(11):1139-1144 (1966).
Osawa et al., "Recent evidence for evolution of the genetic code.," *Microbiol Rev.*, 56(1):229-264 (1992).
Ostermeier et al., "A combinatorial approach to hybrid enzymes independent of DNA homology," *Nat. Biotechnol.*, 17:1205-1209 (1999).
Ostermeier et al., "Combinatorial protein engineering by incremental truncation," *Proc. Natl. Acad. Sci. USA*, 96:3562-3567 (1999).
Otten et al., "Directed evolution: selecting today's biocatalysts," *Biomol. Eng.*, 22:1-9 (2005).
Pal et al., "Studies on xylitol production by metabolic pathway engineered Debaryomyces hansenii," *Bioresour. Technol.*, 147:449-455 (2013).
Parret et al., "Critical reflections on synthetic gene design for recombinant protein expression," *Curr. Opin. Struct. Biol.*, 38:155-162 (2016).
Pasztor et al., "A synthetic O2-tolerant butanol pathway exploiting native fatty acid biosynthesis in *Escherichia coli*," *Biotechnol. Bioeng.*, 112(1):120-128 (2015).
Pitkanen, "Impact of Xylose and Mannose on Central Metabolism of Yeast *Saccharomyces cerevisiae*," Helsinki University of Technology, Department of Chemical Technology, Technical Biochemistry Report, pp. 1-70 (2005).
Porro et al., "Replacement of a metabolic pathway for large-scale production of lactic acid from engineered yeasts," *Appl. Environ. Microbiol.*, 65(9):4211-4215 (1999).
Pourmir et al.,"Production of xylitol by recombinant microalgae," *J. Biotechnol.*, 165:178-183 (2013).
Pritchard et al., "A general model of error-prone PCR," *J. Theor. Biol.*, 234:497-509 (2005).
Rajpal et al., "A general method for greatly improving the affinity of antibodies by using combinatorial libraries" *Proc. Natl. Acad. Sci. USA*, 102(24):8466-8471 (2005).
Rangaswamy et al., "Screening of facultative anaerobic bacteria utilizing D-xylose for xylitol production," *Appl. Microbiol. Biotechnol.*, 60:88-93 (2002).
Rao et al., "Isolation and characterization of ethanol-producing yeasts from fruits and tree barks," *Lett. Appl. Microbiol.*, 47:19-24 (2008).
Reetz et al., "Directed Evolution of an Enantioselective Enzyme through Combinatorial Multiple-Cassette Mutagenesis" *Angew. Chem. Int. Ed Engl.*, 40(19):3589-3591 (2001).
Reetz et al., "Iterative saturation mutagenesis (ISM) for rapid directed evolution of functional enzymes.," *Nat. Protoc.*, 2(4):891-903 (2007).
Reetz et al., "Iterative saturation mutagenesis on the basis of B factors as a strategy for increasing protein thermostability," *Angew. Chem. Int. Ed Engl.*, 45:7745-7751 (2006).
Reidhaar-Olson et al. "Combinatorial cassette mutagenesis as a probe of the informational content of protein sequences," *Science*, 241:53-57 (1988).
Reidhaar-Olson et al., "Random mutagenesis of protein sequences using oligonucleotide cassettes," *Methods Enzymol.*, 208:564-586 (1991).
Rivas et al., "Carbon material and bioenergetic balances of xylitol production from corncobs by Debaryomyces hansenii," *Biotechnol. Prog.*, 19(3):706-713 (2003).
Runquist et al., "Expression of the Gxf1 transporter from Candida intermedia improves fermentation performance in recombinant xylose-utilizing *Saccharomyces cerevisiae*," *Appl. Microbiol. Biotechnol.*, 82(1):123-130 (2009).
Saha et al., "Production of D-arabitol by a newly isolated *Zygosaccharomyces rouxii*," *J. Ind. Microbiol. Biotechnol.*, 34:519-523 (2007).
Sampaio et al., "Screening of filamentous fungi for production of xylitol from D-xylose," *Brazilian J. Microbiol.*, 34:325-328 (2003).
Sasaki et al., "Engineering of pentose transport in Corynebacterium glutamicum to improve simultaneous utilization of mixed sugars," *Appl. Microbiol. Biotechnol.*, 85:105-115 (2009).

(56) References Cited

OTHER PUBLICATIONS

Sasaki et al., "Xylitol production by recombinant Corynebacterium glutamicum under oxygen deprivation" *Appl. Microbiol. Biotechnol.*, 86:1057-1066 (2010).
Selifonova et al., "Rapid evolution of novel traits in microorganisms" *Appl. Environ. Microbiol.*, 67(8):3645-3649 (2001).
Sen et al., "Developments in directed evolution for improving enzyme functions," *Appl. Biochem. Biotechnol.*, 143:212-223 (2007).
Shao et al., "Random-priming in vitro recombination: an effective tool for directed evolution" *Nucleic Acids Res.*, 26(2):681-683 (1998).
Sharma et al., "Enhancement in xylose utilization using Kluyveromyces marxianus NIRE-K1 through evolutionary adaptation approach," *Bioprocess Biosyst. Eng.*, 39:835-843 (2016).
Shi et al., "Metabolic engineering of a synergistic pathway for n-butanol production in *Saccharomyces cerevisiae*," *Sci. Rep.*, 6:25675 (2016).
Sieber et al., "Libraries of hybrid proteins from distantly related sequences," *Nat. Biotechnol.*, 19:456-460 (2001).
Sirisansaneeyakul et al., "Screening of Yeasts for Production of Xylitol from D-Xylose," *J. Ferment. Bioeng.*, 80(6):565-570 (1995).
Slininger et al., "Comparative evaluation of ethanol production by xylose-fermenting yeasts presented high xylose concentrations," *Biotechnol. Lett*, 7(6):431-436 (1985).
Soma et al., "Direct isopropanol production from cellobiose by engineered *Escherichia coli* using a synthetic pathway and a cell surface display system," *J. Biosci. Bioeng.*, 114(1):80-85 (2012).
Steen et al., "Metabolic engineering of *Saccharomyces cerevisiae* for the production of n-butanol," *Microb. Cell. Fact.*, 7:36 (2008).
Steinberg et al., "Remineralizing potential, antiplaque and antigingivitis effects of xylitol and sorbitol sweetened chewing gum," *Clin. Prev. Dent.*, 14(5):31-34 (1992).
Stemmer, "DNA shuffling by random fragmentation and reassembly: in vitro recombination for molecular evolution," *Proc Natl Acad Sci USA*, 91:10747-10751 (1994).
Stemmer, "Rapid evolution of a protein in vitro by DNA shuffling," *Nature*, 370:389-391 (1994).
Su et al., "Efficient production of xylitol from hemicellulosic hydrolysate using engineered *Escherichia coli,*" *Metab. Eng.*, 31:112-122 (2015).
Suzuki et al., "Novel Enzymatic Method for the Production of Xylitol from D-Arabitol by Gluconobacter oxydans," *Biosci. Biotechnol. Biochem.*, 66(12):2614-2620 (2002).
Suzuki et al.,"Expression of xyrA gene encoding for D-xylose reductase of Candida tropicalis and production of xylitol in *Escherichia coli,*" *J. Biosci. Bioeng.*, 87(3):280-284 (1999).
Sybirna et al., "A new Hansenula polymorpha HAP4 homologue which contains only the N-terminal conserved domain of the protein is fully functional in *Saccharomyces cerevisiae,*" *Curr. Genet.*, 47(3):172-181 (2005).
Toivari et al., "Conversion of xylose to ethanol by recombinant *Saccharomyces cerevisiae*: importance of xylulokinase (XKS1) and oxygen availability," *Metab. Eng.*, 3(3):236-249 (2001).
Toivari et al., "Metabolic engineering of *Saccharomyces cerevisiae* for conversion of D-glucose to xylitol and other five-carbon sugars and sugar alcohols," *Appl. Environ. Microbiol.*, 73(17):5471-5476 (2007).
Tung et al., "Computational identification of ubiquitylation sites from protein sequences," *BMC Bioinformatics.* 9:310 (2008).
Ur-Rehman et al., "Xylitol; A review on Bio-production, Application, Health Benefits and Related Safety Issues," *Crit. Rev. Food Sci. Nutr.*, 55:1514-1528 (2015).
Van Den Burg et al., "Engineering an enzyme to resist boiling," *Proc. Natl. Acad. Sci. USA*, 95:2056-2060 (1998).
Van Hoek et al., "Effects of pyruvate decarboxylase overproduction on flux distribution at the pyruvate branch point in *Saccharomyces cerevisiae,*" *Appl. Environ. Microbiol.*, 64(6):2133-2140 (1998).
Vandeska et al., "Effects of environmental conditions on production of xylitol byCandida boidinii," *World J. Microbiol. Biotechnol.*, 11:213-218 (1995).
Volkov et al, "Recombination and chimeragenesis by in vitro heteroduplex formation and in vivo repair" *Nucleic Acids Res.*, 27(18):e18 (1999).
Volkov et al., "Random chimeragenesis by heteroduplex recombination" *Methods Enzymol.*, 328:456-463 (2000).
Voronovsky et al., "Expression of xylA genes encoding xylose isomerases from *Escherichia coli* and Streptomyces coelicolor in the methylotrophic yeast *Hansenula polymorpha,*" *FEMS Yeast Res.*, 5(11):1055-1062 (2005).
West, "Xylitol production by Candida species grown on a grass hydrolysate," *World J. Microbiol. Biotechnol.*, 25:913-916 (2009).
Wong et al., "Sequence saturation mutagenesis (SeSaM): a novel method for directed evolution" *Nucleic Acids Res.*, 32(3):e26 (2004).
Wong et al., "Sequence saturation mutagenesis with tunable mutation frequencies" *Anal. Biochem.*, 341:187-189 (2005).
Wong et al., "Transversion-enriched sequence saturation mutagenesis (SeSaM-Tv+): a random mutagenesis method with consecutive nucleotide exchanges that complements the bias of error-prone PCR." *Biotechnol. J.*, 3:74-82 (2008).
Xiao et al., "Metabolic engineering of D-xylose pathway in Clostridium beijerinckii to optimize solvent production from xylose mother liquid," *Metab. Eng.*, 14(5):569-578 (2012).
Xin et al., Simultaneous fermentation of glucose and xylose to butanol by *Clostridium* sp. strain BOH3 *Appl. Environ. Microbiol.*, 80(15):4771-4778 (2014).
Yang et al., "Metabolic and process engineering of Clostridium cellulovorans for biofuel production from cellulose," *Metab. Eng.*, 32:39-48 (2015).
Yoon et al., "L-arabinose pathway engineering for arabitol-free xylitol production in Candida tropicalis," *Biotechnol. Lett.*, 33:747-753 (2011).
Yoshitake et al., "Production of Polyalcohol by a *Corynebacterium* sp. Part I. Production of Pentitol from Aldopentose" *Agric. Biol. Chem.*, 35(6):905-911 (1971).
Yoshitake et al., "Xylitol Production by an *Enterobacter* Species," *Agric. Biol. Chem.*, 37(10):2261-2267 (1973).
Yoshitake et al., Xylitol Production by Enterobacter liquefaciens, *Agric. Biol. Chem.*, 40(8):1493-1503 (1976).
Yu et al., "Metabolic engineering of Clostridium tyrobutyricum for n-butanol production through co-utilization of glucose and xylose," *Biotechnol. Bioeng.*, 112(10):2134-2141 (2015).
Zha et al., "Optimization of CDT-1 and XYL1 expression for balanced co-production of ethanol and xylitol from cellobiose and xylose by engineered *Saccharomyces cerevisiae,*" *PLoS One*, 8(7):e68317 (2013).
Zhang et al., "Improving xylitol production at elevated temperature with engineered Kluyveromyces marxianus through over-expressing transporters" *Bioresour. Technol.*, pp. 1-17 (2014). doi: http://dx.doi.org/I0.1016/j.biortech.2014.10.150.
Zhang et al., "Metabolic Engineering of a Pentose Metabolism Pathway in Ethanologenic Zymomonas mobilis," *Sceicne*, 267:240-243 (1995).
Zhang et al., "Simultaneous glucose and xylose uptake by an acetone/butanol/ethanol producing laboratory Clostridium beijerinckii strain SE-2," *Biotechnol. Lett.*, 38(4):611-617 (2016).
Zhang et al., "Xylitol production at high temperature by engineered Kluyveromyces marxianus," *Bioresour. Technol.*, 152:192-201 (2014).
Zhao et al., "Molecular evolution by staggered extension process (StEP) in vitro recombination," *Nat. Biotechnol.*, 16:258-261 (1998).
Butler et al., "Uncharacterized protein," Uniprot C4XZX2, retrieved from the internet: https://www.uniprot.org/uniprot/C4XZX2.txt?version=37 on Jun. 30, 2020.
Riley et al., "Glucose/xylose facilitator 1," Uniprot A0A1A0H9B1, retrieved from the internet: https://www.uniprot.org/uniprot/A0A1A0H9B1.txt?version=3 on Jun. 30, 2020.
Riley et al., "General substrate transporter," Uniprot A0A1A0HI81, retrieved from the internet: https://www.uniprot.org/uniprot/A0A1A0HI81.txt?version=3 on Jun. 30, 2020.
Riley et al., "General substrate transporter," Uniprot A0A1A0HK54, retrieved from the internet: https://www.uniprot.org/uniprot/A0A1A0HK54.txt?version=3 on Jun. 30, 2020.

(56) References Cited

OTHER PUBLICATIONS

Riley et al., "General substrate transporter," Uniprot A0A1A0HG07, retrieved from the internet: https://www.uniprot.org/uniprot/A0A1A0HG07.txt?version=3 on Jun. 30, 2020.
Riley et al., "General substrate transporter," Uniprot A0A1A0H5D9, retrieved from the internet: https://www.uniprot.org/uniprot/A0A1A0H5D9.txt?version=3 on Jun. 30, 2020.
Riley et al., "General substrate transporter," Uniprot A0A1A0HJP8, retrieved from the internet: https://www.uniprot.org/uniprot/A0A1A0HJP8.txt?version=3 on Jun. 30, 2020.

* cited by examiner

METHODS AND ORGANISM WITH INCREASED XYLOSE UPTAKE

CROSS-REFERENCE TO RELATED APPLICATION

This application claims the benefit of priority of U.S. Provisional Application No. 62/437,600, filed on Dec. 21, 2016, the content of which is herein incorporated by reference in its entirety.

FIELD

The present invention relates to the field of molecular biology and microbiology. Provided herein are non-naturally occurring microbial organisms having increased xylose uptake and increased production of bioderived compounds using xylose as a substrate, as well as methods to make and use these microbial organisms.

REFERENCE TO SEQUENCE LISTING

The instant application contains a Sequence Listing which has been submitted in ASCII format via EFS-Web and is hereby incorporated by reference in its entirety. Said ASCII copy, created on Dec. 19, 2017, is named 14305-007-999_Sequence_Listing.txt and is 146,836 bytes in size.

BACKGROUND

Xylose is an abundant sugar present in lignocellulosic biomass, a renewable feedstock for producing bioderived chemicals. However, the use of lignocellulosic biomass and the production of bioderived chemicals are limited by the naturally low xylose uptake in microbial organisms. Therefore, methods to increase xylose uptake in microbial organisms to increase the production of bioderived compounds from xylose represent unmet needs. The non-naturally occurring microbial organisms and methods provided herein meet these needs and provide other related advantages.

SUMMARY OF THE INVENTION

Provided herein are non-naturally occurring microbial organism having at least one exogenous nucleic acid encoding a xylose transporter, wherein the xylose transporter has an amino acid sequence that is at least 89% identical to a *Metschnikowia* xylose transporter.

In some embodiments, the non-naturally occurring microbial organism provided herein can have exogenous nucleic acids encoding at least two, at least three, at least four, at least five, at least six, or at least seven xylose transporters. In some embodiments, the xylose transporter can have an amino acid sequence that is at least 90%, at least 95%, at least 98%, or at least 99%, identical to the *Metschnikowia* xylose transporter. In some embodiments, the xylose transporter is a *Metschnikowia* xylose transporter. In some embodiments, the *Metschnikowia* xylose transporter can be, for example, Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p.

In some embodiments, the *Metschnikowia* xylose transporter is from the H0 *Metschnikowia* sp. Accordingly, also provided herein is a non-naturally occurring microbial organism having at least one exogenous nucleic acid encoding a xylose transporter, wherein the xylose transporter has an amino acid sequence that is at least 89% identical to a xylose transporter form the H0 *Metschnikowia* sp. In some embodiments, the xylose transporter has an amino acid sequence that is at least 89% identical to SEQ ID NO: 1, 2, 3, 4, 5, 7, 8, 9, 10, 11, or 12. In some embodiments, the non-naturally occurring microbial organism provided herein can have the exogenous nucleic acid SEQ ID NOs: 13, 14, 15, 16, 17, 19, 20, 21, 22, 23, 24 25, 26, or 27.

In some embodiments, the xylose transporter can be ubiquitin-deficient. In some embodiments, the xylose transporter has an amino acid sequence of SEQ ID NO: 44 or SEQ ID NO: 45. In some embodiments, the non-naturally occurring microbial organism provided herein has the exogenous nucleic acid SEQ ID NO: 49 or SEQ ID NO: 45.

In some embodiments, the exogenous nucleic acid can be codon-optimized for expression in the host microbial organism.

In some embodiments, provided herein is a non-naturally occurring microbial organism having at least one exogenous nucleic acid encoding a xylose transporter, wherein the xylose transporter has an amino acid sequence that is at least 74% identical to Xyt1p of a *Metschnikowia* species. In some embodiments, the *Metschnikowia* species is the H0 *Metschnikowia* sp. In some embodiments, the xylose transporter has an amino acid sequence that is at least 74% identical to SEQ ID NO: 1. In some embodiments, the exogenous nucleic acid has the sequence of SEQ ID NO: 13 or SEQ ID NO: 21.

In some embodiments, provided herein is a non-naturally occurring microbial organism having at least one exogenous nucleic acid encoding a xylose transporter, wherein the xylose transporter has an amino acid sequence that is at least 85% identical to Gxf1p of a *Metschnikowia* species. In some embodiments, the *Metschnikowia* species is the H0 *Metschnikowia* sp. In some embodiments, the xylose transporter has an amino acid sequence that is at least 74% identical to SEQ ID NO: 2. In some embodiments, the exogenous nucleic acid has the sequence of SEQ ID NO: 14.

In some embodiments, provided herein is a non-naturally occurring microbial organism having at least one exogenous nucleic acid encoding a xylose transporter, wherein the xylose transporter has an amino acid sequence that is at least 89% identical to a ΔGxf1p of a *Metschnikowia* species. In some embodiments, the *Metschnikowia* species is the H0 *Metschnikowia* sp. In some embodiments, the xylose transporter has an amino acid sequence that is at least 89% identical to SEQ ID NO: 3. In some embodiments, the exogenous nucleic acid has the sequence of SEQ ID NO: 15.

In some embodiments, provided herein is a non-naturally occurring microbial organism comprising at least one exogenous nucleic acid encoding a xylose transporter, wherein the xylose transporter has an amino acid sequence that is at least 71% identical to a Gxf2p/Gal2p of a *Metschnikowia* species. In some embodiments, the *Metschnikowia* species is the H0 *Metschnikowia* sp. In some embodiments, the xylose transporter has an amino acid sequence that is at least 71% identical to SEQ ID NO: 4. In some embodiments, the exogenous nucleic acid has the sequence of SEQ ID NO: 16.

In some embodiments, provided herein is a non-naturally occurring microbial organism comprising at least one exogenous nucleic acid encoding a xylose transporter, wherein the xylose transporter has an amino acid sequence that is at least 71% identical to a Gxs1p/Hgt12p of a *Metschnikowia* species. In some embodiments, the *Metschnikowia* species is the H0 *Metschnikowia* sp. In some embodiments, the xylose transporter has an amino acid sequence that is at least 71% identical to SEQ ID NO: 7. In some embodiments, the exogenous nucleic acid has the sequence of SEQ ID NO: 19.

In some embodiments, provided herein is a non-naturally occurring microbial organism comprising at least one exogenous nucleic acid encoding a xylose transporter, wherein the xylose transporter has an amino acid sequence that is at least 60% identical to a Hxt5p of a *Metschnikowia* species. In some embodiments, the *Metschnikowia* species is the H0 *Metschnikowia* sp. In some embodiments, the xylose transporter has an amino acid sequence that is at least 60% identical to SEQ ID NO: 8. In some embodiments, the exogenous nucleic acid has the sequence of SEQ ID NO: 20.

In some embodiments, provided herein is a non-naturally occurring microbial organism comprising at least one exogenous nucleic acid encoding a xylose transporter, wherein the xylose transporter has an amino acid sequence that is at least 84% identical to a Hxt2.6p of a *Metschnikowia* species. In some embodiments, the *Metschnikowia* species is the H0 *Metschnikowia* sp. In some embodiments, the xylose transporter has an amino acid sequence that is at least 84% identical to SEQ ID NO: 10. In some embodiments, the exogenous nucleic acid has the sequence of SEQ ID NO: 22 or SEQ ID NO: 23.

In some embodiments, provided herein is a non-naturally occurring microbial organism comprising at least one exogenous nucleic acid encoding a xylose transporter, wherein the xylose transporter has an amino acid sequence that is at least 50% identical to a Qup2p of a *Metschnikowia* species. In some embodiments, the *Metschnikowia* species is the H0 *Metschnikowia* sp. In some embodiments, the xylose transporter has an amino acid sequence that is at least 50% identical to SEQ ID NO: 11. In some embodiments, the exogenous nucleic acid has the sequence of SEQ ID NO: 24 or SEQ ID NO: 25.

In some embodiments, provided herein is a non-naturally occurring microbial organism comprising at least one exogenous nucleic acid encoding a xylose transporter, wherein the xylose transporter has an amino acid sequence that is at least 74% identical to a Aps1p/Hgt19p of a *Metschnikowia* species. In some embodiments, the *Metschnikowia* species is the H0 *Metschnikowia* sp. In some embodiments, the xylose transporter has an amino acid sequence that is at least 74% identical to SEQ ID NO: 12. In some embodiments, the exogenous nucleic acid has the sequence of SEQ ID NO: 26 or SEQ ID NO: 27.

Provided herein are non-naturally occurring microbial organism having at least one exogenous nucleic acid encoding a xylose transporter having an amino acid sequence that is at least 89% identical to a *Metschnikowia* xylose transporter. The exogenous nucleic acid can be a heterologous nucleic acid. The microbial organism can be in an aerobic culture medium or a substantially anaerobic culture medium. The microbial organism can be a species of bacteria or yeast.

In some embodiments, the microbial organism is a species of a yeast, such as *Saccharomyces cerevisiae*, *Schizosaccharomyces pombe*, *Candida albicans*, *Candida tropicalis*, *Debaryomyces hansenii*, *Kluyveromyces lactis*, *Kluyveromyces marxianus*, *Aspergillus terreus*, *Aspergillus niger*, *Chlamydomonas reinhardtii*, *Pichia pastoris*, *Rhizopus arrhizus*, *Rhizopus oryzae*, *Trichoderma reesei*, or *Yarrowia lipolytica*.

In some embodiments, the microbial organism is a species of a bacteria, such as *Escherichia coli*, *Klebsiella oxytoca*, *Anaerobiospirillum succiniciproducens*, *Actinobacillus succinogenes*, *Mannheimia succiniciproducens*, *Rhizobium etli*, *Bacillus subtilis*, *Corynebacterium glutamicum*, *Gluconobacter oxydans*, *Zymomonas mobilis*, *Lactococcus lactis*, *Lactobacillus plantarum*, *Streptomyces coelicolor*, *Clostridium acetobutylicum*, *Pseudomonas fluorescens*, or *Pseudomonas putida*.

The non-naturally occurring microbial organism provided herein can further include a metabolic pathway capable of producing a bioderived compound from xylose, such as xylitol, ethanol, n-butanol, isobutanol, isopropanol, arabitol, ethyl acetate, phenyl-ethyl alcohol, 2-methyl-butanol, or 3-methyl-butanol.

Provided herein is also a method of producing a bioderived compound, including culturing the non-naturally occurring microbial organism provided herein under conditions and for a sufficient period of time to produce said bioderived compound, wherein the microbial organism has a pathway capable of producing the bioderived compound from xylose. The microbial organism can be cultured in medium having xylose and a co-substrate, such as cellobiose, hemicellulose, glycerol, galactose, and glucose, or a combination thereof. The microbial organism can be cultured in batch cultivation, fed-batch cultivation or continuous cultivation.

In some embodiments, the method can further includes separating the bioderived compound from other components in the culture. The separation method can include, for example, extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

Also provided herein is a bioderived compound produced by the method described herein. The bioderived compound can include, for example, glycerol, acetaldehyde, acetate, glyceraldehyde, or a combination thereof as impurities. Also provided herein is a composition having one or more of the bioderived compound described herein. In some embodiments, the composition can have the bioderived xylitol. In some embodiments, the composition can be culture medium. The composition can be culture medium with the microbial organism removed.

DETAILED DESCRIPTION

Figure 1:
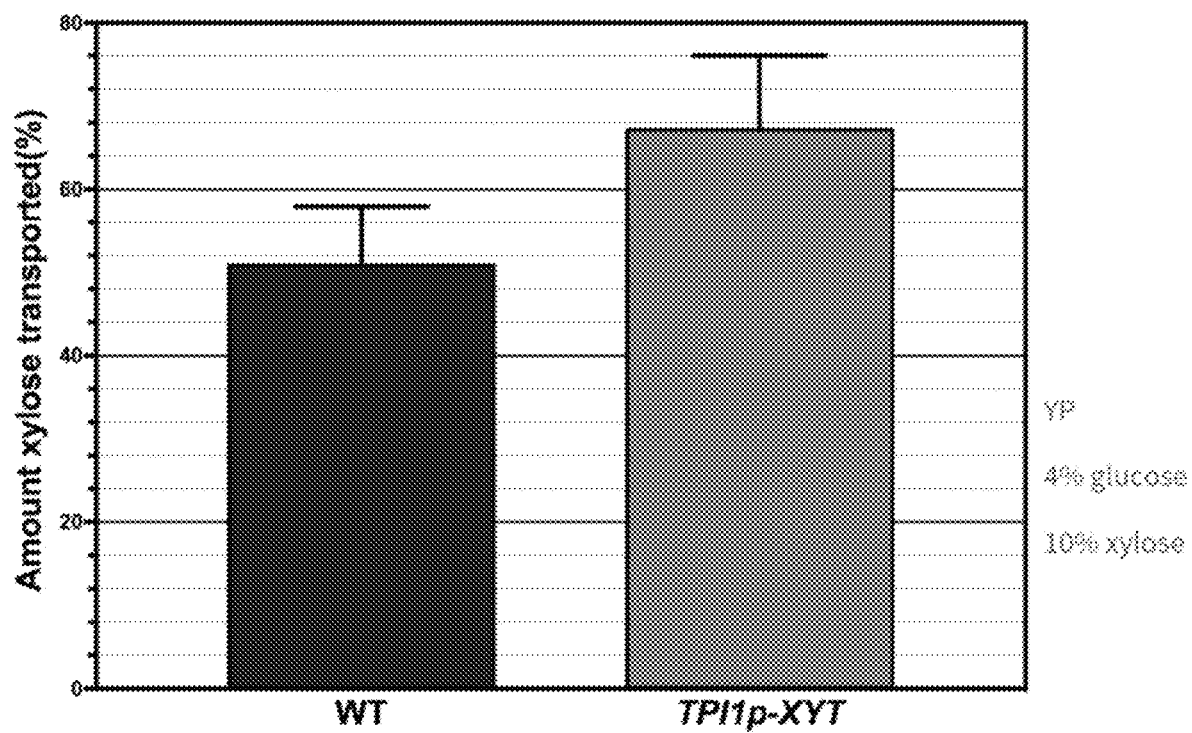
FIG. 1 shows the efficient xylose uptake by the wild type H0 *Metschnikowia* sp. measured by the amount of xylose transported (%), which was further enhanced (from about 55% to about 65%) when XYT1, a xylose transporter of the H0 *Metschnikowia* sp., was overexpressed.

The compositions and methods provided herein are based, in part, on the discovery, cloning and characterization of novel xylose transporters from the *Metschnikowia* genus. Expression of one or more of these xylose transporters or variants thereof in host microbial organisms was found to increase xylose uptake, as well as production of bioderived compounds by these microbial organisms using xylose as a substrate. Provided herein are also nucleic acids that encode these xylose transporters, non-naturally microbial organisms having enhanced xylose uptake by expressing these xylose transporters, as well as bioderived compounds produced by these microbial organisms.

As used herein, the term "non-naturally occurring," when used in reference to a microbial organism or microorganism described herein is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include, but are not limited to, enzymes or proteins within a xylitol biosynthetic pathway.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is also understood that a microbial organism can have one or multiple copies of the same exogenous nucleic acid. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "xylose" refers to a five carbon monosaccharide with a formyl functional group having the chemical formula of $C_5H_{10}O_5$, a Molar mass of 150.13 g/mol, and one IUPAC name of (3R,4S,5R)-oxane-2,3,4,5-tetrol. Xylose is also known in the art as D-xylose, D-xylopyranose, xyloside, d-(+)-xylose, xylopyranose, wood sugar, xylomed and D-xylopentose.

As used herein, the term "xylose transporter" refers to membrane protein that facilitates the movement of xylose across a cell membrane. The term "*Metschnikowia* xylose transporter" refers to a xylose transporter from a *Metschnikowia* species. As used herein, the term "*Metschnikowia* species" refers to any species of yeast that falls within the *Metschnikowia* genus. Exemplary *Metschnikowia* species include, but are not limited to,

*Metschnikowia pulcherrima, Metschnikowia fructicola, Metschnikowia chrysoperlae, Metschnikowia andauensis, Metschnikowia shanxiensis, Metschnikowia sinensis, Metschnikowia zizyphicola, Metschnikowia reukaufii, Metschnikowia bicuspidata, Metschnikowia lunata, Metschnikowia zobellii, Metschnikowia australis, Metschnikowia agaveae, Metschnikowia gruessii, Metschnikowia hawaiiensis, Metschnikowia krissii, Metschnikowia* sp. strain NS-O-85, *Metschnikowia* sp. strain NS-O-89, *Metschnikowia* sp. strain 4MS-2013 and the unique *Metschnikowia* species described herein, *Metschnikowia* sp. H0, alternatively known as the "H0 *Metschnikowia* sp." The *Metschnikowia* species described herein, i.e., the H0 *Metschnikowia* sp., is a newly discovered species, which is identified by the designated Accession No. 081116-01, and deposited at International Depositary Authority of Canada ("IDAC"), an International Depositary Authority, at the address of 1015 Arlington Street, Winnipeg, Manitoba, Canada R3E 3R2, on Nov. 8, 2016, under the terms of the Budapest Treaty.

As used herein, the term "ubiquitin-deficient" when used in connection with a protein refers to an altered form of the protein that is resistant to ubiquitination at one or more ubiquitination sites and proteasome-mediated degradation. The resistance to ubiquitination can range from a decreased frequency of ubiquitination to complete inhibition of ubiquitination. Ubiquitination is an enzymatic post-translational modification by which a ubiquitin protein is attached to a lysine residue of the substrate protein. A chain of multiple ubiquitin proteins can form on a single lysine residue on the substrate protein, and target the substrate protein for proteasome-mediated degradation. Accordingly, a ubiquitin-deficient protein is partially or totally resistant to ubiquitination and proteasome-mediated degradation. In some embodiments, a ubiquitin-deficient protein has an amino acid mutation at or near a lysine residue that can be ubiquitinated. The proximity of the mutation near a lysine residue that can be ubiquitinated can be close within the primary sequence or close within the 3D structure so long as the mutation yields resistance to ubiquitination. Such mutation can be amino acid substitution, deletion, or addition. In some embodiment, the lysine residue that can be ubiquitinated itself is substituted to another amino acid. In some embodiment, the lysine residue is deleted. In some embodiments, one or more amino acid residues near the lysine residue that can be ubiquitinated are mutated such that the lysine residue is not accessible to the ubiquitination machinery. In some embodiments, a ubiquitin-deficient protein has amino acid mutations at or near at least two lysine residues that can be ubiquitinated. In some embodiments, a ubiquitin-deficient protein has amino acid mutations at or near at least three lysine residues that can be ubiquitinated. In some embodiments, a ubiquitin-deficient protein has amino acid mutations at or near at least four lysine residues that can be ubiquitinated. In some embodiments, a ubiquitin-deficient protein has amino acid substitutions at or near all lysine residues that can be ubiquitinated. In some embodiments, a ubiquitin-deficient protein has amino acid substitutions at least all lysine residues that can be ubiquitinated, and is completely resistant to ubiquitination and proteasome-mediated degradation.

As used herein, the term "medium," "culture medium," "growth medium" or grammatical equivalents thereof refers to a liquid or solid (e.g., gelatinous) substance containing nutrients that supports the growth of a cell, including any microbial organism species described herein. Nutrients that support growth include: a substrate that supplies carbon, such as, but are not limited to, xylose, cellobiose, hemicelluloses, glycerol, galactose and glucose; salts that provide essential elements including magnesium, nitrogen, phosphorus, and sulfur; a source for amino acids, such as peptone or tryptone; and a source for vitamin content, such as yeast extract. Specific examples of medium useful in the methods and in characterizing the *Metschnikowia* species described herein include yeast extract peptone (YEP) medium and yeast nitrogen base (YNB) medium having a carbon source such as, but not limited to xylose, glucose, cellobiose, galactose, or glycerol, or a combination thereof. The formulations of YEP and YNB medium are well known in the art. For example, YEP medium having 4% xylose includes, but is not limited to, yeast extract 1.0 g, peptone 2.0 g, xylose 4.0 g, and 100 ml water. As another example, YNB medium having 2% glucose and 2% xylose includes, but is not limited to, biotin 2 μg, calcium pantothenate 400 μg, folic acid 2 μg, inositol 2000 μg, niacin 400 μg, paminobenzoic acid 200 μg, pyridoxine hydrochloride 400 μg, riboflavin 200 μg, thiamine hydrochloride 400 μg, boric acid 500 μg, copper sulfate 40 μg, potassium iodide 100 μg, ferric chloride 200 μg, manganese sulfate 400 μg, sodium molybdate 200 μg, zinc sulfate 400 μg, potassium phosphate monobasic 1 g, magnesium sulfate 500 mg, sodium chloride 100 mg, calcium chloride 100 mg, 20 g glucose, 20 g, xylose and 1 L water. The amount of the carbon source in the medium can be readily determined by a person skilled in the art. When more than one substrate that supplies carbon is present in the medium, these are referred to as "co-substrates." Medium can also include substances other than nutrients needed for growth, such as a substance that only allows select cells to grow (e.g., antibiotic or antifungal), which are generally found in selective medium, or a substance that allows for differentiation of one microbial organism over another when grown on the same medium, which are generally found in differential or indicator medium. Such substances are well known to a person skilled in the art.

As used herein, the term "aerobic" when used in reference to a culture or growth condition is intended to mean that the free oxygen ($O_2$) is available in the culture or growth condition. The term "anaerobic" when used in reference to a culture or growth condition is intended to mean that the culture or growth condition lacks free oxygen ($O_2$). The term "substantially anaerobic" when used in reference to a culture or growth condition is intended to mean that the amount of dissolved oxygen in a liquid medium is less than about 10% of saturation. The term also is intended to include sealed chambers maintained with an atmosphere of less than about 1% oxygen that include liquid or solid medium.

As used herein, the term "bioderived" means derived from or synthesized by a biological organism and can be considered a renewable resource since it can be generated by a biological organism. Such a biological organism, in particular the microbial organism disclosed herein, can utilize feedstock or biomass, such as, sugars (e.g., xylose, glucose, fructose, galactose, sucrose, and arabinose), carbohydrates obtained from an agricultural, plant, bacterial, or animal source, and glycerol.

As used herein, the term "biobased" means a product is composed, in whole or in part, of a bioderived compound. A biobased or bioderived product is in contrast to a petroleum derived product, wherein such a product is derived from or synthesized from petroleum or a petrochemical feedstock.

Provided herein are novel *Metschnikowia* xylose transporters. Expression of these transporters or their variants in microbial organisms (e.g. *Saccharomyces cerevisiae*) can enhance xylose uptake and increase the production of bioderived products from xylose by these microbial organisms. Thus, provided herein is an isolated polypeptide that is a *Metschnikowia* xylose transporter or a variant thereof; an isolated nucleic acid that encodes a *Metschnikowia* xylose transporter or a variant thereof; a vector that has an isolated nucleic acid that encodes a *Metschnikowia* xylose transporter or a variant thereof; as well as a non-naturally occurring microbial organism having enhanced xylose uptake and at least one exogenous nucleic acid encoding a *Metschnikowia* xylose transporter or a variant thereof.

Provided herein are non-naturally occurring microbial organisms having enhanced xylose uptake, which have at least one exogenous nucleic acid encoding a xylose transporter, wherein the xylose transporter has an amino acid sequence that is at least 30% identical to a *Metschnikowia* xylose transporter. The microbial organisms can have one or more copies of the exogenous nucleic acid. In some embodiments, the microbial organisms can have two, three, four, five, six, seven, eight, nine, ten, eleven, twelve, thirteen, fourteen, fifteen, sixteen, seventeen, eighteen, nineteen, twenty, or more copies of the exogenous nucleic acid.

Provided herein are also isolated polypeptides that are at least 30% identical to a *Metschnikowia* xylose transporter. Provided herein are also isolated nucleic acids that encode polypeptides that are at least 30% identical to a *Metschnikowia* xylose transporter. The *Metschnikowia* xylose transporters include, for example, transporters such as Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species. The *Metschnikowia* species include, for example, the *Metschnikowia* sp. H0, *Metschnikowia pulcherrima*, *Metschnikowia fructicola*, *Metschnikowia chrysoperlae*, *Metschnikowia andauensis*, *Metschnikowia shanxiensis*, *Metschnikowia sinensis*, *Metschnikowia zizyphicola*, *Metschnikowia reukaufii*, *Metschnikowia bicuspidata*, *Metschnikowia lunata*, *Metschnikowia zobellii*, *Metschnikowia australis*, *Metschnikowia agaveae*, *Metschnikowia gruessii*, *Metschnikowia hawaiiensis*, *Metschnikowia krissii*, *Metschnikowia* sp. strain NS-O-85, *Metschnikowia* sp. strain NS-O-89, and *Metschnikowia* sp. strain 4MS-2013. The *Metschnikowia* xylose transporter can be a xylose transporter from the H0 *Metschnikowia* sp. In some embodiments, the xylose transporter can include, for example, Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from the H0 *Metschnikowia* sp. Exemplary sequences are provided below.

| SEQ ID NO: | Description | SEQUENCES |
|---|---|---|
| 1 | Amino acid sequence of H0 *Metschnikowia* species Xyt1p | MGYEEKLVAPALKFKNFLDKTPNIHNVYVIAAISCTSGMMFGFDISSMSVF VDQQPYLKMFDNPSSVIQGFITASMSLGSFFGSLTSTFISEPFGRRASLFICGI LWVIGAAVQSSSQNRAQLICGRIIAGWGIGFGSSVAPVYGSEMAPRKIRGTI GGIFQFSVTVGIFIMFLIGYGCSFIQGKASFRIPWGVQMVPGLILLIGLFFIPES PRWLAKQGYWEDAEIIVANVQAKGNRNDANVQIEMSEIKDQLMLDEHLK EFTYADLFTKKYRQRTITAIFAQIWQQLTGMNVMMYYIVYIFQMAGYSGN TNLVPSLIQYIINMAVTVPALFCLDLLGRRTILLAGAAFMMAWQFGVAGIL ATYSEPAYISDTVRITIPDDHKSAAKGVIACCYLFVCSFAFSWGVGIWVYCS EVVVGDSQSRQRGAALATSANWIFNFAIAMFTPSSFKNITWKTYIIYATFCAC MFIHVFFFFPETKGKRLEEIGQLWDEGVPAWRSAKWQPTVPLASDAELAH KMDVAHAEHADLLATHSPSSDEKTGTV |
| 2 | Amino acid sequence of H0 *Metschnikowia* species Gxf1p | MSQDELHTKSGVETPINDSLLEEKHDVTPLAALPEKSFKDYISISIFCLFVAF GGFVFGFDTGTISGFVNMSDFKTRFGEMNAQGEYYLSNVRTGLMVSIFNV GCAVGGIFLCKIADVYGRRIGLMFSMVVYVVGIIIQIASTTKWYQYFIGRLI AGLAVGTVSVISPLFISEVAPKQLRGTLVCCFQLCITLGIFLGYCTTYGTKTY TDSRQWRIPLGICFAWALFLVAGMLNMPESPRYLVEKSRIDDARKSIARSN KVSEEDPAVYTEVQLIQAGIDREALAGSATWMELVTGKPKIFRRVIMGVM LQSLQQLTGDNYFFYYGTTIFKAVGLQDSFQTSIILGIVNFASTFVGIYAIER MGRRLCLLTGSACMFVCFIIYSLIGTQHLYKNGFSNEPSNTYKPSGNAMIFIT CLYIFFFASTWAGGVYCIVSESYPLRIRSKAMSVATAANWMWGFLISFFTPF ITSAIHFYYGFVFTG CLAFSFFYVYFFVVETKGLSLEEVDILYASGTLPWKSS GWVP |
| 3 | Amino acid sequence of H0 *Metschnikowia* species ΔGxf1p (variant of Gxf1p with shorter N-terminus) | MSDFKTRFGEMNAQGEYYLSNVRTGLMVSIFNVGCAVGGIFLCKIADVYG RRIGLMFSMVVYVVGIIIQIASTTKWYQYFIGRLIAGLAVGTVSVISPLFISEV APKQLRGTLVCCFQLCITLGIFLGYCTTYGTKTYTDSRQWRIPLGICFAWAL FLVAGMLNMPESPRYLVEKSRIDDARKSIARSNKVSEEDPAVYTEVQLIQA GIDREALAGSATWMELVTGKPKIFRRVIMGVMLQSLQQLTGDNYFFYYGT TIFKAVGLQDSFQTSIILGIVNFASTFVGIYAIERMGRRLCLLTGSACMFVCFI IYSLIGTQHLYKNGFSNEPSNTYKPSGNAMIFITCLYIFFFASTWAGGVYCIV SESYPLRIRSKAMSVATAANWMWGFLISFFTPFITSAIHFYYGFVFTGCLAFS FFYVYFFVVETKGLSLEEVDILYASGTLPWKSSGWVP |
| 4 | Amino acid sequence of H0 *Metschnikowia* species Gxf2p/Gal2p | MSAEQEQQVSGTSATIDGLASLKQEKTAEEEDAFKPKPATAYFFISFLCGLV AFGGYVFGFDTGTISGFVNMDDYLMRFGQQHADGTYYLSNVRTGLIVSIFN IGCAVGGLALSKVGDIWGRRIGIMVAMIIYMVGIIIQIASQDKWYQYFIGRLI TGLGVGTTSVLSPLFISESAPKHLRGTLVCCFQLMVTLGIFLGYCTTYGTKN YTDSRQWRIPLGLCFAWALLLISGMVFMPESPRFLIERQRFDEAKASVAKS NQVS1EDPAVYTEVELIQAGIDREALAGSAGWKELITGKPKMLQRVILGM MLQSIQQLTGNNYFFYYGTTIFKAVGMSDSFQTSIVLGIVNFASTFVGIWAI ERMGRRSCLLVGSACMSVCFLIYSILGSVNLYIDGYENTPSNTRKPTGNAMI FITCLFIFFFASTWAGGVYSIVSETYPLRIRSKGMAVATAANWMWGFLISFF TPFITSAIHFYYGFVFTGCLIFSFFYVFFFVRETKGLSLEEVDELYATDLPPW KTAGWTPPSAEDMAHTTGFAEAAKPTNKHV |

-continued

| SEQ ID NO: | Description | SEQUENCES |
|---|---|---|
| 5 | Amino acid sequence of H0 Metschnikowia species ΔGxs1p/ΔHgt12p (valiant of Gxs1p/Hgt12p with shorter N-terminus) | MGIFVGVFAALGGVLFGYDTGTISGVMAMPWVKEHFPKDRVAFSASESSLI VSILSAGTFFGAILAPLLTDTLGRRWCIIISSLVVFNLGAALQTAATDIPLLIV GRVIAGLGVGLISSTIPLYQSEALPKWIRGAVVSCYQWAITIGIFLAAVINQG THKINSPASYRIPLGIQMAWGLILGVGMFFLPETPRFYISKGQNAKAAVSLA RLRKLPQDHPELLEELEDIQAAYEFETVHGKSSWSQVFTNKNKQLKKLATG VCLQAFQQLTGVNFIFYFGTTFFNSVGLDGFTTSLATNIVNVGSTIPGILGVE IFGRRKVLLTGAAGMCLSQFIVAIVGVATDSKAANQVLIAFCCIFIAFFAAT WGPTAWVVCGEIFPLRTRAKSIAMCAASNWLLNWAIAYATPYLVDSDKG NLGTNVFFIWGSCNFFCLVFAYFMIYETKGLSLEQVDELYEKVASARKSPG FVPSEHAFREHADVETAMPDNFNLKAEAISVEDASV |
| 6 | NOT USED | |
| 7 | Amino acid sequence of H0 Metschnikowia species Gxs1p/Hgt12 | MGLESNKLIRKYINVGEKRAGSSGMGIFVGVFAALGGVLFGYDTGTISGVM AMPWVKEHFPKDRVAFSASESSLIVSILSAGTFFGAILAPLLTDTLGRRWCII ISSLVVFNLGAALQTAATDIPLLIVGRVIAGLGVGLISSTIPLYQSEALPKWIR GAVVSCYQWAITIGIFLAAVINQGTHKINSPASYRIPLGIQMAWGLILGVGM FFLPETPRFYISKGQNAKAAVSLARLRKLPQDHPELLEELEDIQAAYEFETV HGKSSWSQVFTNKNKQLKKLATGVCLQAFQQLTGVNFIFYFGTTFFNSVG LDGFTTSLATNIVNVGSTIPGILGVEIFGRRKVLLTGAAGMCLSQFIVAIVGV ATDSKAANQVLIAFCCIFIAFFAATWGPTAWVVCGEIFPLRTRAKSIAMCAA SNWLLNWAIAYATPYLVDSDKGNLGTNVFFIWGSCNFFCLVFAYFMIYET KGLSLEQVDELYEKVASARKSPGFVPSEHAFREHADVETAMPDNFNLKAE AISVEDASV |
| 8 | Amino acid sequence of H0 Metschnikowia species Hxt5p | MSIFEGKDGKGVSSTESLSNDVRYDNMEKVDQDVLRHNFNFDKEFEELEIE AAQVNDKPSFVDRILSLEYKLHFENKNHMVVVLLGAFAAAAGLLSGLDQSII SGASIGMNKALNL1EREASLVSSLMPLGAMAGSMIMTPLNEWFGRKSSLITS CIWYTIGSALCAGARDHHMMYAGRFILGVGVGIEGGCVGIYISESVPANVR GSIVSMYQFNIALGEVLGYAVAAIFYTVHGGWRFMVGSSLVFSTILFAGLFF LPESPRWLVHKGRNGMAYDVVVKRLRDINDESAKLEFLEMRQAAYQERER RSQESLFSSWGELFTIARNRRALTYSVIMITLGQLTGVNAVMYYMSTLMGA IGFNEKDSVFMSLVGGGSLLIGTIPAILWMDRFGRRVVVGYNLVGFFVGLVL VGVGYRFNPVTQKAASEGVYLTGLIVYFLFFGSYSTLTWVIPSESFDLRTRS LGMTICSTFLYLWSFTVTYNFTKMSAAFTYTGLTLGFYGGIAFLGLIYQVCF MPETKDKTLEEIDDIFNRSAFSIARENISNLKKGIW |
| 9 | Amino acid sequence of H0 Metschnikowia species Xyt1p with S75L mutation. | MGYEEKLVAPALKFKNFLDKTPNIHNVYVIAAISCTSGMMFGFDISSMSVF VDQQPYLKMFDNPSSVIQGFITALMSLGSFFGSLTSTFISEPFGRRASLFICGI LWVIGAAVQSSSQNRAQLICGRIIAGWGIGFGSSVAPVYGSEMAPRKIRGTI GGIFQFSVTVGIFIMFLIGYGCSFIQGKASFRIPWGVQMVPGLILLIGLFFIPES LPRWLAKQGYWEDAEIIVANVQAKGNRNDANVQIEMSEIKDQLMLDEHLK EFTYADLFTKKYRQRTITAIFAQIWQQLTGMNVMMYYIVYIFQMAGYSGN TNLVPSLIQYIINMAVTVPALFCLDLLGRRTILLAGAAFMMAWQFGVAGIL ATYSEPAYISDTVRITIPDDHKSAAKGVIACCYLFVCSFAFSWGVGIWVYCS EVVVGDSQSRQRGAALATSANWIFNFAIAMFTPSSFKNITWKTYIIYATFCAC MFIHVFFFFPETKGKRLEEIGQLWDEGVPAWRSAKWQPTVPLASDAELAH KMDVAHAEHADLLATHSPSSDEKTGTV |
| 10 | Amino acid sequence of H0 Metschnikowia species Hxt2.6p | MSSTTDTLEKRDIEPFTSDAPVTVHDYIAEERPWWKVPHLRVLTWSVFVIT LTSTNNGYDGSMLNGLQSLDIWQEDLGHPAGQKLGALANGVLFGNLAAV PFASYFCDRFGRRPVICFGQILTIVGAVLQGLSNSYGFFLGSRIVLGFGAMIA TIPSPTLISEIAYPTHRETSTFAYNVCWYLGAIIASWVTYGTRDLQSKACWSI PSYLQAALPFFQVCMIWFVPESPRFLVAKGKIDQARAVLSKYHTGDSTDPR DVALVDFELHEIESALEQEKLNTRSSYFDFFKKRNFRKRGFLCVNIVGVAM QLSGNGLVSYYLSKVLDSIGITETKRQLEINGCLMIYNFVICVSLMSVCRMF KRRVLFLTCFSGMTVCYTIWTILSALNEQRHFEDKGLANGVLAMIFFYYFF YNVGINGLPFLYI1EILPYSHRAKGLNLFQFSQFLTQIYNGYVNPIAMDAISW KYYIVYCCILFVELVIVFFTFPETSGYTLEEVAQVFGDEAPGLHNRQLDVAK ESLEHVEHV |
| 11 | Amino acid sequence of H0 Metschnikowia species Qup2p | MGFRNLKRRLSNVGDSMSVHSVKEEEDFSRVEIPDEIYNYKIVLVALTAAS AAIIIGYDAGFIGGTVSLTAFKSEFGLDKIVISATAASAIEANVVSVFQAGAYF GCLFFYPIGEIWGRKIGLLLSGFLLTFGAAISLISNSSRGLGAIYAGRVLTGLG IGGCSSLAPIYVSEIAPAAIRGKLVGCWEVSWQVGGIVGYWINYGVLQTLPI SSQQWIIPPAVQLIPSGLFWGLCLLIPESPRFLVSKGKIDKARKNLAYLRGLS EDHPSVFELENISKAIEENFEQTGRGFFDPLKALFFSKKMLYRLLLSTSMF MMQNGYGINAVTYYSPTIPFKSLGVQGSNAGLLSTGIFGLLKGAASVFWVFF LVDTFGRRFCLCYLSLPCSICMWYIGAYIKIANPSAKLAAGDTATTPAGTAA KAMLYIWTIFYGITWNGTTWVICAEIFPQSVRTAAQAVNASSNWFWAFMI GHFTGQALENIGYGYYFLFAACSAIFPVVVVVPVYPETKGVPLEAVEYLFEV RPWKAHSYALEKYQIEYNEGEFHQHKPEVLLQGSENSD |

| SEQ ID NO: | Description | SEQUENCES |
|---|---|---|
| 12 | Amino acid sequence of H0 *Metschnikowia* species Aps1p/Hgt19p | MGYEEKLVAPALKFKNFLDKTPNIHNVYVIAAISCTSGMMFGFDISSMSVF<br>VDQQPYLKMFDNPSSVIQGFITASMSLGSFFGSLTSTFISEPFGRRASLFICGI<br>LWVIGAAVQSSSQNRAQLICGRIIAGWGIGFGSSVAPVYGSEMAPRKIRGTI<br>GGIFQFSVTVGIFIMFLIGYGCSFIQGKASFRIPWGVQMVPGLILLIGLFFIPES<br>PRWLAKQGYWEDAEIIVANVQAKGNRNDANVQIEMSEIKDQLMLDEHLK<br>EFTYADLFTKKYRQRTITAIFAQIWQQLTGMNVMMYYIVYIFQMAGYSGN<br>TNLVPSLIQYIINMAVTVPALFCLDLLGRRTILLAGAAFMMAWQFGVAGIL<br>ATYSEPAYISDTVRITIPDDHKSAAKGVIACCYLFVCSFAFSWGVGIWVYCS<br>EVVVGDSQSRQRGAALATSANWIFNFAIAMFTPSSFKNITWKTYIIYATFCAC<br>MFIHVFFFFPETKGKRLEEIGQLWDEGVPAWRSAKWQPTVPLASDAELAH<br>KMDVAHAEHADLLATHSPSSDEKTGTV |
| 13 | Nucleic acid sequence of H0 *Metschnikowia* species XYT1 | ATGGGTTACGAGGAAAAGCTTGTAGCGCCCGCGTTGAAATTCAAAAAC<br>TTTCTTGACAAAACCCCCAATATTCACAATGTCTATGTCATTGCCGCCAT<br>CTCCTGTACATCAGGTATGATGTTTGGATTTGATATCTCGTCGATGTCTG<br>TCTTTGTCGACCAGCAGCCATACTTGAAGATGTTTGACAACCCTAGTTC<br>CGTGATTCAAGGTTTCATTACCGCGCTGATGAGTTTGGGCTCGTTTTTCG<br>GCTCGCTCACATCCACGTTCATCTCTGAGCCTTTTGGTCGTCGTGCATCG<br>TTGTTCATTTGTGGTATTCTTTGGGTAATTGGAGCAGCGGTTCAAAGTTC<br>GTCGCAGAACAGGGCCCAATTGATTTGTGGGCGTATCATTGCAGGATGG<br>GGCATTGGCTTTGGGTCATCGGTGGCTCCTGTTTACGGGTCCGAGATGG<br>CTCCGAGAAAGATCAGAGGCACGATTGGTGGAATCTTCCAGTTCTCCGT<br>CACCGTGGGTATCTTTATCATGTTCTTGATTGGGTACGGATGCTCTTTCA<br>TTCAAGGAAAGGCCTCTTTCCGGATCCCCTGGGGTGTGCAAATGGTTCC<br>CGGCCTTATCCTCTTGATTGGACTTTTCTTTATTCCTGAATCTCCCCGTTG<br>GTTGGCCAAACAGGGCTACTGGGAAGACGCCGAAATCATTGTGGCCAA<br>TGTGCAGGCCAAGGGTAACCGTAACGACGCCAACGTGCAGATTGAAAT<br>GTCGGAGATTAAGGATCAATTGATGCTTGACGAGCACTTGAAGGAGTTT<br>ACGTACGCTGACCTTTTCACGAAGAAGTACCGCCAGCGCACGATCACGG<br>CGATCTTTGCCCAGATCTGGCAACAGTTGACCGGTATGAATGTGATGAT<br>GTACTACATTGTGTACATTTTCCAGATGGCAGGCTACAGCGGCAACACG<br>AACTTGGTGCCCAGTTTGATCCAGTACATCATCAACATGGCGGTCACGG<br>TGCCGGCGCTTTTCTGCTTGGATCTCTTGGGCCGTCGTACCATTTTGCTC<br>GCGGGTGCCGCGTTCATGATGGCGTGGCAATTCGGCGTGGCGGGCATTT<br>TGGCCACTTACTCAGAACCGGCATATATCTCTGACACTGTGCGTATCAC<br>GATCCCCGACGACCACAAGTCTGCTGCAAAAGGTGTGATTGCATGCTGC<br>TATTTGTTTGTGTGCTCGTTTGCATTCTCGTGGGGTGTCGGTATTTGGGT<br>GTACTGTTCCGAGGTTTGGGGTGACTCCCAGTCGAGACAAAGAGGCGCC<br>GCTCTTGCGACGTCGGCCAACTGGATCTTCAACTTCGCCATTGCCATGTT<br>CACGCCGTCCTCATTCAAGAATATCACGTGGAAGACGTATATCATCTAC<br>GCCACGTTCTGTGCGTGCATGTTCATACACGTGTTTTTCTTTTTCCCAGA<br>AACAAAGGGCAAGCGTTTGGAGGAGATAGGCCAGCTTTGGGACGAAGG<br>AGTCCCAGCATGGAGGTCAGCCAAGTGGCAGCCAACAGTGCCGCTCGC<br>GTCCGACGCAGAGCTTGCACACAAGATGGATGTTGCGCACGCGGAGCA<br>CGCGGACTTATTGGCCACGCACTCGCCATCTTCAGACGAGAAGACGGGC<br>ACGGTCTAA |
| 14 | Nucleic acid sequence of H0 *Metschnikowia* species GXF1 | ATGTCTCAAGACGAACTTCATACAAAGTCTGGTGTTGAAACACCAATCA<br>ACGATTCGCTTCTCGAGGAGAAGCACGATGTCACCCCACTCGCGGCATT<br>GCCCGAGAAGTCCTTCAAGGACTACATTTCCATTTCCATTTTCTGTTTGT<br>TTGTGGCATTTGGTGGTTTTGTTTTCGGTTTCGACACCGGTACAGATTTCC<br>GGTTTCGTCAACATGTCCGACTTCAAGACCAGATTTGGTGAGATGAATG<br>CCCAGGGCGAATACTACTTGTCCAATGTTAGAACTGGTTTGATGGTTTC<br>TATTTTCAACGTCGGTTGCGCCGTTGGTGGTATCTTCCTTTGTAAGATTG<br>CCGATGTTTATGGCAGAAGAATTGGTCTTATGTTTTCCATGGTGGTTTAT<br>GTCGTTGGTATCATTATTCAGATTGCCTCCACCACCAAATGGTACCAAT<br>ACTTCATTGGCCGTCTTATTGCTGGCTTGGCTGTGGGTACTGTTTCCGTC<br>ATCTCGCCACTTTTCATTTCCGAGGTTGCTCCTAAACAGCTCAGAGGTAC<br>GCTTGTGTGCTGCTTCCAGTTGTGTATCACCTTGGGTATCTTTTTGGGTT<br>ACTGCACGACCTACGGTACAAAGACTTACACTGACTCCAGACAGTGGA<br>GAATCCCATTGGGTATCTGTTTCGCGTGGGCTTTGTTTTTGGTGGCCGGT<br>ATGTTGAACATGCCCGAGTCTCCTAGATACTTGGTTGAGAAATCGAGAA<br>TCGACGATGCCAGAAAGTCCATTGCCAGATCCAACAAGGTTTCCGAGG<br>AAGACCCCGCCGTGTACACCGAGGTGCAGCTTATCCAGGCTGGTATTGA<br>CAGAGAGGCCCTTGCCGGCAGCGCCACATGGATGGAGCTTGTGACTGG<br>TAAGCCCAAAATCTTCAGAAGAGTCATCATGGGTGTCATGCTTCAGTCC<br>TTGCAACAATTGACTGGTGACAACTACTTTTTCTACTACGGAACCACGA<br>TTTTCAAGGCTGTTGGCTTGCAGGACTCTTTCCAGACGTCGATTATCTTG<br>GGTATTGTCAACTTTGCCTCGACTTTTGTCGGTATTTACGCCATTGAGAG<br>AATGGGCAGAAGATTGTGTTGTTGACCGGATCTGCGTGCATGTTTGTG<br>TGTTTCATCATCTACTCGCTCATTGGTACGCAGCACTTGTACAAGAACG<br>GCTTCTCTAACGAACCTTCCAACACATACAAGCCTTCCGGTAACGCCAT<br>GATCTTCATCACGTGTCTTTACATTTTCTTCTTTGCCTCGACCTGGGCCG<br>GTGGTGTTTACTGTATCGTGTCCGAGTCTTACCCATTGAGAATCAGATCC<br>AAGGCCATGTCTGTCGCCACCGCCGCCAACTGGATGTGGGGTTTCTTGA<br>TCTCGTTCTTCACGCCTTTCATCACCTCCGCCATCCACTTTTACTACGGTT |

| SEQ ID NO: | Description | SEQUENCES |
|---|---|---|
| | | TTGTTTTCACTGGCTGCTTGGCGTTCTCCTTCTTCTACGTCTACTTCTTTG<br>TCGTGGAGACCAAGGGTCTTTCCTTGGAGGAGGTTGACATTTTGTACGC<br>TTCCGGTACGCTTCCATGGAAGTCCTCTGGCTGGGTGCCTCCTACCGCG<br>GACGAAATGGCCCACAACGCCTTCGACAACAAGCCAACTGACGAACAA<br>GTCTAA |
| 15 | Nucleic acid sequence of H0 *Metschnikowia* species ΔGXF1 (variant of GXF1 with shorter N-terminus) | ATGTCCGACTTCAAGACCAGATTTGGTGAGATGAATGCCCAGGGCGAAT<br>ACTACTTGTCCAATGTTAGAACTGGTTTGATGGTTTCTATTTTCAACGTC<br>GGTTGCGCCGTTGGTGGTATCTTCCTTTGTAAGATTGCCGATGTTTATGG<br>CAGAAGAATTGGTCTTATGTTTTCCATGGTGGTTTATGTCGTTGGTATCA<br>TTATTCAGATTGCCTCCACCACCAAATGGTACCAATACTTCATTGGCCGT<br>CTTATTGCTGGCTTGGCTGTGGGTACTGTTTCCGTCATCTCGCCACTTTT<br>CATTTCCGAGGTTGCTCCTAAACAGCTCAGAGGTACGCTTGTGTGCTGC<br>TTCCAGTTGTGTATCACCTTGGGTATCTTTTTGGGTTACTGCACGACCTA<br>CGGTACAAAGACTTACACTGACTCCAGACAGTGGAGAATCCCATTGGGT<br>ATCTGTTTCGCGTGGGCTTTGTTTTTGGTGGCCGGTATGTTGAACATGCC<br>CGAGTCTCCTAGATACTTGGTTGAGAAATCGAGAATCGACGATGCCAGA<br>AAGTCCATTGCCAGATCCAACAAGGTTTCCGAGGAAGACCCCGCCGTGT<br>ACACCGAGGTGCAGCTTATCCAGGCTGGTATTGACAGAGAGGCCCTTGC<br>CGGCAGCGCCACATGGATGGAGCTTGTGACTGGTAAGCCCAAAATCTTC<br>AGAAGAGTCATCATGGGTGTCATGCTTCAGTCCTTGCAACAATTGACTG<br>GTGACAACTACTTTTTCTACTACGGAACCACGATTTTCAAGGCTGTTGG<br>CTTGCAGGACTCTTTCCAGACGTCGATTATCTTGGGTATTGTCAACTTTG<br>CCTCGACTTTTGTCGGTATTTACGCCATTGAGAGAATGGGCAGAAGATT<br>GTGTTTGTTGACCGGATCTGCGTGCATGTTTGTGTGTTTCATCATCTACT<br>CGCTCATTGGTACGCAGCACTTGTACAAGAACGGCTTCTCTAACGAACC<br>TTCCAACACATACAAGCCTTCCGGTAACGCCATGATCTTCATCACGTGT<br>CTTTACATTTTCTTCTTTGCCTCGACCTGGGCCGGTGGTGTTTACTGTAT<br>CGTGTCCGAGTCTTACCCATTGAGAATCAGATCCAAGGCCATGTCTGTC<br>GCCACCGCCGCCAACTGGATGTGGGGTTTCTTGATCTCGTTCTTCACGCC<br>TTTCATCACCTCCGCCATCCACTTTTACTACGGTTTTGTTTTCACTGGCTG<br>CTTGGCGTTCTCCTTCTTCTACGTCTACTTCTTTGTCGTGGAGACCAAGG<br>GTCTTTCCTTGGAGGAGGTTGACATTTTGTACGCTTCCGGTACGCTTCCA<br>TGGAAGTCCTCTGGCTGGGTGCCTCCTACCGCGGACGAAATGGCCCACA<br>ACGCCTTCGACAACAAGCCAACTGACGAACAAGTCTAA |
| 16 | Nucleic acid sequence of H0 *Metschnikowia* species GXF2/GAL2 | ATGAGTGCCGAACAGGAACAACAAGTATCGGGCACATCTGCCACGATA<br>GATGGGCTGGCGTCCTTGAAGCAAGAAAAAACCGCCGAGGAGGAAGAC<br>GCCTTCAAGCCTAAGCCCGCCACGGCGTACTTTTTCATTTCGTTCCTCTG<br>TGGCTTGGTCGCCTTTGGCGGCTACGTTTTCGGTTTCGATACCGGTACGA<br>TTTCCGGGTTTGTTAACATGGACGACTATTTGATGAGATTCGGCCAGCA<br>GCACGCTGATGGCACGTATTACCTTTCCAACGTGAGAACCGGTTTGATC<br>GTGTCCGATCTTCAACATTGGCTGTGCCGTTGGTGGTCTTGCGCTTTCGAA<br>AGTCGGTGACATTTGGGGCAGAAGAATTGGTATTATGGTTGCTATGATC<br>ATCTACATGGTGGGAATCATCATCCAGATCGCTTCACAGGATAAATGGT<br>ACCAGTACTTCATTGGCCGTTTGATCACCGGATTGGGTGTCGGCACCAC<br>GTCCGTGCTTAGTCCTCTTTTCATCTCCGAGTCGGCTCCGAAGCATTTGA<br>GAGGCACCCTTGTGTGTTGTTTCCAGCTCATGGTCACCTTGGGTATCTTT<br>TTGGGCTACTGCACGACCTACGGTACCAAGAACTACACTGACTCGCGCC<br>AGTGGCGGATTCCCTTGGGTCTTTGCTTCGCATGGGCTCTTTTGTTGATC<br>TCGGGAATGGTTTTCATGCCTGAATCCCACGTTTCTTGATTGAGCGCCA<br>GAGATTCGACGAGGCCAAGGCTTCCGTGGCCAAATCGAACCAGGTTTC<br>GACCGAGGACCCCGCCGTGTACACTGAAGTCGAGTTGATCCAGGCCGG<br>TATTGACCGTGAGGCATTGGCCGGATCCGCTGGCTGGAAAGAGCTTATC<br>ACGGGTAAGCCCAAGATGTTGCAGCGTGTGATTTTGGGAATGATGCTCC<br>AGTCGATCCAGCAGCTTACCGGTAACAACTACTTTTTCTACTATGGTAC<br>CACGATCTTCAAGGCCGTGGGCATGTCGGACTCGTTCCAGACCTCGATT<br>GTTTTGGGTATTGTCAACTTCGCCTCCACTTTTGTCGGAATCTGGGCCAT<br>CGAACGCATGGGCCGCAGATCTTGTTTGCTTGTTGGTTCCGCGTGCATG<br>AGTGTGTGTTTCTTGATCTACTCCATCTTGGGTTCCGTCAACCTTTACAT<br>CGACGGCTACGAGAACACGCCTTCCAACACGCGTAAGCCTACCGGTAA<br>CGCCATGATTTTCATCACGTGTTTGTTCATCTTCTTCTTCGCCTCCACCTG<br>GGCCGGTGGTGTGTACAGTATTGTGTCTGAAACATACCCATTGAGAATC<br>CGCTCTAAAGGTATGGCCGTGGCCACCGCTGCCAACTGGATGTGGGGTT<br>TCTTGATTTCGTTCTTCACGCCTTTCATCACCTCGGCCATCCACTTCTACT<br>ACGGGTTTGTGTTCACAGGGTGTCTTATTTTCTCCTTCTTCTACGTGTTCT<br>TCTTTGTTAGGGAAACCAAGGGTCTCTCGTTGGAAGAGGTGGATGAGTT<br>ATATGCCACTGACCTCCCACCATGGAAGACCGCGGGCTGGACGCCTCCT<br>TCTGCTGAGGATATGGCCCACACCACCGGGTTTGCCGAGGCCGCAAAGC<br>CTACGAACAAACACGTTTAA |
| 17 | Nucleic acid sequence of H0 *Metschnikowia* species ΔGXS1/ ΔHGT12 (variant | ATGGGCATTTTCGTTGGCGTTTTCGCCGCGCTTGGCGGTGTTCTCTTTGG<br>CTACGATACCGGTACCATCTCTGGTGTGATGGCCATGCCTTGGGTCAAG<br>GAACATTTCCCAAAAGACCGTGTTGCATTTAGTGCTTCCGAGTCGTCGT<br>TGATTGTGTCTATTTTATCTGCAGGAACTTTCTTTGGAGCCATTCTTGCT<br>CCGCTCTTGACCGATACATTGGGTAGACGCTGGTGTATTATCATCTCTTC |

| SEQ ID NO: | Description | SEQUENCES |
|---|---|---|
| | ofGXS1/HGT12 with shorter N-terminus) | GCTCGTTGTGTTCAATTTGGGTGCTGCTTTGCAGACGGCTGCCACGGAT<br>ATCCCGCTCTTGATTGTTGGTCGTGTCATTGCCGGTTTAGGGGTTGGTTT<br>GATTTCGCTGACGATTCCATTGTACCAGTCCGAAGCGCTTCCCAAATGG<br>ATTAGAGGTGCTGTTGTCTCGTGCTACCAATGGGCCATTACTATTGGTAT<br>CTTTTTGGCTGCCGTGATCAACCAGGGCACTCACAAGATCAACAGCCCT<br>GCGTCGTACAGAATTCCATTGGGTATTCAGATGGCATGGGGTCTTATCT<br>TGGGTGTCGGCATGTTCTTCTTGCCCGAGACGCCTCGTTTCTACATTTCC<br>AAGGGCCAGAATGCGAAGGCTGCTGTTTCATTGGCGCGTTTGAGAAAG<br>CTTCCGCAAGATCACCCGGAGTTGTTGGAGGAATTGGAAGATATCCAGG<br>CGGCATACGAGTTTGAGACTGTCCATGGCAAGTCTTCATGGCTGCAGGT<br>TTTCACCAACAAGAACAAACAATTGAAGAAGTTGGCCACGGGCGTGTG<br>CTTGCAGGCGTTCCAACAATTGACTGGTGTGAACTTCATTTTCTACTTTG<br>GCACGACTTTCTTCAACAGTGTTGGGCTTGACGGATTCACCACCTCCTTG<br>GCCACCAACATTGTCAATGTTGGCTCGACGATCCCTGGTATTTTGGGTG<br>TTGAGATTTTCGGCAGAAGAAAAGTGTTGTTGACCGGCGCTGCTGGTAT<br>GTGTCTTTCGCAATTCATTGTTGCCATTGTTGGTGTAGCCACCGACTCCA<br>AGGCTGCGAACCAAGTTCTTATTGCCTTCTGCTGCATTTTCATTGCGTTC<br>TTTGCAGCCACCTGGGGCCCCACCGCATGGGTTGTTTGTGGCGAGATTT<br>TCCCCTTGAGAACCAGAGCCAAGTCGATTGCCATGTGCGCTGCTTCGAA<br>CTGGTTGTTGAACTGGGCAATTGCATACGCCACGCCATACTTGGTTGAC<br>TCCGATAAGGGTAACTTGGGCACCAATGTGTTTTTCATTTGGGGAAGCT<br>GTAACTTCTTCTGCCTTGTGTTTGCCTACTTCATGATTTACGAGACCAAG<br>GGTCTTTCCTTGGAGCAGGTTGATGAGCTTTACGAGAAGGTTGCCAGCG<br>CCAGAAAGTCGCCTGGCTTCGTGCCAAGCGAGCACGCTTTCAGAGAGC<br>ACGCCGATGTGGAGACCGCCATGCCAGACAACTTCAACTTGAAGGCGG<br>AGGCGATTTCTGTCGAGGATGCCTCTGTTTAA |
| 18 | NOT USED | |
| 19 | Nucleic acid sequence of H0 Metschnikowia species GXS1/HGT12 | ATGAGCATCTTTGAAGGCAAAGACGGGAAGGGGGTATCCTCCACCGAG<br>TCGCTTTCCAATGACGTCAGATATGACAACATGGAGAAAGTTGATCAGG<br>ATGTTCTTAGACACAACTTCAACTTTGACAAAGAATTCGAGGAGCTCGA<br>AATCGAGGCGGCGCAAGTCAACGACAAACCTTCTTTTGTCGACAGGATT<br>TTATCCCTCGAATACAAGCTTCATTTCGAAAACAAGAACCACATGGTGT<br>GGCTCTTGGGCGCTTTCGCAGCCGCCGCAGGCTTATTGTCTGGCTTGGA<br>TCAGTCCATTATTTCTGGTGCATCCATTGGAATGAACAAAGCATTGAAC<br>TTGACTGAACGTGAAGCCTCATTGGTGTCTTCGCTTATGCCTTTAGGCGC<br>CATGGCAGGCTCCATGATTATGACACCTCTTAATGAGTGGTTCGGAAGA<br>AAATCATCGTTGATTATTTCTTGTATTTGGTATACCATCGGATCCGCTTT<br>GTGCGCTGGCGCCAGAGATCACCCACATGATGTACGCTGGCAGATTTATT<br>CTTGGTGTCGGTGTGGGTATAGAAGGTGGGTGTGTGGGCATTTACATTT<br>CCGAGTCTGTCCCAGCCAATGTGCGTGGTAGTATCGTGTCGATGTACCA<br>GTTCAATATTGCTTTGGGTGAAGTTCTAGGGTATGCTGTTGCTGCCATTT<br>TCTACACTGTTCATGGTGGATGGAGGTTCATGGTGGGGTCTTCTTTAGTA<br>TTCTCTACTATATTGTTTGCCGGATTGTTTTTCTTGCCCGAGTCACCTCGT<br>TGGTTGGTGCACAAAGGCAGAAACGGAATGGCATACGATGTGTGGAAG<br>AGATTGAGAGACATAAACGATGAAAGCGCAAAGTTGGAATTTTTGGAG<br>ATGAGACAGGCTGCTTATCAAGAGAGAGAAAGACGCTCGCAAGAGTCT<br>TTGTTCTCCAGCTGGGGCGAATTATTCACCATCGCTAGAAACAGAAGAG<br>CACTTACTTACTCTGTCATAATGATCACTTTGGGTCAATTGACTGGTGTC<br>AATGCCGTCATGTACTACATGTCGACTTTGATGGGTGCAATTGGTTTCA<br>ACGAGAAAGACTCTGTGTTCATGTCCCTTGTGGGAGGCGGTTCTTTGCT<br>TATAGGTACCATTCCTGCCATTTTGTGGATGGACCGTTTCGGCAGAAGA<br>GTTTGGGGTTATAATCTTGTTGGTTTCTTCGTTGGTTTGGTGCTCGTTGG<br>TGTTGGCTACCGTTTCAATCCCGTCACTCAAAAGGCGGCTTCAGAAGGT<br>GTGTACTTGACGGGTCTCATTGTCTATTTCTTGTTCTTTGGTTCCTACTCG<br>ACCTTAACTTGGGTCATTCCATCCGAGTCTTTTGATTTGAGAACAAGATC<br>TTTGGGTATGACAATCTGTTCCACTTTCCTTTACTTGTGGTCTTTCACCGT<br>CACCTACAACTTCACCAAGATGTCCGCCGCCTTCACATACACTGGGTTG<br>ACACTTGGTTTCTACGGTGGCATTGCGTTCCTTGGTTTGATTTACCAGGT<br>CTGCTTCATGCCCGAGACGAAGGACAAGACTTTGGAAGAAATTGACGA<br>TATCTTCAATCGTTCTGCGTTCTCTATCGCGCGCGAGAACATCTCCAACT<br>TGAAGAAGGGTATTTGGTAA |
| 20 | Nucleic acid sequence of H0 Metschnikowia species HXT5 | ATGAGCATCTTTGAAGGCAAAGACGGGAAGGGGGTATCCTCCACCGAG<br>TCGCTTTCCAATGACGTCAGATATGACAACATGGAGAAAGTTGATCAGG<br>ATGTTCTTAGACACAACTTCAACTTTGACAAAGAATTCGAGGAGCTCGA<br>AATCGAGGCGGCGCAAGTCAACGACAAACCTTCTTTTGTCGACAGGATT<br>TTATCCCTCGAATACAAGCTTCATTTCGAAAACAAGAACCACATGGTGT<br>GGCTCTTGGGCGCTTTCGCAGCCGCCGCAGGCTTATTGTCTGGCTTGGA<br>TCAGTCCATTATTTCTGGTGCATCCATTGGAATGAACAAAGCATTGAAC<br>TTGACTGAACGTGAAGCCTCATTGGTGTCTTCGCTTATGCCTTTAGGCGC<br>CATGGCAGGCTCCATGATTATGACACCTCTTAATGAGTGGTTCGGAAGA<br>AAATCATCGTTGATTATTTCTTGTATTTGGTATACCATCGGATCCGCTTT<br>GTGCGCTGGCGCCAGAGATCACCCACATGATGTACGCTGGCAGATTTATT<br>CTTGGTGTCGGTGTGGGTATAGAAGGTGGGTGTGTGGGCATTTACATTT |

| SEQ ID NO: | Description | SEQUENCES |
|---|---|---|
| | | CCGAGTCTGTCCCAGCCAATGTGCGTGGTAGTATCGTGTCGATGTACCA<br>GTTCAATATTGCTTTGGGTGAAGTTCTAGGGTATGCTGTTGCTGCCATTT<br>TCTACACTGTTCATGGTGGATGGAGGTTCATGGTGGGGTCTTCTTTAGTA<br>TTCTCTACTATATTGTTTGCCGGATTGTTTTTCTTGCCCGAGTCACCTCGT<br>TGGTTGGTGCACAAAGGCAGAAACGGAATGGCATACGATGTGTGGAAG<br>AGATTGAGAGACATAAACGATGAAAGCGCAAAGTTGGAATTTTTGGAG<br>ATGAGACAGGCTGCTTATCAAGAGAGAGAAAGACGCTCGCAAGAGTCT<br>TTGTTCTCCAGCTGGGGCGAATTATTCACCATCGCTAGAAACAGAAGAG<br>CACTTACTTACTCTGTCATAATGATCACTTTGGGTCAATTGACTGGTGTC<br>AATGCCGTCATGTACTACATGTCGACTTTGATGGGTGCAATTGGTTTCA<br>ACGAGAAAGACTCTGTGTTCATGTCCCTTGTGGGAGGCGGTTCTTTGCT<br>TATAGGTACCATTCCTGCCATTTTGTGGATGGACCGTTTCGGCAGAAGA<br>GTTTGGGGTTATAATCTTGTTGGTTTCTTCGTTGGTTTGGTGCTCGTTGG<br>TGTTGGCTACCGTTTCAATCCCGTCACTCAAAAGGCGGCTTCAGAAGGT<br>GTGTACTTGACGGGTCTCATTGTCTATTTCTTGTTCTTTGGTTCCTACTCG<br>ACCTTAACTTGGGTCATTCCATCCGAGTCTTTTGATTTGAGAACAAGATC<br>TTTGGGTATGACAATCTGTTCCACTTTCCTTTACTTGTGGTCTTTCACCGT<br>CACCTACAACTTCACCAAGATGTCCGCCGCCTTCACATACACTGGGTTG<br>ACACTTGGTTTCTACGGTGGCATTGCGTTCCTTGGTTTTGATTTACCAGGT<br>CTGCTTCATGCCCGAGACGAAGGACAAGACTTTGGAAGAAATTGACGA<br>TATCTTCAATCGTTCTGCGTTCTCTATCGCGCGCGAGAACATCTCCAACT<br>TGAAGAAGGGTATTTGGTAA |
| 21 | Nucleic acid sequence of H0 Metschnikowia species XYT1 codon optimized for expression in S. cerevisiae | ATGGGATACGAAGAGAAATTAGTGGCCCCCGCTTTGAAATTTAAGAACT<br>TTTTGGATAAGACCCCAAATATACATAACGTTTACGTAATTGCGGCGAT<br>CTCGTGTACCTCAGGTATGATGTTCGGTTTCGATATATCGTCGATGTCCG<br>TGTTCGTGGACCAACAGCCGTATTTAAAAATGTTTGATAACCCTAGCAG<br>CGTGATACAAGGGTTTATAACTGCGTTGATGTCTTTGGGGAGCTTTTTCG<br>GATCGCTAACGTCCACTTTTATTTCAGAACCTTTTGGTAGACGTGCCTCT<br>TTGTTCATATGCGGGATCCTTTGGGTAATTGGGGCGGCAGTTCAAAGTT<br>CTTCTCAGAACCGTGCGCAGCTTATTTGTGGCCGAATTATTGCAGGGTG<br>GGGCATCGGATTCGGTTCTAGCGTTGCGCCGGTATACGGTTCAGAAATG<br>GCCCCACGCAAAATTAGAGGAACAATCGGAGGTATTTTTCAATTTTCTG<br>TCACGGTCGGAATATTCATAATGTTCCTGATTGGCTACGGCTGCTCATTT<br>ATACAAGGCAAGGCCAGTTTTAGAATTCCGTGGGGAGTTCAAATGGTAC<br>CAGGTCTCATTCTGTTGATCGGACTATTCTTCATTCCTGAATCCCCAAGA<br>TGGTTAGCCAAACAAGGCTACTGGGAAGACGCTGAGATCATCGTAGCA<br>AACGTTCAAGCTAAGGGTAACAGGAACGATGCTAATGTGCAAATTGAA<br>ATGTCCGAGATAAAAGATCAGTTAATGCTTGACGAGCATTTAAAGGAGT<br>TTACTTATGCCGATTTGTTTTACCAAAAAATACCGGCAAAGGACGATAAC<br>AGCTATATTTGCCCAAATATGGCAACAGCTGACAGGTATGAATGTCATG<br>ATGTACTACATCGTATATATATTTCAAATGGCAGGTTATTCAGGTAATA<br>CTAATTTAGTTCCTTCACTCATTCAGTATATTATAAATATGGCTGTTACG<br>GTCCCCGCATTGTTCTGTCTTGATCTGCTTGGCAGGAGGACAATTTTATT<br>AGCTGGCGCCGCTTTTATGATGGCCTGGCAATTTGGTGTTGCTGGCATTT<br>TAGCTACTTATTCAGAGCCAGCCTATATTTCAGATACCGTGAGAATTAC<br>AATTCCAGATGACCATAAAAGTGCCGCTAAGGGTGTCATCGCTTGCTGC<br>TATTTGTTTGTTTGTTCCTTCGCCTTTTCCTGGGGTGTAGGTATCTGGGTT<br>TATTGTTCAGAAGTGTGGGGTGATAGTCAATCCAGACAAAGAGGTGCTG<br>CATTGGCAACTTCTGCTAATTGGATCTTCAATTTCGCAATTGCAATGTTT<br>ACACCTTCTTCTTTCAAAAATATCACTTGGAAGACTTATATCATTTATGC<br>TACATTTTGTGCTTGTATGTTCATTCATGTTTTTTTTTTTTCCCTGAAAC<br>AAAGGGTAAGAGACTAGAAGAAATTGGACAGCTATGGGATGAAGGTGT<br>CCCAGCATGGAGATCTGCAAATGGCAACCCACTGTCCCACTAGCAAGT<br>GACGCTGAATTAGCTCACAAAATGGATGTTGCACACGCTGAACACGCA<br>GACTTATTGGCAACCCATTCTCCAAGTAGTGACGAAAAAACTGGTACCG<br>TTTAA |
| 22 | Nucleic acid sequence of H0 Metschnikowia species HXT2.6 | ATGCTGAGCACTACCGATACCCTCGAAAAAGGGACACCGAGCCTTTC<br>ACTTCAGATGCTCCTGTCACAGTCCATGACTATATCGCAGAGGAGCGTC<br>CGTGGTGGAAAGTGCCGCATTTGCGTGTATTGACTTGGTCTGTTTTCGTG<br>ATCACCCTCACCTCCACCAACAACGGGTATGATGGCCTGATGTTGAATG<br>GATTGCAATCCTTGGACATTTGGCAGGAGGATTTGGGTCACCCTGCGGG<br>CCAGAAATTGGGTGCCTTGGCCAACGGTGTTTTGTTTGGTAACCTTGCT<br>GCTGTGCCTTTTGCTTCGTATTTCTGCGATCGTTTTGGTAGAAGGCCGGT<br>CATTTGTTTCGGACAGATCTTGACAATTGTTGGTGCTGTATTACAAGGTT<br>TGTCCAACAGCTATGGATTTTTTTTGGGTTCGAGAATTGTGTTGGGTTTT<br>GGTGCTATGATAGCCACTATTCCGCTGCCAACATTGATTTCCGAAATCG<br>CCTACCCTACGCATAGAGAAACTTCCACTTTCGCCTACAACGTGTGCTG<br>GTATTTGGGAGCCATTATCGCCTCCTGGGTCACATACGGCACCAGAGAT<br>TTACAGAGCAAGGCTTGCTGGTCAATTCCTTCTTATCTCCAGGCCGCCTT<br>ACCTTTCTTTCAAGTGTGCATGATTTGGTTTGTGCCAGAGTCTCCCGGAT<br>TCCTCGTTGCCAAGGGCAAGATCGACCAAGCAAGGGCTGTTTTGTCTAA<br>ATACCATACAGGAGACTCGACTGACCCCAGAGACGTTGCGTTGGTTGAC<br>TTTGAGCTCCATGAGATTGAGAGTGCATTGGAGCAGGAAAAATTGAAC<br>ACTCGCTCGTCATACTTTGACTTTTTCAAGAAGAGAAACTTTAGAAAGA |

| SEQ ID NO: | Description | SEQUENCES |
|---|---|---|
| | | GAGGCTTCTTGTGTGTCATGGTCGGTGTTGCAATGCAGCTTTCTGGAAA<br>CGGCTTAGTGTCCTATTACTTGTCGAAAGTGCTAGACTCGATTGGAATC<br>ACTGAAACCAAGAGACAGCTCGAGATCAATGGCTGCTTGATGATCTATA<br>ACTTTGTCATCTGCGTCTCGTTGATGAGTGTTTGCCGTATGTTCAAAGA<br>AGAGTATTATTTCTCACGTGTTTCTCAGGAATGACGGTTTGCTACACGAT<br>ATGGACGATTTTGTCAGCGCTTAATGAACAGAGACACTTTGAGGATAAA<br>GGCTTGGCCAATGGCGTGTTGGCAATGATCTTCTTCTACTATTTTTTCTA<br>CAACGTTGGCATCAATGGATTGCCATTCCTATACATCACCGAGATCTTG<br>CCTTACTCACACAGAGCAAAAGGCTTGAATTTATTCCAATTCTCGCAAT<br>TTCTCACGCAAATCTACAATGGCTATGTGAACCCAATCGCCATGGACGC<br>AATCAGCTGGAAGTATTACATTGTGTACTGCTGTATTCTCTTCGTGGAGT<br>TGGTGATTGTGTTTTTCACGTTCCCAGAAACTTCGGGATACACTTTGGAG<br>GAGGTCGCCCAGGTATTTGGTGATGAGGCTCCCGGGCTCCACAACAGAC<br>AATTGGATGTTGCGAAAGAATCACTCGAGCATGTTGAGCATGTTTGA |
| 23 | Nucleic acid sequence of H0 Metschnikowia species HXT2.6 codon optimized for expression S. cerevisiae | ATGAGCCAGTCTAAAGAAAAGTCCAACGTTATTACCACCGTCTTGTCTG<br>AAGAATTGCCAGTTAAGTACTCCGAAGAAATCTCCGATTACGTTTACCA<br>TGATCAACATTGGTGGAAGTACAACCACTTCAGAAAATTGCATTGGTAC<br>ATCTTCGTTCTGACTTTGACTTCTACCAACAATGGTTACGATGGCTCTAT<br>GTTGAACGGTCTACAATCTTTGTCTACTTGGAAAGATGCTATGGGTAAT<br>inCCTGAAGGTTACATTTTGGGTGCTTTGGCTAATGGTACTATTTTCGGTGG<br>TGTTTTGGCTGTTGCTTTTGCTTCTTGGGCTTGTGATAGATTTGGTAGAA<br>AGTTGACTACCTGCTTCGGTTCTATCGTTACTGTTATTGGTGCTATATTG<br>CAAGGTGCCTCTACTAATTACGCATTCTTTTTCGTTTCCCGTATGGTTAT<br>TGGTTTTGGTTTCGGTCTAGCTTCTGTTGCTTCTCCAACTTTGATTGCTGA<br>ATTGTCTTTCCCAACTTACAGACCAACTTGTACTGCCTTGTACAATGTTT<br>TTTGGTACTTGGGTGCTGTTATTGCTGCATGGGTTACTTATGGTACTAGA<br>ACTATCGTTTCTGCCTACTCTTGGAGAATTCCATCTTACTTGCAAGGTTT<br>GTTGCCATTGGTTCAAGTTTGTTTGGTTTGGTGGGTTCCAGAATCTCCA<br>GATTCTTGGTTTCTAAGGGTAAGATTGAAAAGGCCAGGGAATTCTTGAT<br>TAAGTTCCATACTGGTAACGACACCCAAGAACAAGCTACTAGATTGGTC<br>GAATTTGAGTTGAAAGAAATTGAAGCCGCCTTGGAGATGGAAAAGATT<br>AACTCTAATTCTAAGTACACCGACTTCATCACCATCAAGACTTTCAGAA<br>AGAGAATCTTCTTGGTTGCTTTCACTGCTTGTATGACTCAATTGTCTGGT<br>AACGGTTTGGTGTCTTACTACTTGTCCAAGGTTTTGATCTCCATTGGTAT<br>TACCGGTGAGAAGAACAATTGCAAATCAACGGTTGCCTGATGATCTAC<br>AACTTGGTTTTGTCTTTAGCTGTTGCCTTCACCTGTTACTTGTTTAGAAG<br>AAAAGGCCCTGTTCATCTTCTCTTGCTCATTCATGTTGTTGTCCTACGTTA<br>TTTGGACCATTCTGTCCGCTATCAATCAACAGAGAAACTTCGAACAAAA<br>AGGTCTAGGTCAAGGTGTCTTGGCTATGATTTTTATCTACTACTTGGCCT<br>ACAACATCGGTTTGAATGGTTTGCCATACTTGTACGTTACCGAAATCTT<br>GCCATATACTCATAGAGCTAAGGGCATCAACTTGTATTCCTTGGTTATT<br>AACATCACCCTGATCTATAACGGTTTCGTTAACGCTATTGCTATGGATG<br>CTATTTCCTGGAAGTACTACATCGTTTACTGCTGCATTATTGCCGTTGAA<br>TTGGTTGTTGTTATCTTCACCTACGTTGAAACTTTCGGTTACACCTTGGA<br>AGAAGTTGCTAGAGTTTTTGAAGGTACTGATTCTTTGGCCATGGACATT<br>AACTTGAACGGTACAGTTTCCAACGAAAAGATCGATATCGTTCACTCTG<br>AAAGAGGTTCCTCTGCTTAA |
| 24 | Nucleic acid sequence of H0 Metschnikowia species QUP2 | ATGGGCTTTCGCAACTTAAAGCGCAGGCTCTCAAATGTTGGCGACTCCA<br>TGTCAGTGCACTCTGTGAAAGAGGAGGAAGACTTCTCCCGCGTGGAAAT<br>CCCGGATGAAATCTACAACTATAGAGATCGTCCTTGTGGCTTTAACAGCG<br>GCGTCGGCTGCCATCATCATCGGCTACGATGCAGGCTTCATTGGTGGCA<br>CGGTTTCGTTGACGGCGTTCAAACTGGAATTTGGCTTGGACAAAATGTC<br>TGCGACGGCGGCTTCTGCTATCGAAGCCAACGTTGTTTCCGTGTTCCAG<br>GCCGGCGCCTACTTTGGGTGTCTTTTCCTTCTATCCGATTGGCGAGATTTG<br>GGGCCGTAAAATCGGTCTTCTTCTTTCCGGCTTTCTTTTGACGTTTGGTG<br>CTGCTATTTCTTTGATTCGAACTCGTCTCGTGGCCTTGGTGCCATATAT<br>GCTGGAAGAGTACTAACAGGTTTGGGGATTGGCGGATGTCTGAGTTTGG<br>CCCCAATCTACGTTTCTGAAATCGCGCCTGCAGCAATCAGAGGCAAGCT<br>TGTGGGCTGCTGGGAAGTGCATGGCAGGTGGGCGGCATTGTTGGCTAC<br>TGGATCAATTACGGAGTCTTGCAGACTCTTCCGATTAGCTCACAACAAT<br>GGATCATCCCGTTTGCTGTACAATTGATCCCATCGGGGCTTTTCTGGGGC<br>CTTTGTCTTTTGATTCCAGAGCTGCCACGTTTTCTTGTATCGAAGGGAAA<br>GATCGATAAGGCGCGCAAAAACTTAGCGTACTTGCGTGGACTTAGCGA<br>GGACCACCCCTATTCTGTTTTTGAGTTGGAGAACATTAGTAAGGCCATT<br>GAAGAGAACTTCGAGCAAACAGGAAGGGGTTTTTTCGACCCATTGAAA<br>GCTTTGTTTTTCAGCAAAAAAATGCTTTACCGCCTTCTCTTGTCCACGTC<br>AATGTTCATGATGCAGAATGGCTATGGAATCAATGCTGTGACATACTAC<br>TCGCCCACGATCTTCAAATCCTTAGGCGTTCAGGGCTCAAACGCCGGTT<br>TGCTCTCAACAGGAATTTTCGGTCTTCTTAAAGGTGCCGCTTCGGTGTTC<br>TGGGTCTTTTTCTTGGTTGACACATTCGGCCGCCGGTTTTGTCTTTGCTA<br>CCTCTCTCTCCCCTGCTCGATCTGCATGTGGTATATTGGCGCATACATCA<br>AGATTGCCAACCCTTCAGCGAAGCTTGCTGCAGGAGACACAGCCACCA<br>CCCCAGCAGGAACTGCAGCGAAAGCGATGCTTTACATATGGACGATTTT<br>CTACGGCATTACGTGGAATGGTACGACCTGGGTGATCTGCGCGGGAGATT |

| SEQ ID NO: | Description | SEQUENCES |
|---|---|---|
| | | TTCCCCCAGTCGGTGAGAACAGCCGCGCAGGCCGTCAACGCTTCTTCTA<br>ATTGGTTCTGGGCTTTCATGATCGGCCACTTCACTGGCCAGGCGCTCGA<br>GAATATTGGGTACGGATACTACTTCTTGTTTGCGGCGTGCTCTGCAATCT<br>TCCCTGTGGTAGTCTGGTTTGTGTACCCCGAAACAAAGGGTGTGCCTTT<br>GGAGGCCGTGGAGTATTTGTTCGAGGTGCGTCCTTGGAAAGCGCACTCA<br>TATGCTTTGGAGAAGTACCAGATTGAGTACAACGAGGGTGAATTCCACC<br>AACATAAGCCCGAAGTACTCTTACAAGGGTCTGAAAACTCGGACACGA<br>GCGAGAAAAGCCTCGCCTGA |
| 25 | Nucleic acid sequence of H0 Metschnikowia species QUP2 codon optimized for expression in S. cerevisiae | ATGGGTTTCAGAAACTTGAAGAGAAGATTGTCTAACGTTGGTGACTCCA<br>TGTCTGTTCACTCTGTTAAGGAAGAAGAAGACTTCTCCAGAGTTGAAAT<br>CCCCAGATGAAATCTACAACTACAAGATCGTCTTGGTTGCTTTGACTGCT<br>GCTTCTGCTGCTATCATCATCGGTTACGATGCTGGTTTCATTGGTGGTAC<br>TGTTTCTTTGACTGCTTTCAAGTCTGAATTCGGTTTGGACAAGATGTCTG<br>CTACTGCTGCTTCTGCTATCGAAATGGGTTTCAGAAACTTGAAGAGGCG<br>TTTGTCTAATGTTGGTGATTCCATGTCTGTTCACTCCGTCAAAGAAGAAG<br>AGGATTTCTCCAGAGTTGAAATCCCAGACGAAATCTACAACTACAAGAT<br>CGTTTTGGTTGCTTTGACTGCTGCTTCTGCTGCTATTATCATTGGTTATG<br>ATGCTGGTTTCATCGGTGGTACTGTTTCTTTGACAGCTTTCAAGTCTGAA<br>TTCGGTTTGGATAAGATGTCTGCTACAGCTGCTTCAGCTATTGAAGCTA<br>ATGTTGTCTCTGTTTTTCAAGCTGGTGCTTACTTTGGTTGCCTGTTTTTTT<br>ACCCAATTGGTGAAATTTGGGGTCGTAAGATTGGTTTGTTGTTGTCTGGT<br>TTCTTGTTGACTTTTGGTGCTGCCATTTCCTTGATCTCTAATTCTTCTAGA<br>GGTTTGGGTGCTATCTATGCTGGTAGAGTTTTGACTGGTTTAGGTATTGG<br>TGGTTGTTCTTCTTTAGCTCCCATCTACGTTAGTGAAATTGCTCCAGCTG<br>CAATTAGAGGTAAGTTAGTTGGTTGTTGGGAAGTTTCTTGGCAAGTTGG<br>TGGTATCGTTGGTTATTGGATTAACTATGGTGCTTGCAAACCCTGCCAA<br>TCTCTTCTCAACAATGGATTATTCCATTCGCCGTTCAATTGATTCCATCT<br>GGTTTGTTTGGGGTTTGTGCTTGTTGATTCCAGAATCTCCAAGATTCTT<br>GGTGTCCAAAGGTAAGATTGATAAGGCCAGAAAGAACTTGGCTTACTT<br>GAGAGGTTTGTCTGAAGATCATCCATACTCCGTTTTTGAGTTGGAGAAC<br>ATTTCCAAGGCCATCGAAGAAAACTTTGAACAAACAGGTAGAGGTTTCT<br>TCGACCCATTGAAGGCTTTGTTTTTCAGCAAGAAAATGCTGTACAGGCT<br>GCTGTTGTCTACTTCTATGTTTATGATGCAAAACGGCTACGGTATTAACG<br>CTGTTACTTATTACTCTCCCACCATCTTTAAGTCCTTGGGTGTTCAAGGT<br>TCTAATGCCGGTTTGTTATCTACTGGTATTTTCGGTTTGTTGAAAGGTGC<br>CGCTTCTGTTTTTTGGGTTTTCTTCTTGGTTGATACCTTCGGTAGAAGATT<br>CTGTTTGTGCTATTTGTCTTTGCCATGCTCTATCTGCATGTGGTATATTG<br>GTGCCTACATTAAGATTGCTAACCCATCTGCTAAATTGGCTGCTGGTGA<br>TACTGCTACTACTCCAGCTGGTACTGCTGCTAAAGCTATGTTGTATATTT<br>GGACCATCTTCTACGGTATCACTTGGAATGGTACTACCTGGGTTATTTGC<br>GCTGAAATTTTTCCACAATCTGTTAGAACAGCTGCTCAAGCTGTTAATG<br>CTTCTTCTAATTGGTTTTGGGCCTTCATGATTGGTCATTTTACTGGTCAA<br>GCTTTGGAAAACATTGGTTACGGTTACTACTTTTTGTTCGCTGCTTGTTC<br>CGCTATTTTCCCAGTTGTAGTTTGGTTCGTTTACCCAGAAACAAAAGGT<br>GTTCCATTGGAAGCTGTTGAATACTTGTTTGAAGTTAGACCATGGAAGG<br>CTCATTCTTACGCTTTAGAAAAGTACCAGATCGAGTACAACGAAGGTGA<br>ATTCCATCAACATAAGCCAGAAGTTTTGTTGCAGGGTTCTGAAAACTCT<br>GATACCTCTGAAAAGTCTTTGGCCTGAAACGAAGGTGAATTCCACCAAC<br>ATAAGCCAGAAGTTTTGTTGCAAGGTTCTGAAAACTCTGACACTTCTGA<br>AAAGTCTTTGGCTTAA |
| 26 | Nucleic acid sequence of H0 Metschnikowia species APS1/HGT19 | ATGTCAGAAAAGCCTGTTGTGTCGCACAGCATCGACACGACGCTGTCTA<br>CGTCATCGAAACAAGTCTATGACGGTAACTCGCTTCTTAAGCCCCTGAA<br>TGAGCGCGATGGCGAACGCGGCAATATCTTGTCGCAGTACACTGAGGA<br>ACAGGCCATGCAAATGGGCCGCAACTATGCGTTGAAGCACAATTTAGA<br>TGCGACACTCTTTGAAAGGCGGCCGCGGTCGCAAGAAACCCATACGA<br>GTTCAATTCGATGAGTTTTTGACCGAAGAGGAAAAAGTCGCGCTTAAC<br>ACGGAGCAGACCAAGAAATGGCACATCCCAAGAAAGTTGGTGGAGGTG<br>ATTGCATTGGGGTCCATGGCCGCTGCGGTGCAGGGTATGGATGAGTCGG<br>TGGTGAATGGTGCAACGCTTTTCTACCCCACGGCAATGGGTATCACAGA<br>TATCAAGAATGCCGATTTGATTGAAGGTTTGATCAACGGTGCGCCCTAT<br>CTTTGCTGCGCCATCATGTGCTGGACATCTGATTACTGGAACAGGAAGT<br>TGGGCCGTAAGTGGACCATTTTCTGGACATGTGCCATTTCTGCAATCAC<br>ATGTATCTGGCAAGGTCTCGTCAATTTGAAATGGTACCATTTGTTCATTG<br>CGCGTTTCTGCTTGGGTTTCGGTATCGGTGTCAAGTCTGCCACCGTGCCT<br>GCGTATGCTGCCGAAACCACCCCGGCCAAAATCAGAGGCTCGTTGGTCA<br>TGCTTTGGCAGTTCTTCACCGCTGTCGGAATCATGCTTGGTTACGTGGCG<br>TCTTTGGCATTCTATTACATTGGTGACAATGGCATTTCTGGCGGCTTGAA<br>CTGGGAGATTGATGCTAGGATCTGCATGTCTTCCAGCTATCGTTGTGTTAG<br>TCCAAGTTCCGTTTGTTCCAGAATCCCCTCGTTGGCTCATGGGTAAGGA<br>AAGACACGCTGAAGCATATGATTCGCTCCGGCAATTGCGGTTCAGTGAA<br>ATCGAGGCGGCCCGTGACTGTTTCTACCAGTACGTGTTGTTGAAAGAGG<br>AGGGCTCTTATGGAACGCAGCCATTCTTCAGCAGAATCAAGGAGATGTT<br>CACCGTGAGAAGAAACAGAAATGGTGCATTGGGCGCGTGGATCGTCAT<br>GTTCATGCAGCAGTTCTGTGGAATCAACGTCATTGCTTACTACTCGTCGT |

| SEQ ID NO: | Description | SEQUENCES |
|---|---|---|
| | | CGATCTTCGTGGAGTCGAATCTTTCTGAGATCAAGGCCATGTTGGCGTC<br>TTGGGGGTTCGGTATGATCAATTTCTTGTTTGCAATTCCAGCGTTCTACA<br>CCATTGACACGTTTGGCCGACGCAACTTGTTGCTCACTACTTTCCCTCTT<br>ATGGCGGTATTCTTACTCATGGCCGGATTCGGGTTCTGGATCCCGTTCG<br>AGACAAACCCACACGGCCGTTTGGCGGTGATCACTATTGGTATCTATTT<br>GTTTGCATGTGTCTACTCTGCGGGCGAGGGACCAGTTCCCTTCACATAC<br>TCTGCCGAAGCATTCCCGTTGTATATCCGTGACTTGGGTATGGGCTTTGC<br>CACGGCCACGTGTTGGTTCTTCAACTTCATTTTGGCATTTTCCTGGCCTA<br>GAATGAAGAATGCATTCAAGCCTCAAGGTGCCTTTGGCTGGTATGCCGC<br>CTGGAACATTGTTGGCTTCTTCTTAGTGTTATGGTTCTTGCCCGAGACAA<br>AGGGCTTGACGTTGGAGGAATTGGACGAAGTGTTTGATGTGCCTTTGAG<br>AAAACACGCGCACTACCGTACCAAAGAATTAGTATACAACTTGCGCAA<br>ATACTTCTTGAGGCAGAACCCTAAGCCATTGCCGCCACTTTATGCACAC<br>CAAAGAATGGCTGTTACCAACCCAGAATGGTTGGAAAAGACCGAGGTC<br>ACGCACGAGGAGAATATCTAG |
| 27 | Nucleic acid sequence of H0 *Metschnikowia* species APS1/HGT19 codon optimized for expression in *S. cerevisiae* | ATGTCTGAAAAGCCAGTTGTTTCTCACTCTATCGACACCACCTCTTCTAC<br>CTCTTCTAAGCAAGTCTACGACGGTAACTCTTTGTTGAAGACCTCTAAC<br>GAAAGAGACGGTGAAAGAGGTAACATCTTGTCTCAATACACTGAAGAA<br>CAAGCAATGCAAATGGGTAGAAACTACGCTTTGAAGCACAACTTGGAC<br>GCTACCTTGTTCGGTAAGGCTGCTGCTGTCGCTAGAAACCCATACGAGT<br>TCAACTCTATGTCTTTCTTGACCGAAGAAGAAAGGTCGCTTTGAACAC<br>CGAACAAACCAAGAAGTGGCACATCCCAAGAAAGTTGGTTGAAGTTAT<br>TGCTTTGGGTTCTATGGCTGCTGCTGTTCAAGGTATGGACGAATCTGTTG<br>TTAACGGTGCTACCTTGTTCTACCCAACCGCTATGGGTATCACCGACAT<br>CAAGAACGCTGACTTGATTGAAGGTTTGATTAACGGTGCCCCATACTTG<br>TGTTGTGCTATTATGTGTTGGACCTCTGACTACGTGGAACAGAAAGTTGG<br>GTAGAAAGTGGACCATTTTCTGGACCTGTGCTATTTCTGCTATCACCTGT<br>ATCTGGCAAGGTTTGGTCAACTTGAAGTGGTATCACTTGTTCATTGCTA<br>GATTCTGTTTGGGTTTCGGTATCGGTGTCAAGTCTGCTACCGTTCCAGCC<br>TACGCTGCTGAAACCACCCCAGCCAAGATTAGAGGTTCTTTGGTTATGT<br>TGTGGCAATTCTTCACCGCTGTCGGTATTATGTTGGGTTACGTTGCTTCT<br>TTGGCTTTCTACTACATTGGTGACAACGGTATTTCTGGTGGTTTGAACTG<br>GAGATTGATGTTGGGTTCTGCTTGTTTGCCAGCCATCGTTGTTTTGGTCC<br>AAGTTCCATTCGTTCCAGAATCTCCAAGATGGTTGATGGGTAAGGAAAG<br>ACACGCTGAAGCCTACGACTCTTTGAGACAATTGAGATTCTCTGAAATC<br>GAAGCCGCTAGAGACTGTTTCTACCAATACGTTTTGTTGAAGGAAGAAG<br>GTTCTTACGGTACTCAACCATTCTTCTCTAGAATCAAGGAAATGTTCACC<br>GTTAGAAGAAACAGAAACGGTGCTTTGGGTGCTTGGATTGTTATGTTTA<br>TGCAACAATTCTGTGGTATCAACGTCATTGCTTACTACTCTTCTTCTATC<br>TTCGTTGAATCTAACTTGTCTGAAATCAAGGCTATGTTGGCTTCTTGGGG<br>TTTTCGGTATGATTAACTTCTTGTTCGCTATTCCAGCCTTCTACACCATTG<br>ACACCTTCGGTAGAAGAAACTTGTTGTTGACTACTTTCCCATTGATGGCT<br>GTTTTCTTGTTGATGGCTGGTTTCGGTTTCTGGATTCCATTCGAAACCAA<br>CCCACACGGTAGATTGGCTGTTATCACTATTGGTATCTACTTGTTCGCTT<br>GTGTCTACTCTGCTGGTGAAGGTCCAGTTCCATTCACCTACTCTGCTGAA<br>GCCTTCCCATTGTACATCAGAGACTTGGGTATGGGTTTCGCTACCGCTA<br>CCTGTTGGTTCTTCAACTTCATTTTGGCTTTCTCTTGGCCAAGAATGAAG<br>AACGCTTTCAAGCCTCAAGGTGCTTTCGGTTGGTACGCTGCTTGGAACA<br>TTGTTGGTTTCTTCTTGGTTTTGTGGTTCTTGCCAGAAACTAAGGGTTTG<br>ACTTTGGAAGAATTGGACGAAGTTTTCGACGTTCCATTGAGAAAGCACG<br>CTCACTACAGAACTAAGGAATTGGTTTACAACTTGAGAAAGTACTTCTT<br>GAGACAAAACCCAAAGCCATTGCCACCATTGTACGCTCACCAAAGAAT<br>GGCTGTTACCAACCCAGAATGGTTGGAAAAGACCGAAGTCACCCACGA<br>AGAAAACATCTAA |
| 44 | Amino Acid sequence of ubiquitin-deficient H0 *Metschnikowia* species Apslp/Hgt19 codon optimized for expression in *S. cerevisiae* (with K4R; K20R; K30R and K93R mutations) | MSERPVVSHSIDTTSSTSSRQVYDGNSLLRTSNERDGERGNILSQYTEEQAM<br>QMGRNYALKHNLDATLFGKAAAVARNPYEFNSMSFLTEEERVALNTEQT<br>KKWHIPRKLVEVIALGSMAAAVQGMDESVVNGATLFYPTAMGITDIKNAD<br>LIEGLINGAPYLCCAIMCWTSDYVVNRKLGRKWTIFWTCAISAITCIWQGLV<br>NLKWYHLFIARFCLGFGIGVKSATVPAYAAETTPAKIRGSLVMLWQFFTAV<br>GIMLGYVASLAFYYIGDNGISGGLNWRLMLGSACLPAIVVLVQVPFVPESP<br>RWLMGKERHAEAYDSLRQLRFSEIEAARDCFYQYVLLKEEGSYGTQPFFSR<br>IKEMFTVRRNRNGALGAWIVMFMQQFCGINVIAYYSSSIFVESNLSEIKAML<br>ASWGFGMINFLFAIPAFYTIDTFGRRNLLLTTPPLMAVFLLMAGFGFWIPFE<br>TNPHGRLAVITIGIYLFACVYSAGEGPVPFTYSAEAFPLYIRDLGMGFATAT<br>CWFFNFILAFSWPRMKNAFKPQGAFGWYAAWNIVGFFLVLWFLPETKGLT<br>LEELDEVFDVPLRKHAHYRTKELVYNLRKYFLRQNPKPLPPLYAHQRMAV<br>TNPEWLEKTEVTHEENI |
| 45 | Amino Acid sequence of ubiquitin-deficient H0 *Metschnikowia* species Hxt5p | MSIFEGRDGRGVSS1ESLSNDVRYDNMERVDQDVLRHNFNFDREFEELEIE<br>AAQVNDRPSFVDRILSLEYKLHFENKNHMVVVLLGAFAAAAGLLSGLDQSII<br>SGASIGMNKALNL1EREASLVSSLMPLGAMAGSMIMTPLNEWFGRKSSLITS<br>CIWYTIGSALCAGARDHHMMYAGRFILGVGVGIEGGCVGIYISESVPANVR<br>GSIVSMYQFNIALGEVLGYAVAAIFYTVHGGWRFMVGSSLVFSTILFAGLFF<br>LPESPRWLVHKGRNGMAYDVVVKRLRDINDESAKLEFLEMRQAAYQERER |

| SEQ ID NO: | Description | SEQUENCES |
|---|---|---|
| | (with K7R; K10R, K29R; K43R and K58R mutations) | RSQESLFSSWGELFTIARNRRALTYSVIMITLGQLTGVNAVMYYMSTLMGA IGFNEKDSVFMSLVGGGSLLIGTIPAILWMDRFGRRVVVGYNLVGFFVGLVL VGVGYRFNPVTQKAASEGVYLTGLIVYFLFFGSYSTLTWVIPSESFDLRTRS LGMTICSTFLYLWSFTVTYNFTKMSAAFTYTGLTLGFYGGIAFLGLIYQVCF MPETKDKTLEEIDDIFNRSAFSIARENISNLKKGIW |
| 46 | Amino Acid sequence of ubiquitin-deficient H0 *Metschnikowia* species Gxf2p/Gal2p (with K23R, K26R, K35R, K542R and K546R mutations) | MSAEQEQQVSGTSATIDGLASLRQERTAEEEDAFRPKPATAYFFISFLCGLV AFGGYVFGFDTGTISGFVNMDDYLMRFGQQHADGTYYLSNVRTGLIVSIFN IGCAVGGLALSKVGDIWGRRIGIMVAMIIYMVGIIIQIASQDKWYQYFIGRLI TGLGVGTTSVLSPLFISESAPKHLRGTLVCCFQLMVTLGIFLGYCTTYGKN YTDSRQWRIPLGLCFAWALLLISGMVFMPESPRFLIERQRFDEAKASVAKS NQVS1EDPAVYTEVELIQAGIDREALAGSAGWKELITGKPKMLQRVILGM MLQSIQQLTGNNYFFYYGTTIFKAVGMSDSFQTSIVLGIVNFASTFVGIWAI ERMGRRSCLLVGSACMSVCFLIYSILGSVNLYIDGYENTPSNTRKPTGNAMI FITCLFIFFFASTWAGGVYSIVSETYPLRIRSKGMAVATAANWMWGFLISFF TPPFITSAIHFYYGFVFTGCLIFSFFYVFFFVRETKGLSLEEVDELYATDLPPW KTAGWTPPSAEDMAHTTGFAEEAARPTNRHV |
| 47 | Amino Acid sequence of ubiquitin-deficient H0 *Metschnikowia* species Gxf1p (with K9R and K24R mutations) | MSQDELHTRSGVETPINDSLLEERHDVTPLAALPEKSFKDYISISIFCLFVAF GGFVFGFDTGTISGFVNMSDFKTRFGEMNAQGEYYLSNVRTGLMVSIFNV GCAVGGIFLCKIADVYGRRIGLMFSMVVYVVGIIIQIASTTKWYQYFIGRLI AGLAVGTVSVISPLFISEVAPKQLRGTLVCCFQLCITLGIFLGYCTTYGTKTY TDSRQWRIPLGICFAWALFLVAGMLNMPESPRYLVEKSRIDDARKSIARSN KVSEEDPAVYTEVQLIQAGIDREALAGSATWMELVTGKPKIFRRVIMGVM LQSLQQLTGDNYFFYYGTTIFKAVGLQDSFQTSIILGIVNFASTFVGIYAIER MGRRLCLLTGSACMFVCFITYSLIGTQHLYKNGFSNEPSNTYKPSGNAMIFIT CLYIFFFASTWAGGVYCIVSESYPLRIRSKAMSVATAANWMWGFLISFFTPF ITSAIHFYYGFVFTGCLAFSFFYVYFFVVETKGLSLEEVDILYASGTLPWKSS GWVPPTADEMAHNAFDNKPTDEQV |
| 48 | Amino Acid sequence of ubiquitin-deficient H0 *Metschnikowia* species Xyt1p (with K6R and S75L mutations) | MGYEERLVAPALKFKNFLDKTPNIHNVYVIAAISCTSGMMFGFDISSMSVF VDQQPYLKMFDNPSSVIQGFITALMSLGSFFGSLTSTFISEPFGRRASLFICGI LWVIGAAVQSSSQNRAQLICGRIIAGWGIGFGSSVAPVYGSEMAPRKIRGTI GGIFQFSVTVGIFIMFLIGYGCSFIQGKASFRIPWGVQMVPGLILLIGLFFIPES PRWLAKQGYWEDAEIIVANVQAKGNRNDANVQIEMSEIKDQLMLDEHLK EFTYADLFTKKYRQRTITAIFAQIWQQLTGMNVMMYYIVYIFQMAGYSGN TNLVPSLIQYIINMAVTVPALFCLDLLGRRTILLAGAAFMMAWQFGVAGIL ATYSEPAYISDTVRITIPDDHKSAAKGVIACCYLFVCSFAFSWGVGIWVYCS EVVVGDSQSRQRGAALATSANWIFNFAIAMFTPSSFKNITWKTYIIYATFCAC MFIHVFFFFPETKGKRLEEIGQLWDEGVPAWRSAKWQPTVPLASDAELAH KMDVAHAEHADLLATHSPSSDEKTGTV |
| 49 | Nucleic acid sequence of ubiquitin-deficient H0 *Metschnikowia* species APS1/HGT19 (with K4R; K20R; K30R and K93R mutations) | ATGTCTGAAAGACCAGTTGTTTCTCACTCTATCGACACCACCTCTTCTAC CTCTTCTAGACAAGTCTACGACGGTAACTCTTTGTTGAGGACCTCTAAC GAAAGAGACGGTGAAAGAGGTAACATCTTGTCTCAATACACTGAAGAA CAAGCAATGCAAATGGGTAGAAACTACGCTTTGAAGCACAACTTGGAC GCTACCTTGTTCGGTAAGGCTGCTGCTGTCGCTAGAAACCCATACGAGT TCAACTCTATGTCTTTCTTGACCGAAGAAGAAAGAGTCGCTTTGAACAC CGAACAAACCAAGAAGTGGCACATCCCAAGAAAGTTGGTTGAAGTTAT TGCTTTGGGTTCTATGGCTGCTGCTGTTCAAGGTATGGACGAATCTGTTG TTAACGGTGCTACCTTGTTCTACCCAACCGCTATGGGTATCACCGACAT CAAGAACGCTGACTTGATTGAAGGTTTGATTAACGGTGCCCCATACTTG TGTTGTGCTATTATGTGTTGGACCTCTGACTACTGGAACAGAAAGTTGG GTAGAAAGTGGACCATTTTCTGGACCTGTGCTATTTCTGCTATCACCTGT ATCTGGCAAGGTTTGGTCAACTTGAAGTGGTATCACTTGTTCATTGCTA GATTCTGTTTGGGTTTCGGTATCGGTGTCAAGTCTGCTACCGTTCCAGCC TACGCTGCTGAAACCACCCCAGCCAAGATTAGAGGTTCTTTGGTTATGT TGTGGCAATTCTTCACCGCTGTCGGTATTATGTTGGGTTACGTTGCTTCT TTGGCTTTCTACTACATTGGTGACAACGGTATTTCTGGTGGTTTGAACTG GAGATTGATGTTGGGTTCTGCTTGTTTGCCAGCCATCGTTGTTTTGGTCC AAGTTCCATTCGTTCCAGAATCTCCAAGATGGTTGATGGGTAAGGAAAG ACACGCTGAAGCCTACGACTCTTTGAGACAATTGAGATTCTCTGAAATC GAAGCCGCTAGAGACTGTTTCTACCAATACGTTTTGTTGAAGGAAGAAG GTTCTTACGGTACTCAACCATTCTTCTCTAGAATCAAGGAAATGTTCACC GTTAGAAGAAACAGAAACGGTGCTTTGGGTGCTTGGATTGTTAGTTTA TGCAACAATTCTGTGGTATCAACGTCATTGCTTACTACTCTTCTTCTATC TTCGTTGAATCTAACTTGTCTGAAATCAAGGCTATGTTGGCTTCTTGGGG TTTCGGTATGATTAACTTCTTGTTCGCTATTCCAGCCTTCTACACCATTG ACACCTTCGGTAGAAGAAACTTGTTGTTGACTACTTTCCCATTGATGGCT GTTTTCTTGTTGATGGCTGGTTTCGGTTTCTGGATTCCATTCGAAACCAA CCCACACGGTAGATTGGCTGTTATCACTATTGGTATCTACTTGTTCGCTT GTGTCTACTCTGCTGGTAAGGTCCAGTTCCATTCACCTACTCTGCTGAA GCCTTCCCATTGTACATCAGAGACTGGGTATGGGTTTCGCTACCGCTA CCTGTTGGTTCTTCAACTTCATTTTGGCTTTCTCTTGGCCAAGAATGAAG AACGCTTTCAAGCCTCAAGGTGCTTTCGGTTGGTACGCTGCTTGGAACA TTGTTGGTTTCTTCTTGGTTTTGTGGTTCTTGCCAGAAACTAAGGGTTTG |

| SEQ ID NO: | Description | SEQUENCES |
|---|---|---|
| | | ACTTTGGAAGAATTGGACGAAGTTTTCGACGTTCCATTGAGAAAGCACG<br>CTCACTACAGAACTAAGGAATTGGTTTACAACTTGAGAAAGTACTTCTT<br>GAGACAAAACCCAAAGCCATTGCCACCATTGTACGCTCACCAAAGAAT<br>GGCTGTTACCAACCCAGAATGGTTGGAAAAGACCGAAGTCACCCACGA<br>AGAAAACATCTAA |
| 50 | Nucleic acid sequence of ubiquitin-deficient H0 *Metschnikowia* species HXT5 (with K7R; K10R, K29R; K43R and K58R mutations) | ATGTCCATTTTCGAAGGTAGGGATGGTAGAGGTGTTTCCTCTACTGAAT<br>CCTTGTCTAACGATGTTAGATACGACAACATGGAAAGAGTTGACCAAG<br>ATGTTTTGAGGCACAATTTCAACTTCGACAGAGAGTTCGAAGAATTGGA<br>AATTGAAGCTGCCCAAGTTAACGATAGACCATCTTTCGTTGATAGGATC<br>TTGTCTTTGGAGTACAAGTTGCACTTCGAAAACAAGAATCACATGGTTT<br>GGTTGTTGGGTGCTTTTGCTGCTGCTGCAGGTTTGTTGTCTGGTTTGGAT<br>CAATCTATTATTTTCCGGTGCCTCTATCGGTATGAACAAGGCTTTGAATTT<br>GACCGAAAGAGAAGCCTCTTGTCAGTTCTTTGATGCCATTGGGTGCT<br>ATGGCTGGTTCTATGATTATGACTCCATTGAATGAATGGTTCGGCCGTA<br>AATCCTCCTTGATTATTTCTTGTATTTGGTACACCATCGGTTCTGCTTTGT<br>GTGCTGGTGCTAGAGATCATCACATGATGTATGCTGGTAGATTCATCTT<br>AGGTGTTGGTGTTGGTATTGAAGGTGGTTGCGTTGGTATCTACATTTCTG<br>AATCTGTTCCAGCCAATGTCAGAGGTTCTATCGTTTCTATGTACCAGTTC<br>AACATTGCCTTGGGTGAAGTTTGGGTTATGCTGTTGCTGCTATTTTCTA<br>CACTGTTCATGGTGGTTGGAGGTTTATGGTTGGTTCTTCTTTGGTTTTCT<br>CCACCATTTTGTTTGCCGGCTTGTTTTTTTTGCCAGAATCTCCAAGATGG<br>TTGGTCCATAAGGGTAGAAATGGTATGGCTTACGATGTTTGGAAGAGAT<br>TGAGAGATATCAACGATGAATCCGCCAAGTTGGAATTCTTGGAAATGA<br>GACAAGCTGCCTACCAAGAAAGAGAAAGAAGATCTCAAGAGTCCTTGT<br>TTTCTTCATGGGGTGAGTTGTTTACCATTGCTAGAAATAGAAGGGCTTT<br>GACCTACTCCGTTATTATGATTACTTTGGGTCAGTTGACTGGTGTTAACG<br>CTGTTATGTATTACATGTCTACTTTGATGGGTGCCATCGGTTTTAACGAA<br>AAGGATTCTGTTTTCATGTCCTTGGTTGGTGGTGGTTCTTTGTTGATTGG<br>TACTATTCCAGCTATCTTGTGGATGGATAGATTCGGTAGAAGAGTTTGG<br>GGTTACAATTTGGTTGGTTTTTCGTCGGTTTGGTATTGGTCGGTGTTGG<br>TTATAGATTCAACCCAGTTACTCAAAAGGCTGCTTCTGAAGGTGTTTATT<br>TGACTGGTTTGATCGTCTACTTCTTGTTCTTCGGTTCTTACTCTACATTGA<br>CCTGGGTTATTCCATCCGAATCTTTCGATTTGAGAACCAGATCTTTGGGT<br>ATGACCATTTGCTCTACTTTCTTGTACTTGTGGTCTTTCACTGTCACTTAC<br>AACTTCACTAAGATGTCTGCTGCTTTCACTTACACAGGTTTGACTTTGGG<br>TTTTTACGGTGGTATTGCTTCTTGGGTTTGATCTACCAAGTTTGCTTTAT<br>GCCAGAAACTAAGGACAAGACCTTGGAAGAAATCGATGACATCTTTAA<br>CAGATCCGCTTTCTCTATTGCCAGGGAAAACATTAGCAACTTGAAGAAA<br>GGTATCTGGTAA |
| 51 | Nucleic acid sequence of ubiquitin-deficient H0 *Metschnikowia* species GXF2/GAL2 (with K23R, K26R, K35R, K542R and K546R mutations) | ATGTCCGCTGAACAAGAACAACAAGTTTCTGGTACTTCTGCCACTATTG<br>ATGGTTTGGCTTCTTTGAGGCAAGAAAGGACTGCTGAAGAAGAAGATG<br>CTTTTAGGCCAAAACCAGCTACTGCCTACTTCTTCATTTCTTTCTTGTGT<br>GGTTTGGTTGCTTTCGGTGGTTACGTTTTTGGTTTTGATACCGGTACTAT<br>CTCCGGTTTCGTTAACATGGATGATTACTTGATGAGATTCGGTCAACAA<br>CATGCTGATGGTACTTACTACTTGTCCAATGTTAGAACCGGTTTGATCGT<br>CAGTATTTTCAACATTGGTTGTGCTGTTGGTGGTTTGGCATTGCTCTAAAG<br>TTGGTGATATTTGGGGTAGAAGAATCGGTATTATGGTTGCCATGATCAT<br>CTACATGGTTGGTATCATTATTCAAATCGCCTCCCAAGACAAGTGGTAT<br>CAATACTTTATTGGTAGATTGATCACCGGTTTGGGTGTTGGTACTACTTC<br>TGTTTTGTCTCCTTTGTTCATTTCCGAATCCGCTCCAAACATTTGAGAG<br>GTACTTTGGTTTGCTGCTTCCAATTGATGGTAACCTTGGGTATTTTCTTG<br>GGTTACTGTACTACTTACGGTACTAAGAACTACACCGATTCTAGACAAT<br>GGAGAATTCCATTGGGTTTGTGTTTTGCTTGGGCCTTGTTGTTGATTTCT<br>GGTATGGTTTTTATGCCAGAATCCCCAAGATTCTTGATCGAAAGACAAA<br>GATTCGATGAAGCTAAGGCTTCTGTTGCCAAGTCTAATCAAGTTTCTAC<br>TGAAGATCCAGCCGTTTACACTGAAGTTGAATTGATTCAAGCCGGTATT<br>GATAGAGAAGCTTTGGCTGGTTCTGCTGGTTGGAAAGAATTGATTACTG<br>GTAAGCCAAAGATGTTGCAAAGAGTCATTTTGGGTATGATGTTACAATC<br>CATCCAACAATTGACCGGTAACAATTACTTCTTCTACTACGGTACAACC<br>ATCTTCAAAGCTGTTGGTATGTCCGATTCTTTTCAAACCTCTATAGTCTT<br>GGGTATCGTTAACTTCGCTTCTACCTTTGTTGGTATTTGGGCCATTGAAA<br>GAATGGGTAGAAGATCTTGTTTGTTGGTTGGTTCAGCTTGTATGTCTGTT<br>TGCTTCTTGATCTACTCTATCTGGGTTCAGTCAACTTGTACATCGATGG<br>TTACGAAAACACTCCATCTAACACTAGAAAGCCAACTGGTAACGCCATG<br>ATTTTCATTACCTGTTTGTTCATCTTTTTCTTCGCCTCTACTTGGGCTGGT<br>GGTGTTTATTCTATAGTTTCTGAAACCTACCCATTGAGAATCAGATCTAA<br>AGGTATGGCTGTTGCTACTGCTGCTAATTGGATGTGGGGTTTTTGATCT<br>CTTTCTTTACCCCATTCATCACCTCCGCTATTCATTTTTACTACGGTTTTG<br>TTTTCACCGGTTGCTTGATCTTCTCATTCTTTTACGTATTCTTTTTCGTCC<br>GTGAAACTAAGGGTTTGTCCTTGGAAGAAGTTGACGAATTATACGCTAC<br>TGATTTGCCACCATGGAAAACTGCAGGTTGGACTCCACCATCAGCTGAA<br>GATATGGCTCATACAACTGGTTTTGCTGAAGCTGCTAGGCCTACAAACA<br>GACACGTTTGA |

| SEQ ID NO: | Description | SEQUENCES |
|---|---|---|
| 52 | Nucleic acid sequence of ubiquitin-deficient H0 Metschnikowia species GXF1 (with K9R and K24R mutations) | ATGTCTCAAGATGAATTGCACACCAGATCTGGTGTTGAAACTCCAATCA ACGACTCCTTGTTGGAAGAAAGACATGATGTTACTCCATTGGCTGCTTT GCCAGAAAAATCTTTCAAGGACTACATCTCCATCTCCATTTTCTGTTTGT TTGTTGCTTTCGGTGGTTTCGTTTTCGGTTTTGATACTGGTACTATTTCCG GTTTCGTTAACATGTCTGATTTCAAGACTAGGTTCGGTGAAATGAATGC TCAGGGTGAATATTACTTGTCCAACGTTAGAACTGGCCTGATGGTTTCT ATTTTCAATGTTGGTTGTGCTGTCGGTGGTATTTTCTTGTGTAAAATTGC TGATGTCTACGGTAGAAGGATCGGTTTGATGTTTTCTATGGTTGTCTACG TTGTCGGTATCATTATTCAAATTGCTTCTACCACCAAGTGGTATCAGTAC TTCATTGGTAGATTGATTGCTGGTTTGGCTGTTGGTACTGTTTCTGTTAT TTCCCCTTTGTTCATTTCCGAAGTTGCTCCAAAACAATTGAGAGGTACTT TGGTTTGCTGTTTCCAATTGTGTATTACCTTGGGTATCTTCTTGGGTTACT GTACTACTTACGGTACTAAGACTTACACCGATTCTAGACAATGGCGTAT TCCATTGGGTATTTGTTTTGCTTGGGCTTTGTTTTTGGTTGCCGGTATGTT GAATATGCCAGAATCTCCAAGATACTTGGTCGAAAAGTCCAGAATTGAT GATGCCAGAAAGTCCATTGCTAGGTCTAACAAAGTTTCCGAAGAAGATC CAGCTGTTTACACCGAAGTTCAATTGATTCAAGCCGGTATTGATAGAGA AGCTTTGGCTGGTTCTGCTACTTGGATGGAATTGGTTACTGGTAAGCCT AAGATCTTTAGAAGAGTTATCATGGGTGTCATGTTGCAATCCTTGCAAC AATTGACTGGTGACAACTACTTTTTCTACTACGGTACAACCATTTTCAAG GCTGTCGGTTTACAAGATTCTTTCCAAACCTCCATCATTTTGGGTATCGT TAACTTCGCTTCTACCTTCGTTGGTATCTACGCTATTGAAAGAATGGGTA GAAGATTGTGTTTGTTGACAGGTTCTGCTTGTATGTTCGTTTGCTTCATC ATCTACTCATTGATCGGTACTCAGCACTTGTACAAAAACGGTTTTTCTAA CGAACCCTCCAACACTTACAAACCATCTGGTAATGCCATGATCTTCATT ACCTGCCTGTACATTTTCTTTTTCGCTTCAACTTGGGCTGGTGGTGTTTA CTGTATAGTTTCTGAATCTTACCCACTGAGGATCAGATCTAAAGCTATG TCTGTTGCTACTGCTGCAAATTGGATGTGGGGTTTTTTGATTTCTTTCTTT ACCCCATTCATCACCTCCGCTATCCATTTTTACTATGGTTTTGTTTTCACC GGTTGCTTGGCTTTCTCTTTCTTTTACGTTTACTTCTTCGTCGTCGAGACT AAGGGTTTGTCTTTGGAAGAGGTTGATATCTTGTATGCCTCTGGTACTTT GCCATGGAAATCTTCAGGTTGGGTTCCACCAACTGCTGACGAAATGGCT CATAATGCTTTTGATAACAAACCAACCGATGAACAGGTTTAA |
| 53 | Nucleic acid sequence of ubiquitin-deficient H0 Metschnikowia species XYT1 (with K6R and S75L mutations) | ATGGGATACGAAGAGAGATTAGTGGCCCCCGCTTTGAAATTTAAGAACT TTTTGGATAAGACCCCAAATATACATAACGTTTACGTAATTGCGGCGAT CTCGTGTACCTCAGGTATGATGTTCGGTTTCGATATATCGTCGATGTCCG TGTTCGTGGACCAACAGCCGTATTTAAAAATGTTTGATAACCCTAGCAG CGTGATACAAGGGTTTATAACTGCGTTGATGTCTTTGGGGAGCTTTTTCG GATCGCTAACGTCCACTTTTATTTCAGAACCTTTTGGTAGACGTGCCTCT TTGTTCATATGCGGGATCCCTTTGGGTAATTGGGGCGGCAGTTCAAAGTT CTTCTCAGAACCGTGCGCAGCTTATTTGTGGCCGAATTATTGCAGGGTG GGGCATCGGATTCGGTTCTAGCGTTGCGCCGGTATACGGTTCAGAAATG GCCCCACGCAAAATTAGAGGAACAATCGGAGGTATTTTTCAATTTTCTG TCACGGTCGGAATATTCATAATGTTCCTGATTGGCTACGGCTGCTCATTT ATACAAGGCAAGGCCAGTTTTAGAATTCCGTGGGGAGTTCAAATGGTAC CAGGTCTCATTCTGTTGATCGGACTATTCTTCATTCCTGAATCCCCAAGA TGGTTAGCCAAACAAGGCTACTGGGAAGACGCTGAGATCATCGTAGCA AACGTTCAAGCTAAGGGTAACAGGAACGATGCTAATGTGCAAATTGAA ATGTCCGAGATAAAAGATCAGTTAATGCTTGACGAGCATTTAAGGAGT TTACTTATGCCGATTTGTTTACCAAAAAATACCGGCAAAGGACGATAAC AGCTATATTTGCCCAAATATGGCAACAGCTGACAGGTATGAATGTCATG ATGTACTACATCGTATATATATTTCAAATGGCAGGTTATTCAGGTAATA CTAATTTAGTTCCTTCACTCATTCAGTATATTATAAAATATGGCTGTTACG GTCCCCGCATTGTTCGTCTTGATCTGCTTGGCAGGAGGACAATTTTATT AGCTGGCGCCGCTTTTATGATGGCCTGGCAATTTGGTGTTGCTGGCATTT TAGCTACTTATTCAGAGCCAGCCTATATTTCAGATACCGTGAGAATTAC AATTCCAGATGACCATAAAAGTGCCGCTAAGGGTGTCATCGCTTGCTGC TATTTGTTTGTTTGTTCCTTCGCCTTTTCCTGGGGTGTAGGTATCTGGGTT TATTGTTCAGAAGTGTGGGTGATAGTCAATCCAGACAAAGAGGTGCTG CATTGGCAACTTCTGCTAATTGGATCTTCAATTTCGCAATTGCAATGTTT ACACCTTCTTCTTTCAAAAATATCACTTGGAAGACTTATATCATTTATGC TACATTTTGTGCTTGTATGTTCATTCATGTTTTTTTTTTTTCCCTGAAAC AAAGGGTAAGAGACTAGAAGAAATTGGACAGCTATGGGATGAAGGTGT CCCAGCATGGAGATCTGCAAAATGGCAACCCACTGTCCCACTAGCAAGT GACGCTGAATTAGCTCACAAAATGGATGTTGCACACGCTGAACACGCA GACTTATTGGCAACCCATTCTCCAAGTAGTGACGAAAAAACTGGTACCG TTTAA |
| 54 | Amino Acid sequence of ubiquitin-deficient H0 | MSQDELHTRSGVETPINDSLLEERHDVTPLAALPEKSFKDYISISIFCLFVAF GGFVFGFDTGTISGFVNMSDFKTRFGEMNAQGEYYLSNVRTGLMVSIFNV GCAVGGIFLCKIADVYGRRIGLMFSMVYVVGIIIQIASTTKWYQYFIGRLI AGLAVGTVSVISPLFISEVAPKQLRGTLVCCFQLCITLGIFLGYCTTYGTKTY |

| SEQ ID NO: | Description | SEQUENCES |
|---|---|---|
| | *Metschnikowia* species Gxf1p (with K9R; K24R, K538R mutations) | TDSRQWRIPLGICFAWALFLVAGMLNMPESPRYLVEKSRIDDARKSIARSN KVSEEDPAVYTEVQLIQAGIDREALAGSATWMELVTGKPKIFRRVIMGSN LQSLQQLTGDNYFFYYGTTIFKAVGLQDSFQTSIILGIVNFASTFVGIYAIER MGRRLCLLTGSACMFVCFI1YSLIGTQHLYKNGFSNEPSNTYKPSGNAMIFIT CLYIFFFASTWAGGVYCIVSESYPLRIRSKAMSVATAANWMWGFLISFFTPF ITSAIHFYYGFVFTGCLAFSFFYVYFFVVETKGLSLEEVDILYASGTLPWKSS GWVPPTADEMAHNAFDNRPTDEQV |
| 55 | Amino Acid sequence of ubiquitin-deficient H0 *Metschnikowia* species Xyt1p (with K6R, S75L, K517R, K539R mutations) | MGYEERLVAPALKFKNFLDKTPNIHNVYVIAAISCTSGMMFGFDISSMSVF VDQQPYLKMFDNPSSVIQGFITALMSLGSFFGSLTSTFISEPFGRRASLFICGI LWVIGAAVQSSSQNRAQLICGRIIAGWGIGFGSSVAPVYGSEMAPRKIRGTI GGIFQFSVTVGIFIMFLIGYGCSFIQGKASFRIPWGVQMVPGLILLIGLFFIPES PRWLAKQGYWEDAEIIVANVQAKGNRNDANVQIEMSEIKDQLMLDEHLK EFTYADLFTKKYRQRTITAIFAQIWQQLTGMNVMMYYIVYIFQMAGYSGN TNLVPSLIQYIINMAVTVPALFCLDLLGRRTILLAGAAFMMAWQFGVAGIL ATYSEPAYISDTVRITIPDDHKSAAKGVIACCYLFVCSFAFSWGVGIWVYCS EVVVGDSQSRQRGAALATSANWIFNFAIAMFTPSSFKNITWKTYIIYATFCAC MFIHVFFFFPETKGKRLEEIGQLWDEGVPAWRSAKWQPTVPLASDAELAH RMDVAHAEHADLLATHSPSSDERTGTV |
| 56 | Nucleic acid sequence of ubiquitin-deficient H0 *Metschnikowia* speciesGXF1 (with K9R; K24R, K538R mutations) | ATGTCTCAAGATGAATTGCACACCAGATCTGGTGTTGAAACTCCAATCA ACGACTCCTTGTTGGAAGAAAGACATGATGTTACTCCATTGGCTGCTTT GCCAGAAAAATCTTTCAAGGACTACATCTCCATCTCCATTTTCTGTTTGT TTGTTGCTTTCGGTGGTTTCGTTTTCGGTTTTGATACTGGTACTATTTCCG GTTTCGTTAACATGTCTGATTTCAAGACTAGGTTCGGTGAAATGAATGC TCAGGGTGAATATTACTTGTCCAACGTTAGAACTGGCCTGATGGTTTCT ATTTTCAATGTTGGTTGTGCTGTCGGTGGTTATTTTCTTGTGTAAAATTGC TGATGTCTACGGTAGAAGGATCGGTTGATGTTTTCTATGGTTGTCTACG TTGTCGGTATCATTATTCAAATTGCTTCTACCACCAAGTGGTATCAGTAC TTCATTGGTAGATTGATTGCTGGTTTGGCTGTTGGTACTGTTTCTGTTAT TTCCCCTTTGTTCATTTCCGAAGTTGCTCCAAAACAATTGAGAGGTACTT TGGTTTGCTGTTTCCAATTGTGTATTACCTTGGGTATCTTCTTGGGTTACT GTACTACTTACGGTACTAAGACTTACACCGATTCTAGACAATGGCGTAT TCCATTGGGTATTTGTTTTGCTTGGGCTTTGTTTTTGGTTGCCGGTATGTT GAATATGCCAGAATCTCCAAGATACTTGGTCGAAAAGTCCAGAATTGAT GATGCCAGAAAGTCCATTGCTAGGTCTAACAAAGTTTCCGAAGAAGATC CAGCTGTTTACACCGAAGTTCAATTGATTCAAGCCGGTATTGATAGAGA AGCTTTGGCTGGTTCTGCTACTTGGATGGAATTGGTTACTGGTAAGCCT AAGATCTTTAGAAGAGTTATCATGGGTGTCATGTTGCAATCCTTGCAAC AATTGACTGGTGACAACTACTTTTTCTACTACGGTACAACCATTTTCAAG GCTGTCGGTTTACAAGATTCTTTCCAAACCTCCATCATTTTGGGTATCGT TAACTTCGCTTCTACCTTCGTTGGTATCTACGCTATTGAAAGAATGGGTA GAAGATTGTGTTTGTTGACAGGTTCTGCTTGTATGTTCGTTTGCTTCATC ATCTACTCATTGATCGGTACTCAGCACTTGTACAAAAACGGTTTTTCTAA CGAACCCTCCAACACTTACAAACCATCTGGTAATGCCATGATCTTCATT ACCTGCCTGTACATTTTCTTTTTCGCTTCAACTTGGGCTGGTGGTGTTTA CTGTATAGTTTCTGAATCTTACCCACTGAGGATCAGATCTAAAGCTATG TCTGTTGCTACTGCTGCAAATTGGATGTGGGGTTTTTTGATTTCTTTCTTT ACCCCATTCATCACCTCCGCTATCCATTTTTACTATGGTTTTGTTTTCACC GGTTGCTTGGCTTTCTCTTTCTTTTACGTTTACTTCTTCGTCGTCGAGACT AAGGGTTTGTCTTTGGAAGAGGTTGATATCTTGTATGCCTCTGGTACTTT GCCATGGAAATCTTCAGGTTGGGTTCCACCAACTGCTGACGAAATGGCT CATAATGCTTTTGATAACAGACCAACCGATGAACAGGTTTAA |
| 57 | Nucleic acid sequence of ubiquitin-deficient H0 *Metschnikowia* species XYT1 (with K6R, S75L, K517R, K539R mutations) | ATGGGATACGAAGAGAGATTAGTGGCCCCCGCTTTGAAATTTAAGAACT TTTTGGATAAGACCCCAAATATACATAACGTTTACGTAATTGCGGCGAT CTCGTGTACCTCAGGTATGATGTTCGGTTTCGATATATCGTCGATGTCCG TGTTCGTGGACCAACAGCCGTATTTAAAAATGTTTGATAACCCTAGCAG CGTGATACAAGGGTTTATAACTGCGTTGATGTCTTTGGGGAGCTTTTTCG GATCGCTAACGTCCACTTTTATTTCAGAACCTTTTGGTAGACGTGCCTCT TTGTTCATATGCGGGATCCTTTGGGTAATTGGGCGGCAGTTCAAAGTTC CTTCTCAGAACCGTGCGCAGCTTATTTGTGGCCGAATTATTGCAGGGTG GGGCATCGGATTCGGTTCTAGCGTTGCGCCGGTATACGGTTCAGAAATG GCCCCACGCAAAATTAGAGGAACAATCGGAGGTATTTTTCAATTTTCTG TCACGGTCGGAATATTCATAATGTTCCTGATTGGCTACGGCTGCTCATTT ATACAAGGCAAGGCCAGTTTTAGAATTCCGTGGGGAGTTCAAATGGTAC CAGGTCTCATTCTGTTGATCGGACTATTCTTCATTCCTGAATCCCCAAGA TGGTTAGCCAACAAGGCTACTGGGAAGACGCTGAGATCATCGTAGCA AACGTTCAAGCTAAGGGTAACAGGAACGATGCTAATGTGCAAATTGAA ATGTCCGAGATAAAGATCAGTTAATGCTTGACGAGCATTTAAAGGAGT TTACTTATGCCGATTTGTTTACCAAAAAATACCGGCAAAGGACGATAAC AGCTATATTTGCCCAAATATGGCAACAGCTGACAGGTATGAATGTCATG ATGTACTACATCGTATATATATTTCAAATGGCAGGTTATTCAGGTAATA CTAATTTAGTTCCTTCACTCATTCAGTATATTATAAATATGGCTGTTACG GTCCCCGCATTGTTCTGTCTTGATCTGCTTGGCAGGAGGCAATTTTATT AGCTGGCGCCGCTTTTATGATGGCCTGGCAATTTGGTGTTGCTGGCATTT |

| SEQ ID NO: | Description | SEQUENCES |
|---|---|---|
| | | TAGCTACTTATTCAGAGCCAGCCTATATTTCAGATACCGTGAGAATTAC<br>AATTCCAGATGACCATAAAAGTGCCGCTAAGGGTGTCATCGCTTGCTGC<br>TATTTGTTTGTTTGTTCCTTCGCCTTTTCCTGGGGTGTAGGTATCTGGGTT<br>TATTGTTCAGAAGTGTGGGGTGATAGTCAATCCAGACAAAGAGGTGCTG<br>CATTGGCAACTTCTGCTAATTGGATCTTCAATTTCGCAATTGCAATGTTT<br>ACACCTTCTTCTTTCAAAAATATCACTTGGAAGACTTATATCATTTATGC<br>TACATTTTGTGCTTGTATGTTCATTCATGTTTTTTTTTTTCCCTGAAAC<br>AAAGGGTAAGAGACTAGAAGAAATTGGACAGCTATGGGATGAAGGTGT<br>CCCAGCATGGAGATCTGCAAAATGGCAACCCACTGTCCCACTAGCAAGT<br>GACGCTGAATTAGCTCACAGAATGGATGTTGCACACGCTGAACACGCA<br>GACTTATTGGCAACCCATTCTCCAAGTAGTGACGAAAGAACTGGTACCG<br>TTTAA |
| 58 | Amino Acid sequence of ubiquitin-deficient H0 *Metschnikowia* species Gxf2p/Gal2p (with K23R, K26R, and K35R, mutations) | MSAEQEQQVSGTSATIDGLASLRQERTAEEEDAFRPKPATAYFFISFLCGLV<br>AFGGYVFGFDTGTISGFVNMDDYLMRFGQQHADGTYYLSNVRTGLIVSIFN<br>IGCAVGGLALSKVGDIWGRRIGIMVAMIIYMVGIIIQIASQDKWYQYFIGRLI<br>TGLGVGTTSVLSPLFISESAPKHLRGTLVCCFQLMVTLGIFLGYCTTYGTKN<br>YTDSRQWRIPLGLCFAWALLLISGMVFMPESPRFLIERQRFDEAKASVAKS<br>NQVS1EDPAVYTEVELIQAGIDREALAGSAGWKELITGKPKMLQRVILGM<br>MLQSIQQLTGNNYFFYYGTTIFKAVGMSDSFQTSIVLGIVNFASTFVGIWAI<br>ERMGRRSCLLVGSACMSVCFLIYSILGSVNLYIDGYENTPSNTRKPTGNAMI<br>FITCLFIPFFASTWAGGVYSIVSETYPLRIRSKGMAVATAANWMWGFLISFF<br>TPFITSAIHFYYGFVFTGCLIFSFFYVFFFVRETKGLSLEEVDELYATDLPPW<br>KTAGWTPPSAEDMAHTTGFAEAAKPTNKHV |
| 59 | NucleicAcid sequence of ubiquitin-deficient H0 *Metschnikowia* species Gxf2p/Gal2p (with K23R, K26R, and K35R, mutations) | ATGTCCGCTGAACAAGAACAACAAGTTTCTGGTACTTCTGCCACTATTG<br>ATGGTTTGGCTTCTTTGAGGCAAGAAAGGACTGCTGAAGAAGAAGATG<br>CTTTTAGGCCAAAACCAGCTACTGCCTACTTCTTCATTTCTTTCTTGTGT<br>GGTTTGGTTGCTTTCGGTGGTTACGTTTTTGGTTTTGATACCGGTACTAT<br>CTCCGGTTTCGTTAACATGGATGATTACTTGATGAGATTCGGTCAACAA<br>CATGCTGATGGTACTTACTACTTGTCCAATGTTAGAACCGGTTTGATCGT<br>CAGTATTTTCAACATTGGTTGTGCTGTTGGTGGTTTGGCATTGTCTAAAG<br>TTGGTGATATTTGGGGTAGAAGAATCGGTATTATGGTTGCCATGATCAT<br>CTACATGGTTGGTATCATTATTCAAATCGCCTCCCAAGACAAGTGGTAT<br>CAATACTTTATTGGTAGATTGATCACCGGTTTGGGTGTTGGTACTACTTC<br>TGTTTTGTCTCCTTTGTTCATTTCCGAATCCGCTCCAAAACATTTGAGAG<br>GTACTTTGGTTTGCTGCTTCCAATTGATGGTAACCTTGGGTATTTTCTTG<br>GGTTACTGTACTACTTACGGTACTAAGAACTACACCGATTCTAGACAAT<br>GGAGAATTCCATTGGGTTTGTGTTTTGCTTGGGCCTTGTTGTTGATTTCT<br>GGTATGGTTTTTATGCCAGAATCCCCAAGATTCTTGATCGAAAGACAAA<br>GATTCGATGAAGCTAAGGCTTCTGTTGCCAAGTCTAATCAAGTTTCTAC<br>TGAAGATCCAGCCGTTTACACTGAAGTTGAATTGATTCAAGCCGGTATT<br>GATAGAGAAGCTTTGGCTGGTTCTGCTGGTTGGAAAGAATTGATTACTG<br>GTAAGCCAAAGATGTTGCAAAGAGTCATTTTGGGTATGATGTTACAATC<br>CATCCAACAATTGACCGGTAACAATTACTTCTTCTACTACGGTACAACC<br>ATCTTCAAAGCTGTTGGTATGTCCGATTCTTTTCAAACCTCTATAGTCTT<br>GGGTATCGTTAACTTCGCTTCTACCTTTGTTGGTATTTGGGCCATTGAAA<br>GAATGGGTAGAAGATCTTGTTTGTTGGTTGGTTCAGCTTGTATGTCTGTT<br>TGCTTCTTGATCTACTCTATCTTGGGTTCAGTCAACTTGTACATCGATGG<br>TTACGAAAACACTCCATCTAACACTAGAAAGCCAACTGGTAACGCCATG<br>ATTTTCATTACCTGTTTGTTCATCTTTTTCTTCGCCTCTACTTGGGCTGGT<br>GGTGTTTATTCTATAGTTTCTGAAACCTACCCATTGAGAATCAGATCTAA<br>AGGTATGGCTGTTGCTACTGCTGCTAATTGGATGTGGGGTTTTTTGATCT<br>CTTTCTTTACCCCATTCATCACCTCCGCTATTCATTTTTACTACGGTTTTG<br>TTTTCACCGGTTGCTTGATCTTCTCATTCTTTTACGTATTCTTTTTCGTCC<br>GTGAAACTAAGGGTTTGTCCTTGGAAGAAGTTGACGAATTATACGCTAC<br>TGATTTGCCACCATGGAAAACTGCAGGTTGGACTCCACCATCAGCTGAA<br>GATATGGCTCATACAACTGGTTTTGCTGAAGCTGCTAAGCCTACAAACA<br>AACACGTTTGA |

Expression of more than one xylose transporters can further improve xylose uptake. As such, the non-naturally occurring microbial organisms can have at least one exogenous nucleic acid, or at least two, at least three, at least four, at least five, at least six, at least seven, at least eight, at least nine, at least ten, or at least eleven nucleic acids each encoding a xylose transporter. In some embodiments, the microbial organisms have at least two exogenous nucleic acids each encoding a xylose transporter. In some embodiments, the microbial organisms have at least three exogenous nucleic acids each encoding a xylose transporter. In some embodiments, the microbial organisms have at least four exogenous nucleic acids each encoding a xylose transporter. In some embodiments, the microbial organisms have at least five exogenous nucleic acids each encoding a xylose transporter. In some embodiments, the microbial organisms have at least six exogenous nucleic acids each encoding a xylose transporter. In some embodiments, the microbial organisms have at least seven exogenous nucleic acids each encoding a xylose transporter. In some embodiments, the microbial organisms have at least eight exogenous nucleic acids each encoding a xylose transporter. In some embodiments, the microbial organisms have at least nine exogenous nucleic acids each encoding a xylose transporter. In some embodiments, the microbial organisms have at least ten exogenous nucleic acids each encoding a xylose transporter.

In some embodiments, the microbial organisms have at least eleven exogenous nucleic acids each encoding a xylose transporter.

The xylose transporters provided herein can be a *Metschnikowia* xylose transporter, including such as those from H0 *Metschnikowia* sp. having amino acid sequences as shown in sequence listing, as well as their variants that retain their transporter function. For example, provided herein is Xyt1p from H0 *Metschnikowia* sp. that has an amino acid sequence of SEQ ID NO: 1, as well as variants thereof that retain the transporter function of Xyt1p. The transporter function of Xyt1p includes, but is not limited to, transport of xylose across cell wall and/or cell membrane, which can be determined, for example, by subjecting the variant to a transporter assay as described herein or otherwise known in the art. The xylose transporter function can be determined, for example, by expressing the transporter in a microbial organism and measuring the increase in xylose uptake by the microbial organism. In an exemplary assay, a non-xylose utilizing microbial organism expressing an exogenous transporter can be cultured in a xylose-containg medium and the decrease of xylose in the culture medium can be measured by high performance liquid chromatography (HPLC) using Rezex RPM-monosaccharide Pb+2 column (Phenomenex), refractive index detector and water as a mobile phase at 0.6 ml/min. In another exemplary assay, starter cultures for wild type and transgenic microbial organisms expressing various transporters can be grown in YP base medium with controlled amounts of glucose and xylose (%; w/v). Uninoculated medium is used a reference for a given sampling time; the medium indicates 100% of the starting xylose or xylose at time 0 h. At 24 h intervals, samples at volumes of 300-1000 µL can be removed from the culture aseptically and filtered through a 0.2 m syringe filter, physically separating medium and yeast. The medium can be transferred to glass vials and the xylose content can be examined by HPLC. The amount of xylose remaining in the sampled medium can be determined by comparison with a predefined calibration curve, and the remaining sample is normalized to the xylose content in the uninoculated medium, which is counted as containing 100% of the xylose at the initiation of the culture. The non-naturally occurring microbial organisms expressing an exogenous xylose transporter can consume xylose at a higher rate than their wild type counterparts, and the differences in the decrease rate of xylose in the culture medium between wild type and non-naturally occurring microbial organisms expressing an exogenous xylose transporter can indicate the transporter function of the exogenous xylose transporter.

In some embodiments, provided herein are also isolated polypeptides that are variants of a *Metschnikowia* xylose transporter that retains its transporter function. Provided herein are also isolated nucleic acids that encode polypeptides that are variants to a *Metschnikowia* xylose transporter that retains its transporter function. In some embodiments, the variant of a *Metschnikowia* xylose transporter is ubiquitin-deficient. In some embodiments, the ubiquitin-deficient *Metschnikowia* xylose transporter has amino acid mutation at or near at least one lysine residue that can be ubiquitinated. In some embodiments, the ubiquitin-deficient *Metschnikowia* xylose transporter has amino acid mutations at or near at least two lysine residue that can be ubiquitinated. In some embodiments, the ubiquitin-deficient *Metschnikowia* xylose transporter has amino acid mutations at or near at least three lysine residue that can be ubiquitinated. In some embodiments, the ubiquitin-deficient *Metschnikowia* xylose transporter has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient *Metschnikowia* xylose transporter has amino acid mutation near the lysine residue that can be ubiquitinated such that the lysine residue is not accessible to the ubiquitination machinery. In some embodiments, provided herein are non-naturally occurring microbial organisms having an exogenous nucleic acid encoding a xylose transporter, wherein the xylose transporter is a variant of a *Metschnikowia* xylose transporter that retains its transporter function. In some embodiments, the xylose transporter is a variant of the xylose transporters from the H0 *Metschnikowia* sp. as described herein that retains its transporter function. In some embodiments, the variant of a H0 *Metschnikowia* sp. xylose transporter is ubiquitin-deficient.

In some embodiments, provided herein are also isolated polypeptides that are variants of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species that retain the transporter function. Provided herein are also isolated polypeptides that are variants of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from the H0 *Metschnikowia* sp. that retain the transporter function. In some embodiments, the variant is ubiquitin-deficient. In some embodiments, provided herein are also isolated nucleic acids that encode polypeptides that are variants of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species that retain the transporter function. In some embodiments, provided herein are also isolated nucleic acids that encode polypeptides that are variants of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from the H0 *Metschnikowia* sp. that retain the transporter function.

In some embodiments, provided herein are non-naturally occurring microbial organisms having an exogenous nucleic acid encoding a xylose transporter, wherein the xylose transporter is a variant of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species that retains the transporter function. In some embodiments, provided herein are non-naturally occurring microbial organisms having an exogenous nucleic acid encoding a xylose transporter, wherein the xylose transporter is a variant of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from H0 *Metschnikowia* sp. that retains the transporter function. In some embodiments, the variant is ubiquitin-deficient.

The xylose transporters described herein can have amino acid sequence of at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity, or is identical, to the amino acid sequences disclosed herein by SEQ ID NO, GenBank and/or GI number. In some embodiments, the xylose transporters described herein can have amino acid sequence of 35%, 40%, 45%, 50%, 55%, 65%, 70%, 75%, 80%, 85%, 90%, 91%, 92%, 93%, 94%, 95%, 96%, 97%, 98% or 99% sequence identity, or be identical, to amino acids described herein by SEQ ID NO, GenBank and/or GI number. In some embodiments, the xylose transporters described herein can have amino acid sequence of 35%, 40%, 45%, 50%, 55%, 65%, 70%, 75%, 80%, 85%, 90%, 91%, 92%, 93%, 94%, 95%, 96%, 97%, 98% or 99% sequence identity, or be identical, to any one of SEQ ID NOs: 1-5 and 7-12.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* xylose transporter such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* xylose transporter such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p.

In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* xylose transporter such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p. In some embodiments, the exogenous nucleic acid encodes a *Metschnikowia* xylose transporter such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

Variants of a specific xylose transporter can also include, for example, amino acid substitutions, deletions, fusions, or truncations when compared to the reference xylose transporter. Variants of the *Metschnikowia* xylose transporters described herein can also contain conservatively amino acids substitution, meaning that one or more amino acid can be replaced by an amino acid that does not alter the secondary and/or tertiary stricture of the xylose transporter. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Phenotypically silent amino acid exchanges are described more fully in Bowie et al., *Science* 247:1306-10 (1990). In addition, variants of *Metschnikowia* xylose transporters include those having amino acid substitutions, deletions, or additions to the amino acid sequence outside functional regions of the protein so long as the substitution, deletion, or addition does not affect xylose transport function of the resulting polypeptide. In some embodiments, the variant is ubiquitin-deficient. Techniques for making these substitutions and deletions are well known in the art and include, for example, site-directed mutagenesis.

In some embodiments, provided herein are non-naturally occurring microbial organisms having an exogenous nucleic acid encoding a xylose transporter, wherein the xylose transporter has 1 to 50, 1 to 45, 1 to 40, 1 to 35, 1 to 30, 1 to 25, 1 to 20, 1 to 15, 1 to 10, or 1 to 5, amino acid substitutions, deletions or insertions of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species and retains the transporter function. The *Metschnikowia* species can be the H0 *Metschnikowia* sp. In some embodiments, the xylose transporter has 1 to 10 amino acid substitutions, deletions or insertions of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species and retains the transporter function. The *Metschnikowia* species can be the H0 *Metschnikowia* sp. In some embodiments, the xylose transporter has 1 to 5 amino acid substitutions, deletions or insertions of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species and retains the transporter function. The *Metschnikowia* species can be the H0 *Metschnikowia* sp. In some embodiment, the xylose transporter is a ubiquitin-deficient Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from a *Metschnikowia* species and retains the transporter function. The *Metschnikowia* species can be the H0 *Metschnikowia* sp.

The xylose transporters provided herein also include functional fragments of specific *Metschnikowia* xylose transporters that retain their transporter function. In some embodiments, provided herein is an isolated polypeptide that is a functional fragment of a specific *Metschnikowia* xylose transporter. In some embodiments, provided herein is an isolated nucleic acid that encodes a polypeptide that is functional fragment of a specific *Metschnikowia* xylose transporter. In some embodiments, the xylose transporter can be fragments of a xylose transporter such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p retains the transporter function. In some embodiments, the xylose transporter can be fragments of a xylose transporter such as Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p from the H0 *Metschnikowia* sp. retains the transporter function.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a function fragment of a *Metschnikowia* xylose transporter including such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a function fragment of a *Metschnikowia* xylose transporter including such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to a function fragment of a xylose transporter of H0 *Metschnikowia* sp. including such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a function fragment of a xylose transporter of H0 *Metschnikowia* sp. including such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p.

In some embodiments, provided herein are non-naturally occurring microbial organisms having an exogenous nucleic acid encoding a functional fragment of a *Metschnikowia* xylose transporter that retains its transporter function. In some embodiments, the non-naturally occurring microbial organisms provided herein have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a function fragment of a *Metschnikowia* xylose transporter including such as *Metschnikowia* Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p. In some embodiments, the non-naturally occurring microbial organisms provided herein have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a function fragment of a xylose transporter of H0 *Metschnikowia* sp. such as Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, or Aps1p/Hgt19p.

In some embodiments, variants of *Metschnikowia* xylose transporters described herein include covalent modification or aggregative conjugation with other chemical moieties, such as glycosyl groups, polyethylene glycol (PEG) groups, lipids, phosphate, acetyl groups, and the like. In some embodiments, variants of the *Metschnikowia* xylose transporters described herein further include, for example, fusion proteins formed of xylose transporter polypeptide and another polypeptide. The added polypeptides for constructing the fusion protein include those that facilitate purification or oligomerization of xylose transporters, or those that enhance stability and/or transport capacity or transport rate of xylose transporters. In some embodiments, the added polypeptides gain enhanced transport capability when fused with the xylose transporters described herein.

The *Metschnikowia* xylose transporters described herein can be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin, GST, and the OmpA signal sequence tag. A binding partner that recognizes and binds to the heterologous peptide tags can be any molecule or compound, including metal ions (for example, metal affinity columns), antibodies, antibody fragments, or any protein or peptide that selectively or specifically binds the heterologous peptide to permit purification of the fusion protein.

The *Metschnikowia* xylose transporters can also be modified to facilitate formation of oligomers. For example, the Xyt1p polypeptides can be fused to peptide moieties that promote oligomerization, such as leucine zippers and certain antibody fragment polypeptides, such as Fc polypeptides. Techniques for preparing these fusion proteins are known, and are described, for example, in WO 99/31241 and in Cosman et al., *Immunity* 14:123-133 (2001). Fusion to an Fc polypeptide offers the additional benefit of facilitating purification by affinity chromatography over Protein A or Protein G columns. Fusion to a leucine-zipper (LZ), for example, a repetitive heptad repeat, often with four or five leucine residues interspersed with other amino acids, is described in Landschulz et al., *Science* 240:1759-64 (1988).

The xylose transporters described herein can be provided in an isolated form, or in a substantially purified form. The polypeptides can be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. In some embodiments, protein chromatography is employed for purification.

The *Metschnikowia* xylose transporters described herein can be recombinantly expressed by suitable hosts. When heterologous expression of the *Metschnikowia* xylose transporters is desired, the coding sequences of specific *Metschnikowia* xylose transporters can be modified in accordance with the codon usage of the host. The standard genetic code is well known in the art, as reviewed in, for example, Osawa et al., Microbiol Rev. 56(1):229-64 (1992). Yeast species, including but not limited to *Saccharomyces cerevisiae, Candida azyma, Candida diversa, Candida magnoliae, Candida rugopelliculosa, Yarrowia lipolytica*, and *Zygoascus hellenicus*, use the standard code. Certain yeast species use alternative codes. For example, "CUG," standard codon for "Leu," encodes "Ser" in species such as *Candida albicans, Candida cylindracea, Candida melibiosica, Candida parapsilosis, Candida rugose, Pichia stipitis*, and *Metschnikowia* species. The codon table for the H0 *Metschnikowia* sp. is provided below. The DNA codon CTG in a foreign gene from a non "CUG" clade species need to be changed to TTG, CTT, CTC, TTA, or CTA for a functional expression of a protein in the *Metschnikowia* species. Other codon optimization can result in increase of protein expression of a foreign gene in the *Metschnikowia* species. Codon optimization can result in increase protein expression of a foreign gene in the host. Methods of Codon optimization are well known in the art (e.g. Chung et al., *BMC Syst Biol.* 6:134 (2012); Chin et al., *Bioinformatics* 30(15):2210-12 (2014)), and various tools are available (e.g. DNA2.0 at dna20.com/services/genegps; and OPTIMIZER at genomes.urv.es/OPTIMIZER).

TABLE

Codons for H0 *Metschnikowia* sp.

| Amino Acid | SLC | DNAcodons | | | | |
|---|---|---|---|---|---|---|
| Isoleucine | I | ATT | ATC | ATA | | |
| Leucine | L | CTT | CTC | CTA | TTA | TTG |
| Valine | V | GTT | GTC | GTA | GTG | |
| Phenylalanine | F | TTT | TTC | | | |
| Methionine | M | ATG | | | | |
| Cysteine | C | TGT | TGC | | | |
| Alanine | A | GCT | GCC | GCA | GCG | |
| Glycine | G | GGT | GGC | GGA | GGG | |
| Proline | P | CCT | CCC | CCA | CCG | |
| Threonine | T | ACT | ACC | ACA | ACG | |
| Serine | S | TCT | TCC | TCA | TCG | AGT | AGC CTG |
| Tyrosine | Y | TAT | TAC | | | |
| Tryptophan | W | TGG | | | | |
| Glutamine | Q | CAA | CAG | | | |
| Asparagine | N | AAT | AAC | | | |
| Histidine | H | CAT | CAC | | | |
| Glutamic acid | E | GAA | GAG | | | |
| Aspartic acid | D | GAT | GAC | | | |
| Lysine | K | AAA | AAG | | | |
| Arginine | R | CGT | CGC | CGA | CGG | AGA | AGG |
| Stop codons | Stop | TAA | TAG | TGA | | |

Furthermore, the hosts can simultaneously produce other transporters such that multiple transporters are expressed in the same cell, wherein the different transporters can form oligomers to transport the same sugar. Alternatively, the different transporters can function independently to transport different sugars.

Variants of *Metschnikowia* xylose transporters can be generated by conventional methods known in the art, such as by introducing mutations at particular locations by oligonucleotide-directed site-directed mutagenesis. Site-directed-mutagenesis is considered an informational approach to protein engineering and can rely on high-resolution crystallographic structures of target proteins for specific amino acid changes (Van Den Burg et al., *PNAS* 95:2056-60 (1998)). Computational methods for identifying site-specific changes for a variety of protein engineering objectives are also known in the art (Hellinga, *Nature Structural Biology* 5:525-27 (1998)).

Other techniques known in the art include, but are not limited to, non-informational mutagenesis techniques (referred to generically as "directed evolution"). Directed evolution, in conjunction with high-throughput screening, allows testing of statistically meaningful variations in protein conformation (Arnold, 1998). Directed evolution technology can include diversification methods similar to that described by Crameri et al., *Nature* 391:288-91 (1998), site-saturation mutagenesis, staggered extension process (StEP) (Zhao et al., *Nature Biotechnology* 16:258-61 (1998)), and DNA synthesis/reassembly (U.S. Pat. No. 5,965,408).

As disclosed herein, a nucleic acid encoding xylose transporter can be introduced into a host organism. In some cases, it can also be desirable to modify an activity of a biosynthesis pathway enzyme or protein to increase production of a desired product. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a xylose transporter or a biosynthesis pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional ts mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein or otherwise known in the art.

Provided herein are also isolated nucleic acids encoding the *Metschnikowia* xylose transporters described herein.

Nucleic acids provided herein include those having the nucleic acid sequence provided in the sequence listing; those that hybridize to the nucleic acid sequences provided in the sequence listing, under high stringency hybridization conditions (for example, 42°, 2.5 hr., 6×SCC, 0.1% SDS); and those having substantial nucleic acid sequence identity with the nucleic acid sequence provided in the sequence listing. The nucleic acids provided herein also encompass equivalent substitutions of codons that can be translated to produce the same amino acid sequences. Provided herein are also vectors including the nucleic acids described herein. The vector can be an expression vector suitable for expression in a host microbial organism. The vector can be a 2 vector. The vector can be an ARS vector.

The nucleic acids provided herein include those encoding xylose transporters having an amino acid sequence as described herein, as well as their variants that retain transporter activity. The nucleic acids provided herein can be cDNA, chemically synthesized DNA, DNA amplified by PCR, RNA, or combinations thereof. Due to the degeneracy of the genetic code, two DNA sequences can differ and yet encode identical amino acid sequences.

Provided herein are also useful fragments of nucleic acids encoding the *Metschnikowia* xylose transporters described herein, include probes and primers. Such probes and primers can be used, for example, in PCR methods to amplify or detect the presence of nucleic acids encoding the *Metschnikowia* xylose transporters in vitro, as well as in Southern and Northern blots for analysis. Cells expressing the *Metschnikowia* xylose transporters can also be identified by the use of such probes. Methods for the production and use of such primers and probes are known.

Provided herein are also fragments of nucleic acids encoding the *Metschnikowia* xylose transporters that are antisense or sense oligonucleotides having a single-stranded nucleic acid capable of binding to a target mRNA or DNA sequence of a *Metschnikowia* xylose transporter.

A nucleic acid encoding a xylose transporter described herein can include nucleic acids that hybridize to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein.

Stringent hybridization refers to conditions under which hybridized polynucleotides are stable. As known to those of skill in the art, the stability of hybridized polynucleotides is reflected in the melting temperature (Tm) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5×Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrilodone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Nucleic acids encoding a xylose transporter provided herein include those having a certain percent sequence identity to a nucleic acid disclosed herein by SEQ ID NO, GenBank and/or GI number. For example, the nucleic acids encoding a xylose transporter can have at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity, or be identical, to a nucleic acid described herein by SEQ ID NO, GenBank and/or GI number. In some embodiments, the nucleic acid molecule can have 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity, or be identical, to a sequence selected from SEQ ID NOs: 10-16 and 19-27.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Xyt1p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Xyt1p. In some embodiments, provided herein are non-naturally occurring microbial organisms having at least one exogenous nucleic acid encoding a xylose transporter, wherein the xylose transporter has an amino acid sequence that is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Xyt1p. In some embodiments, the xylose transporter can be a *Metschnikowia* Xyt1p. In some embodiments, the xylose transporter can be a variant of a *Metschnikowia* Xyt1p that retains its transporter function. The xylose transporter can be a functional fragment of a *Metschnikowia* Xyt1p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Xyt1p from a *Metschnikowia* species. In some embodiments, the xylose transporter has 1 to 10 amino acid substitutions, deletions or insertions of Xyt1p from a *Metschnikowia* species. In some embodiments, the xylose transporter has 1 to 5 amino acid substitutions, deletions or insertions of Xyt1p from a *Metschnikowia* species.

In some embodiment, the xylose transporter is an ubiquitin-deficient Xyt1p from a *Metschnikowia* species. In some embodiments, the ubiquitin-deficient Xyt1p has amino acid mutation at or near at least one lysine residue that can be ubiquitinated. In some embodiments, the ubiquitin-deficient Xyt1p has amino acid mutations at or near at least two lysine residues that can be ubiquitinated. In some embodiments, the ubiquitin-deficient Xyt1p has amino acid mutations at or near at least three lysine residues that can be ubiquitinated. In some embodiments, the ubiquitin-deficient Xyt1p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Xyt1p has amino acid mutation near the lysine residue that can be ubiquitinated such that the lysine residue is not accessible to the ubiquitination machinery. In some embodiments, the lysine residues that can be ubiquitinated include K6, K517 and K539 of Xyt1p. In some embodiments, the ubiquitin-deficient Xyt1p has amino acid substitutions at one of K6, K517 and K539. In some embodiments, the ubiquitin-deficient Xyt1p has amino acid substitution at K6. In some embodiments, the ubiquitin-deficient Xyt1p has amino acid substitution at K517. In some embodiments, the ubiquitin-deficient Xyt1p has amino acid substitution at K539. In some embodiments, the ubiquitin-deficient Xyt1p has amino acid substitutions at two of K6, K517 and K539. In some embodiments, the ubiquitin-deficient Xyt1p has amino acid substitutions at K517 and K539. In some embodiments, the ubiquitin-deficient Xyt1p has amino acid substitutions at K539 and K6. In some embodiments, the ubiquitin-deficient Xyt1p has amino acid substitutions at K6 and K517. In some embodiments, the ubiquitin-deficient Xyt1p has amino acid substitutions at three of K6, K517 and K539.

The *Metschnikowia* species can be the H0 *Metschnikowia* sp. In some embodiments, provided herein is an isolated polypeptide that has an amino acid sequence that is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Xyt1p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Xyt1p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Xyt1p of H0 *Metschnikowia* sp. In some embodiments, the xylose transporter is Xyt1p of H0 *Metschnikowia* sp. In some embodiments, the xylose transporter can be a variant of Xyt1p of H0 *Metschnikowia* sp. that retains its transporter function. In some embodiment, the xylose transporter is a ubiquitin-deficient Xyt1p from H0 *Metschnikowia* sp. In some embodiments, the xylose transporter is a functional fragment of Xyt1p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Xyt1p from H0 *Metschnikowia* sp. In some embodiments, the xylose transporter has 1 to 10 amino acid substitutions, deletions or insertions of Xyt1p from H0 *Metschnikowia* sp. In some embodiments, the xylose transporter has 1 to 5 amino acid substitutions, deletions or insertions of Xyt1p from H0 *Metschnikowia* sp. In some embodiments, the xylose transporter has the amino acid sequence of SEQ ID NO: 1. In some embodiments, the amino acid sequence of the xylose transporter is SEQ ID NO: 1. In some embodiments, the nucleic acid has the sequence of SEQ ID NO: 13. In some embodiments, the sequence of the nucleic acid is SEQ ID NO: 13. In some embodiments, the ubiquitin-deficient Xyt1p has the amino acid sequence of SEQ ID NO: 48. In some embodiments, the nucleic acid has the sequence of SEQ ID NO: 53. The nucleic acid encoding Xyt1p from a *Metschnikowia* species can be codon optimized for heterologous expression. In some embodiments, the nucleic acid encoding *Metschnikowia* Xyt1p is codon optimized for expression in a yeast host strain. The yeast host strain can be any yeast host strain described herein, such as *Saccharomyces cerevisiae*. In some embodiments, the nucleic acid encoding *Metschnikowia* Xyt1p is codon optimized for expression in a bacterial host strain. The bacterial host strain can be any bacterial host strain described herein, such as *E. coli*. In some embodiments, the nucleic acid encoding Xyt1p from H0 *Metschnikowia* sp. is codon optimized for expression in *Saccharomyces cerevisiae*. For example, in some embodiments, the nucleic acid encoding Xyt1p of H0 *Metschnikowia* sp. is codon optimized for expression in *Saccharomyces cerevisiae*. The nucleic acid can have the sequence of SEQ ID NO: 21.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxf1p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxf1p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxf1p. In some embodiments, the xylose transporter is a *Metschnikowia* Gxf1p. In some embodiments, the xylose transporter is a variant of a *Metschnikowia* Gxf1p that retains its transporter function. The xylose transporter can be a functional fragment of a *Metschnikowia* Gxf1p. In some embodiments, the nucleic acid encodes a xylose transporter having 1 to 50, 1 to 45, 1 to 40, 1 to 35, 1 to 30, 1 to 25, 1 to 20, 1 to 15, 1 to 10, or 1 to 5, amino acid substitutions, deletions or insertions of Gxf1p from a *Metschnikowia* species. In some embodiments, the xylose transporter has 1 to 10 amino acid substitutions, deletions or insertions of Gxf1p from a *Metschnikowia* species. In some embodiments, the xylose transporter has 1 to 5 amino acid substitutions, deletions or insertions of Gxf1p from a *Metschnikowia* species.

In some embodiment, the xylose transporter is a ubiquitin-deficient Gxf1p from a *Metschnikowia* species. In some embodiments, the ubiquitin-deficient Gxf1p has amino acid mutation at or near at least one lysine residue that can be ubiquitinated. In some embodiments, the ubiquitin-deficient Gxf1p has amino acid mutations at or near at least two lysine residue that can be ubiquitinated. In some embodiments, the ubiquitin-deficient Gxf1p has amino acid mutations at or near at least three lysine residue that can be ubiquitinated. In some embodiments, the ubiquitin-deficient Gxf1p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Gxf1p has amino acid mutation near the lysine residue that can be ubiquitinated such that the lysine residue is not accessible to the ubiquitination machinery. In some embodiments, the lysine residues that can be ubiquitinated include K9, K24, and K538 of Gxf1p. In some embodiments, the ubiquitin-deficient Gxf1p has amino acid substitutions at one of K9, K24, and K538. In some embodiments, the ubiquitin-deficient Gxf1p has amino acid substitution at K9. In some embodiments, the ubiquitin-deficient Gxf1p has amino acid substitution at K24. In some embodiments, the ubiquitin-deficient Gxf1p has amino acid substitution at K538. In some embodiments, the ubiquitin-deficient Gxf1p has amino acid substitutions at two of K9, K24, and K538. In some embodiments, the ubiquitin-deficient Gxf1p has amino acid substitutions at K9 and K24. In some embodiments, the ubiquitin-deficient Gxf1p has amino acid substitutions at K538 and K9. In some embodiments, the ubiquitin-deficient Gxf1p has amino acid substitutions at K24 and K538. In some embodiments, the ubiquitin-deficient Gxf1p has amino acid substitutions at three of K9, K24, and K538. In some embodiments, the ubiquitin-deficient Gxf1p has amino acid substitutions at K9, K24, K538. In some embodiments, the ubiquitin-deficient Gxf1p has amino acid substitutions at K9, K24, and K538.

The *Metschnikowia* species can be the H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Gxf1p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Gxf1p of H0 *Metschnikowia* sp. In some embodiments, the xylose transporter is Gxf1p of H0 *Metschnikowia* sp. In some embodiments, the xylose transporter can be a variant of Gxf1p of H0 *Metschnikowia* sp. that retains its transporter function. In some embodiment, the xylose transporter is a ubiquitin-deficient Gxf1p from H0 *Metschnikowia* sp. In some embodiments, the xylose transporter is a functional fragment of Gxf1p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Gxf1p from H0 *Metschnikowia* sp. In some embodiments, the xylose transporter has 1 to 10 amino acid substitutions, deletions or insertions of Gxf1p from H0 *Metschnikowia* sp. In some embodiments, the xylose transporter has 1 to 5 amino acid substitutions, deletions or insertions of Gxf1p from H0 *Metschnikowia* sp. In some embodiments, the xylose transporter has the amino acid sequence of SEQ ID NO: 2. In some embodiments, the amino acid sequence of the xylose transporter is SEQ ID NO: 2. In some embodiments, the nucleic acid has the sequence of SEQ ID NO: 14. In some embodiments, the sequence of the nucleic acid is SEQ ID NO: 14. In some embodiments, the ubiquitin-deficient Gxf1p has the amino acid sequence of SEQ ID NO: 47. In some embodiments, the nucleic acid has the sequence of SEQ ID NO: 52. In some embodiments, the nucleic acid encodes a functional fragment of Gxf1p of H0 *Metschnikowia* sp. For example, the fragment of Gxf1p can be a variant of Gxf1p that has a shorter N-terminus, and referred to as ΔGxf1p. In some embodiments, the amino acid sequence of the xylose transporter is SEQ ID NO: 3. In some embodiments, the nucleic acid has the sequence of SEQ ID NO: 15. The nucleic acid encoding Gxf1p from a *Metschnikowia* species can be codon optimized for heterologous expression. In some embodiments, the nucleic acid encoding *Metschnikowia* Gxf1p is codon optimized for expression in a yeast host strain. The yeast host strain can be any yeast host strain described herein, such as *Saccharomyces cerevisiae*. In some embodiments, the nucleic acid encoding *Metschnikowia* Gxf1p is codon optimized for expression in a bacterial host strain. The bacterial host strain can be any bacterial host strain described herein, such as *E. coli*. In some embodiments, the nucleic acid encoding Gxf1p from H0 *Metschnikowia* sp. is codon optimized for expression in *Saccharomyces cerevisiae*.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxf2p/Gal2p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxf2p/Gal2p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxf2p/Gal2p. In some embodiments, the xylose transporter is a *Metschnikowia* Gxf2p/Gal2p. In some embodiments, the xylose transporter is a variant of a *Metschnikowia* Gxf2p/Gal2p that retains its transporter function. The xylose transporter can be a functional fragment of a *Metschnikowia* Gxf2p/Gal2p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Gxf2p/Gal2p from a *Metschnikowia* species. In some embodiments, the xylose transporter has 1 to 10 amino acid substitutions, deletions or insertions of Gxf2p/Gal2p from a *Metschnikowia* species. In some embodiments, the xylose transporter has 1 to 5 amino acid substitutions, deletions or insertions of Gxf2p/Gal2p from a *Metschnikowia* species.

In some embodiment, the xylose transporter is a ubiquitin-deficient Gxf2p/Gal2p from a *Metschnikowia* species. In some embodiments, the ubiquitin-deficient Gxf2p/Gal2p has amino acid mutation at or near at least one lysine residue that can be ubiquitinated. In some embodiments, the ubiquitin-deficient Gxf2p/Gal2p has amino acid mutations at or near at least two lysine residue that can be ubiquitinated. In some embodiments, the ubiquitin-deficient Gxf2p/Gal2p has amino acid mutations at or near at least three lysine residue that can be ubiquitinated. In some embodiments, the ubiquitin-deficient Gxf2p/Gal2p has amino acid mutations at or near at least four lysine residue that can be ubiquitinated. In some embodiments, the ubiquitin-deficient Gxf2p/Gal2p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Gxf2p/Gal2p has amino acid mutation near the lysine residue that can be ubiquitinated such that the lysine residue is not accessible to the ubiquitination machinery. In some embodiments, the lysine residues that can be ubiquitinated include K23, K26, K35, K542 and K546 of Gxf2p/Gal2p. In some embodiments, the ubiquitin-deficient Xyt1p has amino acid substitutions at one of K23, K26, K35, K542 and K546. In some embodiments, the ubiquitin-deficient Gxf2p/Gal2p has amino acid substitution at K23. In some embodiments, the ubiquitin-deficient Gxf2p/Gal2p has amino acid substitution at K26. In some embodiments, the ubiquitin-deficient Gxf2p/Gal2p has amino acid substitution at K35. In some embodiments, the ubiquitin-deficient Gxf2p/Gal2p has amino acid substitution at K542. In some embodiments, the ubiquitin-deficient Gxf2p/Gal2p has amino acid substitution at K546. In some embodiments, the ubiquitin-deficient Gxf2p/Gal2p has amino acid substitutions at two of K23, K26, K35, K542 and K546. In some embodiments, the ubiquitin-deficient Gxf2p/Gal2p has amino acid substitutions at three of K23, K26, K35, K542 and K546. In some embodiments, the ubiquitin-deficient Gxf2p/Gal2p has amino acid substitutions at four of K23, K26, K35, K542 and K546. In some embodiments, the ubiquitin-deficient Gxf2p/Gal2p has amino acid substitutions at K23, K26, K35, K542 and K546.

The *Metschnikowia* species can be the H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Gxf2p/Gal2p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Gxf2p/Gal2p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to Gxf2p/Gal2p of H0 *Metschnikowia* sp. In some embodiments, the xylose transporter is Gxf2p/Gal2p of H0 *Metschnikowia* sp. In some embodiments, the xylose transporter can be a variant of Gxf2p/Gal2p of H0 *Metschnikowia* sp. that retains its transporter function. In some embodiment, the xylose transporter is a ubiquitin-deficient Gxf2p/Gal2p from H0 *Metschnikowia* sp. In some embodiments, the xylose transporter is a functional fragment of Gxf2p/Gal2p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Gxf2p/Gal2p from H0 *Metschnikowia* sp. In some embodiments, the xylose transporter has 1 to 10 amino acid substitutions, deletions or insertions of Gxf2p/Gal2p from H0 *Metschnikowia* sp. In some embodiments, the xylose transporter has 1 to 5 amino acid substitutions, deletions or insertions of Gxf2p/Gal2p from H0 *Metschnikowia* sp. In some embodiments, the xylose transporter has the amino acid sequence of SEQ ID NO: 4. In some embodiments, the amino acid sequence of the xylose transporter is SEQ ID NO: 4. In some embodiments, the nucleic acid has the sequence of SEQ ID NO: 16. In some embodiments, the sequence of the nucleic acid is SEQ ID NO: 16. In some embodiments, the ubiquitin-deficient Gxf2p/Gal2p has the amino acid sequence of SEQ ID NO: 46. In some embodiments, the nucleic acid has the sequence of SEQ ID NO: 51. The nucleic acid encoding Gxf2p/Gal2p from a *Metschnikowia* species can be codon optimized for heterologous expression. In some embodiments, the nucleic acid encoding *Metschnikowia* Gxf2p/Gal2p is codon optimized for expression in a yeast host strain. The yeast host strain can be any yeast host strain described herein, such as *Saccharomyces cerevisiae*. In some embodiments, the nucleic acid encoding *Metschnikowia* Gxf2p/Gal2p is codon optimized for expression in a bacterial host strain. The bacterial host strain can be any bacterial host strain described herein, such as *E. coli*. In some embodiments, the nucleic acid encoding Gxf2p/Gal2p from H0 *Metschnikowia* sp. is codon optimized for expression in *Saccharomyces cerevisiae*.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxs1p/Hgt12p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxs1p/Hgt12p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Gxs1p/Hgt12p. In some embodiments, the xylose transporter is a *Metschnikowia* Gxs1p/Hgt12p. In some embodiments, the xylose transporter is a variant of a *Metschnikowia* Gxs1p/Hgt12p that retains its transporter function. The xylose transporter can be a functional fragment of a *Metschnikowia* Gxs1p/Hgt12p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Gxs1p/Hgt12p from a *Metschnikowia* species. In some embodiments, the xylose transporter has 1 to 10 amino acid substitutions, deletions or insertions of Gxs1p/Hgt12p from a *Metschnikowia* species. In some embodiments, the xylose transporter has 1 to 5 amino acid substitutions, deletions or insertions of Gxs1p/Hgt12p from a *Metschnikowia* species.

The *Metschnikowia* species can be the H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Gxs1p/Hgt12p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Gxs1p/Hgt12p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to Gxs1p/Hgt12p of H0 *Metschnikowia* sp. In some embodiments, the xylose transporter is Gxs1p/Hgt12p of H0 *Metschnikowia* sp. In some embodiments, the xylose transporter can be a variant of Gxs1p/Hgt12p of H0 *Metschnikowia* sp. that retains its transporter function. In some embodiments, the xylose transporter is a functional fragment of Gxs1p/Hgt12p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Gxs1p/Hgt12p from H0 *Metschnikowia* sp. In some embodiments, the xylose transporter has 1 to 10 amino acid substitutions, deletions or insertions of Gxs1p/Hgt12p from H0 *Metschnikowia* sp. In some embodiments, the xylose transporter has 1 to 5 amino acid substitutions, deletions or insertions of Gxs1p/Hgt12p from H0 *Metschnikowia* sp. In some embodiments, the xylose transporter has the amino acid sequence of SEQ ID NO: 7. In some embodiments, the amino acid sequence of the xylose transporter is SEQ ID NO: 7. In some embodiments, the nucleic acid has the sequence of SEQ ID NO: 19. In some embodiments, the sequence of the nucleic acid is SEQ ID NO: 19. In some embodiments, the nucleic acid encodes a functional fragment of Gxs1p/Hgt12p of H0 *Metschnikowia* sp. For example, the fragment of Gxs1p/Hgt12p can be a variant of Gxs1p/Hgt12p that has a shorter N-terminus, and referred to as ΔGxs1p/ΔHgt12p. In some embodiments, the amino acid sequence of the xylose transporter is SEQ ID NO: 5. In some embodiments, the nucleic acid has the sequence of SEQ ID NO: 17. The nucleic acid encoding Gxs1p/Hgt12p from a *Metschnikowia* species can be codon optimized for heterologous expression. In some embodiments, the nucleic acid encoding *Metschnikowia* Gxs1p/Hgt12p is codon optimized for expression in a yeast host strain. The yeast host strain can be any yeast host strain described herein, such as *Saccharomyces cerevisiae*. In some embodiments, the nucleic acid encoding *Metschnikowia* Gxs1p/Hgt12p is codon optimized for expression in a bacterial host strain. The bacterial host strain can be any bacterial host strain described herein, such as *E. coli*. In some embodiments, the nucleic acid encoding Gxs1p/Hgt12p from H0 *Metschnikowia* sp. is codon optimized for expression in *Saccharomyces cerevisiae*.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Hxt5p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Hxt5p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Hxt5p. In some embodiments, the xylose transporter is a *Metschnikowia* Hxt5p. In some embodiments, the xylose transporter is a variant of a *Metschnikowia* Hxt5p that retains its transporter function. The xylose transporter can be a functional fragment of a *Metschnikowia* Hxt5p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Hxt5p from a *Metschnikowia* species. In some embodiments, the xylose transporter has 1 to 10 amino acid substitutions, deletions or insertions of Hxt5p from a *Metschnikowia* species. In some embodiments, the xylose transporter has 1 to 5 amino acid substitutions, deletions or insertions of Hxt5p from a *Metschnikowia* species.

In some embodiment, the xylose transporter is a ubiquitin-deficient Hxt5p from a *Metschnikowia* species. In some embodiments, the ubiquitin-deficient Hxt5p has amino acid mutation at or near at least one lysine residue that can be ubiquitinated. In some embodiments, the ubiquitin-deficient Hxt5p has amino acid mutations at or near at least two lysine residue that can be ubiquitinated. In some embodiments, the ubiquitin-deficient Hxt5p has amino acid mutations at or near at least three lysine residue that can be ubiquitinated. In some embodiments, the ubiquitin-deficient Hxt5p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Hxt5p has amino acid mutation near the lysine residue that can be ubiquitinated such that the lysine residue is not accessible to the ubiquitination machinery. In some embodiments, the lysine residues that can be ubiquitinated include K7, K10, K29, K43 and K58 of Hxt5p. In some embodiments, the ubiquitin-deficient Hxt5p has amino acid substitutions at one of K7, K10, K29, K43 and K58. In some embodiments, the ubiquitin-deficient Hxt5p has amino acid substitution at K7. In some embodiments, the ubiquitin-deficient Hxt5p has amino acid substitution at K10. In some embodiments, the ubiquitin-deficient Hxt5p has amino acid substitution at K29. In some embodiments, the ubiquitin-deficient Hxt5p has amino acid substitution at K43. In some embodiments, the ubiquitin-deficient Hxt5p has amino acid substitution at K58. In some embodiments, the ubiquitin-deficient Hxt5p has amino acid substitutions at two of K7, K10, K29, K43, and K58. In some embodiments, the ubiquitin-deficient Hxt5p has amino acid substitutions at K7 and K10. In some embodiments, the ubiquitin-deficient Hxt5p has amino acid substitutions at K7 and K29. In some embodiments, the ubiquitin-deficient Hxt5p has amino acid substitutions at K7 and K58. In some embodiments, the ubiquitin-deficient Hxt5p has amino acid substitutions at K10 and K29. In some embodiments, the ubiquitin-deficient Hxt5p has amino acid substitutions at K10 and K58. In some embodiments, the ubiquitin-deficient Hxt5p has amino acid substitutions at K10 and K43. In some embodiments, the ubiquitin-deficient Hxt5p has amino acid substitutions at K29 and K43. In some embodiments, the ubiquitin-deficient Hxt5p has amino acid substitutions at K43 and K7. In some embodiments, the ubiquitin-deficient Hxt5p has amino acid substitutions at K29 and K58. In some embodiments, the ubiquitin-deficient Hxt5p has amino acid substitutions at K43 and K58. In some embodiments, the ubiquitin-deficient Hxt5p has amino acid substitutions at three of K7, K10, K29, K43 and K58. In some embodiments, the ubiquitin-deficient Hxt5p has amino acid substitutions at K7, K10, and K29. In some embodiments, the ubiquitin-deficient Hxt5p has amino acid substitutions at K7, K10, and K43. In some embodiments, the ubiquitin-deficient Hxt5p has amino acid substitutions at K7, K10, and K58. In some embodiments, the ubiquitin-deficient Hxt5p has amino acid substitutions at K10, K29 and K43. In some embodiments, the ubiquitin-deficient Hxt5p has amino acid substitutions at K10, K29 and K58. In some embodiments, the ubiquitin-deficient Hxt5p has amino acid substitutions at K29, K43 and K58. In some embodiments, the ubiquitin-deficient Hxt5p has amino acid substitutions at four of K7, K10, K29, K43 and K58. In some embodiments, the ubiquitin-deficient Hxt5p has amino acid substitutions at K7, K10, K29 and K43. In some embodiments, the ubiquitin-deficient Hxt5p has amino acid substitutions at K7, K10, K29 and K58. In some embodiments, the ubiquitin-deficient Hxt5p has amino acid substitutions at K7, K10, K43 and K58. In some embodiments, the ubiquitin-deficient Hxt5p has amino acid substitutions at K7, K29, K43 and K58. In some embodiments, the ubiquitin-deficient Hxt5p has amino acid substitutions at K10, K29, K43, and K58. In some embodiments, the ubiquitin-deficient Hxt5p has amino acid substitutions at K7, K10, K29, K43 and K58.

The *Metschnikowia* species can be the H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Hxt5p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Hxt5p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to Hxt5p of H0 *Metschnikowia* sp. In some embodiments, the xylose transporter is Hxt5p of H0 *Metschnikowia* sp. In some embodiments, the xylose transporter can be a variant of Hxt5p of H0 *Metschnikowia* sp. that retains its transporter function. In some embodiment, the xylose transporter is a ubiquitin-deficient Hxt5p from H0 *Metschnikowia* sp. In some embodiments, the xylose transporter is a functional fragment of Hxt5p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Hxt5p from H0 *Metschnikowia* sp. In some embodiments, the xylose transporter has 1 to 10 amino acid substitutions, deletions or insertions of Hxt5p from H0 *Metschnikowia* sp. In some embodiments, the xylose transporter has 1 to 5 amino acid substitutions, deletions or insertions of Hxt5p from H0 *Metschnikowia* sp. In some embodiments, the xylose transporter has the amino acid sequence of SEQ ID NO: 8. In some embodiments, the amino acid sequence of the xylose transporter is SEQ ID NO: 8. In some embodiments, the nucleic acid has the sequence of SEQ ID NO: 20. In some embodiments, the sequence of the nucleic acid is SEQ ID NO: 20. In some embodiments, the ubiquitin-deficient Hxt5p has the amino acid sequence of SEQ ID NO: 45. In some embodiments, the nucleic acid has the sequence of SEQ ID NO: 50. The nucleic acid encoding Hxt5p from a *Metschnikowia* species can be codon optimized for heterologous expression. In some embodiments, the nucleic acid encoding *Metschnikowia* Hxt5p is codon optimized for expression in a yeast host strain. The yeast host strain can be any yeast host strain described herein, such as *Saccharomyces cerevisiae*. In some embodiments, the nucleic acid encoding *Metschnikowia* Hxt5p is codon optimized for expression in a bacterial host strain. The bacterial host strain can be any bacterial host strain described herein, such as *E. coli*. In some embodiments, the nucleic acid encoding Hxt5p from H0 *Metschnikowia* sp. is codon optimized for expression in *Saccharomyces cerevisiae*.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Hxt2.6p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Hxt2.6p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Hxt2.6p. In some embodiments, the xylose transporter is a *Metschnikowia* Hxt2.6p. In some embodiments, the xylose transporter is a variant of a *Metschnikowia* Hxt2.6p that retains its transporter function. The xylose transporter can be a functional fragment of a *Metschnikowia* Hxt2.6p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Hxt2.6p from a *Metschnikowia* species. In some embodiments, the xylose transporter has 1 to 10 amino acid substitutions, deletions or insertions of Hxt2.6p from a *Metschnikowia* species. In some embodiments, the xylose transporter has 1 to 5 amino acid substitutions, deletions or insertions of Hxt2.6p from a *Metschnikowia* species. In some embodiment, the xylose transporter is a ubiquitin-deficient Hxt2.6p from a *Metschnikowia* species. In some embodiments, the ubiquitin-deficient Hxt2.6p has amino acid mutation at or near at least one lysine residue that can be ubiquitinated. In some embodiments, the ubiquitin-deficient Hxt2.6p has amino acid mutations at or near at least two lysine residue that can be ubiquitinated. In some embodiments, the ubiquitin-deficient Hxt2.6p has amino acid mutations at or near at least three lysine residue that can be ubiquitinated. In some embodiments, the ubiquitin-deficient Hxt2.6p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Hxt2.6p has amino acid mutation near the lysine residue that can be ubiquitinated such that the lysine residue is not accessible to the ubiquitination machinery.

The *Metschnikowia* species can be the H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to Hxt2.6p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Hxt2.6p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to Hxt2.6p of H0 *Metschnikowia* sp. In some embodiments, the xylose transporter is Hxt2.6p of H0 *Metschnikowia* sp. In some embodiments, the xylose transporter can be a variant of Hxt2.6p of H0 *Metschnikowia* sp. that retains its transporter function. In some embodiments, the xylose transporter is a functional fragment of Hxt2.6p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Hxt2.6p from H0 *Metschnikowia* sp. In some embodiments, the xylose transporter has 1 to 10 amino acid substitutions, deletions or insertions of Hxt2.6p from H0 *Metschnikowia* sp. In some embodiments, the xylose transporter has 1 to 5 amino acid substitutions, deletions or insertions of Hxt2.6p from H0 *Metschnikowia* sp. In some embodiments, the xylose transporter has the amino acid sequence of SEQ ID NO: 10. In some embodiments, the amino acid sequence of the xylose transporter is SEQ ID NO: 10. In some embodiments, the nucleic acid has the sequence of SEQ ID NO: 22. In some embodiments, the sequence of the nucleic acid is SEQ ID NO: 22. The Hxt2.6p from a *Metschnikowia* species can be codon optimized for heterologous expression. In some embodiments, the nucleic acid encoding *Metschnikowia* Hxt2.6p is codon optimized for expression in a yeast host strain. The yeast host strain can be any yeast host strain described herein, such as *Saccharomyces cerevisiae*. In some embodiments, the nucleic acid encoding *Metschnikowia* Hxt2.6p is codon optimized for expression in a bacterial host strain. The bacterial host strain can be any bacterial host strain described herein, such as *E. coli*. In some embodiments, the nucleic acid encoding Hxt2.6p from H0 *Metschnikowia* sp. is codon optimized for expression in *Saccharomyces cerevisiae*. For example, in some embodiments, the nucleic acid encodes Hxt2.6p of H0 *Metschnikowia* sp. that is codon optimized for expression in *Saccharomyces cerevisiae*. The nucleic acid can have the sequence of SEQ ID NO: 23.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Qup2p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Qup2p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Qup2p. In some embodiments, the xylose transporter is a *Metschnikowia* Qup2p. In some embodiments, the xylose transporter is a variant of a *Metschnikowia* Qup2p that retains its transporter function. The xylose transporter can be a functional fragment of a *Metschnikowia* Qup2p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Qup2p from a *Metschnikowia* species. In some embodiments, the xylose transporter has 1 to 10 amino acid substitutions, deletions or insertions of Qup2p from a *Metschnikowia* species. In some embodiments, the xylose transporter has 1 to 5 amino acid substitutions, deletions or insertions of Qup2p from a *Metschnikowia* species. In some embodiment, the xylose transporter is a ubiquitin-deficient Qup2p from a *Metschnikowia* species. In some embodiments, the ubiquitin-deficient Qup2p has amino acid mutation at or near at least one lysine residue that can be ubiquitinated. In some embodiments, the ubiquitin-deficient Qup2p has amino acid mutations at or near at least two lysine residue that can be ubiquitinated. In some embodiments, the ubiquitin-deficient Qup2p has amino acid mutations at or near at least three lysine residue that can be ubiquitinated. In some embodiments, the ubiquitin-deficient Qup2p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Qup2p has amino acid mutation near the lysine residue that can be ubiquitinated such that the lysine residue is not accessible to the ubiquitination machinery.

The *Metschnikowia* species can be the H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Qup2p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Qup2p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to Qup2p of H0 *Metschnikowia* sp. In some embodiments, the xylose transporter can be Qup2p of H0 *Metschnikowia* sp. In some embodiments, the xylose transporter can be a variant of Qup2p of H0 *Metschnikowia* sp. that retains its transporter function. In some embodiments, the xylose transporter can be a functional fragment of Qup2p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Qup2p from H0 *Metschnikowia* sp. In some embodiments, the xylose transporter has 1 to 10 amino acid substitutions, deletions or insertions of Qup2p from H0 *Metschnikowia* sp. In some embodiments, the xylose transporter has 1 to 5 amino acid substitutions, deletions or insertions of Qup2p from H0 *Metschnikowia* sp. In some embodiments, the xylose transporter has the amino acid sequence of SEQ ID NO: 11. In some embodiments, the amino acid sequence of the xylose transporter is SEQ ID NO: 11. In some embodiments, the nucleic acid has the sequence of SEQ ID NO: 24. In some embodiments, the sequence of the nucleic acid is SEQ ID NO: 24. The Qup2p from a *Metschnikowia* species can be codon optimized for heterologous expression. In some embodiments, the nucleic acid encoding *Metschnikowia* Qup2p is codon optimized for expression in a yeast host strain. The yeast host strain can be any yeast host strain described herein, such as *Saccharomyces cerevisiae*. In some embodiments, the nucleic acid encoding *Metschnikowia* Qup2p is codon optimized for expression in a bacterial host strain. The bacterial host strain can be any bacterial host strain described herein, such as *E. coli*. In some embodiments, the nucleic acid encoding Qup2p from H0 *Metschnikowia* sp. is codon optimized for expression in *Saccharomyces cerevisiae*. For example, in some embodiments, the nucleic acid encodes Qup2p of H0 *Metschnikowia* sp. that is codon optimized for expression in *Saccharomyces cerevisiae*. The nucleic acid can have the sequence of SEQ ID NO: 25.

In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Aps1p/Hgt19p. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Aps1p/Hgt19p. In some embodiments, provided herein are non-naturally occurring microbial organisms having at least one exogenous nucleic acid encoding a xylose transporter, wherein the xylose transporter has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a *Metschnikowia* Aps1p/Hgt19p. In some embodiments, the xylose transporter is a *Metschnikowia* Aps1p/Hgt19p. In some embodiments, the xylose transporter is a variant of a *Metschnikowia* Aps1p/Hgt19p that retains its transporter function. The xylose transporter can be a functional fragment of a *Metschnikowia* Aps1p/Hgt19p. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Aps1p/Hgt19p from a *Metschnikowia* species. In some embodiments, the xylose transporter has 1 to 10 amino acid substitutions, deletions or insertions of Aps1p/Hgt19p from a *Metschnikowia* species. In some embodiments, the xylose transporter has 1 to 5 amino acid substitutions, deletions or insertions of Aps1p/Hgt19p from a *Metschnikowia* species.

In some embodiment, the xylose transporter is a ubiquitin-deficient Aps1p/Hgt19p from a *Metschnikowia* species. In some embodiments, the ubiquitin-deficient Aps1p/Hgt19p has amino acid mutation at or near at least one lysine residue that can be ubiquitinated. In some embodiments, the ubiquitin-deficient Aps1p/Hgt19p has amino acid mutations at or near at least two lysine residue that can be ubiquitinated. In some embodiments, the ubiquitin-deficient Aps1p/Hgt19p has amino acid mutations at or near at least three lysine residue that can be ubiquitinated. In some embodiments, the ubiquitin-deficient Aps1p/Hgt19p has amino acid mutations at or near all lysine residue that can be ubiquitinated. In some embodiment, the amino acid mutation is substitution of the lysine residue. In some embodiment, the amino acid mutation is deletion of the lysine residue. In some embodiment, the ubiquitin-deficient Aps1p/Hgt19p has amino acid mutation near the lysine residue that can be ubiquitinated such that the lysine residue is not accessible to the ubiquitination machinery. In some embodiments, the lysine residues that can be ubiquitinated include K4, K20, K30 and K93 of Aps1p/Hgt19p. In some embodiments, the ubiquitin-deficient Aps1p/Hgt19p has amino acid substitutions at one of K4, K20, K30 and K93. In some embodiments, the ubiquitin-deficient Aps1p/Hgt19p has amino acid substitution at K4. In some embodiments, the ubiquitin-deficient Aps1p/Hgt19p has amino acid substitution at K20. In some embodiments, the ubiquitin-deficient Aps1p/Hgt19p has amino acid substitution at K30. In some embodiments, the ubiquitin-deficient Aps1p/Hgt19p has amino acid substitution at K93. In some embodiments, the ubiquitin-deficient Aps1p/Hgt19p has amino acid substitutions at two of K4, K20, K30 and K93. In some embodiments, the ubiquitin-deficient Aps1p/Hgt19p has amino acid substitutions at K4 and K20. In some embodiments, the ubiquitin-deficient Aps1p/Hgt19p has amino acid substitutions at K20 and K30. In some embodiments, the ubiquitin-deficient Aps1p/Hgt19p has amino acid substitutions at K30 and K93. In some embodiments, the ubiquitin-deficient Aps1p/Hgt19p has amino acid substitutions at K93 and K4. In some embodiments, the ubiquitin-deficient Aps1p/Hgt19p has amino acid substitutions at K4 and K30. In some embodiments, the ubiquitin-deficient Aps1p/Hgt19p has amino acid substitutions at K20 and K93. In some embodiments, the ubiquitin-deficient Aps1p/Hgt19p has amino acid substitutions at three of K4, K20, K30 and K93. In some embodiments, the ubiquitin-deficient Aps1p/Hgt19p has amino acid substitutions at K4, K20, and K30. In some embodiments, the ubiquitin-deficient Aps1p/Hgt19p has amino acid substitutions at K20, K30 and K93. In some embodiments, the ubiquitin-deficient Aps1p/Hgt19p has amino acid substitutions at K30, K93 and K4. In some embodiments, the ubiquitin-deficient Aps1p/Hgt19p has amino acid substitutions at K4, K20, and K93. In some embodiments, the ubiquitin-deficient Aps1p/Hgt19p has amino acid substitutions at K4, K20, K30 and K93.

The *Metschnikowia* species can be the *Metschnikowia* H0 *Metschnikowia* sp. In some embodiments, provided herein is an isolated polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Aps1p/Hgt19p of H0 *Metschnikowia* sp. In some embodiments, provided herein is an isolated nucleic acid that encodes a polypeptide that has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a Aps1p/Hgt19p of H0 *Metschnikowia* sp. In some embodiments, the non-naturally occurring microbial organisms have at least one exogenous nucleic acid encoding a xylose transporter that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to Aps1p/Hgt19p of H0 *Metschnikowia* sp. In some embodiments, the xylose transporter is Aps1p/Hgt19p of H0 *Metschnikowia* sp. In some embodiments, the xylose transporter can be a variant of Aps1p/Hgt19p of H0 *Metschnikowia* sp. that retains its transporter function. In some embodiment, the xylose transporter is a ubiquitin-deficient Aps1p/Hgt19p from H0 *Metschnikowia* sp. In some embodiments, the xylose transporter is a functional fragment of Aps1p/Hgt19p of H0 *Metschnikowia* sp. In some embodiments, the xylose transporter can have 1 to 50, 1 to 45, 1 to 40, 1 to 35, 1 to 30, 1 to 25, 1 to 20, 1 to 15, 1 to 10, or 1 to 5, amino acid substitutions, deletions or insertions of Aps1p/Hgt19p from H0 *Metschnikowia* sp. In some embodiments, the xylose transporter has 1 to 10 amino acid substitutions, deletions or insertions of Aps1p/Hgt19p from H0 *Metschnikowia* sp. In some embodiments, the xylose transporter has 1 to 5 amino acid substitutions, deletions or insertions of Aps1p/Hgt19p from H0 *Metschnikowia* sp. In some embodiments, the xylose transporter has the amino acid sequence of SEQ ID NO: 12. In some embodiments, the amino acid sequence of the xylose transporter is SEQ ID NO: 12. In some embodiments, the nucleic acid has the sequence of SEQ ID NO: 26. In some embodiments, the sequence of the nucleic acid is SEQ ID NO: 26. In some embodiments, the ubiquitin-deficient Aps1p/Hgt19p has the amino acid sequence of SEQ ID NO: 44. In some embodiments, the nucleic acid has the sequence of SEQ ID NO: 49. The Aps1p/Hgt19p from a *Metschnikowia* species can be codon optimized for heterologous expression. In some embodiments, the nucleic acid encoding *Metschnikowia* Aps1p/Hgt19p is codon optimized for expression in a yeast host strain. The yeast host strain can be any yeast host strain described herein, such as *Saccharomyces cerevisiae*. In some embodiments, the nucleic acid encoding *Metschnikowia* Aps1p/Hgt19p is codon optimized for expression in a bacterial host strain. The bacterial host strain can be any bacterial host strain described herein, such as *E. coli*. In some embodiments, the nucleic acid encoding Aps1p/Hgt19p from H0 *Metschnikowia* sp. is codon optimized for expression in *Saccharomyces cerevisiae*. For example, in some embodiments, the nucleic acid encodes Aps1p/Hgt19p of H0 *Metschnikowia* sp. that is codon optimized for expression in *Saccharomyces cerevisiae*. The nucleic acid can have the sequence of SEQ ID NO: 27.

As provided above, the non-naturally occurring microbial organisms can have at least one exogenous nucleic acid, or at least two, at least three, at least four, at least five, at least six, at least seven, at least eight, or at least nine nucleic acids encoding a combination of xylose transporters described herein. In some embodiments, the non-naturally occurring microbial organisms express two xylose transporters described herein. In some embodiments, the non-naturally occurring microbial organisms express three xylose transporters described herein. In some embodiments, the non-naturally occurring microbial organisms express four xylose transporters described herein. In some embodiments, the non-naturally occurring microbial organisms express five xylose transporters described herein. In some embodiments, the non-naturally occurring microbial organisms express six xylose transporters described herein. In some embodiments, the non-naturally occurring microbial organisms express seven xylose transporters described herein. In some embodiments, the non-naturally occurring microbial organisms express eight xylose transporters described herein. In some embodiments, the non-naturally occurring microbial organisms express nine xylose transporters described herein. In some embodiments, the non-naturally occurring microbial organisms express ten xylose transporters described herein. In some embodiments, the non-naturally occurring microbial organisms express eleven xylose transporters described herein. In some embodiments, the combination of xylose transporters include two, three, four, five, six, seven, eight, nine, or ten xylose transporters of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, and Aps1p/Hgt19p from a *Metschnikowia* species as well as variants thereof. In some embodiments, the combination of xylose transporters include two, three, four, five, six, seven, eight, nine, or ten xylose transporters of Xyt1p, Gxf1p, ΔGxf1p, Gxf2p/Gal2p, Gxs1p/Hgt12p, ΔGxs1p/ΔHgt12p, Hxt5p, Hxt2.6p, Qup2p, and Aps1p/Hgt19p from H0 *Metschnikowia* sp. as well as variants thereof.

The xylose transporter provided herein can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology*, Vol. 182 (Academic Press, (1990)). Alternatively, the isolated xylose transporter provided herein can be obtained using well-known recombinant methods (see, for example, Sambrook et al., supra, 1989; Ausubel et al., supra, 1999). The methods and conditions for biochemical purification of the isolated xylose transporter provided herein can be chosen by those skilled in the art, and purification monitored, for example, by a functional assay.

One non-limiting example of a method for preparing the xylose transporter is to express nucleic acids encoding the xylose transporter in a suitable host cell, such as a bacterial cell, a yeast cell, or other suitable cell, using methods well known in the art, and recovering the expressed xylose transporter, again using well-known purification methods, as described herein. The xylose transporter provided herein can be isolated directly from cells that have been transformed with expression vectors as described herein. Recombinantly expressed xylose transporters can also be expressed as fusion proteins with appropriate affinity tags, such as glutathione S transferase (GST), poly His, streptavidin, and the like, and affinity purified, if desired. The polypeptide of the xylose transporters described herein can retain the affinity tag, if desired, or optionally the affinity tag can be removed from the polypeptide using well known methods to remove an affinity tag, for example, using appropriate enzymatic or chemical cleavage. Thus, provided herein are polypeptide of xylose transporters without or optionally with an affinity tag. Accordingly, in some embodiments, provided herein is a host cell expressing a polypeptide of the xylose transporters herein. A polypeptide of the xylose transporters described herein can also be produced by chemical synthesis using a method of polypeptide synthesis well know to one of skill in the art.

In some embodiments, provided herein are methods of constructing a host strain that can include, among other steps, introducing a vector disclosed herein into a host cell that is capable of fermentation. Vectors of the invention can be introduced stably or transiently into a host cell using techniques well known in the art including, but not limited to, conjugation, electroporation, chemical transformation, transduction, transfection, and ultrasound transformation. Additional methods are disclosed herein, any one of which can be used in the method of the invention.

Provided herein are also vectors containing the polynucleotide molecules encoding xylose transporters, as well as host cells transformed with such vectors. Any of the polynucleotide molecules of the disclosure can be contained in a vector, which generally includes a selectable marker and an origin of replication, for propagation in a host. The vectors can further include suitable transcriptional or translational regulatory sequences, such as those derived from a mammalian, fungal, bacterial, viral, or insect genes, operably linked to the polynucleotide molecule that encode xylose transporter. Examples of such regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a xylose transporter if the promoter nucleotide sequence directs the transcription of the xylose transporter sequence.

Selection of suitable vectors for the cloning of nucleic acid molecules encoding the xylose transporter of this disclosure depends upon the host cell in which the vector will be transformed, and, where applicable, the host cell from which the xylose transporter is to be expressed. Suitable host cells for expression of xylose transporter include prokaryotes and yeasts, which are discussed below. Selection of suitable combinations of vectors and host organisms is a routine matter from a perspective of skill.

The xylose transporter to be expressed in such host cells can also be fusion proteins that include sequences from other proteins. As discussed above, such regions can be included to allow, for example, enhanced functionality, improved stability, or facilitated purification of the xylose transporter. For example, a nucleic acid sequence encoding a peptide that binds strongly to xylose can be fused in-frame to the transmembrane sequence of a xylose transporter so that the resulting fusion protein binds xylose and transports the sugar across the cell membrane at a higher rate than the wild type transporter.

The non-naturally occurring microbial organisms provided herein can be produced by introducing expressible nucleic acids encoding one or more of the xylose transporters. In some embodiments, the host microbial organisms have one or more biosynthetic pathways for producing products such as xylitol, ethanol, n-butanol, isobutanol, isopropanol, arabitol, ethyl acetate, phenyl-ethyl alcohol, 2-methyl-butanol, and 3-methyl-butanol from xylose. The expression of xylose transporters described herein can enhance xylose uptake and increase the production of these bioderived products of these microbial organisms.

Host microbial organisms can be selected from, and the non-naturally occurring microbial organisms generated in, for example, bacteria, yeast, fungus or any of a variety of other microorganisms applicable or suitable to fermentation processes. Similarly, exemplary species of yeast or fungi species include any species selected from the order Saccharomycetales, family Saccaromycetaceae, including the genera *Saccharomyces, Debaryomyces, Candida, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Candida albicans, Candida tropicalis, Debaryomyces hansenii, Kluyveromyces lactis, Kluyveromyces marxianus, Aspergillus terreus, Aspergillus niger, Chlamydomonas reinhardtii, Pichia pastoris, Rhizopus arrhizus, Rhizopus oryzae, Trichoderma reesei, Yarrowia lipolytica*, and the like.

The xylose transporters described herein can also be expressed in yeast host cells from genera including *Saccharomyces, Pichia*, and *Kluveromyces*. In one embodiment, the yeast host is *S. cerevisiae*. Yeast vectors can contain an origin of replication sequence from a 2 yeast plasmid for high copy vectors and a CEN sequence for a low copy number vector. Other sequences on a yeast vector can include an autonomously replicating sequence (ARS), a promoter region, sequences for polyadenylation, sequences for transcription termination, and a selectable marker gene. In some embodiments, vectors are replicable in both yeast and bacteria such as *E. coli* (termed shuttle vectors). In addition to the above-mentioned features of yeast vectors, a shuttle vector also includes sequences for replication and selection in bacteria such as *E. coli*.

Exemplary bacteria include, for example, any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include, for example, *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Expression vectors for use in prokaryotic hosts generally comprise one or more phenotypic selectable marker genes. Such genes encode, for example, a protein that confers antibiotic resistance or that supplies an auxotrophic requirement. A wide variety of such vectors are readily available from commercial sources. Examples include, for example, pSPORT vectors, pGEM vectors (Promega, Madison, Wis.), pPROEX vectors (LTI, Bethesda, Md.), Bluescript vectors (Stratagene), and pQE vectors (Qiagen).

Insect host cell culture systems can also be used for the expression of the xylose transporters described herein. The target xylose transporters can be expressed using a baculovirus expression system, as described, for example, in the review by Luckow and Summers, 1988.

*Saccharomyces cerevisiae* is a particularly useful host organism since it is a well characterized microbial organism suitable for genetic engineering. Other particularly useful host organisms include bacteria such as *E. coli*. It is understood that any suitable microbial host organism can be used to express xylose transporters described herein to enhance xylose uptake. The microbial host organism can also be modified to introduce metabolic and/or genetic modifications to produce a desired product or to further enhance the production of a desired product, such as xylitol, ethanol, n-butanol, isobutanol, isopropanol, arabitol, ethyl acetate, phenyl-ethyl alcohol, 2-methyl-butanol, and 3-methyl-butanol from xylose.

The choice of a suitable expression vector for expression of xylose transporters described herein depend upon the host cell to be used. Examples of suitable expression vectors for *E. coli* include pET, pUC, and similar vectors as is known in the art. In some embodiments, the vectors for expression of the xylose transporters include the shuttle plasmid pIJ702 for *Streptomyces lividans*, pGAPZalpha-A, B, C and pPIC-Zalpha-A, B, C (Invitrogen) for *Pichia pastoris*, and pFE-1 and pFE-2 for filamentous fungi and similar vectors as is known in the art.

Modification of nucleic acids encoding xylose transporters described herein to facilitate insertion into a particular vector (for example, by modifying restriction sites), ease of use in a particular expression system or host (for example, using preferred host codons), and the like, are known and are contemplated for use. Genetic engineering methods for the production of xylose transporters include the expression of the polynucleotide molecules in cell free expression systems, in host cells, in tissues, and in animal models, according to known methods.

Methods for constructing and testing the expression levels of xylose transporter in a non-naturally occurring host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of a bioderived product can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins. Available tools for codon optimization include "UpGene," described in Gao et al., *Biotechnology progress* 20.2 (2004): 443-448; "Codon optimizer," described in Fuglsang, *Protein expression and purification* 31.2 (2003): 247-249. As a person of ordinary skill would understand, it would have been a routine practice to use these or any other available tools in the art to codon optimize the specific nucleic acid sequences described herein to express the corresponding gene in a specific host strain.

An expression vector or vectors can be constructed to include one or more nucleic acids encoding xylose transporters and/or other enzymes of a biosynthesis pathway operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Provided herein are also reagents, compositions, and methods that are useful for analysis of xylose transporter activity and for assessing the amount and rate of xylose transport.

The polypeptide of xylose transporters of the present disclosure, in whole or in part, can be used to raise polyclonal and monoclonal antibodies that are useful in purifying the xylose transporters, or detecting their expression, as well as a reagent tool for characterizing the molecular actions of the xylose transporters. Preferably, a peptide containing a unique epitope of the xylose transporters is used in preparation of antibodies, using conventional techniques. Methods for the selection of peptide epitopes and production of antibodies are known. See, for example, Antibodies: A Laboratory Manual, Harlow and Land (eds.), 1988 Cold Spring Harbor Laboratory Press, Cold Spring Harbor, N.Y.; Monoclonal Antibodies, Hybridomas: A New Dimension in Biological Analyses, Kennet et al. (eds.), 1980 Plenum Press, New York.

The non-naturally occurring microbial organisms provided herein have enhanced xylose uptake by expressing xylose transporter described herein. In some embodiments, the microbial organisms provided herein can have one or more biosynthetic pathways to produce compounds such as xylitol, ethanol, n-butanol, isobutanol, isopropanol, arabitol, ethyl acetate, phenyl-ethyl alcohol, 2-methyl-butanol, or 3-methyl-butanol from xylose, and the enhanced xylose uptake increases production of such compound. The biosynthetic pathway can be an endogenous pathway or an exogenous pathway. The microbial organisms provided herein can further have expressible nucleic acids encoding one or more of the enzymes or proteins participating in one or more biosynthetic pathways for products such as xylitol, ethanol, n-butanol, isobutanol, isopropanol, arabitol, ethyl acetate, phenyl-ethyl alcohol, 2-methyl-butanol, and 3-methyl-butanol. Depending on the host microbial organism chosen for biosynthesis, nucleic acids for some or all of a particular biosynthetic pathway can be expressed. In some embodiments, the host microbial organism can have endogenous expression of all enzymes of a biosynthetic pathway to produce a compound from xylose and naturally produces the compound, which can be improved by further expressing a xylose transporter described herein. In some embodiments, the host microbial organism can be deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve biosynthesis of the desired compound. Thus, a non-naturally occurring microbial organism can further include exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as xylitol, ethanol, n-butanol, isobutanol, isopropanol, arabitol, ethyl acetate, phenyl-ethyl alcohol, 2-methyl-butanol, or 3-methyl-butanol from xylose.

Microbial organisms having a biosynthesis pathway to produce xylitol from xylose are known in the art. In some embodiments, provided herein are non-naturally occurring microbial organisms having at least one exogenous nucleic acid encoding a xylose transporter as described herein, as well as a biosynthesis pathway for producing xylitol from xylose. With enhanced xylose uptake the microbial organism can also have improved production of xylitol from xylose. Provided herein are also methods of producing a bioderived xylitol by culturing the non-naturally occurring microbial organism provided herein having a xylitol biosynthesis pathway under conditions and for a sufficient period of time to produce xylitol.

Xylitol is a five-carbon sugar alcohol widely used as a low-calorie, low-carbohydrate alternative to sugar; xylitol does not affect insulin levels of people with diabetes and individuals with hyperglycemia (Drucker et al., *Arch of Oral Biol.* 24:965-970 (1979)). Xylitol is approximately as sweet as sucrose but has 33% fewer calories. The consumption of xylitol is also beneficial for dental health as it reduces caries by 33%; xylitol has also been reported to inhibit demineralization of healthy tooth enamel and to re-mineralize damaged tooth enamel (Steinberg et al., *Clinical Preventive Dentistry* 14:31-34 (1992); Maguire et al., *British Dental J.* 194:429-436 (2003); Grillaud et al., *Arch of Pediatrics andAdolescent Medicine* 12:1180-1186 (2005)). In addition, xylitol in chewing gum inhibits growth of *Streptoccocus mutans* (Haresaku et al., *Caries Res.* 41:198-203 (2007)), and it reduces the incidence of acute middle ear infection (Azarpazhooh et al., *Cochrane Database of Systematic Reviews* 11:CD007095 (2011)).

Microbial production of xylitol offers cost effective downstream processing that can reduce manufacturing cost (Rivas et al., *Biotechnol. Prog.* 19:706-713 (2003)). Such process would reduce the need for purified xylose, producing highly pure, easy to separate product, and be adaptable to wide variety of raw material source from different geographical locations (Ur-Rehman et al., *Critical Reviews in Food Science and Nutrition* 55:1514-1528 (2013)).

Many yeast species (*Candida* spp., *Debaryomyces hansenii, Pichia anomala, Kluyveromvces* spp, *Pachysolen tannophilus, Saccharomyces* spp. and *Schizosaccharomyces pombe*) have been identified with the ability to convert xylose to xylitol (Sirisansaneeyakul et al., *J. Ferment. Bioeng.* 80:565-570 (1995); Onishi et al., *Agric. Biol. Chem.* 30:1139-1144 (1966); Barbosa et al., *J. Ind. Microbiol.* 3:241-251 (1988); Gong et al., *Biotechnol. Lett.* 3:125-130 (1981); Vandeska et al., *World J. Microbiol. Biotechnol.* 11:213-218 (1995); Dahiya et al., *Cabdirect.org* 292-303 (1990); Gong et al., *Biotechnol. Bioeng.* 25:85-102 (1983)). The ability to produce xylitol from xylulose has also been discovered in various yeast (*Saccharomyces* spp., *D. hansenii, P. farinose, Hansenula* spp., *Endomycopsis chodatii, Candida* spp. and *Cryptococcus neoformans*) (Onishi et al., *Appl. Microbiol.* 18:1031-1035 (1969)). The majority of research into the biological production of xylitol is with yeast, and novel yeast species capable of converting xylose to xylitol continue to be discovered (Kamat et al., *J. App. Microbiol.* 115: 1357-1367 (2013); Bura et al., *J. Ind. Microbiol. Biotechnol.* 39:1003-1011 (2012); Junyapate et al., *Antonie Van Leeuwenhoek* 105:471-480 (2014); Guaman-Burneo et al., *Antonie Van Leeuwenhoek* 108: 919-931 (2015); Cadete et al., *Int. J. Syst. Evolv. Microbiol.* 65:2968-2974 (2015)).

*S. cerevisiae* is a yeast organism that is used in many food processes, but does not naturally utilize xylose efficiently. It has been engineered to produce xylitol from xylose by expressing xylose reductases from other yeast species such as *S. stipitis* (*P. stipitis*) and *C. shehatae* (Hallborn et al., *Bio/Technology* 9:1090-1095; Hallborn et al., *Appl. Microbiol. Biotechol.* 42:326-333 (1994); Lee et al., *Process Biochem.* 35:1199-1203 (2000); Giovinden et al., *Appl. Microbiol. Biotechnol.* 55:76-80 (2001); Chung et al., *Enzyme Microb. Technol.* 30:809-816 (2002)).

Alternate pathways for xylitol production in *S. cerevisiae* have been explored. Expression of *S. stipitis* xylitol dehydrogenase and deletion of the xylulokinase gene in a transketolase-deficient strain of *S. cerevisiae* allowed conversion of glucose to xylitol through a multistep pathway (Toivari et al., *Appl. Enviorn. Microbiol.* 73:5471-5476 (2007)).

Expression of *Neurospora crassa* cellodextrin transporter and intracellular β-glucosidase allowed it to simultaneously utilize cellobiose and xylose during xylitol production (Oh et al., *Metab. Eng.* 15:226-234 (2013); Zha et al., *PLoS One* 8:e68317 (2013)). Furthermore, the overexpression of *S. cerevisae* ALD5, IDP2 or *S. stipitis* ZWF1 lead to increased NADPH levels, resulting in higher xylitol productivity (Oh et al., *Metab. Eng.* 15:226-234 (2013)).

Xylitol production can be improved by the use of both NADPH-preferring and NADH-preferring xylose reductases to decrease the limitation of NAD(P)H cofactors. This strategy was used in *S. cerevisiae* with the expression of wild-type NADPH-preferring and mutant NADH-preferring *S. stipitis* xylose reductase and *S. cerevisiae* ZWF1 and ACS1 (Jo et al., *Biotechnol. J.* 10:1935-1943 (2015)).

In order to decrease processing costs of xylitol production, *S. stipitis* xylose reductase, *Aspergillus aculeatus* β-glucosidase, *A. oryzae* β-xylosidase, and *Trichoderma reesei* endoxylanase were expressed in *S. cerevisiae* (Guirimand et al., *Appl. Microbiol. Biotechnol.* 100:3477-3487 (2016)). Expression of these fungal enzymes allowed direct degradation of hemicellulose without the addition of exogenous enzymes.

*C. tropicalis* is pathogenic, but is also one of the natural producers of xylitol. Several patents and literature have described the application of yeast from genus *Candida* as the host strain for xylitol production from xylose; i.e. *C. tropicalis* ATCC 13803 (PCT/IN2009/000027 & KR100259470), *C. tropicalis* ATCC 9968 (PCT/FI1990/000015), *C. tropicalis* KFCC 10960 (KR100199819), *C. tropicalis* (NRRL 12968) (PCT/IN2013/000523), *C. tropicalis* ATCC 750 (West et al., *World J. Mircrobiol. Biotechnol.* 25:913-916 (2009)) and *C. tropicalis* ATCC 7349 (SAROTE et al., *J. Ferment. and Bioeng.* 80:565-570 (1995)). One strategy used to improve xylitol production in *C. tropicalis* was the expression of an NADH-preferring xylose reductase from *C. parapsilosis*, which allowed reduction of xylose with both NADPH and NADH (Lee et al., *Appl. Enviorn. Microbiol.* 69:6179-6188 (2003)). Deletion of xylitol dehydrogenase increases xylitol production by blocking xylitol catabolism, but a co-substate such as glucose or glycerol is needed to regenerate NADPH for xylose reductase activity (Ko et al., *Appl. Environ. Microbiol.* 72:4207-4213 (2006); Ko et al., *Biotechnol. Lett.* 28:1159-1162 (2006)). Further improvements for xylitol production were made by combining deletion of the xylitol dehydrogenase gene with expression of *N. crassa* xylose reductase (Jeon et al., *Bioprocess Biosyst. Eng.* 35:191-198 (2012)). The xylose uptake and xylitol productivity of this strain was again further improved by expressing a xylose transporter from *Arabidopsis thaliana* (Jeon et al., *Bioprocess Biosyst. Eng.* 36:809-817 (2013)).

If glycerol is provided as a co-substrate, NADPH regeneration can be enhanced by expressing glucose-6-phosphate dehydrogenase and 6-phosphogluconate dehydrogenase in *C. tropicalis* (Ahmad et al., *Bioprocess Biosyst. Eng.* 35:199-204 (2012)). Xylitol production can also be enhanced by deleting glycerol kinase and expressing three NADPH-regenerating glycerol dehydrogenases from *S. stipitis* (Ahmad et al., *Bioprocess Biosyst. Eng.* 36:1279-1284 (2013)). One of the problems with producing xylitol from mixed sugar substrates is that the xylose reductase from *C. tropicalis* can convert arabinose to arabitol, a contaminant in xylitol production. To prevent this, the endogenous xylose reductase was deleted and a mutant xylose-specific xylose reductase from *N. crassa* was expressed along with bacterial arabinose assimilation enzymes (Yoon et al., *Biotechnol. Lett.* 33:747-753 (2011); Nair et al., *Chem Bio Chem* 9:1213-1215 (2008)). This minimized arabitol formation while allowing arabinose assimilation for cell growth.

*K. marxianus* is a thermotolerant yeast often found in dairy products. It can be used for xylitol production due to its high growth rate, tolerance to temperatures up to 52° C., and ability to utilize various sugars. Expression of the *N. crassa* xylose reductase alone or in conjunction with deletion of the xylitol dehydrogenase gene in *K. marxianus* led to xylitol production optimally at 42° C. (Zhang et al., *Bioresour. Technol.* 152:192-201 (2014)). Further improvements to xylitol production were made by testing the expression of various xylose transporters: *K. marxianus* aquaglyceroporin, *C. intermedia* glucose/xylose facilitator, or *C. intermedia* glucose/xylose symporter (Zhang et al., *Bioresour. Technol.* 175:642-645 (2015)). The expression of the *C. intermedia* glucose/xylose facilitator was found to be effective at increasing xylitol yield and productivity, and notably, produced the highest reported final xylitol concentration. *K. marxianus* was also used in an evolutionary adaptation experiment that resulted in a strain with improved xylose utilization and xylitol production capabilities (Sharma et al., *Bioprocess Biosyst. Eng.* 39:835-843 (2016)).

Two other yeast species have been genetically engineered to explore xylitol production. *D. hansenii* is another natural producer of xylitol that is osmotolerant and non-pathogenic. Xylitol production was enhanced in this species by deletion of the xylitol dehydrogenase gene (Pal et al., *Bioresour. Technol.* 147:449-455 (2013)). *P. pastoris* is a yeast commonly used for protein expression. It has been engineered to produce xylitol directly from glucose through the glucose-arabitol-xylulose-xylitol pathway (Cheng et al., *Appl. Microbiol. Biotechnol.* 98:3539-3552 (2014)). This was achieved by expressing xylitol dehydrogenase from *Gluconobacter oxydans* and the xylulose-forming arabitol dehydrogenase from *Klebsiella pneumoniae*.

In addition to filamentous fungi and yeast, a limited number of bacterial species (*Corynebacterium* sp. and *Enterobacter liquefaciens*) have been observed to produce xylitol from xylose (Yoshitake et al., *Agric. Biol. Chem.* 35:905-911 (1971); Yoshitake et al., *Agric. Biol. Chem.* 37:2261-2267 (1973); Yoshitake et al., *Agric. Biol. Chem.* 40:1493-1503 (1976); Rangaswamy et al., *Appl. Microbiol. Biotechnol.* 60:88-93 (2002)). *Mycobacterium smegmatis* has also been reported to be able to produce xylitol from xylulose (Izumori et al., *J. Ferment. Technol.* 66:33-36 (1988)). A subsequent screen of bacteria discovered that *Gluconobacter* spp. and *Acetobacter xylinum* are capable of converting arabitol to xylitol through the sequential conversion of arabitol to xylulose and xylulose to xylitol (Suzuki et al., *Biosci. Biotechnol. Biochem.* 66:2614-2620 (2002)).

Microalgae are an attractive platform for the production of renewable resources. Xylitol production in microalgae has been reported once, where expression of the xylose reductase from *Neurospora crassa* in *Chlamydomonas reinhardtii* allowed it to convert a small amount of xylose to xylitol (Pourmir et al., *J. Biotechnol.* 165:178-183 (2013)).

The extracts of various filamentous fungi (*Penicillium* spp., *Aspergillus* spp., *Rhizopus nigricans*, *Gliocladium roseum*, *Byssochlamys fulva*, *Myrothecium verrucaria*, *Neurospora crassa*, *Rhodotorula glutinis* and *Torulopsis utilis*) have been observed to contain an enzyme capable of converting xylose to xylitol (Chiang et al., *Nature* 188:79-81 (1960); Chiang et al., *Biochem. Biophys. Res. Commun.* 3:554-559 (1960); Chiang et al., *Biochem. Biophys. Acta.* 29:664-5 (1958)). Subsequent studies identified additional filamentous fungi (*Petromyces albertensis*, *Penicillium* spp. and *A. niger*) capable of converting xylose to xylitol with varying degrees of efficiency (Dahiya et al., *Can. J. Microbiol.* 37:14-18 (1991); Sampaio et al., *Brazilian J. Microbiol.* 34:325-328 (2003)).

*Trichoderma reesei*, a filamentous fungus that secretes celluloytic enzymes, produced more xylitol when the genes for xylitol dehydrogenase and L-arabinitol-4-dehydrogenase were deleted in order to block xylitol metabolism (Dashtban et al., *Appl. Biochem. Biotechnol.* 169:554-569(2013)). Xylitol production also increased in *T. reesei* when xylose reductase was overexpressed and xylulokinase was inhibited (Hong et al., *Biomed Res. Int.* 2014:169705 (2014)). *Phanerochaete sordida*, a white-rot fungus with ligninolytic activity, produced more xylitol when it expressed the xylose reductase gene from *P. chrysosporium* (Hirabayashi et al., *J. Biosci. Bioeng.* 120:6-8 (2015)).

Bacteria metabolize xylose with xylose isomerases instead of with the xylose reductase-xylitol dehydrogenase pathway. Therefore, the use of bacterial hosts for xylitol production typically involves recombinant expression of xylose reductases. Xylose reductase from *C. tropicalis* was expressed in *E. coli* and was found to be functional for xylitol production from xylose (Suzuki et al., *J. Biosci. Bioeng.* 87:280-284 (1999)). A subsequent study expressed xylose reductases from *C. boidinii*, *C. tenuis* and *S. stipitis* in conjunction with a deletion of the endogenous xylulokinase gene (Cirino et al., *Biotechnol. Bioeng.* 95:1167-1176 (2006)). In order to improve xylitol production from mixtures of glucose and xylose, the cyclic AMP receptor protein was replaced with a mutant that circumvents glucose repression of xylose metabolism. Expressing the xylose transporters, XylE or XylFGH, has similar effects to replacing the cyclic AMP receptor protein with a mutant form (Khankal et al., *J. Biotechnol.* 134:246-252 (2008)).

Cofactor regeneration is also important for improving xylitol production in bacteria, which has been explored in *E. coli* through a large number of gene deletions and expression of cofactor regenerating pathways (Chin et al., *Biotechnol. Bioeng.* 102:209-220 (2009); Chin et al., *Biotechnol. Prog.* 27:333-341 (2011); Iverson et al., *World J. Microbiol. Biotechnol.* 29:1225-1232 (2013); Iverson et al., *BMC Syst. Biol.* 10:31 (2016)). Another study aimed at improving xylitol production from mixtures of glucose and xylose disrupted the phosphoenolpyruvate-dependent glucose phosphotransferase system to eliminate catabolite repression (Su et al., *Metab. Eng.* 31:112-122 (2015)). Endogenous xylose metabolism was blocked in this strain by disrupting xylose isomerase, xylulose kinase, and the phosphoenolpyruvate-dependent fructose phosphotransferase system, and the *N. crassa* xylose reductase was expressed to optimize xylitol production.

*L. lactis* is a well-characterized bacterium commonly used for dairy processes such as cheese production, and could be adopted for other food-related processes. *L. lactis* was able to produce xylitol from xylose when it expressed the *S. stipitis* xylose reductase and the *L. brevis* xylose transporter (Nyyossola et al., *J. Biotechnol.* 118:55-56 (2005)).

C. glutamicum is a bacterium with many industrial uses such as the production of MSG. It has been engineered to co-utilize xylose and glucose, which is an important trait for xylitol productivity (Sasaki et al., *Appl. Microbiol. Biotechnol.* 85:105-115 (2009)). To optimize xylitol production in C. glutamicum, it has been engineered to express a pentose transporter and a mutant xylose reductase from C. tenuis in conjunction with disruptions of its lactate dehydrogenase, xylulokinase, and phosphoenolpyruvate-dependent fructose phosphotransferase genes (Sasaki et al., *Appl. Microbiol. Biotechnol.* 86:1057-1066 (2010)). Xylitol production in C. glutamicum was also achieved by expressing S. stipitis xylose reductase (Kim et al., *Enzyme Microb. Technol.* 46:366-371 (2010)). Expression of *Rhodotorula mucilaginosa* xylose reductase, E. coli 1-arabinose isomerase, *Agrobacterium tumefaciens* d-psicose-3-epimerase, *Mycobacterium smegmatis* 1-xylulose reductase, and a fusion pentose transporter allowed the production of xylitol from mixtures of xylose and arabinose without the formation of arabitol (Dhar et al., *J. Biotechnol.* 230:63-71 (2016)).

It is understood that microbial organisms provided herein or otherwise known in the art with either natural or engineered biosynthesis pathways to produce xylitol from xylose can be used as the host strain, which can have enhanced xylose uptake and improved production of xylitol from xylose when expressing an exogenous nucleic acid encoding a xylose transporter as described herein. Further metabolic engineering can be adopted to further increase xylitol production in these host strains.

Microbial organisms having a biosynthesis pathway to produce ethanol from xylose are known in the art. In some embodiments, provided herein are non-naturally occurring microbial organisms having at least one exogenous nucleic acid encoding a xylose transporter as described herein, as well as a biosynthesis pathway for producing ethanol from xylose. With enhanced xylose uptake the microbial organism can also have improved production of ethanol from xylose. Provided herein are also methods of producing a bioderived ethanol by culturing the non-naturally occurring microbial organism provided herein having an ethanol biosynthesis pathway under conditions and for a sufficient period of time to produce ethanol.

Ethanol has a number of uses and is most commonly used as a fuel additive. As a fuel additive, ethanol is a low value product with much of the cost of its production attributed to the cost of raw materials. It would be desirable, therefore, to develop ethanologens and fermentation processes for the production of ethanol from readily available, inexpensive starting materials, such as lignocellulose. Fermentation of both glucose and xylose is currently regarded as a high priority for economical conversion of biomass into ethanol. Most microorganisms are able to ferment glucose but few have been reported to utilize xylose efficiently and even fewer ferment this pentose to ethanol.

A relatively small number of wild type microorganisms can ferment D-xylose. These microorganisms are generally not suitable for large-scale fermentation. This unfavorability may arise, for example, as a result of unfamiliarity with the microorganisms, difficulty obtaining the microorganisms, poor productivity and/or growth on pretreated lignocellulosics or unsatisfactory yield when grown on mixed sugars derived from biomass. (C. Abbas, "Lignocellulosics to ethanol: meeting ethanol demand in the future," The Alcohol Textbook, 4$^{th}$ Edition. (K. A. Jacques, T. P. Lyons and D. R. Kelsall, eds). Nottingham University Press, Nottingham, U K, 2003, pp. 41-57.; C. Abbas, "Emerging biorefineries and biotechnological applications of nonconventional yeast: now and in the future," The Alcohol Textbook, 4$^{th}$ Edition. (K. A. Jacques, T. P. Lyons and D. R. Kelsall, eds). Nottingham University Press, Nottingham, United Kingdom, 2003, pp. 171-191).

Yeasts are considered promising microorganisms for alcoholic fermentation of xylose (see Ryabova, supra). They have larger cells than bacteria, are resistant to viral infection, and tend to be more resistant to negative feedback from ethanol. Furthermore, yeast growth and metabolism have been extensively studied for a number of species.

A number of yeasts are known to naturally ferment D-xylose. These include, for example, P. stipitis, C. shehatae, and P. tannophilus (see Ryabova, supra; Cite 2, C. Abbas 2003). The common brewer's yeast S. cerevisiae is not known to ferment D-xylose naturally, but a number of strains of metabolically engineered S. cerevisiae that do ferment D-xylose have been reported.

Numerous studies have described the metabolism of D-xylose by recombinant S. cerevisiae (see, e.g., Matsushika et al., *Applied Microbiology and Biotechnology* 84, no. 1 (2009): 37-53; U.S. Pat. Pub. No. 2005/0153411A1 (Jul. 14, 2005); U.S. Pat. Pub. No. 2004/0231661A1 (Nov. 25, 2004); U.S. Pat. No. 4,368,268 (Jan. 11, 1983); U.S. Pat. No. 6,582,944 (Jun. 24, 2003); U.S. Pat. No. 7,226,735 (Jun. 5, 2007); U.S. Pat. Pub. No. 2004/0142456A1 (Jul. 22, 2004); Jeffries, T. W. & Jin, Y-S., *Appl. Microbiol. Biotechnol.* 63: 495-509 (2004); Jin, Y-S., *Met. Eng.* 6: 229-238 (2004); Pitkanen, J-Y., Helsinki Univ. of Tech., Dept. of Chem. Tech., Technical Biochemistry Report (January 2005); Porro, D. et al., *App. & Env. Microbiol.* 65(9): 4211-4215 (1999); Jin, Y-S., et al., *App. & Env. Microbiol.* 70(11): 6816-6825 (2004); Sybirna, K, et al., *Curr. Genetics* 47(3): 172-181 (2005); Toivari, M. H., et al., *Metabolic Eng.* 3:236-249 (2001).

D-Xylose metabolism in yeast proceeds along a pathway similar to that of glucose via pentose phosphate pathway. Carbon from D-xylose is processed to ethanol via the glycolytic cycle or to $CO_2$ via respiratory TCA cycle. Fermentation to ethanol relies in part on the metabolism of pyruvate, which is a metabolite that may be used in either respiration or fermentation (see van Hoek, P., et al., *Appl. & Enviro. Microbiol.* 64(6); 2133-2140 (1998)). Pyruvate enters fermentation following decarboxylation of pyruvate to acetaldehyde by the enzyme pyruvate decarboxylase (E.C. 4.1.1.1). Pyruvate decarboxylase is a member of the family of biotin-dependent carboxylases. It catalyzes the decarboxylation of pyruvate to form oxaloacetate with ATP cleavage. The oxaloacetate can be used for synthesis of fat, glucose, and some amino acids or other derivatives. The enzyme is highly conserved and found in a variety of prokaryotes and eukaryotes.

Other microbial organisms capable of ethanol production from xylose are also known in the art. The thermotolerant methylotrophic yeast *Hansenula polymorpha* (also known as *P. angusta*) was reported to have optimum and maximum growth temperatures of 37° C. and 48° C., respectively, and can naturally ferment D-xylose under certain conditions. (U.S. Pat. No. 8,071,298; Voronovsky et al., *FEMS Yeast Res.* 5(11): 1055-62 (2005)). Additionally, three strains of *P. stipitis* and three of *C. shehatae* were reported to ferment xylose when subjected to both aerobic and microaerophilic conditions. Of the strains considered, P. stipitis NRRL Y-7124 was able to utilize all but 7 g/L of 150 g/L xylose supplied aerobically to produce 52 g/L ethanol at a yield of 0.39 g per gram xylose (76% of theoretical yield) and at a rate comparable to the fastest shown by C. shehatae NRRL Y-12878. For all strains tested, fermentation results from aerobic cultures were more favorable than those from microaerophilic cultures. Slininger, P. J. et al., *Biotechnol Lett* (1985) 7: 431.

For example, *Zymomonas mobilis*, a bacterial ethanologen that grows on glucose, fructose, and sucrose, metabolizing these sugars to $CO_2$ and ethanol via the Entner-Douderoff pathway. Though wild type strains cannot use xylose as a carbon source, recombinant strains of *Z. mobilis* that are able to grow on this sugar have been engineered (U.S. patent publication No. 20080187973, U.S. Pat. Nos. 5,514,583, 5,712,133, WO 95/28476, Feldmann et al. (1992) *Appl Microbiol Biotechnol* 38: 354-361, Zhang et al. (1995) *Science* 267:240-243).

The conversion of xylose to ethanol by recombinant *E. coli* has been reported. The addition of small amounts of calcium, magnesium, and ferrous ions stimulated fermentation. Beall et al., *Biotechnology and Bioengineering* 38, no. 3 (1991): 296-303.

It is understood that microbial organisms provided herein or otherwise known in the art with either natural or engineered biosynthesis pathways to produce ethanol from xylose can be used as the host strain, which can have enhanced xylose uptake and improved production of ethanol from xylose when expressing an exogenous nucleic acid encoding a xylose transporter as described herein. Further metabolic engineering can be adopted to further increase ethanol production in these host strains.

Microbial organisms having a biosynthesis pathway to produce n-butanol from xylose are known in the art. See e.g. Kudahettige-Nilsson R L, et al., *Bioresour Technol*. 176: 71-9 (2015); Xin F, et al., *Appl Environ Microbiol.*, 80(15): 4771-8 (2014); Xiao H, et al., *Metab Eng*. 14(5):569-78 (2012); Zhang J, et al., *Biotechnol Lett*. 38(4):611-7 (2016); Yu L, et al. *Biotechnol Bioeng*. 112(10):2134-41 (2015); Steen, et al, *Microb Cell Fact*. 7:36 (2008); Pásztor A, et al., *Biotechnol Bioeng.*, 112(1):120-8 (2015); Shi S, et al., *Sci Rep*. 6:25675(2016); Dellomonaco C, et al., *Nature,* 10:476 (7360):355-9 (2011). In some embodiments, provided herein are non-naturally occurring microbial organisms having at least one exogenous nucleic acid encoding a xylose transporter as described herein, as well as a biosynthesis pathway for producing n-butanol from xylose. With enhanced xylose uptake the microbial organism can also have improved production of n-butanol from xylose. Provided herein are also methods of producing a bioderived n-butanol by culturing the non-naturally occurring microbial organism provided herein having a n-butanol biosynthesis pathway under conditions and for a sufficient period of time to produce n-butanol.

Butanol offers a number of benefits as a fuel. Butanol is a four-carbon alcohol, a clear neutral liquid miscible with most solvents (alcohols, ether, aldehydes, ketones and hydrocarbons) and is sparingly soluble in water (water solubility 6.3% as compared to ethanol which is totally miscible). It has an octane rating comparable to gasoline, making it a valuable fuel for any internal combustion engine made for burning gasoline. Fuel testing also has proven that butanol does not phase separate in the presence of water, and has no negative impact on elastomer swelling. Butanol not only has a higher energy content that is closer to that of gasoline than ethanol, so it is less of a compromise on fuel economy, but it also can be easily added to conventional gasoline due to its low vapor pressure.

Butanol biosynthesis can be achieved through the acetone, butanol, and ethanol fermentation pathway (the "ABE pathway"). The products of this butanol fermentative production pathway using a solvent-producing species of the bacterium *Clostridium acetobutylicum* are six parts butanol, three parts acetone, and one part ethanol, Butanol-production pathway has been introduced to various host organisms. For instance, the pathway was expressed in *Escherichia coli* (Atsumi et al., *Nature* 451:86-89 (2008)) and *S. cerevisiae* (Steen et al., *Microb. Cell Fact* 7:36 (2008)) for their high growth rates and the efficiency of genetic tools. *P. putida, L. brevis* and *B. subtilis* were used for their potentially higher solvent tolerance (Nielsen et al., *Metab. Eng.* 11:262-273 (2009); Berezina et al., *Appl. Microbiol. Biot.* 87:635-646 (2010)).

An alternative to the use of food crops as starting material for butanol production is biomass, specifically lignocellulosic biomass. *Clostridium* spp. strains have been engineered to produce butanol for xylose, such as *C. saccharoperbutylacetonicum* (e.g., *C. saccharoperbutylacetonicum* strain ATCC 27021 or *C. saccharoperbutylacetonicum* strain ATCC 27022). See e.g. U.S. Pat. No. 8,900,841. *C. cellulolyticum* was engineered to divert its native valine synthesis pathway for isobutanol production from crystalline cellulose (Higashide et al., *Appl. Environ. Microb.* 77:2727-2733 (2011)). *C. cellulovorans*, which natively produces butyric acid as the main metabolic product, was introduced with an aldehyde/alcohol dehydrogenase (AdhE2) to convert precursor butyryl-CoA to 1-butanol from cellulose (Yang et al., *Metab. Eng.* 32:39-48 (2015)). 1-Butanol production from xylose was also demonstrated using *Thermoanaerobacterium saccharolyticum* (Bhandiwad et al., *Metab. Eng.* 21:17-25 (2014)).

To increase the cellulose decomposition rate and to reduce chance of contamination, thermophilic organisms were used. The first example of isobutanol production in thermophiles was demonstrated in *Geobacillus thermoglucosidasius* using cellobiose as substrate (Lin et al., *Metab. Eng.* 24:1-8 (2014)). In this work, thermostabilities of enzymes involved in isobutanol synthesis were investigated. The result of this study was applied to the direct conversion of cellulose to isobutanol in *C. thermocellum* by expressing and optimizing the isobutanol biosynthesis pathway (Lin et al., *Metab. Eng.* 31:44-52 (2015)).

*S. cerevisiae* has several benefits such as high ethanol production from hexoses and high tolerance to ethanol and other inhibitory compounds in the acid hydrolysates of lignocellulose biomass. Although standard strains of this yeast cannot utilize pentoses, such as xylose, a recombinant yeast strain can be provided that can ferment xylose and cellooligosaccharides by integrating genes for the intercellular expression of xylose assimilation pathways, such as xylose reductase and xylitol dehydrogenase from *P. stipitis* and a gene for displaying β-glucosidase from *A. acleatus*. See e.g. U.S. Patent Publication No. 20100129885; U.S. Patent Publication No. 20100261241.

It is understood that microbial organisms provided herein or otherwise known in the art with either natural or engineered biosynthesis pathways to produce n-butanol from xylose can be used as the host strain. These microbial organisms can have enhanced xylose uptake and improved production of n-butanol from xylose when expressing an exogenous nucleic acid encoding a xylose transporter as described herein. Further metabolic engineering can be adopted to further increase n-butanol production in these host strains.

Microbial organisms having a biosynthesis pathway to produce isobutanol from xylose are known in the art. See e.g. Felpeto-Santero C, et al., *AMB Express* 5(1):119 (2015). In some embodiments, provided herein are non-naturally occurring microbial organisms having at least one exogenous nucleic acid encoding a xylose transporter as described herein, as well as a biosynthesis pathway for producing isobutanol from xylose. With enhanced xylose uptake the microbial organism can also have improved production of isobutanol from xylose. Provided herein are also methods of producing a bioderived isobutanol by culturing the non-naturally occurring microbial organism provided herein having a isobutanol biosynthesis pathway under conditions and for a sufficient period of time to produce isobutanol.

Isobutanol, also a biofuel candidate, has been produced in recombinant microorganisms expressing a heterologous, five-step metabolic pathway (See, e.g., WO/2007/050671, WO/2008/098227, and WO/2009/103533). Other pathways for isobutanol production are also known in the art. See e.g., U.S. Pat. No. 8,530,226 B2; U.S. Pat. No. 8,114,641 B2; U.S. Pat. No. 8,975,049 B2. The recombinant microorganism including a pathway for the production of isobutanol from five-carbon (pentose) sugars including xylose is also known in the art. (See e.g., WO 2012173659; WO 2011153144). The recombinant microorganism can be engineered to express a functional exogenous xylose isomerase. Exogenous xylose isomerases functional in yeast are known in the art. See, e.g., US2006/0234364. The exogenous xylose isomerase gene can be operatively linked to promoter and terminator sequences that are functional in the yeast cell. Various methods of genetic engineering to improve isobutanol production are also known in the art. (See e.g., Avalos et al., *Nature Biotechnology* 31, 335-41 (2013).)

For example, recombinant *S. cerevisiae* was known to produce isobutanol from xylose. See e.g. US20130035515, Brat et al., *FEMS yeast research* 13.2 (2013): 241-244; Lee, Won-Heong et al. *Bioprocess and biosystems engineering* 35.9 (2012): 1467-1475; Simultaneous overexpression of an optimized, cytosolically localized valine biosynthesis pathway together with overexpression of xylose isomerase XylA from *C. phytofermentans*, transaldolase Tal1 and xylulokinase Xks1 enabled recombinant *S. cerevisiae* cells to complement the valine auxotrophy of ilv2,3,5 triple deletion mutants for growth on D-xylose as the sole carbon source. Moreover, after additional overexpression of ketoacid decarboxylase Aro10 and alcohol dehydrogenase Adh2, the cells were able to ferment D-xylose directly to isobutanol.

It is understood that microbial organisms provided herein or otherwise known in the art with either natural or engineered biosynthesis pathways to produce isobutanol from xylose can be used as the host strain, which can have enhanced xylose uptake and improved production of isobutanol from xylose when expressing an exogenous nucleic acid encoding a xylose transporter as described herein. Further metabolic engineering can be adopted to further increase isobutanol production in these host strains.

Microbial organisms having a biosynthesis pathway to produce isopropanol are known in the art. Hanai T, et al., *Appl Environ Microbiol.*, 73(24):7814-8 (2007). In some embodiments, provided herein are non-naturally occurring microbial organisms having at least one exogenous nucleic acid encoding a xylose transporter as described herein, as well as a biosynthesis pathway for producing isopropanol from xylose. With enhanced xylose uptake the microbial organism can also have improved production of isopropanol from xylose. Provided herein are also methods of producing a bioderived isopropanol by culturing the non-naturally occurring microbial organism provided herein having an isopropanol biosynthesis pathway under conditions and for a sufficient period of time to produce isopropanol.

Polymerization of ethylene provides polyethylene, a type of plastic with a wide range of useful applications. Ethylene is traditionally produced by refined non-renewable fossil fuels, but dehydration of biologically-derived ethanol to ethylene offers an alternative route to ethylene from renewable carbon sources, i.e., ethanol from fermentation of fermentable sugars. Similarly, isopropanol and n-propanol can be dehydrated to propylene, which in turn can be polymerized to polypropylene. As with polyethylene, using biologically-derived propanol starting material (i.e., isopropanol or n-propanol) would result in "Green Polypropylene." See e.g. WO 2009/049274, WO 2009/103026, WO 2009/131286, WO 2010/071697, WO 2011/031897, WO 2011/029166, WO 2011/022651, WO 2012/058603.

Production of isopropanol has been observed in recombinant *Lactobacillus* host cells (e.g., *Lactobacillus reuteri*) engineered to have an isopropanol pathway and produce increased amounts of isopropanol. See e.g. WO2013178699 A1. Direct isopropanol production from cellobiose by engineered *Escherichia coli* using a synthetic pathway was also observed. See e.g. Soma et al., *Journal of bioscience and bioengineering* 114.1: 80-85 (2012).

It is understood that microbial organisms provided herein or otherwise known in the art with either natural or engineered biosynthesis pathways to produce isopropanol from xylose can be used as the host strain, which can have enhanced xylose uptake and improved production of isopropanol from xylose when expressing an exogenous nucleic acid encoding a xylose transporter as described herein. Further metabolic engineering can be adopted to further increase isopropanol production in these host strains.

Arabitol belongs to the pentitol family and is used in the food industry as a sweetener and in the production of human therapeutics as an anticariogenic agent and an adipose tissue reducer. It can also be utilized as a substrate for chemical products such as arabinoic and xylonic acids, propylene, ethylene glycol, xylitol and others. It is included on the list of 12 building block C3-C6 compounds, designated for further biotechnological research. This polyol can be produced by yeasts in the processes of bioconversion or biotransformation of waste materials from agriculture, the forest industry (L-arabinose, glucose) and the biodiesel industry (glycerol). There are native yeasts from the genera *Candida, Pichia, Debaryomyces* and *Zygosaccharomyces* as well as genetically modified strains of *Saccharomyces cerevisiae* that are able to utilize biomass hydrolysates to effectively produce L- or D-arabitol. Kordowska-Wiater, *Journal of Applied Microbiology* 119, 303-314 (2015).

Microbial organisms having a biosynthesis pathway to produce arabitol are known in the art. (See e.g. Kordowska-Wiater, *Journal of Applied Microbiology* 119, 303-314 (2015); Nozaki et al., *Biosci. Biotechnol. Biochem.*, 67(9): 1923-29 (2003).) For example, the recently identified *Zygocaccharomyces rouxxii* NRRL 27,624 strain is known to produce D-arabitol as the main metabolic product from glucose (Saha et al., *J Ind Microbiol Biotechnol* 34:519-523 (2007)). However, it also was identified as producing D-arabitol and xylitol from xylose and from a mixture of xylose and xylulose (Saha et al., 2007). Based on these results, the pathway for production of D-arabitol from xylose included a xylose reductase, a xylitol dehydrogenase and an arabitol dehydrogenase (Saha et al., 2007). Additionally, *Candida maltosa* has been shown to produce D-arabitol from D-xylulose by a xylulose reductase (Cheng et al., Microbial. Cell Factories, 10:5 (2011)). Production of arabitol was also found to be improved by the addition of xylose with glycerol in the yeast species within the genus of *Debaryomyces*,

*Geotrichum* and *Metschnikowia* (International Application Publication WO 2012/011962 (2012)).

In some embodiments, provided herein are non-naturally occurring microbial organisms having at least one exogenous nucleic acid encoding a xylose transporter as described herein, as well as a biosynthesis pathway for producing arabitol from xylose. With enhanced xylose uptake the microbial organism can also have improved production of arabitol from xylose. Provided herein are also methods of producing a bioderived arabitol by culturing the non-naturally occurring microbial organism provided herein having an arabitol biosynthesis pathway under conditions and for a sufficient period of time to produce arabitol.

It is understood that microbial organisms provided herein or otherwise known in the art with either natural or engineered biosynthesis pathways to produce arabitol from xylose can be used as the host strain, which can have enhanced xylose uptake and improved production of arabitol from xylose when expressing an exogenous nucleic acid encoding a xylose transporter as described herein. Further metabolic engineering can be adopted to further increase arabitol production in these host strains.

Microbial organisms having a biosynthesis pathway to produce ethyl acetate from xylose are known in the art. Morrissey J P, et al., *Yeast*, 32(1):3-16 (2015). In some embodiments, provided herein are non-naturally occurring microbial organisms having at least one exogenous nucleic acid encoding a xylose transporter as described herein, as well as a biosynthesis pathway for producing ethyl acetate from xylose. With enhanced xylose uptake the microbial organism can also have improved production of ethyl acetate from xylose. Provided herein are also methods of producing a bioderived ethyl acetate by culturing the non-naturally occurring microbial organism provided herein having an ethyl acetate biosynthesis pathway under conditions and for a sufficient period of time to produce ethyl acetate.

Ethyl acetate is an environmentally friendly solvent with many industrial applications. Microbial synthesis of ethyl acetate is desirable. The ability of yeasts for producing larger amounts of this ester is known for a long time and can be applied to large-scale ester production from renewable raw materials. *P. anomala*, *C. utilis*, and *K. marxianus* are yeasts which convert sugar into ethyl acetate with a high yield. Löser et al., *Appl Microbiol Biotechnol* (2014) 98:5397-5415.

Synthesis of much ethyl acetate requires oxygen which is usually supplied by aeration. Ethyl acetate is highly volatile so that aeration results in its phase transfer and stripping. This stripping process cannot be avoided but requires adequate handling during experimentation and offers a chance for a cost-efficient process-integrated recovery of the synthesized ester.

It is understood that microbial organisms provided herein or otherwise known in the art with either natural or engineered biosynthesis pathways to produce ethyl acetate from xylose can be used as the host strain, which can have enhanced xylose uptake and improved production of ethyl acetate from xylose when expressing an exogenous nucleic acid encoding a xylose transporter as described herein. Further metabolic engineering can be adopted to further increase ethyl acetate production in these host strains.

Microbial organisms having a biosynthesis pathway to produce phenyl-ethyl alcohol are known in the art. See e.g. Kim B, et al., *Biotechnol Bioeng*. 111(1):115-24 (2014). In some embodiments, provided herein are non-naturally occurring microbial organisms having at least one exogenous nucleic acid encoding a xylose transporter as described herein, as well as a biosynthesis pathway for producing phenyl-ethyl alcohol from xylose. With enhanced xylose uptake the microbial organism can also have improved production of phenyl-ethyl alcohol from xylose. Provided herein are also methods of producing a bioderived phenyl-ethyl alcohol by culturing the non-naturally occurring microbial organism provided herein having an phenyl-ethyl alcohol biosynthesis pathway under conditions and for a sufficient period of time to produce phenyl-ethyl alcohol.

Phenyl-ethyl alcohol a colorless, transparent, slightly viscous liquid that can be produced by microbial organisms. Phenyl-ethyl alcohol has been found in a number of natural essential oils, in food, spices and tobacco, and in undistilled alcoholic beverages, beers and wines. It prevents or retards bacterial growth, and thus protects cosmetics and personal care products from spoilage. Phenyl-ethyl alcohol also imparts a fragrance to a product.

It is understood that microbial organisms provided herein or otherwise known in the art with either natural or engineered biosynthesis pathways to produce phenyl-ethyl alcohol from xylose can be used as the host strain, which can have enhanced xylose uptake and improved production of phenyl-ethyl alcohol from xylose when expressing an exogenous nucleic acid encoding a xylose transporter as described herein. Further metabolic engineering can be adopted to further increase phenyl-ethyl alcohol production in these host strains.

Microbial organisms having a biosynthesis pathway to produce 2-methyl-butanol are known in the art. See e.g. U.S. Pat. No. 8,114,641 B2; U.S. Pat. No. 8,975,049 B2. In some embodiments, provided herein are non-naturally occurring microbial organisms having at least one exogenous nucleic acid encoding a xylose transporter as described herein, as well as a biosynthesis pathway for producing 2-methyl-butanol from xylose. With enhanced xylose uptake the microbial organism can also have improved production of 2-methyl-butanol from xylose. Provided herein are also methods of producing a bioderived 2-methyl-butanol by culturing the non-naturally occurring microbial organism provided herein having a 2-methyl-butanol biosynthesis pathway under conditions and for a sufficient period of time to produce 2-methyl-butanol.

2-methyl-butanol can be used as a solvent and an intermediate in the manufacture of other chemicals. 2-methyl-butanol also has applications in fuel and lubricating oil additives, flotation aids, manufacture of corrosion inhibitors, pharmaceuticals, paint solvent, and extraction agent.

It is understood that microbial organisms provided herein or otherwise known in the art with either natural or engineered biosynthesis pathways to produce 2-methyl-butanol from xylose can be used as the host strain, which can have enhanced xylose uptake and improved production of 2-methyl-butanol from xylose when expressing an exogenous nucleic acid encoding a xylose transporter as described herein. Further metabolic engineering can be adopted to further increase 2-methyl-butanol production in these host strains.

Microbial organisms having a biosynthesis pathway to produce 3-methyl-butanol are known in the art. See e.g. U.S. Pat. No. 8,114,641 B2; U.S. Pat. No. 8,975,049 B2; U.S. Pat. No. 7,985,567 B2. In some embodiments, provided herein are non-naturally occurring microbial organisms having at least one exogenous nucleic acid encoding a xylose transporter as described herein, as well as a biosynthesis pathway for producing 3-methyl-butanol from xylose. With enhanced xylose uptake the microbial organism also has improved production of 3-methyl-butanol from xylose. Provided herein are also methods of producing a bioderived 3-methyl-butanol by culturing the non-naturally occurring microbial organism provided herein having a 3-methyl-butanol biosynthesis pathway under conditions and for a sufficient period of time to produce 3-methyl-butanol.

3-methyl-butanol (also known as isoamyl alcohol or isopentyl alcohol) is a clear, colorless alcohol. 3-methyl-butanol is a main ingredient in the production of banana oil, an ester found in nature and also produced as a flavouring in industry. It is also the main ingredient of Kovac's reagent, used for the bacterial diagnostic indole test. 3-methyl-butanol is also used as an antifoaming agent in the chloroform:isomyl alcohol reagent.

It is understood that microbial organisms provided herein or otherwise known in the art with either natural or engineered biosynthesis pathways to produce 3-methyl-butanol from xylose can be used as the host strain, which can have enhanced xylose uptake and improved production of 3-methyl-butanol from xylose when expressing an exogenous nucleic acid encoding a xylose transporter as described herein. Further metabolic engineering can be adopted to further increase 3-methyl-butanol production in these host strains.

Depending on the biosynthetic pathway constituents of a selected host microbial organism for a particular compound, the non-naturally occurring microbial organisms provided herein can include at least one exogenously expressed biosynthetic pathway-encoding nucleic acid and up to all encoding nucleic acids for one or more biosynthetic pathways of the compound. The compound can be, for example, xylitol, ethanol, n-butanol, isobutanol, isopropanol, arabitol, ethyl acetate, phenyl-ethyl alcohol, 2-methyl-butanol, or 3-methyl-butanol. For example, ethanol biosynthesis can be established in a host deficient in a pathway enzyme or protein that is required to produce ethanol from xylose through exogenous expression of the corresponding encoding nucleic acid. In other words, in a host deficient in all enzymes or proteins of an ethanol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of ethanol can be included in *S. cerevisiae* to enhance the production of ethanol from xylose, although *S. cerevisiae* has endogenous expression for all enzymes of the ethanol biosynthesis pathway from xylose except a xylose transporter.

Given the teachings and guidance provided herein, those skilled in the art will understand that the number of encoding nucleic acids to introduce in an expressible form will, at least, parallel the pathway deficiencies of the selected host microbial organism. Therefore, a non-naturally occurring microbial organism of the invention can have one, two, three, four, five, six, seven or eight up to all nucleic acids encoding the enzymes or proteins constituting a biosynthetic pathway. In some embodiments, the non-naturally occurring microbial organisms also can include other genetic modifications that facilitate or optimize biosynthesis of a particular compound or that confer other useful functions onto the host microbial organism. One such other functionality can include, for example, augmentation of the synthesis of one or more of the pathway precursors for a particular compound.

Generally, a host microbial organism is selected such that it produces the desired product or the precursor of a desired product, either as a naturally produced molecule or as an engineered product that either provides de novo production of a desired precursor or increased production of a precursor naturally produced by the host microbial organism. For example, ethanol is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a particular biosynthesis pathway.

In some embodiments, a non-naturally occurring microbial organism provided herein is generated from a host that contains the enzymatic capability to synthesize compounds such as xylitol, ethanol, n-butanol, isobutanol, isopropanol, arabitol, ethyl acetate, phenyl-ethyl alcohol, 2-methyl-butanol, or 3-methyl-butanol from xylose. In this specific embodiment it can be useful to increase the synthesis or accumulation of the desired product to, for example, drive the biosynthesis pathway reactions toward the production of the desired product. Increased synthesis or accumulation can be accomplished by, for example, overexpression of nucleic acids encoding one or more of the biosynthesis pathway enzymes or proteins for producing compounds such as xylitol, ethanol, n-butanol, isobutanol, isopropanol, arabitol, ethyl acetate, phenyl-ethyl alcohol, 2-methyl-butanol, or 3-methyl-butanol from xylose. Overexpression of the enzyme or enzymes and/or protein or proteins of the biosynthesis pathways of desired pathway can occur, for example, through exogenous expression of the endogenous gene or genes, or through exogenous expression of the heterologous gene or genes. Therefore, the microbial organisms with enhanced xylose uptake as provided herein can be readily modified for producing a desired compound, for example, through overexpression of one, two, three, four, five, and up to all nucleic acids encoding the biosynthetic pathway enzymes or proteins for the desired product. In addition, a non-naturally occurring organism can be generated by mutagenesis of an endogenous gene that results in an increase in activity of an enzyme in the biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that any of the one or more exogenous nucleic acids can be introduced into a microbial organism to produce a non-naturally occurring microbial organism with increased production of a desired product, such as xylitol, ethanol, n-butanol, isobutanol, isopropanol, arabitol, ethyl acetate, phenyl-ethyl alcohol, 2-methyl-butanol, or 3-methyl-butanol. The nucleic acids can be introduced so as to confer, for example, a biosynthetic pathway to produce ethanol from xylose onto the microbial organism. Alternatively, encoding nucleic acids can be introduced to produce an intermediate microbial organism having the biosynthetic capability to catalyze some of the required reactions to confer biosynthetic capability. For example, a non-naturally occurring microbial organism having a biosynthetic pathway can comprise at least two exogenous nucleic acids encoding desired enzymes or proteins. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of a desired product as described herein, the non-naturally occurring microbial organisms and methods provided herein also can be utilized in various combinations with each other and/or with other microbial organisms and methods well known in the art to achieve product biosynthesis by other routes. For example, one alternative to produce ethanol other than use of the ethanol producers is through addition of another microbial organism capable of converting an ethanol pathway intermediate to ethanol. One such procedure includes, for example, the fermentation of a microbial organism that produces an ethanol pathway intermediate. The ethanol pathway intermediate can then be used as a substrate for a second microbial organism that converts the ethanol pathway intermediate to ethanol. The ethanol pathway intermediate can be added directly to another culture of the second organism or the original culture of the ethanol pathway intermediate producers can be depleted of these microbial organisms by, for example, cell separation, and then subsequent addition of the second organism to the fermentation broth can be utilized to produce the final product without intermediate purification steps. Although ethanol is used as an example here, the same approach can be used for production of other desired products such as xylitol, ethanol, n-butanol, isobutanol, isopropanol, ethyl acetate, phenyl-ethyl alcohol, 2-methyl-butanol, or 3-methyl-butanol.

In other embodiments, the non-naturally occurring microbial organisms and methods provided herein can be assembled in a wide variety of subpathways to achieve biosynthesis of a desired product. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of a desired product can be accomplished by constructing a microbial organism that contains biosynthetic pathways for conversion of one pathway intermediate to another pathway intermediate or the product. Alternatively, a desired product also can be biosynthetically produced from microbial organisms through co-culture or co-fermentation using two organisms in the same vessel, where the first microbial organism produces an intermediate for the desired product and the second microbial organism converts the intermediate to the desired product. The desired product can be xylitol, ethanol, n-butanol, isobutanol, isopropanol, arabitol, ethyl acetate, phenyl-ethyl alcohol, 2-methyl-butanol, or 3-methyl-butanol.

Given the teachings and guidance provided herein, those skilled in the art will understand that a wide variety of combinations and permutations exist for the non-naturally occurring microbial organisms and methods provided herein, together with other microbial organisms, with the co-culture of other non-naturally occurring microbial organisms having subpathways and with combinations of other chemical and/or biochemical procedures well known in the art to produce a desired product In some embodiments, the methods provided herein to produce a bioderived compound further include separated from other components in the culture using a variety of methods well known in the art. The bioderived compound can be xylitol, ethanol, n-butanol, isobutanol, isopropanol, arabitol, ethyl acetate, phenyl-ethyl alcohol, 2-methyl-butanol, or 3-methyl-butanol. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, ultrafiltration, activated charcoal adsorption, pH adjustment and precipitation, or a combination of one or more methods enumerated above. All of the above methods are well known in the art.

Any of the non-naturally occurring microbial organisms described herein can be cultured to produce and/or secrete the desired bioderived compound including such as xylitol, ethanol, n-butanol, isobutanol, isopropanol, arabitol, ethyl acetate, phenyl-ethyl alcohol, 2-methyl-butanol, or 3-methyl-butanol. For example, the microbial organisms provided herein can be cultured for the biosynthetic production of a desired compound. Accordingly, in some embodiments, provided herein are culture media containing a desired bioderived compound described herein or intermediate thereof. In some aspects, the culture medium can also be separated from the non-naturally occurring microbial organisms that produced the a desired bioderived compound or intermediate thereof. Methods for separating a microbial organism from culture medium are well known in the art. Exemplary methods include filtration, flocculation, precipitation, centrifugation, sedimentation, and the like.

For the production of the desired bioderived compound including such as xylitol, ethanol, n-butanol, isobutanol, isopropanol, arabitol, ethyl acetate, phenyl-ethyl alcohol, 2-methyl-butanol, or 3-methyl-butanol, the microbial organisms provided herein are cultured in a medium with carbon source and other essential nutrients. In some embodiments, the microbial organisms provided herein are cultured in an aerobic culture medium. In some embodiments, the microbial organisms provided herein are cultured in a substantially anaerobic culture medium. As described herein, one exemplary growth condition for achieving biosynthesis of a desired product such as xylitol, ethanol, n-butanol, isobutanol, isopropanol, arabitol, ethyl acetate, phenyl-ethyl alcohol, 2-methyl-butanol, or 3-methyl-butanol includes anaerobic culture or fermentation conditions. In certain embodiments, the non-naturally occurring microbial organisms provided herein can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United States publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The culture medium for the microbial organisms provided herein can include xylose, either as the sole source of carbon or in combination with one or more co-substrates described herein or known in the art. The culture medium can further include other supplements, such as yeast extract, and/or peptone. The culture medium can further include, for example, any other carbohydrate source which can supply a source of carbon to the non-naturally occurring microorganism. Such sources include, for example: other sugars such as cellobiose, hemicelluloses, glucose, arabinose, galactose, mannose, fructose, sucrose and starch; or glycerol. The source can be biomass hydrolysate. Thus, the culture medium can include xylose and the co-substrate glucose. The culture medium can include xylose and the co-substrate cellobiose. The culture medium can include xylose and the co-substrate hemicellulose. The culture medium can include xylose and the co-substrate galactose. The culture medium can include xylose and the co-substrate glycerol.

The culture medium can have 1%, 2%, 3%, 4%, 5%, 6%, 7%, 8%, 9%, 10%, 11%, 12%, 13%, 14%, 15%, 16%, 17%, 18%, 19%, 20%, or higher amount of sugar (w/v). In some embodiments, the culture medium can have 2% sugar. In some embodiments, the culture medium can have 4% sugar. In some embodiments, the culture medium can have 10% sugar. In some embodiments, the culture medium can have 1%, 2%, 3%, 4%, 5%, 6%, 7%, 8%, 9%, 10%, 11%, 12%, 13%, 14%, 15%, 16%, 17%, 18%, 19%, 20%, or higher amount of xylose (w/v). The culture medium can have 1% xylose. The culture medium can have 2% xylose. The culture medium can have 3% xylose. The culture medium can have 4% xylose. The culture medium can have 5% xylose. The culture medium can have 6% xylose. The culture medium can have 7% xylose. The culture medium can have 8% xylose. The culture medium can have 9% xylose. The culture medium can have 10% xylose. The culture medium can have 11% xylose. The culture medium can have 12% xylose. The culture medium can have 12% xylose. The culture medium can have 13% xylose. The culture medium can have 14% xylose. The culture medium can have 15% xylose. The culture medium can have 16% xylose. The culture medium can have 17% xylose. The culture medium can have 18% xylose. The culture medium can have 19% xylose. The culture medium can have 20% xylose.

The culture medium can be a C5-rich medium, with a five carbon sugar (such as xylose) as the primary carbon source. The culture medium can also have a C6 sugar (six-carbon sugar). In some embodiments, the culture medium can have a C6 sugar as the primary carbon source. In some embodiments, the C6 sugar is glucose. The culture can have both a C6 sugar and a C5 sugar as the carbon source can have the C6 sugar and the C5 sugar present at different ratios. In some embodiment, the ratio of the amount of C6 sugar to that of the C5 sugar (the C6:C5 ratio) in the culture medium is between about 10:1 and about 1:10. For example, the C6:C5 ratio in the culture medium can be about 10:1, 9:1, 8:1, 7:1, 6:1, 5:1, 3:1, 2:1, 1:1, 1:2, 1:3, 1:4, 1:5, 1:6, 1:7, 1:8, 1:9 or 1:10. In some embodiments, the C6:C5 ratio in the culture medium is about 3:1. In some embodiments, the C6:C5 ratio in the culture medium is about 1:1. In some embodiments, the C6:C5 ratio in the culture medium is about 1:5. In some embodiments, the C6:C5 ratio in the culture medium is about 1:10. The C5 sugar can be xylose, and the C6 sugar can be glucose. In some embodiment, the ratio of the amount of glucose to that of xylose (the glucose:xylose ratio) in the culture medium is between about 10:1 and about 1:10. For example, the glucose:xylose ratio in the culture medium can be about 10:1, 9:1, 8:1, 7:1, 6:1, 5:1, 3:1, 2:1, 1:1, 1:2, 1:3, 1:4, 1:5, 1:6, 1:7, 1:8, 1:9 or 1:10. In some embodiments, the glucose:xylose ratio in the culture medium is about 3:1. In some embodiments, the glucose:xylose ratio in the culture medium is about 1:1. In some embodiments, the glucose:xylose ratio in the culture medium is about 1:5. In some embodiments, the glucose:xylose ratio in the culture medium is about 1:10.

Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as xylose, glucose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of the desired bioderived compound including such as xylitol, ethanol, n-butanol, isobutanol, isopropanol, arabitol, ethyl acetate, phenyl-ethyl alcohol, 2-methyl-butanol, or 3-methyl-butanol.

Accordingly, given the teachings and guidance provided herein, those skilled in the art will understand that a non-naturally occurring microbial organism can be produced that secretes the biosynthesized compounds described herein when grown on xylose as a carbon source. Such compounds include, for example, xylitol, ethanol, n-butanol, isobutanol, isopropanol, arabitol, ethyl acetate, phenyl-ethyl alcohol, 2-methyl-butanol, or 3-methyl-butanol and any of the intermediate metabolites thereof. All that is required is to engineer in one or more of the required enzyme or protein activities to achieve biosynthesis of the desired compound or intermediate including, for example, inclusion of some or all of the biosynthetic pathways for producing the desired product. Accordingly, provided herein is a non-naturally occurring microbial organism that produces and/or secretes a desired product such as xylitol, ethanol, n-butanol, isobutanol, isopropanol, arabitol, ethyl acetate, phenyl-ethyl alcohol, 2-methyl-butanol, or 3-methyl-butanol when grown on a carbohydrate or other carbon source and produces and/or secretes an intermediate metabolites shown in the biosynthesis pathway of the desired compound when grown on xylose and optionally other carbohydrate or carbon source.

The non-naturally occurring microbial organisms provided herein are constructed using methods well known in the art as exemplified herein to exogenously express at least one nucleic acid encoding a xylose transporter in sufficient amounts to enhance xylose uptake and increase the production of a desired product from xylose. It is understood that the microbial organisms provided herein are cultured under conditions sufficient to produce a desired product such as xylitol, ethanol, n-butanol, isobutanol, isopropanol, arabitol, ethyl acetate, phenyl-ethyl alcohol, 2-methyl-butanol, or 3-methyl-butanol. Following the teachings and guidance provided herein, the non-naturally occurring microbial organisms provided herein can achieve biosynthesis of the desired product resulting in intracellular concentrations between about 0.1-200 mM or more. Generally, the intracellular concentration of the desired product between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms provided herein.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719. Any of these conditions can be employed with the non-naturally occurring microbial organisms as well as other anaerobic conditions well known in the art. Under such anaerobic or substantially anaerobic conditions, the producer strains can synthesize the desired product at intracellular concentrations of 5-10 mM or more as well as all other concentrations exemplified herein. It is understood that, even though the above description refers to intracellular concentrations, the producing microbial organisms can produce the desired product intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary fed-batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a fed-batch fermentation process, the time period for the fermentation is generally in the range of several hours to several days, for example, 8 to 24 hours, or 1, 2, 3, 4 or 5 days, or up to two weeks, depending on the desired culture conditions. The pH can be controlled or not, as desired, in which case a culture in which pH is not controlled will typically decrease to pH 3-6 by the end of the run. In some embodiment, the initial pH can first decrease and then increase during the cultivation period. In one embodiment, the initial pH of the medium is around 6, and during the cultivation period, the pH decreased first to 5.5 and later increased to around 6.5. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, usually with relatively high sugar concentration, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of the desired product can include the addition of an osmoprotectant to the culturing conditions. In certain embodiments, the non-naturally occurring microbial organisms provided herein can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylsulfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products can be obtained under anaerobic or substantially anaerobic culture conditions.

The culture conditions described herein can be scaled up and grown continuously for manufacturing of a desired product. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of a desired product. Generally, and as with non-continuous culture procedures, the continuous and/or near-continuous production includes culturing the microbial organisms provided herein in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism provided herein is for a sufficient period of time to produce a sufficient amount of product for a desired purpose.

Fermentation procedures are well known in the art. Briefly, fermentation for the biosynthetic production of a desired product can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using producer strains provided herein using continuous production of substantial quantities of a desire product, the bio-derived product also can be, for example, simultaneously subjected to chemical synthesis and/or enzymatic procedures to convert the product to other compounds, or the bioderived product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of a desired product.

Provided herein are also compositions having a bio-derived compound produced by the microbial organisms described herein, and an additional component. The component other than the bioderived product can be a cellular portion, for example, a trace amount of a cellular portion of the culture medium, or can be fermentation broth or culture medium or a purified or partially purified fraction thereof produced in the presence of, a non-naturally occurring microbial organism provided herein having a xylose transporter. The composition can have, for example, a reduced level of a byproduct when produced by the microbial organism disclosed herein. The composition can have, for example, one or more bioderived compound such as xylitol, ethanol, n-butanol, isobutanol, isopropanol, arabitol, ethyl acetate, phenyl-ethyl alcohol, 2-methyl-butanol, or 3-methyl-butanol, and a cell lysate or culture supernatant of a microbial organism provided herein. The additional component can be a byproduct, or an impurity, such as glycerol, acetaldehyde, acetate, glyceraldehyde, or a combination thereof. The byproduct can be glycerol. The byproduct can be acetaldehyde. The byproduct can be glyceraldehyde. The byproduct can be acetate. The impurity can be glycerol. The impurity can be acetaldehyde. The impurity can be glyceraldehyde. The impurity can be acetate.

In some embodiments, the carbon feedstock and other cellular uptake sources such as phosphate, ammonia, sulfate, chloride and other halogens can be chosen to alter the isotopic distribution of the atoms present in the bioderived compound produced by microbial organisms provided herein. The various carbon feedstock and other uptake sources enumerated above will be referred to herein, collectively, as "uptake sources." Uptake sources can provide isotopic enrichment for any atom present in the bioderived compound produced by microbial organisms provided herein, or in the byproducts or impurities. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S-B)/(M-B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}=-19$ per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}=-19$ per mil. This is equivalent to an absolute (AD 1950)$^{14}C/^{12}C$ ratio of $1.176\pm0.010\times10^{-12}$ (Karlen et al., *Arkiv Geofysik*, 4:465-471 (1968)). The standard calculations take into account the differential uptake of one isotope with respect to another, for example, the preferential uptake in biological systems of $^{12}C$ over $^{13}C$ over $^{14}C$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B,* 172:281-287 (2000)). For example, carbon-14 dating has been used to quantify bio-based content in terephthalate-containing materials (Colonna et al., *Green Chemistry,* 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, provided herein are bioderived compounds that have a carbon-12, carbon-13, and carbon-14 ratio that reflects an atmospheric carbon, also referred to as environmental carbon, uptake source. The bioderived compounds include such as xylitol, ethanol, n-butanol, isobutanol, isopropanol, arabitol, ethyl acetate, phenyl-ethyl alcohol, 2-methyl-butanol, or 3-methyl-butanol. For example, in some aspects the bioderived compound can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, provided herein are bioderived compounds that have a carbon-12, carbon-13, and carbon-14 ratio that reflects petroleum-based carbon uptake source. In this aspect, the bioderived compounds provided herein can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, bioderived compounds provided herein can have a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, provided herein are also the products derived the bioderived compounds including such as xylitol, ethanol, n-butanol, isobutanol, isopropanol, arabitol, ethyl acetate, phenyl-ethyl alcohol, 2-methyl-butanol, or 3-methyl-butanol, wherein the bioderived compounds has a carbon-12, carbon-13, and carbon-14 isotope ratio of about the same value as the $CO_2$ that occurs in the environment. For example, in some aspects, provided herein are bioderived compounds having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived compounds as disclosed herein, wherein the bioderived product is chemically modified to generate a final product. Methods of chemically modifying a bioderived product to generate a desired product are well known to those skilled in the art, as described herein.

Provided herein are also compositions having a bioderived compound produced by the microbial organisms described herein, and an additional component. The component other than the bioderived product can be a cellular portion, for example, a trace amount of a cellular portion of the culture medium, or can be fermentation broth or culture medium or a purified or partially purified fraction thereof produced in the presence of, a non-naturally occurring microbial organism provided herein having a xylose transporter. The composition can have, for example, a reduced level of a byproduct when produced by the microbial organism disclosed herein. The composition can have, for example, one or more bioderived compound such as xylitol, ethanol, n-butanol, isobutanol, isopropanol, arabitol, ethyl acetate, phenyl-ethyl alcohol, 2-methyl-butanol, or 3-methyl-butanol, and a cell lysate or culture supernatant of a microbial organism provided herein. The additional component can be a byproduct, or an impurity, such as glycerol, acetaldehyde, acetate, glyceraldehyde, or a combination thereof. The byproduct can be glycerol. The byproduct can be acetaldehyde. The byproduct can be glyceraldehyde. The byproduct can be acetate. The impurity can be glycerol. The impurity can be acetaldehyde. The impurity can be glyceraldehyde. The impurity can be acetate.

In some embodiments, the compositions provided herein can have a bioderived xylitol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived xylitol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived ethanol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived ethanol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived n-butanol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived n-butanol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived isobutanol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived isobutanol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived isopropanol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived isopropanol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived arabitol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived arabitol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived ethyl acetate and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived ethyl acetate. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived phenyl-ethyl alcohol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived phenyl-ethyl alcohol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived 2-methyl-butanol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived 2-methyl-butanol. The additional component can be the cell lysate of the microbial organism provided herein. The additional component can be a byproduct, such as glycerol, acetaldehyde, acetate, glyceraldehyde, or a combination thereof.

In some embodiments, the compositions provided herein can have a bioderived 3-methyl-butanol and an additional component. The additional component can be fermentation broth or culture medium. The additional component can be the supernatant of fermentation broth or culture medium. The additional component can be a cellular portion of fermentation broth or culture medium. The additional component can be the microbial organisms having an exogenous nucleic acid encoding a xylose transporter as described herein used to produce the bioderived 3-methyl-butanol. The additional component can be the cell lysate of the microbial organism provided herein. The additional component can be a byproduct, such as glycerol, acetaldehyde, acetate, glyceraldehyde, or a combination thereof.

Provided herein are also biobased products having one or more bioderived compound produced by a non-naturally occurring microorganism described herein or produced using a method described herein. In some embodiments, provided herein are biobased products produced using a bioderived compound described herein, such as xylitol, ethanol, n-butanol, isobutanol, isopropanol, arabitol, ethyl acetate, phenyl-ethyl alcohol, 2-methyl-butanol, or 3-methyl-butanol. Such manufacturing can include chemically reacting the bioderived compound (e.g. chemical conversion, chemical functionalization, chemical coupling, oxidation, reduction, polymerization, copolymerization and the like) into the final product. In some embodiments, provided herein are biobased products having a bioderived compound described herein, such as xylitol, ethanol, n-butanol, isobutanol, isopropanol, arabitol, ethyl acetate, phenyl-ethyl alcohol, 2-methyl-butanol, or 3-methyl-butanol. In some embodiments, provided herein are biobased products having at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived compound as disclosed herein.

It is understood that modifications which do not substantially affect the activity of the various embodiments of this invention are also provided within the definition of the invention provided herein. Accordingly, the following examples are intended to illustrate but not limit the present invention. Throughout this application various publications have been referenced. The disclosures of these publications in their entireties, including GenBank and GI number publications, are hereby incorporated by reference in this application in order to more fully describe the state of the art to which this invention pertains.

Example I

Expression of Xylose Transporters in H0 *Metschnikowia* sp.

The yeast of H0 *Metschnikowia* sp. was grown in various culture media, and the expression of various xylose transporters was measured by transcriptome analysis. As referred to in the Table below, "FPKM" refers to "Fragments Per Kilobase of transcript per Million mapped reads"; all media included the standard formulation of 2% peptone and 1% yeast extract; final sugar concentrations were 2% total in all culture media; "High" and "Low" refer to the maximum and minimum FPKM values found in the three biological replicates tested.

Example II

Engineering Enhanced Xylose Uptake in H0 *Metschnikowia* sp.

Figure 2:
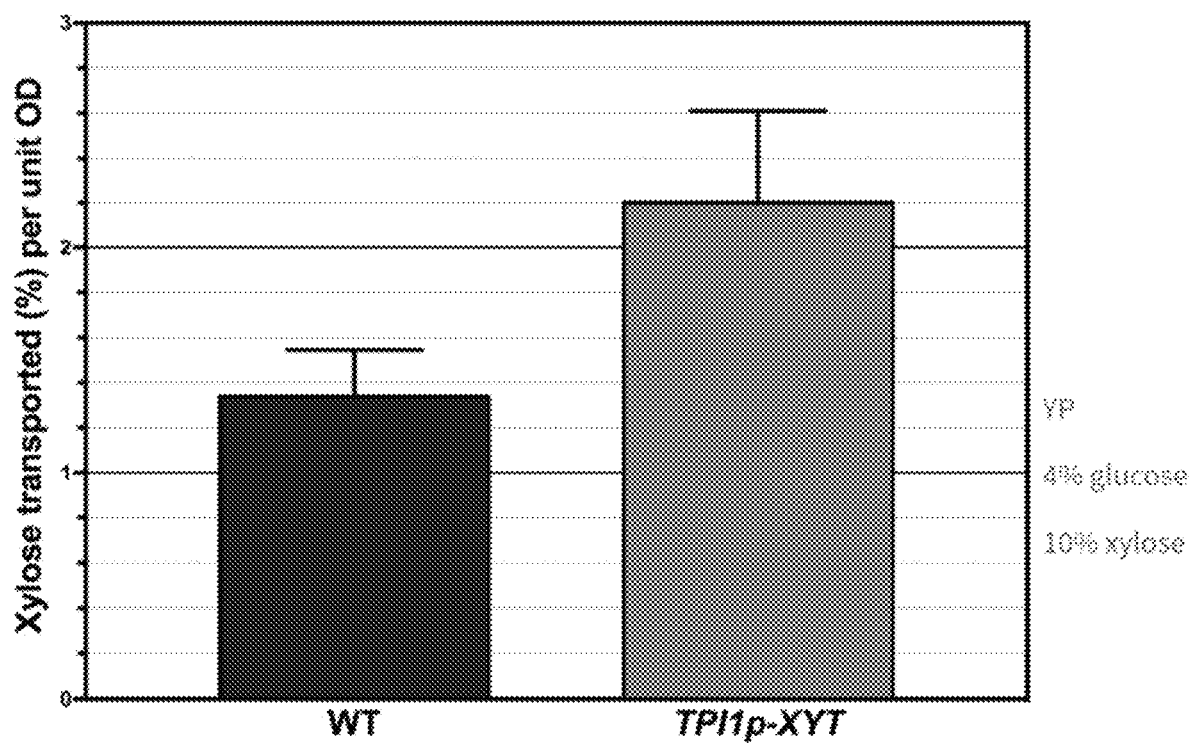
FIG. 2 shows the efficient xylose uptake by the wild type H0 *Metschnikowia* sp. measured by xylose transported (%) per unit $OD_{600}$, which was further enhanced (from about 1.3 to 2.2) when the XYT1 was overexpressed.

H0 *Metschnikowia* sp. was confirmed to have a robust xylose uptake and metabolism machinery, with the ability to consume and metabolize xylose as its sole carbon source. Xylose uptake is measured by growing H0 in known quantities of xylose and measuring the xylose remaining in the medium by high performance liquid chromatography. The quantity of xylose remaining is compared with a standard curve and the amount of said sugar in the inoculation medium. As shown in FIG. 1 and FIG. 2, efficient xylose transport was observed in wild type H0 *Metschnikowia* sp. The xylose uptake by the H0 *Metschnikowia* sp. was measured to be between 24 to 48 grams in 48 hours and 90 grams in 6 days (initial $OD_{600}$=0.2), which is significantly higher than the xylose uptake rate by yeasts known in the art. See Hector, et al., *Applied microbiology and biotechnology* 80(4): 675-684 (2008) (reporting xylose uptake rate of 10-15 grams in 48 h by *S. cerevisiae* with initial $OD_{600}$=1.0 at aerobic conditions); Runquist, et al., *Appl Microbiol Biotechnol* 82:123 (2009) (reporting xylose uptake rate of 4 grams in 48 h by yeast (TMB34XX) at anaerobic conditions); Apel et al., *Scientific reports* 6 (2016)(reporting xylose uptake rate of 9 grams in 48 h by yeast at aerobic conditions). The xylose transport was further enhanced in H0 *Metschnikowia* sp. overexpressing Xyt1p, as also shown in FIG. 1 and FIG. 2. To overexpress Xyt1p, the H0 XYT1 cassette was used which is comprised of H0 TPI1 promoter driving XYT1 and blasticidin expressed from the H0 PGK1

TABLE

Transcriptome Analysis of Xylose Transporters in H0 *Metschnikowia* sp.

| Gene | Glucose_FPKM | | | Xylose_FPKM | | |
|---|---|---|---|---|---|---|
| | Average | Low | High | Average | Low | High |
| GXF1 | 3137.35 | 2408.44 | 3866.25 | 860.96 | 671.36 | 1050.56 |
| XYT1 | 31.9043 | 21.8232 | 41.9855 | 1758.64 | 1354.27 | 2163.01 |
| HXT5 | 3.52499 | 0 | 8.25012 | 322.102 | 247.985 | 396.218 |
| GXS1/HGT12 | 1.78735 | 0 | 5.2273 | 42.4692 | 28.2335 | 56.705 |
| HGT19/APS1 | 22.3382 | 13.4993 | 31.1771 | 2254.54 | 1738.24 | 2770.83 |
| QUP2 | 25.0151 | 15.6231 | 34.4071 | 46.223 | 32.1743 | 60.2716 |
| GXF2/GAL2 | 302.552 | 232.996 | 372.107 | 69.8126 | 50.0024 | 89.6228 |

| Gene | Galactose_FPKM | | | Cellobiose_FPKM | | |
|---|---|---|---|---|---|---|
| | Average | Low | High | Average | Low | High |
| GXF1 | 1865.95 | 1442.41 | 2289.49 | 321.954 | 248.525 | 395.383 |
| XYT1 | 1309.91 | 1016.34 | 1603.48 | 900.511 | 701.542 | 1099.48 |
| HXT5 | 386.68 | 298.795 | 474.564 | 614.885 | 477.428 | 752.342 |
| GXS1/HGT12 | 150.957 | 112.586 | 189.328 | 119.261 | 88.3474 | 150.175 |
| HGT19/APS1 | 2915.42 | 2230.39 | 3600.46 | 3723.89 | 2821.8 | 4625.99 |
| QUP2 | 43.0144 | 29.7968 | 56.2321 | 51.0531 | 36.0561 | 66.0501 |
| GXF2/GAL2 | 89.9721 | 65.6522 | 114.292 | 31.5998 | 19.9003 | 43.2992 |

| Gene | FP_media_FPKM | | |
|---|---|---|---|
| | Average | Low | High |
| GXF1 | 2238.27 | 1726.85 | 2749.7 |
| XYT1 | 461.868 | 359.76 | 563.975 |
| HXT5 | 61.3177 | 42.1094 | 80.5259 |
| GXS1/HGT12 | 5.15064 | 0 | 10.7361 |
| HGT19/APS1 | 830.711 | 644.877 | 1016.54 |
| QUP2 | 39.3644 | 26.9207 | 51.8081 |
| GXF2/GAL2 | 40.5208 | 26.9909 | 54.0507 | promoter. The primers Y33 and Y33R amplified XYT1 OFR from H0 genomic DNA with homology 30 and 31 bp of homology with the H0 TPI1 promoter and H0 RPL15A terminator in vector DeBONO_E28.7. The XYT1 amplicon was Gibson assembled into the EcoRI and SalI sites of DeBONO_E28.7. The resulting Xyt1p vector was linearized with NdeI. Primers Y41 and Y41R were used to amplify H0 PGK1pro-Blasticidin-H0PGK1terminator was amplified from DeBONO_E29. The resulting amplicon was recombined into the NdeI site of the digested H0TPI1pro-XYL1-RPL15Aterminator. The vector was electroporated into H0 at 1.5 kv and 25 uF and 200 ohm in a 0.1 cm cuvette. Electroporated cells were recovered in liquid YPD for 4 hours. Finally, cells were diluted to 30% with liquid YPD and 100 uL of cell mixture was plated on YPD agar containing 350 ug/mL of blasticidin. Individual colonies were picked after 48 h and restreaked onto YPD agar blasticidin medium. The blasticidin concentration required to select transgenic H0 was determined empirically.

Example III

Engineering *S. cerevisiae* with Enhanced Xylose Uptake

*S. cerevisiae* does not have the functional machinery to efficiently utilize xylose as the carbon source. *S. cerevisiae* has a fully annotated genome, complete transcriptomic data and hundreds of tools developed for genetic and biochemical manipulation. The xylose transporters from the H0 *Metschnikowia* sp. were introduced into *S. cerevisiae* to increase xylose uptake and to synthesize bioderived product from renewable biomass. *S. cerevisiae* BY4742 was used as the genetic platform to heterologously over-express xylose transporter from the H0 *Metschnikowia* sp.

Figure 3:
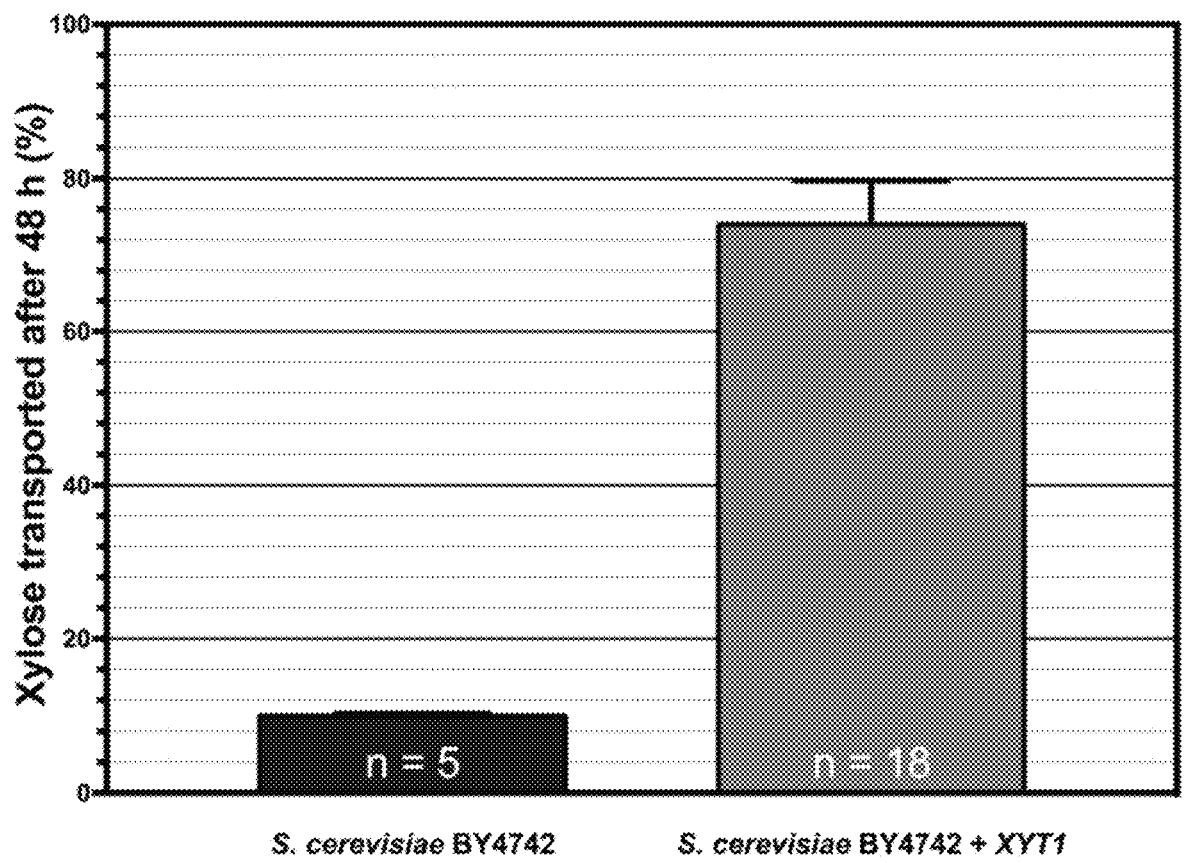
FIG. 3 shows that the expression of H0 XYT1 in *Saccharomyces* increased the xylose transport from about 10% to about 74% (48 hours) in *Saccharomyces*.

Genes encoding the following xylose transporters from the H0 *Metschnikowia* sp. were cloned Xyt1p, Gxf1p, ΔGxf1p (variant of Gxf1p with shorter N-terminus), Gxs1p/Hgt12p, and Hxt5p, and codon optimized for expression in BY4742. As shown in FIG. 3, the expression of Xyt1p, the xylose transferred in 48 hours from the medium increased from about 10% in BY4742 to about 74% in BY4742 expressing Xyt1p.

Genes encoding Gxf1p, ΔGxf1p, Gxs1p/Hgt12p, and Hxt5p from H0 *Metschnikowia* sp. were synthesized and transformed into BY4742 for xylose transport testing by HPLC. Following the design for Xyt1p, genes encoding each of Gxf1p, ΔGxf1p, Gxs1p/Hgt12p, and Hxt5p was expressed from the TEF promoter and terminator derived from the plasmid pUG6. All open reading frames (ORFs) were selected for with nourseothricin.

Due to H0 CTG codon usage, all ORFs corresponding to H0 transporters were synthesized by ThermoFisher as double stranded "gene strings." H0 transporter ORFs were translated with the codon translation table provided above. The resulting amino acid sequence was converted back to DNA. The resulting DNA was entered into the ThermoFisher genestrings web interface. The web interface modified the nucleotide sequence such that the amino acid remained as desired but the nucleotides would be altered such to achieve nearly balanced ratio of adenine-thymidine to guanine-cytosine. The synthetic XYT1 ORF was flanked by approximately 25 bp of homology with the TEF promoter at the 5' terminus and TEF terminator at the 3' terminus on pUG6 in order to facilitate Gibson assembly, respectively. The ORF was Gibson assembled into the pUG6, linearized with Y10, Y10R primers, deleting the G418resistance ORF.

Using primers Y15 and Y15R, H0 ADH1promoter-NAT-H0 PGK1 terminator was amplified from pZL29 and assembled into the TEF promoter-XYT1-TEF terminator plasmid. The complete plasmid containing XYT1 is designated DeBONO_E35.3. E35.3 was used as base vector clone all of GXF1, ΔGXF1, GXS1/HGT12, HXT5, HGT19. The DeBONO_E35.3 vector was amplified with Y53 and Y53R primers to linearize the vector and simultaneously, omitting XYL1, creating fragment Y53 (fY53). Each of the synthesized, codon optimized transporters were cloned into fY53 by Gibson assembly. The cassettes expressing transporters and NAT resistance were linearized by PCR with primers Y16, Y16R or Y96i and Y95Ri for integration into dubious ORFs at loci YIL100W and YLR123C. The linearized transporters were integrated into said dubious loci using standard *Saccharomyces* electroporation or chemical transformation methods.

Transgenic yeasts were recovered with 100 ug/mL NAT in solid YPD medium. GXF2/GAL2 was synthesized as described above. GXF2/GAL2 was cloned into a G418 resistance vector with general structure: CCW12 promoter-GXF2/GAL2-H0 DIT1 terminator. The promoter-terminator sequences were amplified from vector DeBONO_E54. This vector was linearized with primers Y83 and Y83R to yield fY83. The GXF2/GAL2 genestring was Gibson assembled into fY83. The transporter cassette was linearized by PCR with primers Y91i+Y93Ri for integration into the dubious ORF at locus YLR122C. The linearized cassette was transformed as described above and GXF2/GAL2 transgenics were selected with 200 ug/mL of G418.

Relevant primer sequences used in this example are provided below.

| SEQ ID NO: | Primer | Sequences |
|---|---|---|
| 28 | Primer Y10 | GAAAAAACTGGTACCGTTTAATCAGTACTGACA ATAAAAAGATTCTTGT |
| 29 | Primer Y10R | TAATTTCTCTTCGTATCCCATGGTTGTTTATGTTC GGATGTGATGTGAG |
| 30 | Primer Y15 | ACGCCGCCATCCAGTGTCGAAAACGAGCTTTGT CTTGTAAAGAGTCTTCGGTCATTTTTA |
| 31 | Primer Y15R | GCGGCCGCATAGGCCACTAGTGGATCTGATCAA TACATACAAGCATCTCACAATCACAAG |
| 32 | Primer Y33 | TTTTTCACCCACAACAAATAATATCAAAAGATG GGTTACGAGGAAAAGCTTGTAGCGCCC |
| 33 | Primer Y33R | ACGAGAACACCCAGCTAAACGCGGTGCGCGTTA GACCGTGCCCGTCTTCTCGTCTGAAGA |
| 34 | Primer Y41 | CAGAGCAGATTGTACTGAGAGTGCACCAGGCGC GCCCCATCCAGTGTCGAACCATCATTAAAAGAT |
| 35 | Primer Y41R | CTCCTTACGCATCTGTGCGGTATTTCACACCGCA CTAGACAATACATACAAGCATCTCACAATCACA A |
| 36 | Primer Y53 | TCAGTACTGACAATAAAAAGATTCTTGTTTTCAA GAAC |
| 37 | Primer YS3R | CTCACATCACATCCGAACATAAACAACC |
| 38 | Primer Y83 | TATCCCGTCACTTCCACATTCG |
| 39 | Primer Y83R | TATTGATATAGTGTTTAAGCGAATGACAGAAG |

-continued

| SEQ ID NO: | Primer Sequences |
|---|---|
| 40 | Primer Y96i ATAGAAAGCAAATAGTTATATAATTTTTCATGG ACGTAGGTCTAGAGATCTGTTTAGCTTGC |
| 41 | Primer Y95Ri AATGCAAAAGCGGCTCCTAAACAGAAATTCTTC AGTCAATACATACAAGCATCTCACAATCACAAG |
| 42 | Primer Y93Ri TCGTCTATATCAAAACTGCATGTTTCTCTACGTC TAATTAAGGGTTCTCGAGAGCTCG |
| 43 | Primer Y91i ACTTCAATAGACTTCAATAGAAAGCAAATAGTT ATATGCCCTGAGGATGTATCTGG |

Example IV

Xylose Uptake by Wildtype and Ubiquitin-Deficient Xylose Transporters

The primary sequences of the H0 *Metschnikowia* sp. transporters described herein were examined for ubiquitination sites/residues with predictive tool 'UbiPred' (Tung and Ho, (2008), *BMC Bioinformatics*, 9, 310). Ubiquitin-deficient mutants of Hxt5p, Hgt19p, Xyt1p, Gxf1p and Gal2p, were engineered to replace all their cytoplasmic facing lysine ("K") residues that were identified as ubiquitination sites to Arginine ("R").

TABLE

Cytoplasmic facing lysine ("K") residues (ATG/M is Residue No. 1))

| Transporter | Residue No. | Transporter | Residue No. | Transporter | Residue No. |
|---|---|---|---|---|---|
| Hgt19p (SEQ ID NO: 44) | 4 20 30 93 | Xyt1p (SEQ ID NO: 55) | 6 517 539 | Gal2p (SEQ ID NO: 46) | 23 26 35 542 546 |
| Hxt5p (SEQ ID NO: 45) | 7 10 29 43 58 | Gxf1p (SEQ ID NO: 54) | 9 24 538 | | |

Figure 4A:
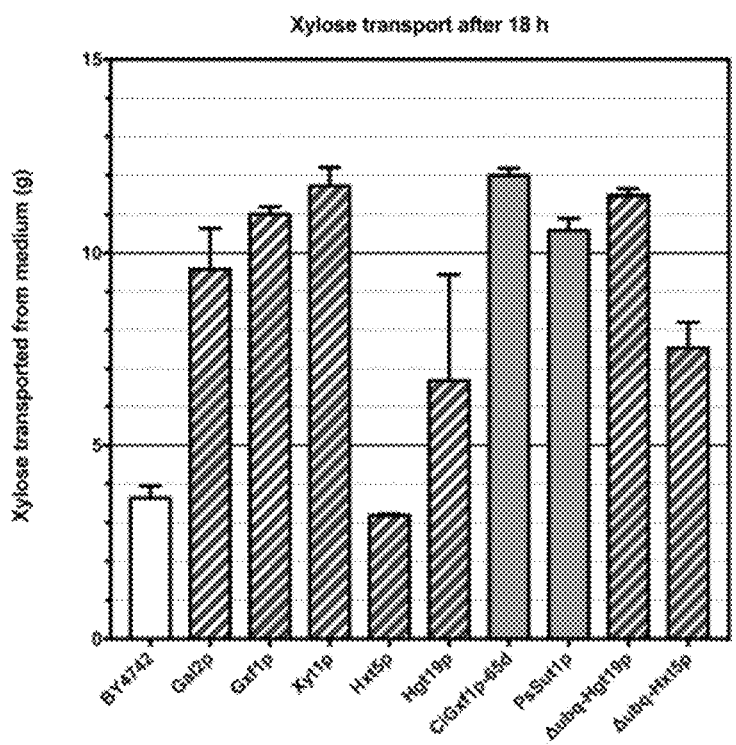
FIGS. 4A-4C show the xylose uptake by host strain BY4742 (*Saccharomyces cerevisiae*), and BY4742 strains expressing xylose transports H0 *Metschnikowia* sp. Gxf2p/Gal2p ("Gal2p"), H0 *Metschnikowia* sp. Gxf1p ("Gxf1p"), H0 *Metschnikowia* sp. Xyt1p ("Xyt1p"), H0 *Metschnikowia* sp. Hxt5p ("Hxt5p"), H0 *Metschnikowia* sp. Aps1p/Hgt19p ("Hgt19p"), *Candida intermedia* Gxf1p ("CiGxf1p-65d"), *Pichia stipis* Sut1p ("PsSut1p"), ubiquitin-deficient H0 *Metschnikowia* sp. Aps1p/Hgt19p ("Δubq-Hgt19p"), or ubiquitin-deficient H0 *Metschnikowia* sp. Hxt5p ("Δubq-Hxt5p"), at 18 h (FIG. 4A), 64 h (FIG. 4B), and 88 h (FIG. 4C)
Figure 4B:
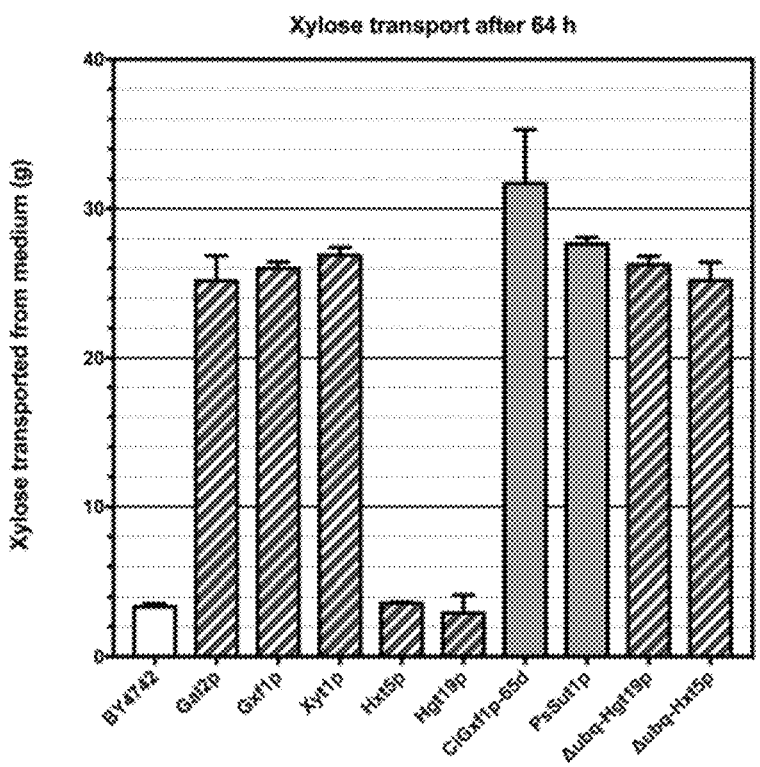
Figure 4C:
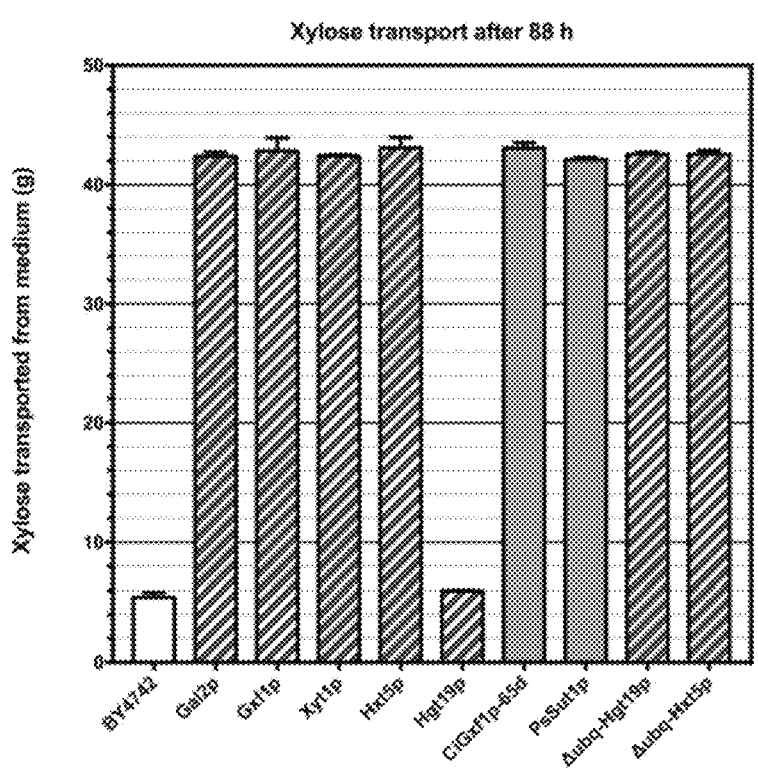

As shown in the xylose update assay, replacing K with R doubled and quadrupled xylose uptake for each of Δubq-Hxt5p and Δubq-HGT19p compared with the native transporters at 18 h and 64 h (FIGS. 4A and 4B). When all ubiquitination sites were removed from H0 *Metschnikowia* sp. Xyt1p and H0 *Metschnikowia* sp. Gal2p and expressed in host strain BY4742, the transporters were no longer functional. The recovered transgenic yeasts, producing ubiquitin free transporters were slow growing, requiring doubled growing time compared to yeasts expressing unmodified H0 *Metschnikowia* sp. Xyt1p and Gal2p. Ubiquitin free Gxf1p producing cells could not be recovered. These results indicate that ubiquitination sites, although inhibitory in Hxt5p and Hgt19p, are required in Xyt1p, Gxf1p and Gal2p for xylose transport and/or protein stability.

We claim:

1. A non-naturally occurring microbial organism comprising at least one heterologous nucleic acid encoding a xylose transporter, wherein said xylose transporter comprises an amino sequence that is at least 95% identical to an amino acid sequence selected from the group consisting of the amino acid sequence of SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, and SEQ ID NO: 12.

2. The non-naturally occurring microbial organism of claim 1, comprising at least two heterologous nucleic acids encoding at least two xylose transporters.

3. The non-naturally occurring microbial organism of claim 1, wherein said heterologous nucleic acid encodes a xylose transporter comprising an amino acid sequence that is at least 98% identical to an amino acid sequence selected from the group consisting of the amino acid sequence of SEQ ID NO: 1 SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, and SEQ ID NO: 12.

4. The non-naturally occurring microbial organism of claim 1, wherein said heterologous nucleic acid encodes a xylose transporter comprising an amino acid sequence that is at least 99% identical to an amino acid sequence selected from the group consisting of the amino acid sequence of SEQ ID NO: 1 SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, and SEQ ID NO: 12.

5. The non-naturally occurring microbial organism of claim 1, comprising at least three heterologous nucleic acids encoding at least three xylose transporters.

6. The non-naturally occurring microbial organism of claim 1, comprising at least four heterologous nucleic acids encoding at least four xylose transporters.

7. The non-naturally occurring microbial organism of claim 1, comprising at least five heterologous nucleic acids encoding at least five xylose transporters.

8. The non-naturally occurring microbial organism of claim 1, wherein said at least one heterologous nucleic acid comprises a nucleic acid sequence selected from the group consisting of the nucleotide sequence of SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

9. The non-naturally occurring microbial organism of claim 1, wherein at least one heterologous nucleic acid encodes a xylose transporter comprising the amino acid sequence of:
(a) SEQ ID NO: 1; or
(b) SEQ ID NO: 12.

10. The non-naturally occurring microbial organism of claim 1, wherein said xylose transporter is ubiquitin-deficient.

11. The non-naturally occurring microbial organism of claim 10, wherein said xylose transporter comprises amino acid substitutions at at least two lysine residues.

12. The non-naturally occurring microbial organism of claim 10, wherein said heterologous nucleic acid encodes said xylose transporter comprising the amino acid sequence of SEQ ID NO: 44 or SEQ ID NO: 45.

13. The non-naturally occurring microbial organism of claim 1, wherein said heterologous nucleic acid is codon-optimized to express said xylose transporter in said non-naturally occurring microbial organism.

14. The non-naturally occurring microbial organism of claim 1, wherein said non-naturally occurring microbial organism is in an aerobic culture medium.

15. The non-naturally occurring microbial organism of claim 1, wherein said non-naturally occurring microbial organism is in (i) a liquid culture medium comprising dissolved oxygen of less than 10% of saturation or (ii) a sealed chamber maintained with an atmosphere of less than 1% oxygen.

16. The non-naturally occurring microbial organism of claim 1, wherein said non-naturally occurring microbial organism is a species of bacteria or yeast.

17. The non-naturally occurring microbial organism of claim 16, wherein said non-naturally occurring microbial organism is a species of yeast, and wherein said species of yeast is *Saccharomyces cerevisiae*.

18. The non-naturally occurring microbial organism of claim 17, wherein said non-naturally occurring microbial organism comprises:
   (i) at least one heterologous nucleic acid encoding the xylose transporter comprising the amino acid sequence of:
      (a) SEQ ID NO: 1; or
      (b) SEQ ID NO: 12; or
   (ii) at least one heterologous nucleic acid comprising the nucleotide sequence of:
      (c) SEQ ID NO: 21; or
      (d) SEQ ID NO: 27.

19. The non-naturally occurring microbial organism of claim 1, wherein said non-naturally occurring microbial organism further comprises a metabolic pathway capable of producing a bioderived compound from xylose, wherein said bioderived compound is selected from the group consisting of xylitol, ethanol, n-butanol, isobutanol, isopropanol, arabitol, ethyl acetate, phenyl-ethyl alcohol, 2-methyl-butanol, and 3-methyl-butanol.

20. A method of producing a bioderived compound comprising:
   culturing the non-naturally occurring microbial organism of claim 19 under conditions and for a sufficient period of time to produce said bioderived compound.

21. The method of claim 20, wherein the conditions comprise culturing the non-naturally occurring microbial organism in a medium comprising xylose and a co-substrate selected from the group consisting of cellobiose, hemicellulose, glycerol, galactose, and glucose, or a combination thereof.

* * * * *

SEQUENCE LISTING

<160> NUMBER OF SEQ ID NOS: 59

<210> SEQ ID NO 1
<211> LENGTH: 543
<212> TYPE: PRT
<213> ORGANISM: Artificial Sequence
<220> FEATURE:
<223> OTHER INFORMATION: sequence of H0 Metschnikowia species Xyt1p

<400> SEQUENCE: 1

```
Met Gly Tyr Glu Glu Lys Leu Val Ala Pro Ala Leu Lys Phe Lys Asn
1               5                   10                  15

Phe Leu Asp Lys Thr Pro Asn Ile His Asn Val Tyr Val Ile Ala Ala
                20                  25                  30

Ile Ser Cys Thr Ser Gly Met Met Phe Gly Phe Asp Ile Ser Ser Met
            35                  40                  45

Ser Val Phe Val Asp Gln Gln Pro Tyr Leu Lys Met Phe Asp Asn Pro
        50                  55                  60

Ser Ser Val Ile Gln Gly Phe Ile Thr Ala Ser Met Ser Leu Gly Ser
65                  70                  75                  80

Phe Phe Gly Ser Leu Thr Ser Thr Phe Ile Ser Glu Pro Phe Gly Arg
                85                  90                  95

Arg Ala Ser Leu Phe Ile Cys Gly Ile Leu Trp Val Ile Gly Ala Ala
                100                 105                 110

Val Gln Ser Ser Ser Gln Asn Arg Ala Gln Leu Ile Cys Gly Arg Ile
            115                 120                 125

Ile Ala Gly Trp Gly Ile Gly Phe Gly Ser Ser Val Ala Pro Val Tyr
        130                 135                 140

Gly Ser Glu Met Ala Pro Arg Lys Ile Arg Gly Thr Ile Gly Gly Ile
145                 150                 155                 160
```

```
Phe Gln Phe Ser Val Thr Val Gly Ile Phe Ile Met Phe Leu Ile Gly
            165                 170                 175

Tyr Gly Cys Ser Phe Ile Gln Gly Lys Ala Ser Phe Arg Ile Pro Trp
            180                 185                 190

Gly Val Gln Met Val Pro Gly Leu Ile Leu Leu Ile Gly Leu Phe Phe
            195                 200                 205

Ile Pro Glu Ser Pro Arg Trp Leu Ala Lys Gln Gly Tyr Trp Glu Asp
210                 215                 220

Ala Glu Ile Ile Val Ala Asn Val Gln Ala Lys Gly Asn Arg Asn Asp
225                 230                 235                 240

Ala Asn Val Gln Ile Glu Met Ser Glu Ile Lys Asp Gln Leu Met Leu
            245                 250                 255

Asp Glu His Leu Lys Glu Phe Thr Tyr Ala Asp Leu Phe Thr Lys Lys
            260                 265                 270

Tyr Arg Gln Arg Thr Ile Thr Ala Ile Phe Ala Gln Ile Trp Gln Gln
            275                 280                 285

Leu Thr Gly Met Asn Val Met Met Tyr Tyr Ile Val Tyr Ile Phe Gln
            290                 295                 300

Met Ala Gly Tyr Ser Gly Asn Thr Asn Leu Val Pro Ser Leu Ile Gln
305                 310                 315                 320

Tyr Ile Ile Asn Met Ala Val Thr Val Pro Ala Leu Phe Cys Leu Asp
                325                 330                 335

Leu Leu Gly Arg Arg Thr Ile Leu Leu Ala Gly Ala Ala Phe Met Met
            340                 345                 350

Ala Trp Gln Phe Gly Val Ala Gly Ile Leu Ala Thr Tyr Ser Glu Pro
            355                 360                 365

Ala Tyr Ile Ser Asp Thr Val Arg Ile Thr Ile Pro Asp Asp His Lys
370                 375                 380

Ser Ala Ala Lys Gly Val Ile Ala Cys Cys Tyr Leu Phe Val Cys Ser
385                 390                 395                 400

Phe Ala Phe Ser Trp Gly Val Gly Ile Trp Val Tyr Cys Ser Glu Val
                405                 410                 415

Trp Gly Asp Ser Gln Ser Arg Gln Arg Gly Ala Ala Leu Ala Thr Ser
            420                 425                 430

Ala Asn Trp Ile Phe Asn Phe Ala Ile Ala Met Phe Thr Pro Ser Ser
            435                 440                 445

Phe Lys Asn Ile Thr Trp Lys Thr Tyr Ile Ile Tyr Ala Thr Phe Cys
            450                 455                 460

Ala Cys Met Phe Ile His Val Phe Phe Phe Pro Glu Thr Lys Gly Lys
465                 470                 475                 480

Lys Arg Leu Glu Glu Ile Gly Gln Leu Trp Asp Glu Gly Val Pro Ala
                485                 490                 495

Trp Arg Ser Ala Lys Trp Gln Pro Thr Val Pro Leu Ala Ser Asp Ala
            500                 505                 510

Glu Leu Ala His Lys Met Asp Val Ala His Ala Glu His Ala Asp Leu
            515                 520                 525

Leu Ala Thr His Ser Pro Ser Ser Asp Glu Lys Thr Gly Thr Val
            530                 535                 540

<210> SEQ ID NO 2
<211> LENGTH: 524
<212> TYPE: PRT
<213> ORGANISM: Artificial Sequence
<220> FEATURE:
<223> OTHER INFORMATION: sequence of H0 Metschnikowia species Gxf1p
```

```
<400> SEQUENCE: 2

Met Ser Gln Asp Glu Leu His Thr Lys Ser Gly Val Glu Thr Pro Ile
1               5                   10                  15

Asn Asp Ser Leu Leu Glu Glu Lys His Asp Val Thr Pro Leu Ala Ala
            20                  25                  30

Leu Pro Glu Lys Ser Phe Lys Asp Tyr Ile Ser Ile Ser Ile Phe Cys
        35                  40                  45

Leu Phe Val Ala Phe Gly Gly Phe Val Phe Gly Phe Asp Thr Gly Thr
    50                  55                  60

Ile Ser Gly Phe Val Asn Met Ser Asp Phe Lys Thr Arg Phe Gly Glu
65                  70                  75                  80

Met Asn Ala Gln Gly Glu Tyr Tyr Leu Ser Asn Val Arg Thr Gly Leu
                85                  90                  95

Met Val Ser Ile Phe Asn Val Gly Cys Ala Val Gly Gly Ile Phe Leu
            100                 105                 110

Cys Lys Ile Ala Asp Val Tyr Gly Arg Arg Ile Gly Leu Met Phe Ser
        115                 120                 125

Met Val Val Tyr Val Val Gly Ile Ile Ile Gln Ile Ala Ser Thr Thr
    130                 135                 140

Lys Trp Tyr Gln Tyr Phe Ile Gly Arg Leu Ile Ala Gly Leu Ala Val
145                 150                 155                 160

Gly Thr Val Ser Val Ile Ser Pro Leu Phe Ile Ser Glu Val Ala Pro
                165                 170                 175

Lys Gln Leu Arg Gly Thr Leu Val Cys Cys Phe Gln Leu Cys Ile Thr
            180                 185                 190

Leu Gly Ile Phe Leu Gly Tyr Cys Thr Thr Tyr Gly Thr Lys Thr Tyr
        195                 200                 205

Thr Asp Ser Arg Gln Trp Arg Ile Pro Leu Gly Ile Cys Phe Ala Trp
    210                 215                 220

Ala Leu Phe Leu Val Ala Gly Met Leu Asn Met Pro Glu Ser Pro Arg
225                 230                 235                 240

Tyr Leu Val Glu Lys Ser Arg Ile Asp Asp Ala Arg Lys Ser Ile Ala
                245                 250                 255

Arg Ser Asn Lys Val Ser Glu Glu Asp Pro Ala Val Tyr Thr Glu Val
            260                 265                 270

Gln Leu Ile Gln Ala Gly Ile Asp Arg Glu Ala Leu Ala Gly Ser Ala
        275                 280                 285

Thr Trp Met Glu Leu Val Thr Gly Lys Pro Lys Ile Phe Arg Arg Val
    290                 295                 300

Ile Met Gly Val Met Leu Gln Ser Leu Gln Gln Leu Thr Gly Asp Asn
305                 310                 315                 320

Tyr Phe Phe Tyr Tyr Gly Thr Thr Ile Phe Lys Ala Val Gly Leu Gln
                325                 330                 335

Asp Ser Phe Gln Thr Ser Ile Ile Leu Gly Ile Val Asn Phe Ala Ser
            340                 345                 350

Thr Phe Val Gly Ile Tyr Ala Ile Glu Arg Met Gly Arg Arg Leu Cys
        355                 360                 365

Leu Leu Thr Gly Ser Ala Cys Met Phe Val Cys Phe Ile Ile Tyr Ser
    370                 375                 380

Leu Ile Gly Thr Gln His Leu Tyr Lys Asn Gly Phe Ser Asn Glu Pro
385                 390                 395                 400

Ser Asn Thr Tyr Lys Pro Ser Gly Asn Ala Met Ile Phe Ile Thr Cys
                405                 410                 415
```

```
Leu Tyr Ile Phe Phe Ala Ser Thr Trp Ala Gly Gly Val Tyr Cys
                420             425             430

Ile Val Ser Glu Ser Tyr Pro Leu Arg Ile Arg Ser Lys Ala Met Ser
    435             440             445

Val Ala Thr Ala Ala Asn Trp Met Trp Gly Phe Leu Ile Ser Phe Phe
    450             455             460

Thr Pro Phe Ile Thr Ser Ala Ile His Phe Tyr Tyr Gly Phe Val Phe
465             470             475             480

Thr Gly Cys Leu Ala Phe Ser Phe Phe Tyr Val Tyr Phe Val Val
                485             490             495

Glu Thr Lys Gly Leu Ser Leu Glu Glu Val Asp Ile Leu Tyr Ala Ser
                500             505             510

Gly Thr Leu Pro Trp Lys Ser Ser Gly Trp Val Pro
                515             520
```

<210> SEQ ID NO 3
<211> LENGTH: 454
<212> TYPE: PRT
<213> ORGANISM: Artificial Sequence
<220> FEATURE:
<223> OTHER INFORMATION: sequence of H0 Metschnikowia species ?Gxf1p
      (variant of Gxf1p with shorter N-terminus)

<400> SEQUENCE: 3

```
Met Ser Asp Phe Lys Thr Arg Phe Gly Glu Met Asn Ala Gln Gly Glu
1               5                   10                  15

Tyr Tyr Leu Ser Asn Val Arg Thr Gly Leu Met Val Ser Ile Phe Asn
                20                  25                  30

Val Gly Cys Ala Val Gly Gly Ile Phe Leu Cys Lys Ile Ala Asp Val
                35                  40                  45

Tyr Gly Arg Arg Ile Gly Leu Met Phe Ser Met Val Val Tyr Val Val
    50                  55                  60

Gly Ile Ile Ile Gln Ile Ala Ser Thr Thr Lys Trp Tyr Gln Tyr Phe
65                  70                  75                  80

Ile Gly Arg Leu Ile Ala Gly Leu Ala Val Gly Thr Val Ser Val Ile
                85                  90                  95

Ser Pro Leu Phe Ile Ser Glu Val Ala Pro Lys Gln Leu Arg Gly Thr
                100                 105                 110

Leu Val Cys Cys Phe Gln Leu Cys Ile Thr Leu Gly Ile Phe Leu Gly
                115                 120                 125

Tyr Cys Thr Thr Tyr Gly Thr Lys Thr Tyr Thr Asp Ser Arg Gln Trp
                130                 135                 140

Arg Ile Pro Leu Gly Ile Cys Phe Ala Trp Ala Leu Phe Leu Val Ala
145                 150                 155                 160

Gly Met Leu Asn Met Pro Glu Ser Pro Arg Tyr Leu Val Glu Lys Ser
                165                 170                 175

Arg Ile Asp Asp Ala Arg Lys Ser Ile Ala Arg Ser Asn Lys Val Ser
                180                 185                 190

Glu Glu Asp Pro Ala Val Tyr Thr Glu Val Gln Leu Ile Gln Ala Gly
                195                 200                 205

Ile Asp Arg Glu Ala Leu Ala Gly Ser Ala Thr Trp Met Glu Leu Val
                210                 215                 220

Thr Gly Lys Pro Lys Ile Phe Arg Arg Val Ile Met Gly Val Met Leu
225                 230                 235                 240

Gln Ser Leu Gln Gln Leu Thr Gly Asp Asn Tyr Phe Phe Tyr Tyr Gly
                245                 250                 255
```

```
Thr Thr Ile Phe Lys Ala Val Gly Leu Gln Asp Ser Phe Gln Thr Ser
            260                 265                 270

Ile Ile Leu Gly Ile Val Asn Phe Ala Ser Thr Phe Val Gly Ile Tyr
        275                 280                 285

Ala Ile Glu Arg Met Gly Arg Arg Leu Cys Leu Leu Thr Gly Ser Ala
    290                 295                 300

Cys Met Phe Val Cys Phe Ile Ile Tyr Ser Leu Ile Gly Thr Gln His
305                 310                 315                 320

Leu Tyr Lys Asn Gly Phe Ser Asn Glu Pro Ser Asn Thr Tyr Lys Pro
                325                 330                 335

Ser Gly Asn Ala Met Ile Phe Ile Thr Cys Leu Tyr Ile Phe Phe Phe
            340                 345                 350

Ala Ser Thr Trp Ala Gly Gly Val Tyr Cys Ile Val Ser Glu Ser Tyr
        355                 360                 365

Pro Leu Arg Ile Arg Ser Lys Ala Met Ser Val Ala Thr Ala Ala Asn
    370                 375                 380

Trp Met Trp Gly Phe Leu Ile Ser Phe Phe Thr Pro Phe Ile Thr Ser
385                 390                 395                 400

Ala Ile His Phe Tyr Tyr Gly Phe Val Phe Thr Gly Cys Leu Ala Phe
                405                 410                 415

Ser Phe Phe Tyr Val Tyr Phe Val Val Glu Thr Lys Gly Leu Ser
            420                 425                 430

Leu Glu Glu Val Asp Ile Leu Tyr Ala Ser Gly Thr Leu Pro Trp Lys
        435                 440                 445

Ser Ser Gly Trp Val Pro
    450

<210> SEQ ID NO 4
<211> LENGTH: 548
<212> TYPE: PRT
<213> ORGANISM: Artificial Sequence
<220> FEATURE:
<223> OTHER INFORMATION: sequence of H0 Metschnikowia species Gxf2p/
      Gal2p

<400> SEQUENCE: 4

Met Ser Ala Glu Gln Glu Gln Gln Val Ser Gly Thr Ser Ala Thr Ile
1               5                   10                  15

Asp Gly Leu Ala Ser Leu Lys Gln Glu Lys Thr Ala Glu Glu Asp
            20                  25                  30

Ala Phe Lys Pro Lys Pro Ala Thr Ala Tyr Phe Phe Ile Ser Phe Leu
        35                  40                  45

Cys Gly Leu Val Ala Phe Gly Gly Tyr Val Phe Gly Phe Asp Thr Gly
    50                  55                  60

Thr Ile Ser Gly Phe Val Asn Met Asp Asp Tyr Leu Met Arg Phe Gly
65                  70                  75                  80

Gln Gln His Ala Asp Gly Thr Tyr Tyr Leu Ser Asn Val Arg Thr Gly
                85                  90                  95

Leu Ile Val Ser Ile Phe Asn Ile Gly Cys Ala Val Gly Gly Leu Ala
            100                 105                 110

Leu Ser Lys Val Gly Asp Ile Trp Gly Arg Arg Ile Gly Ile Met Val
        115                 120                 125

Ala Met Ile Ile Tyr Met Val Gly Ile Ile Gln Ile Ala Ser Gln
    130                 135                 140
```

```
Asp Lys Trp Tyr Gln Tyr Phe Ile Gly Arg Leu Ile Thr Gly Leu Gly
145                 150                 155                 160

Val Gly Thr Thr Ser Val Leu Ser Pro Leu Phe Ile Ser Glu Ser Ala
            165                 170                 175

Pro Lys His Leu Arg Gly Thr Leu Val Cys Cys Phe Gln Leu Met Val
        180                 185                 190

Thr Leu Gly Ile Phe Leu Gly Tyr Cys Thr Thr Tyr Gly Thr Lys Asn
    195                 200                 205

Tyr Thr Asp Ser Arg Gln Trp Arg Ile Pro Leu Gly Leu Cys Phe Ala
    210                 215                 220

Trp Ala Leu Leu Leu Ile Ser Gly Met Val Phe Met Pro Glu Ser Pro
225                 230                 235                 240

Arg Phe Leu Ile Glu Arg Gln Arg Phe Asp Glu Ala Lys Ala Ser Val
                245                 250                 255

Ala Lys Ser Asn Gln Val Ser Thr Glu Asp Pro Ala Val Tyr Thr Glu
            260                 265                 270

Val Glu Leu Ile Gln Ala Gly Ile Asp Arg Glu Ala Leu Ala Gly Ser
        275                 280                 285

Ala Gly Trp Lys Glu Leu Ile Thr Gly Lys Pro Lys Met Leu Gln Arg
    290                 295                 300

Val Ile Leu Gly Met Met Leu Gln Ser Ile Gln Gln Leu Thr Gly Asn
305                 310                 315                 320

Asn Tyr Phe Phe Tyr Tyr Gly Thr Thr Ile Phe Lys Ala Val Gly Met
                325                 330                 335

Ser Asp Ser Phe Gln Thr Ser Ile Val Leu Gly Ile Val Asn Phe Ala
            340                 345                 350

Ser Thr Phe Val Gly Ile Trp Ala Ile Glu Arg Met Gly Arg Arg Ser
        355                 360                 365

Cys Leu Leu Val Gly Ser Ala Cys Met Ser Val Cys Phe Leu Ile Tyr
    370                 375                 380

Ser Ile Leu Gly Ser Val Asn Leu Tyr Ile Asp Gly Tyr Glu Asn Thr
385                 390                 395                 400

Pro Ser Asn Thr Arg Lys Pro Thr Gly Asn Ala Met Ile Phe Ile Thr
                405                 410                 415

Cys Leu Phe Ile Phe Phe Phe Ala Ser Thr Trp Ala Gly Gly Val Tyr
            420                 425                 430

Ser Ile Val Ser Glu Thr Tyr Pro Leu Arg Ile Arg Ser Lys Gly Met
        435                 440                 445

Ala Val Ala Thr Ala Ala Asn Trp Met Trp Gly Phe Leu Ile Ser Phe
    450                 455                 460

Phe Thr Pro Phe Ile Thr Ser Ala Ile His Phe Tyr Tyr Gly Phe Val
465                 470                 475                 480

Phe Thr Gly Cys Leu Ile Phe Ser Phe Tyr Val Phe Phe Phe Val
                485                 490                 495

Arg Glu Thr Lys Gly Leu Ser Leu Glu Glu Val Asp Glu Leu Tyr Ala
            500                 505                 510

Thr Asp Leu Pro Pro Trp Lys Thr Ala Gly Trp Thr Pro Pro Ser Ala
        515                 520                 525

Glu Asp Met Ala His Thr Thr Gly Phe Ala Glu Ala Ala Lys Pro Thr
    530                 535                 540

Asn Lys His Val
545
```

<210> SEQ ID NO 5
<211> LENGTH: 502
<212> TYPE: PRT
<213> ORGANISM: Artificial Sequence
<220> FEATURE:
<223> OTHER INFORMATION: sequence of H0 Metschnikowia species delta-Gxs1p/Delta-Hgt12p (variant of Gxs1p/Hgt12p with shorter N-terminus)

<400> SEQUENCE: 5

```
Met Gly Ile Phe Val Gly Val Phe Ala Ala Leu Gly Gly Val Leu Phe
1               5                   10                  15

Gly Tyr Asp Thr Gly Thr Ile Ser Gly Val Met Ala Met Pro Trp Val
            20                  25                  30

Lys Glu His Phe Pro Lys Asp Arg Val Ala Phe Ser Ala Ser Glu Ser
        35                  40                  45

Ser Leu Ile Val Ser Ile Leu Ser Ala Gly Thr Phe Phe Gly Ala Ile
    50                  55                  60

Leu Ala Pro Leu Leu Thr Asp Thr Leu Gly Arg Arg Trp Cys Ile Ile
65                  70                  75                  80

Ile Ser Ser Leu Val Val Phe Asn Leu Gly Ala Ala Leu Gln Thr Ala
                85                  90                  95

Ala Thr Asp Ile Pro Leu Leu Ile Val Gly Arg Val Ile Ala Gly Leu
            100                 105                 110

Gly Val Gly Leu Ile Ser Ser Thr Ile Pro Leu Tyr Gln Ser Glu Ala
        115                 120                 125

Leu Pro Lys Trp Ile Arg Gly Ala Val Val Ser Cys Tyr Gln Trp Ala
    130                 135                 140

Ile Thr Ile Gly Ile Phe Leu Ala Ala Val Ile Asn Gln Gly Thr His
145                 150                 155                 160

Lys Ile Asn Ser Pro Ala Ser Tyr Arg Ile Pro Leu Gly Ile Gln Met
                165                 170                 175

Ala Trp Gly Leu Ile Leu Gly Val Gly Met Phe Phe Leu Pro Glu Thr
            180                 185                 190

Pro Arg Phe Tyr Ile Ser Lys Gly Gln Asn Ala Lys Ala Ala Val Ser
        195                 200                 205

Leu Ala Arg Leu Arg Lys Leu Pro Gln Asp His Pro Glu Leu Leu Glu
    210                 215                 220

Glu Leu Glu Asp Ile Gln Ala Ala Tyr Glu Phe Glu Thr Val His Gly
225                 230                 235                 240

Lys Ser Ser Trp Ser Gln Val Phe Thr Asn Lys Asn Lys Gln Leu Lys
                245                 250                 255

Lys Leu Ala Thr Gly Val Cys Leu Gln Ala Phe Gln Gln Leu Thr Gly
            260                 265                 270

Val Asn Phe Ile Phe Tyr Phe Gly Thr Thr Phe Phe Asn Ser Val Gly
        275                 280                 285

Leu Asp Gly Phe Thr Thr Ser Leu Ala Thr Asn Ile Val Asn Val Gly
    290                 295                 300

Ser Thr Ile Pro Gly Ile Leu Gly Val Glu Ile Phe Gly Arg Arg Lys
305                 310                 315                 320

Val Leu Leu Thr Gly Ala Ala Gly Met Cys Leu Ser Gln Phe Ile Val
                325                 330                 335

Ala Ile Val Gly Val Ala Thr Asp Ser Lys Ala Ala Asn Gln Val Leu
            340                 345                 350

Ile Ala Phe Cys Cys Ile Phe Ile Ala Phe Phe Ala Ala Thr Trp Gly
        355                 360                 365
```

```
Pro Thr Ala Trp Val Val Cys Gly Glu Ile Phe Pro Leu Arg Thr Arg
    370                 375                 380

Ala Lys Ser Ile Ala Met Cys Ala Ala Ser Asn Trp Leu Leu Asn Trp
385                 390                 395                 400

Ala Ile Ala Tyr Ala Thr Pro Tyr Leu Val Asp Ser Asp Lys Gly Asn
                405                 410                 415

Leu Gly Thr Asn Val Phe Phe Ile Trp Gly Ser Cys Asn Phe Phe Cys
            420                 425                 430

Leu Val Phe Ala Tyr Phe Met Ile Tyr Glu Thr Lys Gly Leu Ser Leu
        435                 440                 445

Glu Gln Val Asp Glu Leu Tyr Glu Lys Val Ala Ser Ala Arg Lys Ser
    450                 455                 460

Pro Gly Phe Val Pro Ser Glu His Ala Phe Arg Glu His Ala Asp Val
465                 470                 475                 480

Glu Thr Ala Met Pro Asp Asn Phe Asn Leu Lys Ala Glu Ala Ile Ser
                485                 490                 495

Val Glu Asp Ala Ser Val
            500

<210> SEQ ID NO 6

<400> SEQUENCE: 6

000

<210> SEQ ID NO 7
<211> LENGTH: 526
<212> TYPE: PRT
<213> ORGANISM: Artificial Sequence
<220> FEATURE:
<223> OTHER INFORMATION: sequence of H0 Metschnikowia species Gxs1p/
      Hgt12

<400> SEQUENCE: 7

Met Gly Leu Glu Ser Asn Lys Leu Ile Arg Lys Tyr Ile Asn Val Gly
1               5                   10                  15

Glu Lys Arg Ala Gly Ser Ser Gly Met Gly Ile Phe Val Gly Val Phe
            20                  25                  30

Ala Ala Leu Gly Gly Val Leu Phe Gly Tyr Asp Thr Gly Thr Ile Ser
        35                  40                  45

Gly Val Met Ala Met Pro Trp Val Lys Glu His Phe Pro Lys Asp Arg
    50                  55                  60

Val Ala Phe Ser Ala Ser Glu Ser Leu Ile Val Ser Ile Leu Ser
65                  70                  75                  80

Ala Gly Thr Phe Phe Gly Ala Ile Leu Ala Pro Leu Leu Thr Asp Thr
                85                  90                  95

Leu Gly Arg Arg Trp Cys Ile Ile Ile Ser Ser Leu Val Val Phe Asn
            100                 105                 110

Leu Gly Ala Ala Leu Gln Thr Ala Ala Thr Asp Ile Pro Leu Leu Ile
        115                 120                 125

Val Gly Arg Val Ile Ala Gly Leu Gly Val Gly Leu Ile Ser Ser Thr
    130                 135                 140

Ile Pro Leu Tyr Gln Ser Glu Ala Leu Pro Lys Trp Ile Arg Gly Ala
145                 150                 155                 160
```

Val Val Ser Cys Tyr Gln Trp Ala Ile Thr Ile Gly Ile Phe Leu Ala
            165                 170                 175

Ala Val Ile Asn Gln Gly Thr His Lys Ile Asn Ser Pro Ala Ser Tyr
        180                 185                 190

Arg Ile Pro Leu Gly Ile Gln Met Ala Trp Gly Leu Ile Leu Gly Val
            195                 200                 205

Gly Met Phe Phe Leu Pro Glu Thr Pro Arg Phe Tyr Ile Ser Lys Gly
    210                 215                 220

Gln Asn Ala Lys Ala Ala Val Ser Leu Ala Arg Leu Arg Lys Leu Pro
225                 230                 235                 240

Gln Asp His Pro Glu Leu Leu Glu Gly Leu Glu Asp Ile Gln Ala Ala
                245                 250                 255

Tyr Glu Phe Glu Thr Val His Gly Lys Ser Ser Trp Ser Gln Val Phe
            260                 265                 270

Thr Asn Lys Asn Lys Gln Leu Lys Lys Leu Ala Thr Gly Val Cys Leu
        275                 280                 285

Gln Ala Phe Gln Gln Leu Thr Gly Val Asn Phe Ile Phe Tyr Phe Gly
    290                 295                 300

Thr Thr Phe Phe Asn Ser Val Gly Leu Asp Gly Phe Thr Thr Ser Leu
305                 310                 315                 320

Ala Thr Asn Ile Val Asn Val Gly Ser Thr Ile Pro Gly Ile Leu Gly
                325                 330                 335

Val Glu Ile Phe Gly Arg Arg Lys Val Leu Leu Thr Gly Ala Ala Gly
            340                 345                 350

Met Cys Leu Ser Gln Phe Ile Val Ala Ile Val Gly Val Ala Thr Asp
        355                 360                 365

Ser Lys Ala Ala Asn Gln Val Leu Ile Ala Phe Cys Cys Ile Phe Ile
    370                 375                 380

Ala Phe Phe Ala Ala Thr Trp Gly Pro Thr Ala Trp Val Val Cys Gly
385                 390                 395                 400

Glu Ile Phe Pro Leu Arg Thr Arg Ala Lys Ser Ile Ala Met Cys Ala
                405                 410                 415

Ala Ser Asn Trp Leu Leu Asn Trp Ala Ile Ala Tyr Ala Thr Pro Tyr
            420                 425                 430

Leu Val Asp Ser Asp Lys Gly Asn Leu Gly Thr Asn Val Phe Phe Ile
        435                 440                 445

Trp Gly Ser Cys Asn Phe Phe Cys Leu Val Phe Ala Tyr Phe Met Ile
    450                 455                 460

Tyr Glu Thr Lys Gly Leu Ser Leu Glu Gln Val Asp Glu Leu Tyr Glu
465                 470                 475                 480

Lys Val Ala Ser Ala Arg Lys Ser Pro Gly Phe Val Pro Ser Glu His
                485                 490                 495

Ala Phe Arg Glu His Ala Asp Val Glu Thr Ala Met Pro Asp Asn Phe
            500                 505                 510

Asn Leu Lys Ala Glu Ala Ile Ser Val Glu Asp Ala Ser Val
        515                 520                 525

<210> SEQ ID NO 8
<211> LENGTH: 548
<212> TYPE: PRT
<213> ORGANISM: Artificial Sequence
<220> FEATURE:
<223> OTHER INFORMATION: sequence of H0 Metschnikowia species Hxt5p

<400> SEQUENCE: 8

```
Met Ser Ile Phe Glu Gly Lys Asp Gly Lys Gly Val Ser Ser Thr Glu
1               5                   10                  15

Ser Leu Ser Asn Asp Val Arg Tyr Asp Asn Met Glu Lys Val Asp Gln
            20                  25                  30

Asp Val Leu Arg His Asn Phe Asn Phe Asp Lys Glu Phe Glu Glu Leu
        35                  40                  45

Glu Ile Glu Ala Ala Gln Val Asn Asp Lys Pro Ser Phe Val Asp Arg
    50                  55                  60

Ile Leu Ser Leu Glu Tyr Lys Leu His Phe Glu Asn Lys Asn His Met
65                  70                  75                  80

Val Trp Leu Leu Gly Ala Phe Ala Ala Ala Gly Leu Leu Ser Gly
                85                  90                  95

Leu Asp Gln Ser Ile Ile Ser Gly Ala Ser Ile Gly Met Asn Lys Ala
                100                 105                 110

Leu Asn Leu Thr Glu Arg Glu Ala Ser Leu Val Ser Ser Leu Met Pro
            115                 120                 125

Leu Gly Ala Met Ala Gly Ser Met Ile Met Thr Pro Leu Asn Glu Trp
130                 135                 140

Phe Gly Arg Lys Ser Ser Leu Ile Ile Ser Cys Ile Trp Tyr Thr Ile
145                 150                 155                 160

Gly Ser Ala Leu Cys Ala Gly Ala Arg Asp His His Met Met Tyr Ala
                165                 170                 175

Gly Arg Phe Ile Leu Gly Val Gly Val Gly Ile Glu Gly Gly Cys Val
            180                 185                 190

Gly Ile Tyr Ile Ser Glu Ser Val Pro Ala Asn Val Arg Gly Ser Ile
        195                 200                 205

Val Ser Met Tyr Gln Phe Asn Ile Ala Leu Gly Glu Val Leu Gly Tyr
    210                 215                 220

Ala Val Ala Ala Ile Phe Tyr Thr Val His Gly Gly Trp Arg Phe Met
225                 230                 235                 240

Val Gly Ser Ser Leu Val Phe Ser Thr Ile Leu Phe Ala Gly Leu Phe
                245                 250                 255

Phe Leu Pro Glu Ser Pro Arg Trp Leu Val His Lys Gly Arg Asn Gly
            260                 265                 270

Met Ala Tyr Asp Val Trp Lys Arg Leu Arg Asp Ile Asn Asp Glu Ser
        275                 280                 285

Ala Lys Leu Glu Phe Leu Glu Met Arg Gln Ala Ala Tyr Gln Glu Arg
    290                 295                 300

Glu Arg Arg Ser Gln Glu Ser Leu Phe Ser Ser Trp Gly Glu Leu Phe
305                 310                 315                 320

Thr Ile Ala Arg Asn Arg Arg Ala Leu Thr Tyr Ser Val Ile Met Ile
                325                 330                 335

Thr Leu Gly Gln Leu Thr Gly Val Asn Ala Val Met Tyr Tyr Met Ser
            340                 345                 350

Thr Leu Met Gly Ala Ile Gly Phe Asn Glu Lys Asp Ser Val Phe Met
        355                 360                 365

Ser Leu Val Gly Gly Ser Leu Leu Ile Gly Thr Ile Pro Ala Ile
    370                 375                 380

Leu Trp Met Asp Arg Phe Gly Arg Arg Val Trp Gly Tyr Asn Leu Val
385                 390                 395                 400

Gly Phe Phe Val Gly Leu Val Leu Val Gly Val Gly Tyr Arg Phe Asn
                405                 410                 415
```

-continued

```
Pro Val Thr Gln Lys Ala Ala Ser Glu Gly Val Tyr Leu Thr Gly Leu
                420             425                 430

Ile Val Tyr Phe Leu Phe Phe Gly Ser Tyr Ser Thr Leu Thr Trp Val
            435                 440                 445

Ile Pro Ser Glu Ser Phe Asp Leu Arg Thr Arg Ser Leu Gly Met Thr
        450                 455                 460

Ile Cys Ser Thr Phe Leu Tyr Leu Trp Ser Phe Thr Val Thr Tyr Asn
465                 470                 475                 480

Phe Thr Lys Met Ser Ala Ala Phe Thr Tyr Thr Gly Leu Thr Leu Gly
                485                 490                 495

Phe Tyr Gly Gly Ile Ala Phe Leu Gly Leu Ile Tyr Gln Val Cys Phe
            500                 505                 510

Met Pro Glu Thr Lys Asp Lys Thr Leu Glu Glu Ile Asp Asp Ile Phe
        515                 520                 525

Asn Arg Ser Ala Phe Ser Ile Ala Arg Glu Asn Ile Ser Asn Leu Lys
530                 535                 540

Lys Gly Ile Trp
545

<210> SEQ ID NO 9
<211> LENGTH: 543
<212> TYPE: PRT
<213> ORGANISM: Artificial Sequence
<220> FEATURE:
<223> OTHER INFORMATION: sequence of H0 Metschnikowia species Xyt1p with
      S75L mutation

<400> SEQUENCE: 9

Met Gly Tyr Glu Glu Lys Leu Val Ala Pro Ala Leu Lys Phe Lys Asn
1               5                   10                  15

Phe Leu Asp Lys Thr Pro Asn Ile His Asn Val Tyr Val Ile Ala Ala
                20                  25                  30

Ile Ser Cys Thr Ser Gly Met Met Phe Gly Phe Asp Ile Ser Ser Met
            35                  40                  45

Ser Val Phe Val Asp Gln Gln Pro Tyr Leu Lys Met Phe Asp Asn Pro
        50                  55                  60

Ser Ser Val Ile Gln Gly Phe Ile Thr Ala Leu Met Ser Leu Gly Ser
65                  70                  75                  80

Phe Phe Gly Ser Leu Thr Ser Thr Phe Ile Ser Glu Pro Phe Gly Arg
                85                  90                  95

Arg Ala Ser Leu Phe Ile Cys Gly Ile Leu Trp Val Ile Gly Ala Ala
            100                 105                 110

Val Gln Ser Ser Ser Gln Asn Arg Ala Gln Leu Ile Cys Gly Arg Ile
        115                 120                 125

Ile Ala Gly Trp Gly Ile Gly Phe Gly Ser Ser Val Ala Pro Val Tyr
130                 135                 140

Gly Ser Glu Met Ala Pro Arg Lys Ile Arg Gly Thr Ile Gly Gly Ile
145                 150                 155                 160

Phe Gln Phe Ser Val Thr Val Gly Ile Phe Ile Met Phe Leu Ile Gly
                165                 170                 175

Tyr Gly Cys Ser Phe Ile Gln Gly Lys Ala Ser Phe Arg Ile Pro Trp
            180                 185                 190

Gly Val Gln Met Val Pro Gly Leu Ile Leu Ile Gly Leu Phe Phe
        195                 200                 205

Ile Pro Glu Ser Pro Arg Trp Leu Ala Lys Gln Gly Tyr Trp Glu Asp
210                 215                 220
```

Ala Glu Ile Ile Val Ala Asn Val Gln Ala Lys Gly Asn Arg Asn Asp
225                 230                 235                 240

Ala Asn Val Gln Ile Glu Met Ser Glu Ile Lys Asp Gln Leu Met Leu
            245                 250                 255

Asp Glu His Leu Lys Glu Phe Thr Tyr Ala Asp Leu Phe Thr Lys Lys
        260                 265                 270

Tyr Arg Gln Arg Thr Ile Thr Ala Ile Phe Ala Gln Ile Trp Gln Gln
    275                 280                 285

Leu Thr Gly Met Asn Val Met Met Tyr Tyr Ile Val Tyr Ile Phe Gln
290                 295                 300

Met Ala Gly Tyr Ser Gly Asn Thr Asn Leu Val Pro Ser Leu Ile Gln
305                 310                 315                 320

Tyr Ile Ile Asn Met Ala Val Thr Val Pro Ala Leu Phe Cys Leu Asp
                325                 330                 335

Leu Leu Gly Arg Arg Thr Ile Leu Leu Ala Gly Ala Ala Phe Met Met
            340                 345                 350

Ala Trp Gln Phe Gly Val Ala Gly Ile Leu Ala Thr Tyr Ser Glu Pro
        355                 360                 365

Ala Tyr Ile Ser Asp Thr Val Arg Ile Thr Ile Pro Asp Asp His Lys
    370                 375                 380

Ser Ala Ala Lys Gly Val Ile Ala Cys Cys Tyr Leu Phe Val Cys Ser
385                 390                 395                 400

Phe Ala Phe Ser Trp Gly Val Gly Ile Trp Val Tyr Cys Ser Glu Val
                405                 410                 415

Trp Gly Asp Ser Gln Ser Arg Gln Arg Gly Ala Ala Leu Ala Thr Ser
            420                 425                 430

Ala Asn Trp Ile Phe Asn Phe Ala Ile Ala Met Phe Thr Pro Ser Ser
        435                 440                 445

Phe Lys Asn Ile Thr Trp Lys Thr Tyr Ile Ile Tyr Ala Thr Phe Cys
    450                 455                 460

Ala Cys Met Phe Ile His Val Phe Phe Phe Pro Glu Thr Lys Gly
465                 470                 475                 480

Lys Arg Leu Glu Glu Ile Gly Gln Leu Trp Asp Glu Gly Val Pro Ala
                485                 490                 495

Trp Arg Ser Ala Lys Trp Gln Pro Thr Val Pro Leu Ala Ser Asp Ala
            500                 505                 510

Glu Leu Ala His Lys Met Asp Val Ala His Glu His Ala Asp Leu
        515                 520                 525

Leu Ala Thr His Ser Pro Ser Ser Asp Glu Lys Thr Gly Thr Val
    530                 535                 540

<210> SEQ ID NO 10
<211> LENGTH: 524
<212> TYPE: PRT
<213> ORGANISM: Artificial Sequence
<220> FEATURE:
<223> OTHER INFORMATION: sequence of H0 Metschnikowia species Hxt2.6p

<400> SEQUENCE: 10

Met Ser Ser Thr Thr Asp Thr Leu Glu Lys Arg Asp Thr Glu Pro Phe
1               5                   10                  15

Thr Ser Asp Ala Pro Val Thr Val His Asp Tyr Ile Ala Glu Glu Arg
            20                  25                  30

Pro Trp Trp Lys Val Pro His Leu Arg Val Leu Thr Trp Ser Val Phe
        35                  40                  45

```
Val Ile Thr Leu Thr Ser Thr Asn Asn Gly Tyr Asp Gly Ser Met Leu
 50                  55                  60

Asn Gly Leu Gln Ser Leu Asp Ile Trp Gln Glu Asp Leu Gly His Pro
 65                  70                  75                  80

Ala Gly Gln Lys Leu Gly Ala Leu Ala Asn Gly Val Leu Phe Gly Asn
                 85                  90                  95

Leu Ala Ala Val Pro Phe Ala Ser Tyr Phe Cys Asp Arg Phe Gly Arg
            100                 105                 110

Arg Pro Val Ile Cys Phe Gly Gln Ile Leu Thr Ile Val Gly Ala Val
            115                 120                 125

Leu Gln Gly Leu Ser Asn Ser Tyr Gly Phe Phe Leu Gly Ser Arg Ile
130                 135                 140

Val Leu Gly Phe Gly Ala Met Ile Ala Thr Ile Pro Ser Pro Thr Leu
145                 150                 155                 160

Ile Ser Glu Ile Ala Tyr Pro Thr His Arg Glu Thr Ser Thr Phe Ala
                165                 170                 175

Tyr Asn Val Cys Trp Tyr Leu Gly Ala Ile Ile Ala Ser Trp Val Thr
            180                 185                 190

Tyr Gly Thr Arg Asp Leu Gln Ser Lys Ala Cys Trp Ser Ile Pro Ser
            195                 200                 205

Tyr Leu Gln Ala Ala Leu Pro Phe Phe Gln Val Cys Met Ile Trp Phe
210                 215                 220

Val Pro Glu Ser Pro Arg Phe Leu Val Ala Lys Gly Lys Ile Asp Gln
225                 230                 235                 240

Ala Arg Ala Val Leu Ser Lys Tyr His Thr Gly Asp Ser Thr Asp Pro
                245                 250                 255

Arg Asp Val Ala Leu Val Asp Phe Glu Leu His Glu Ile Glu Ser Ala
            260                 265                 270

Leu Glu Gln Glu Lys Leu Asn Thr Arg Ser Ser Tyr Phe Asp Phe Phe
            275                 280                 285

Lys Lys Arg Asn Phe Arg Lys Arg Gly Phe Leu Cys Val Met Val Gly
            290                 295                 300

Val Ala Met Gln Leu Ser Gly Asn Gly Leu Val Ser Tyr Tyr Leu Ser
305                 310                 315                 320

Lys Val Leu Asp Ser Ile Gly Ile Thr Glu Thr Lys Arg Gln Leu Glu
                325                 330                 335

Ile Asn Gly Cys Leu Met Ile Tyr Asn Phe Val Ile Cys Val Ser Leu
            340                 345                 350

Met Ser Val Cys Arg Met Phe Lys Arg Arg Val Leu Phe Leu Thr Cys
            355                 360                 365

Phe Ser Gly Met Thr Val Cys Tyr Thr Ile Trp Thr Ile Leu Ser Ala
370                 375                 380

Leu Asn Glu Gln Arg His Phe Glu Asp Lys Gly Leu Ala Asn Gly Val
385                 390                 395                 400

Leu Ala Met Ile Phe Phe Tyr Tyr Phe Phe Tyr Asn Val Gly Ile Asn
                405                 410                 415

Gly Leu Pro Phe Leu Tyr Ile Thr Glu Ile Leu Pro Tyr Ser His Arg
            420                 425                 430

Ala Lys Gly Leu Asn Leu Phe Gln Phe Ser Gln Phe Leu Thr Gln Ile
            435                 440                 445

Tyr Asn Gly Tyr Val Asn Pro Ile Ala Met Asp Ala Ile Ser Trp Lys
450                 455                 460
```

```
Tyr Tyr Ile Val Tyr Cys Cys Ile Leu Phe Val Glu Leu Val Ile Val
465                 470                 475                 480

Phe Phe Thr Phe Pro Glu Thr Ser Gly Tyr Thr Leu Glu Glu Val Ala
                485                 490                 495

Gln Val Phe Gly Asp Glu Ala Pro Gly Leu His Asn Arg Gln Leu Asp
            500                 505                 510

Val Ala Lys Glu Ser Leu Glu His Val Glu His Val
            515                 520

<210> SEQ ID NO 11
<211> LENGTH: 556
<212> TYPE: PRT
<213> ORGANISM: Artificial Sequence
<220> FEATURE:
<223> OTHER INFORMATION: sequence of H0 Metschnikowia species Qup2p

<400> SEQUENCE: 11

Met Gly Phe Arg Asn Leu Lys Arg Arg Leu Ser Asn Val Gly Asp Ser
1               5                   10                  15

Met Ser Val His Ser Val Lys Glu Glu Asp Phe Ser Arg Val Glu
            20                  25                  30

Ile Pro Asp Glu Ile Tyr Asn Tyr Lys Ile Val Leu Val Ala Leu Thr
        35                  40                  45

Ala Ala Ser Ala Ala Ile Ile Ile Gly Tyr Asp Ala Gly Phe Ile Gly
    50                  55                  60

Gly Thr Val Ser Leu Thr Ala Phe Lys Ser Glu Phe Gly Leu Asp Lys
65                  70                  75                  80

Met Ser Ala Thr Ala Ala Ser Ala Ile Glu Ala Asn Val Val Ser Val
                85                  90                  95

Phe Gln Ala Gly Ala Tyr Phe Gly Cys Leu Phe Phe Tyr Pro Ile Gly
            100                 105                 110

Glu Ile Trp Gly Arg Lys Ile Gly Leu Leu Leu Ser Gly Phe Leu Leu
        115                 120                 125

Thr Phe Gly Ala Ala Ile Ser Leu Ile Ser Asn Ser Ser Arg Gly Leu
130                 135                 140

Gly Ala Ile Tyr Ala Gly Arg Val Leu Thr Gly Leu Gly Ile Gly Gly
145                 150                 155                 160

Cys Ser Ser Leu Ala Pro Ile Tyr Val Ser Glu Ile Ala Pro Ala Ala
                165                 170                 175

Ile Arg Gly Lys Leu Val Gly Cys Trp Glu Val Ser Trp Gln Val Gly
            180                 185                 190

Gly Ile Val Gly Tyr Trp Ile Asn Tyr Gly Val Leu Gln Thr Leu Pro
        195                 200                 205

Ile Ser Ser Gln Gln Trp Ile Ile Pro Phe Ala Val Gln Leu Ile Pro
210                 215                 220

Ser Gly Leu Phe Trp Gly Leu Cys Leu Leu Ile Pro Glu Ser Pro Arg
225                 230                 235                 240

Phe Leu Val Ser Lys Gly Lys Ile Asp Lys Ala Arg Lys Asn Leu Ala
                245                 250                 255

Tyr Leu Arg Gly Leu Ser Glu Asp His Pro Tyr Ser Val Phe Glu Leu
            260                 265                 270

Glu Asn Ile Ser Lys Ala Ile Glu Glu Asn Phe Glu Gln Thr Gly Arg
        275                 280                 285

Gly Phe Phe Asp Pro Leu Lys Ala Leu Phe Phe Ser Lys Lys Met Leu
290                 295                 300
```

Tyr Arg Leu Leu Leu Ser Thr Ser Met Phe Met Met Gln Asn Gly Tyr
305                 310                 315                 320

Gly Ile Asn Ala Val Thr Tyr Tyr Ser Pro Thr Ile Phe Lys Ser Leu
            325                 330                 335

Gly Val Gln Gly Ser Asn Ala Gly Leu Leu Ser Thr Gly Ile Phe Gly
        340                 345                 350

Leu Leu Lys Gly Ala Ala Ser Val Phe Trp Val Phe Leu Val Asp
    355                 360                 365

Thr Phe Gly Arg Arg Phe Cys Leu Cys Tyr Leu Ser Leu Pro Cys Ser
370                 375                 380

Ile Cys Met Trp Tyr Ile Gly Ala Tyr Ile Lys Ile Ala Asn Pro Ser
385                 390                 395                 400

Ala Lys Leu Ala Ala Gly Asp Thr Ala Thr Thr Pro Ala Gly Thr Ala
            405                 410                 415

Ala Lys Ala Met Leu Tyr Ile Trp Thr Ile Phe Tyr Gly Ile Thr Trp
        420                 425                 430

Asn Gly Thr Thr Trp Val Ile Cys Ala Glu Ile Phe Pro Gln Ser Val
    435                 440                 445

Arg Thr Ala Ala Gln Ala Val Asn Ala Ser Ser Asn Trp Phe Trp Ala
450                 455                 460

Phe Met Ile Gly His Phe Thr Gly Gln Ala Leu Glu Asn Ile Gly Tyr
465                 470                 475                 480

Gly Tyr Tyr Phe Leu Phe Ala Ala Cys Ser Ala Ile Phe Pro Val Val
            485                 490                 495

Val Trp Phe Val Tyr Pro Glu Thr Lys Gly Val Pro Leu Glu Ala Val
        500                 505                 510

Glu Tyr Leu Phe Glu Val Arg Pro Trp Lys Ala His Ser Tyr Ala Leu
    515                 520                 525

Glu Lys Tyr Gln Ile Glu Tyr Asn Glu Gly Glu Phe His Gln His Lys
530                 535                 540

Pro Glu Val Leu Leu Gln Gly Ser Glu Asn Ser Asp
545                 550                 555

<210> SEQ ID NO 12
<211> LENGTH: 543
<212> TYPE: PRT
<213> ORGANISM: Artificial Sequence
<220> FEATURE:
<223> OTHER INFORMATION: sequence of H0 Metschnikowia species Aps1p/
      Hgt19p

<400> SEQUENCE: 12

Met Gly Tyr Glu Glu Lys Leu Val Ala Pro Ala Leu Lys Phe Lys Asn
1               5                   10                  15

Phe Leu Asp Lys Thr Pro Asn Ile His Asn Val Tyr Val Ile Ala Ala
            20                  25                  30

Ile Ser Cys Thr Ser Gly Met Met Phe Gly Phe Asp Ile Ser Ser Met
        35                  40                  45

Ser Val Phe Val Asp Gln Gln Pro Tyr Leu Lys Met Phe Asp Asn Pro
    50                  55                  60

Ser Ser Val Ile Gln Gly Phe Ile Thr Ala Ser Met Ser Leu Gly Ser
65                  70                  75                  80

Phe Phe Gly Ser Leu Thr Ser Thr Phe Ile Ser Glu Pro Phe Gly Arg
            85                  90                  95

Arg Ala Ser Leu Phe Ile Cys Gly Ile Leu Trp Val Ile Gly Ala Ala
        100                 105                 110

-continued

```
Val Gln Ser Ser Gln Asn Arg Ala Gln Leu Ile Cys Gly Arg Ile
    115                 120                 125
Ile Ala Gly Trp Gly Ile Gly Phe Gly Ser Ser Val Ala Pro Val Tyr
130                 135                 140
Gly Ser Glu Met Ala Pro Arg Lys Ile Arg Gly Thr Ile Gly Gly Ile
145                 150                 155                 160
Phe Gln Phe Ser Val Thr Val Gly Ile Phe Ile Met Phe Leu Ile Gly
                165                 170                 175
Tyr Gly Cys Ser Phe Ile Gln Gly Lys Ala Ser Phe Arg Ile Pro Trp
            180                 185                 190
Gly Val Gln Met Val Pro Gly Leu Ile Leu Leu Ile Gly Leu Phe Phe
        195                 200                 205
Ile Pro Glu Ser Pro Arg Trp Leu Ala Lys Gln Gly Tyr Trp Glu Asp
    210                 215                 220
Ala Glu Ile Ile Val Ala Asn Val Gln Ala Lys Gly Asn Arg Asn Asp
225                 230                 235                 240
Ala Asn Val Gln Ile Glu Met Ser Glu Ile Lys Asp Gln Leu Met Leu
                245                 250                 255
Asp Glu His Leu Lys Glu Phe Thr Tyr Ala Asp Leu Phe Thr Lys Lys
            260                 265                 270
Tyr Arg Gln Arg Thr Ile Thr Ala Ile Phe Ala Gln Ile Trp Gln Gln
        275                 280                 285
Leu Thr Gly Met Asn Val Met Met Tyr Tyr Ile Val Tyr Ile Phe Gln
    290                 295                 300
Met Ala Gly Tyr Ser Gly Asn Thr Asn Leu Val Pro Ser Leu Ile Gln
305                 310                 315                 320
Tyr Ile Ile Asn Met Ala Val Thr Val Pro Ala Leu Phe Cys Leu Asp
                325                 330                 335
Leu Leu Gly Arg Arg Thr Ile Leu Leu Ala Gly Ala Ala Phe Met Met
            340                 345                 350
Ala Trp Gln Phe Gly Val Ala Gly Ile Leu Ala Thr Tyr Ser Glu Pro
        355                 360                 365
Ala Tyr Ile Ser Asp Thr Val Arg Ile Thr Ile Pro Asp Asp His Lys
    370                 375                 380
Ser Ala Ala Lys Gly Val Ile Ala Cys Cys Tyr Leu Phe Val Cys Ser
385                 390                 395                 400
Phe Ala Phe Ser Trp Gly Val Gly Ile Trp Val Tyr Cys Ser Glu Val
                405                 410                 415
Trp Gly Asp Ser Gln Ser Arg Gln Arg Gly Ala Ala Leu Ala Thr Ser
            420                 425                 430
Ala Asn Trp Ile Phe Asn Phe Ala Ile Ala Met Phe Thr Pro Ser Ser
        435                 440                 445
Phe Lys Asn Ile Thr Trp Lys Thr Tyr Ile Ile Tyr Ala Thr Phe Cys
    450                 455                 460
Ala Cys Met Phe Ile His Val Phe Phe Phe Pro Glu Thr Lys Gly
465                 470                 475                 480
Lys Arg Leu Glu Glu Ile Gly Gln Leu Trp Asp Glu Gly Val Pro Ala
                485                 490                 495
Trp Arg Ser Ala Lys Trp Gln Pro Thr Val Pro Leu Ala Ser Asp Ala
            500                 505                 510
```

Glu Leu Ala His Lys Met Asp Val Ala His Ala Glu His Ala Asp Leu
    515                 520                 525

Leu Ala Thr His Ser Pro Ser Ser Asp Glu Lys Thr Gly Thr Val
    530                 535                 540

<210> SEQ ID NO 13
<211> LENGTH: 1632
<212> TYPE: DNA
<213> ORGANISM: Artificial Sequence
<220> FEATURE:
<223> OTHER INFORMATION: sequence of H0 Metschnikowia species XYT1

<400> SEQUENCE: 13

| | | |
|---|---|---|
| atgggttacg aggaaaagct tgtagcgccc gcgttgaaat tcaaaaactt tcttgacaaa | 60 |
| acccccaata ttcacaatgt ctatgtcatt gccgccatct cctgtacatc aggtatgatg | 120 |
| tttggatttg atatctcgtc gatgtctgtc tttgtcgacc agcagccata cttgaagatg | 180 |
| tttgacaacc ctagttccgt gattcaaggt ttcattaccg cgctgatgag tttgggctcg | 240 |
| ttttttcggct cgctcacatc cacgttcatc tctgagcctt tggtcgtcg tgcatcgttg | 300 |
| ttcatttgtg gtattctttg ggtaattgga gcagcggttc aaagttcgtc gcagaacagg | 360 |
| gcccaattga tttgtgggcg tatcattgca ggatgggca ttggctttgg gtcatcggtg | 420 |
| gctcctgttt acgggtccga gatggctccg agaaagatca gaggcacgat tggtggaatc | 480 |
| ttccagttct ccgtcaccgt gggtatcttt atcatgttct tgattgggta cggatgctct | 540 |
| ttcattcaag gaaaggcctc tttccggatc cctggggtg tgcaaatggt tcccggcctt | 600 |
| atcctcttga ttggactttt ctttattcct gaatctcccc gttggttggc caaacagggc | 660 |
| tactgggaag acgccgaaat cattgtggcc aatgtgcagg ccaagggtaa ccgtaacgac | 720 |
| gccaacgtgc agattgaaat gtcggagatt aaggatcaat tgatgcttga cgagcacttg | 780 |
| aaggagttta cgtacgctga cctttttcacg aagaagtacc gccagcgcac gatcacggcg | 840 |
| atctttgccc agatctggca acagttgacc ggtatgaatg tgatgatgta ctacattgtg | 900 |
| tacattttcc agatggcagg ctacagcggc aacacgaact tggtgcccag tttgatccag | 960 |
| tacatcatca acatgcggt cacggtgccg gcgcttttct gcttggatct cttgggccgt | 1020 |
| cgtaccattt tgctcgcggg tgccgcgttc atgatggcgt ggcaattcgg cgtggcgggc | 1080 |
| attttggcca cttactcaga accggcatat atctctgaca ctgtgcgtat cacgatcccc | 1140 |
| gacgaccaca gtctgctgc aaaaggtgtg attgcatgct gctatttgtt tgtgtgctcg | 1200 |
| tttgcattct cgtgggggtgt cggtatttgg gtgtactgtt ccgaggtttg gggtgactcc | 1260 |
| cagtcgagac aaagaggcgc cgctcttgcg acgtcggcca actggatctt caacttcgcc | 1320 |
| attgccatgt tcacgccgtc ctcattcaag aatatcacgt ggaagacgta tatcatctac | 1380 |
| gccacgttct gtgcgtgcat gttcatacac gtgttttttct tttcccaga aacaaagggc | 1440 |
| aagcgtttgg aggagatagg ccagctttgg gacgaaggag tcccagcatg gaggtcagcc | 1500 |
| aagtggcagc caacagtgcc gctcgcgtcc gacgcagagc ttgcacacaa gatggatgtt | 1560 |
| gcgcacgcgg agcacgcgga cttattggcc acgcactcgc catcttcaga cgagaagacg | 1620 |
| ggcacggtct aa | 1632 |

<210> SEQ ID NO 14
<211> LENGTH: 1635
<212> TYPE: DNA
<213> ORGANISM: Artificial Sequence
<220> FEATURE:
<223> OTHER INFORMATION: sequence of H0 Metschnikowia species GXF1

<400> SEQUENCE: 14

```
atgtctcaag acgaacttca tacaaagtct ggtgttgaaa caccaatcaa cgattcgctt    60
ctcgaggaga agcacgatgt caccccactc gcggcattgc ccgagaagtc cttcaaggac   120
tacatttcca tttccatttt ctgtttgttt gtggcatttg gtggttttgt tttcggtttc   180
gacaccggta cgatttccgg tttcgtcaac atgtccgact caagaccag atttggtgag    240
atgaatgccc agggcgaata ctacttgtcc aatgttagaa ctggtttgat ggtttctatt   300
ttcaacgtcg gttgcgccgt tggtggtatc ttcctttgta agattgccga tgtttatggc   360
agaagaattg gtcttatgtt ttccatggtg gtttatgtcg ttggtatcat tattcagatt   420
gcctccacca ccaaatggta ccaatacttc attggccgtc ttattgctgg cttggctgtg   480
ggtactgttt ccgtcatctc gccactttc atttccgagg ttgctcctaa acagctcaga   540
ggtacgcttg tgtgctgctt ccagttgtgt atccacttgg gtatctttt gggttactgc    600
acgacctacg gtacaaagac ttacactgac tccagacagt ggagaatccc attgggtatc   660
tgtttcgcgt gggctttgtt tttggtgcc ggtatgttga acatgccga gtctcctaga    720
tacttggttg agaaatcgag aatcgacgat gccagaaagt ccattgccag atccaacaag   780
gtttccgagg aagaccccgc cgtgtacacc gaggtgcagc ttatccaggc tggtattgac   840
agagaggccc ttgccggcag cgccacatgg atggagcttg tgactggtaa gcccaaaatc   900
ttcagaaagg tcatcatggg tgtcatgctt cagtccttgc aacaattgac tggtgacaac   960
tactttttct actacggaac cacgattttc aaggctgttg gcttgcagga ctctttccag  1020
acgtcgatta tcttgggtat tgtcaacttt gcctcgactt tgtcggtat ttacgccatt   1080
gagagaatgg gcagaagatt gtgtttgttg accggatctg cgtgcatgtt tgtgtgtttc  1140
atcatctact cgctcattgg tacgcagcac ttgtacaaga acggcttctc taacgaacct   1200
tccaacacat acaagccttc cggtaacgcc atgatcttca tcacgtgtct ttacattttc  1260
ttctttgcct cgacctgggc cggtggtgtt tactgtatcg tgtccgagtc ttacccattg   1320
agaatcagat ccaaggccat gtctgtcgcc accgccgcca actggatgtg gggtttcttg   1380
atctcgttct tcacgccttt catcacctcc gccatccact tttactacgg ttttgttttc   1440
actggctgct tggcgttctc cttcttctac gtctacttct ttgtcgtgga gaccaagggt   1500
ctttccttgg aggaggttga catttgtac gcttccggta cgcttccatg gaagtcctct   1560
ggctgggtgc ctcctaccgc ggacgaaatg gcccacaacg ccttcgacaa caagccaact   1620
gacgaacaag tctaa                                                   1635
```

<210> SEQ ID NO 15
<211> LENGTH: 1425
<212> TYPE: DNA
<213> ORGANISM: Artificial Sequence
<220> FEATURE:
<223> OTHER INFORMATION: sequence of H0 Metschnikowia species delta-GXF1 (variant of GXF1 with shorter N-terminus)

<400> SEQUENCE: 15

```
atgtccgact caagaccag atttggtgag atgaatgccc agggcgaata ctacttgtcc    60
aatgttagaa ctggtttgat ggtttctatt ttcaacgtcg gttgcgccgt tggtggtatc   120
ttcctttgta agattgccga tgtttatggc agaagaattg gtcttatgtt ttccatggtg   180
gtttatgtcg ttggtatcat tattcagatt gcctccacca ccaaatggta ccaatacttc   240
attggccgtc ttattgctgg cttggctgtg ggtactgttt ccgtcatctc gccactttc    300
```

-continued

| | |
|---|---|
| atttccgagg ttgctcctaa acagctcaga ggtacgcttg tgtgctgctt ccagttgtgt | 360 |
| atcaccttgg gtatcttttt gggttactgc acgacctacg gtacaaagac ttacactgac | 420 |
| tccagacagt ggagaatccc attgggtatc tgtttcgcgt gggctttgtt tttggtggcc | 480 |
| ggtatgttga acatgcccga gtctcctaga tacttggttg agaaatcgag atcgacgat | 540 |
| gccagaaagt ccattgccag atccaacaag gtttccgagg aagacccgc cgtgtacacc | 600 |
| gaggtgcagc ttatccaggc tggtattgac agagaggccc ttgccggcag cgccacatgg | 660 |
| atggagcttg tgactggtaa gcccaaaatc ttcagaagag tcatcatggg tgtcatgctt | 720 |
| cagtccttgc aacaattgac tggtgacaac tactttttct actacggaac cacgattttc | 780 |
| aaggctgttg gcttgcagga ctctttccag acgtcgatta tcttgggtat tgtcaacttt | 840 |
| gcctcgactt ttgtcggtat ttacgccatt gagagaatgg gcagaagatt gtgtttgttg | 900 |
| accggatctg cgtgcatgtt tgtgtgtttc atcatctact cgctcattgg tacgcagcac | 960 |
| ttgtacaaga acggcttctc taacgaacct tccaacacat acaagccttc cggtaacgcc | 1020 |
| atgatcttca tcacgtgtct ttacattttc ttctttgcct cgacctgggc cggtggtgtt | 1080 |
| tactgtatcg tgtccgagtc ttacccattg agaatcagat ccaaggccat gtctgtcgcc | 1140 |
| accgccgcca actggatgtg gggtttcttg atctcgttct tcacgccttt catcacctcc | 1200 |
| gccatccact tttactacgg ttttgttttc actggctgct ggcgttctc cttcttctac | 1260 |
| gtctacttct ttgtcgtgga gaccaagggt ctttccttgg aggaggttga cattttgtac | 1320 |
| gcttccggta cgcttccatg gaagtcctct ggctgggtgc ctcctaccgc ggacgaaatg | 1380 |
| gcccacaacg ccttcgacaa caagccaact gacgaacaag tctaa | 1425 |

<210> SEQ ID NO 16
<211> LENGTH: 1647
<212> TYPE: DNA
<213> ORGANISM: Artificial Sequence
<220> FEATURE:
<223> OTHER INFORMATION: sequence of H0 Metschnikowia species GXF2/GAL2

<400> SEQUENCE: 16

| | |
|---|---|
| atgagtgccg aacaggaaca acaagtatcg ggcacatctg ccacgataga tgggctggcg | 60 |
| tccttgaagc aagaaaaaac cgccgaggag gaagacgcct tcaagcctaa gcccgccacg | 120 |
| gcgtactttt tcatttcgtt cctctgtggc ttggtcgcct ttggcggcta cgttttcggt | 180 |
| ttcgataccg gtacgatttc cgggtttgtt aacatggacg actatttgat gagattcggc | 240 |
| cagcagcacg ctgatggcac gtattacctt tccaacgtga gaaccggttt gatcgtgtcg | 300 |
| atcttcaaca ttggctgtgc cgttggtggt cttgcgcttt cgaaagtcgg tgacatttgg | 360 |
| ggcagaagaa ttggtattat ggttgctatg atcatctaca tggtgggaat catcatccag | 420 |
| atcgcttcac aggataaatg gtaccagtac ttcattggcc gtttgatcac cggattgggt | 480 |
| gtcggcacca cgtccgtgct tagtcctctt ttcatctccg agtcggctcc gaagcatttg | 540 |
| agaggcaccc ttgtgtgttg tttccagctc atggtcacct gggtatctt tttgggctac | 600 |
| tgcacgacct acggtaccaa gaactacact gactcgcgcc agtggcggat tcccttgggt | 660 |
| ctttgcttcg catgggctct tttgttgatc tcgggaatgg ttttcatgcc tgaatcccca | 720 |
| cgtttcttga ttgagcgcca gagattcgac gaggccaagg cttccgtggc caaatcgaac | 780 |
| caggtttcga ccgaggaccc cgccgtgtac actgaagtcg agttgatcca ggccggtatt | 840 |
| gaccgtgagc cattggccgg atccgctggc tggaaagagc ttatcacggg taagcccaag | 900 |
| atgttgcagc gtgtgattttt gggaatgatg ctccagtcga tccagcagct taccggtaac | 960 |

```
aactactttt tctactatgg taccacgatc ttcaaggccg tgggcatgtc ggactcgttc    1020
cagacctcga ttgttttggg tattgtcaac ttcgcctcca cttttgtcgg aatctgggcc    1080
atcgaacgca tgggccgcag atcttgtttg cttgttggtt ccgcgtgcat gagtgtgtgt    1140
ttcttgatct actccatctt gggttccgtc aacctttaca tcgacggcta cgagaacacg    1200
ccttccaaca cgcgtaagcc taccggtaac gccatgattt tcatcacgtg tttgttcatc    1260
ttcttcttcg cctccacctg ggccggtggt gtgtacagta ttgtgtctga aacataccca    1320
ttgagaatcc gctctaaagg tatggccgtg ccaccgctg ccaactggat gtggggtttc     1380
ttgatttcgt tcttcacgcc tttcatcacc tcggccatcc acttctacta cgggtttgtg    1440
ttcacagggt gtcttatttt ctccttcttc tacgtgttct tctttgttag ggaaaccaag    1500
ggtctctcgt tggaagaggt ggatgagtta tatgccactg acctcccacc atggaagacc    1560
gcgggctgga cgcctccttc tgctgaggat atggcccaca ccaccgggtt tgccgaggcc    1620
gcaaagccta cgaacaaaca cgtttaa                                       1647

<210> SEQ ID NO 17
<211> LENGTH: 1509
<212> TYPE: DNA
<213> ORGANISM: Artificial Sequence
<220> FEATURE:
<223> OTHER INFORMATION: sequence of H0 Metschnikowia species delta-GXS1
      /delta-HGT12 (variant of GXS1 /HGT12 with shorter N-terminus)

<400> SEQUENCE: 17
atgggcattt tcgttggcgt tttcgccgcg cttggcggtg ttctctttgg ctacgatacc      60
ggtaccatct ctggtgtgat ggccatgcct tgggtcaagg aacatttccc aaaagaccgt    120
gttgcattta gtgcttccga gtcgtcgttg attgtgtcta ttttatctgc aggaactttc    180
tttggagcca ttcttgctcc gctcttgacc gatacattgg gtagacgctg gtgtattatc    240
atctcttcgc tcgttgtgtt caatttgggt gctgctttgc agacggctgc cacggatatc    300
ccgctcttga ttgttggtcg tgtcattgcc ggtttagggg ttggtttgat ttcgctgacg    360
attccattgt accagtccga agcgcttccc aaatggatta gaggtgctgt tgtctcgtgc    420
taccaatggg ccattactat tggtatcttt ttggctgccg tgatcaacca gggcactcac    480
aagatcaaca gccctgcgtc gtacagaatt ccattgggta ttcagatggc atggggtctt    540
atctggggtg tcggcatgtt cttcttgccc gagacgcctc gtttctacat ttccaagggc    600
cagaatgcga aggctgctgt tcattggcg cgtttgagaa agcttccgca agatcacccg     660
gagttgttgg aggaattgga agatatccag gcggcatacg agtttgagac tgtccatggc    720
aagtcttcat ggctgcaggt tttcaccaac aagaacaaac aattgaagaa gttggccacg    780
ggcgtgtgct tgcaggcgtt ccaacaattg actggtgtga acttcatttt ctactttggc    840
acgactttct tcaacagtgt tgggcttgac ggattcacca cctccttggc caccaacatt    900
gtcaatgttg gctcgacgat ccctggtatt ttgggtgttg agattttcgg cagaagaaaa    960
gtgttgttga ccggcgctgc tggtatgtgt ctttcgcaat tcattgttgc cattgttggt    1020
gtagccaccg actccaaggc tgcgaaccaa gttcttattg ccttctgctg cattttcatt    1080
gcgttctttg cagccacctg ggcccccacc gcatggggttg tttgtggcga gtttttcccc    1140
ttgagaacca gagccaagtc gattgccatg tgcgctgctt cgaactggtt gttgaactgg    1200
gcaattgcat acgccacgcc atacttggtt gactccgata agggtaactt gggcaccaat    1260 gtgttttca tttgggggaag ctgtaacttc ttctgccttg tgtttgccta cttcatgatt    1320
```

```
tacgagacca agggtctttc cttggagcag gttgatgagc tttacgagaa ggttgccagc    1380
gccagaaagt cgcctggctt cgtgccaagc gagcacgctt tcagagagca cgccgatgtg    1440
gagaccgcca tgccagacaa cttcaacttg aaggcggagg cgatttctgt cgaggatgcc    1500
tctgtttaa                                                              1509

<210> SEQ ID NO 18

<400> SEQUENCE: 18

000

<210> SEQ ID NO 19
<211> LENGTH: 1647
<212> TYPE: DNA
<213> ORGANISM: Artificial Sequence
<220> FEATURE:
<223> OTHER INFORMATION: sequence of H0 Metschnikowia species GXS1/HGT12

<400> SEQUENCE: 19
atgagcatct tgaaggcaa agacgggaag ggggtatcct ccaccgagtc gctttccaat      60
gacgtcagat atgacaacat ggagaaagtt gatcaggatg ttcttagaca caacttcaac    120
tttgacaaag aattcgagga gctcgaaatc gaggcggcgc aagtcaacga caaaccttct    180
tttgtcgaca ggattttatc cctcgaatac aagcttcatt tcgaaaacaa gaaccacatg    240
gtgtggctct gggcgctttt cgcagccgcc gcaggcttat tgtctggctt ggatcagtcc    300
attatttctg gtgcatccat tggaatgaac aaagcattga acttgactga acgtgaagcc    360
tcattggtgt cttcgcttat gccttaggc gccatggcag gctccatgat tatgacacct      420
cttaatgagt ggttcggaag aaaatcatcg ttgattattt cttgtatttg gtataccatc    480
ggatccgctt tgtgcgctgg cgccagagat caccacatga gtacgctgg cagatttatt     540 cttggtgtcg gtgtgggtat agaaggtggg tgtgtgggca tttacatttc cgagtctgtc    600
ccagccaatg tgcgtggtag tatcgtgtcg atgtaccagt tcaatattgc tttgggtgaa    660
gttctagggt atgctgttgc tgccattttc tacactgttc atggtggatg gaggttcatg    720
gtggggtctt ctttagtatt ctctactata ttgtttgccg gattgttttt cttgcccgag    780
tcacctcgtt ggtggtgca caaaggcaga acggaatgg catacgatgt gtggaagaga       840
ttgagagaca taaacgatga agcgcaaag ttggaatttt ggagatgag acaggctgct       900 tatcaagaga gagaaagacg ctcgcaagag tctttgttct ccagctgggg cgaattattc    960
accatcgcta gaaacagaag agcacttact tactctgtca aatgatcac tttgggtcaa    1020 ttgactggtg tcaatgccgt catgtactac atgtcgactt tgatgggtgc aattggtttc   1080
aacgagaaag actctgtgtt catgtcccct gtgggaggcg gttcttttgct tataggtacc    1140 attcctgcca ttttgtggat ggaccgtttc ggcagaagag tttggggtta taatcttgtt    1200
ggtttcttcg ttggttggt gctcgttggt gttggctacc gtttcaatcc cgtcactcaa    1260
aaggcggctt cagaaggtgt gtacttgacg ggtctcattg tctatttctt gttctttggt   1320
tcctactcga ccttaactgg ggtcattcca tccgagtctt tgatttgag acaagatct     1380 ttgggtatga caatctgttc cactttcctt tacttgtggt ctttcaccgt cacctacaac    1440
ttcaccaaga tgtccgccgc cttcacatac actgggttga cacttggttt ctacggtggc    1500
attgcgttcc ttggtttgat taccaggtc tgcttcatgc ccgagacgaa ggacaagact     1560
```

```
ttggaagaaa ttgacgatat cttcaatcgt tctgcgttct ctatcgcgcg cgagaacatc      1620
tccaacttga agaagggtat ttggtaa                                          1647

<210> SEQ ID NO 20
<211> LENGTH: 1647
<212> TYPE: DNA
<213> ORGANISM: Artificial Sequence
<220> FEATURE:
<223> OTHER INFORMATION: sequence of H0 Metschnikowia species HXT5

<400> SEQUENCE: 20
atgagcatct tgaaggcaaa gacgggaag ggggtatcct ccaccgagtc gctttccaat        60
gacgtcagat atgacaacat ggagaaagtt gatcaggatg ttcttagaca caacttcaac      120
tttgacaaag aattcgagga gctcgaaatc gaggcggcgc aagtcaacga caaaccttct      180
tttgtcgaca ggatttttatc cctcgaatac aagcttcatt cgaaaacaa gaaccacatg      240 gtgtggctct gggcgctttt cgcagccgcc gcaggcttat tgtctggctt ggatcagtcc      300
attatttctg gtgcatccat ggaatgaac aaagcattga acttgactga acgtgaagcc       360
tcattggtgt cttcgcttat gcctttaggc gccatggcag ctccatgat tatgacacct       420 cttaatgagt ggttcggaag aaaatcatcg ttgattattt cttgtatttg gtataccatc      480
ggatccgctt tgtgcgctgg cgccagagat caccacatga tgtacgctgg cagatttatt      540
cttggtgtcg gtgtgggtat agaaggtggg tgtgtgggca tttacatttc cgagtctgtc      600
ccagccaatg tgcgtggtag tatcgtgtcg atgtaccagt tcaatattgc tttgggtgaa      660
gttctagggt atgctgttgc tgccattttc tacactgttc atggtggatg gaggttcatg      720
gtggggtctt ctttagtatt ctctactata ttgtttgccg gattgttttt cttgcccgag      780
tcacctcgtt ggttggtgca caaaggcaga acggaatgg catacgatgt gtggaagaga       840
ttgagagaca taaacgatga aagcgcaaag ttggaatttt tggagatgag acaggctgct      900
tatcaagaga gagaaagacg ctcgcaagag tctttgttct ccagctgggg cgaattattc      960
accatcgcta gaaacagaag agcacttact tactctgtca taatgatcac tttgggtcaa     1020
ttgactggtg tcaatgccgt catgtactac atgtcgactt tgatgggtgc aattggtttc     1080
aacgagaaag actctgtgtt catgtccctt gtgggaggcg gttctttgct tataggtacc     1140
attcctgcca ttttgtggat ggaccgtttc ggcagaagag tttggggtta taatcttgtt     1200
ggtttcttcg ttggtttggt gctcgttggt gttggctacc gtttcaatcc cgtcactcaa     1260
aaggcggctt cagaaggtgt gtacttgacg ggtctcattg tctatttctt gttctttggt     1320
tcctactcga ccttaacttg ggtcattcca tccgagtctt tgatttgag aacaagatct      1380 ttgggtatga caatctgttc cactttcctt tacttgtggt ctttcaccgt cacctacaac     1440
ttcaccaaga tgtccgccgc cttcacatac actgggttga cacttggttt ctacggtggc     1500
attgcgttcc ttggttttgat ttaccaggtc tgcttcatgc ccgagacgaa ggacaagact     1560
ttggaagaaa ttgacgatat cttcaatcgt tctgcgttct ctatcgcgcg cgagaacatc     1620
tccaacttga agaagggtat ttggtaa                                         1647

<210> SEQ ID NO 21
<211> LENGTH: 1632
<212> TYPE: DNA
<213> ORGANISM: Artificial Sequence
<220> FEATURE:
<223> OTHER INFORMATION: sequence of H0 Metschnikowia species XYT1 codon
      optimized for expression in S. cerevisiae
```

<400> SEQUENCE: 21

```
atgggatacg aagagaaatt agtggccccc gctttgaaat ttaagaactt tttggataag      60
accccaaata tacataacgt ttacgtaatt gcggcgatct cgtgtacctc aggtatgatg     120
ttcggtttcg atatatcgtc gatgtccgtg ttcgtggacc aacagccgta tttaaaaatg     180
tttgataacc ctagcagcgt gatacaaggg tttataactg cgttgatgtc tttggggagc     240
tttttcggat cgctaacgtc cacttttatt tcagaacctt ttggtagacg tgcctctttg     300
ttcatatgcg ggatcctttg ggtaattggg gcggcagttc aaagttcttc tcagaaccgt     360
gcgcagctta tttgtggccg aattattgca gggtggggca tcggattcgg ttctagcgtt     420
gcgccggtat acggttcaga atggccccca cgcaaaatta gaggaacaat cggaggtatt     480
tttcaatttt ctgtcacggt cggaatattc ataatgttcc tgattggcta cggctgctca     540
tttatacaag gcaaggccag ttttagaatt ccgtggggag ttcaaatggt accaggtctc     600
attctgttga tcggactatt cttcattcct gaatccccaa gatggttagc caaacaaggc     660
tactgggaag acgctgagat catcgtagca aacgttcaag ctaagggtaa caggaacgat     720
gctaatgtgc aaattgaaat gtccgagata aagatcagt taatgcttga cgagcattta     780
aaggagttta cttatgccga tttgtttacc aaaaaatacc ggcaaaggac gataacagct     840
atatttgccc aaatatggca acagctgaca ggtatgaatg tcatgatgta ctacatcgta     900
tatatatttc aaatggcagg ttattcaggt aatactaatt tagttccttc actcattcag     960
tatattataa atatggctgt tacggtcccc gcattgttct gtcttgatct gcttggcagg    1020
aggacaattt tattagctgg cgccgctttt atgatggcct ggcaatttgg tgttgctggc    1080
attttagcta cttattcaga gccagcctat atttcagata ccgtgagaat tacaattcca    1140
gatgaccata aaagtgccgc taagggtgtc atcgcttgct gctatttgtt tgtttgttcc    1200
ttcgcctttt cctggggtgt aggtatctgg gtttattgtt cagaagtgtg gggtgatagt    1260
caatccagac aaagaggtgc tgcattggca acttctgcta attggatctt caatttcgca    1320
attgcaatgt ttacaccttc ttctttcaaa aatatcactt ggaagactta tcatttat     1380
gctacatttt gtgcttgtat gttcattcat gtttttttt ttttccctga acaaagggt     1440
aagagactag aagaaattgg acagctatgg gatgaaggtg tcccagcatg gagatctgca    1500
aaatggcaac ccactgtccc actagcaagt gacgctgaat tagctcacaa aatggatgtt    1560
gcacacgctg aacacgcaga cttattggca acccattctc caagtagtga cgaaaaaact    1620
ggtaccgttt aa                                                       1632
```

<210> SEQ ID NO 22
<211> LENGTH: 1575
<212> TYPE: DNA
<213> ORGANISM: Artificial Sequence
<220> FEATURE:
<223> OTHER INFORMATION: sequence of H0 Metschnikowia species HXT2.6

<400> SEQUENCE: 22

```
atgctgagca ctaccgatac cctcgaaaaa agggacaccg agcctttcac ttcagatgct      60
cctgtcacag tccatgacta tatcgcagag gagcgtccgt ggtggaaagt gccgcatttg     120
cgtgtattga cttggtctgt tttcgtgatc accctcacct ccaccaacaa cgggtatgat     180
ggcctgatgt tgaatggatt gcaatccttg gacatttggc aggaggattt gggtcaccct     240
gcgggccaga aattgggtgc cttggccaac ggtgttttgt ttggtaacct tgctgctgtg     300
ccttttgctt cgtatttctg cgatcgtttt ggtagaaggc cggtcatttg tttcggacag     360
```

```
atcttgacaa ttgttggtgc tgtattacaa ggtttgtcca acagctatgg atttttttg      420
ggttcgagaa ttgtgttggg ttttggtgct atgatagcca ctattccgct gccaacattg     480
atttccgaaa tcgcctaccc tacgcataga gaaacttcca ctttcgccta caacgtgtgc     540
tggtatttgg gagccattat cgcctcctgg gtcacatacg gcaccagaga tttacagagc     600
aaggcttgct ggtcaattcc ttcttatctc caggccgcct tacctttctt tcaagtgtgc     660
atgatttggt ttgtgccaga gtctcccaga ttcctcgttg ccaagggcaa gatcgaccaa     720
gcaagggctg ttttgtctaa ataccataca ggagactcga ctgacccag agacgttgcg      780
ttggttgact ttgagctcca tgagattgag agtgcattgg agcaggaaaa attgaacact     840
cgctcgtcat actttgactt tttcaagaag agaaacttta gaaagagagg cttcttgtgt     900
gtcatggtcg gtgttgcaat gcagctttct ggaaacggct tagtgtccta ttacttgtcg     960
aaagtgctag actcgattgg aatcactgaa accaagagac agctcgagat caatggctgc    1020
ttgatgatct ataactttgt catctgcgtc tcgttgatga gtgtttgccg tatgttcaaa    1080
agaagagtat tatttctcac gtgtttctca ggaatgacgg tttgctacac gatatggacg    1140
attttgtcag cgcttaatga acagagacac tttgaggata aaggcttggc caatggcgtg    1200
ttggcaatga tcttcttcta ctattttttc tacaacgttg gcatcaatgg attgccattc    1260
ctatacatca ccgagatctt gccttactca cacagagcaa aaggcttgaa tttattccaa    1320
ttctcgcaat ttctcacgca aatctacaat ggctatgtga cccaatcgc catggacgca     1380
atcagctgga agtattacat tgtgtactgc tgtattctct tcgtggagtt ggtgattgtg    1440
tttttcacgt tcccagaaac ttcgggatac actttggagg aggtcgccca ggtatttggt    1500
gatgaggctc ccgggctcca acagacaa ttggatgttg cgaaagaatc actcgagcat      1560
gttgagcatg tttga                                                     1575

<210> SEQ ID NO 23
<211> LENGTH: 1605
<212> TYPE: DNA
<213> ORGANISM: Artificial Sequence
<220> FEATURE:
<223> OTHER INFORMATION: sequence of H0 Metschnikowia species HXT2.6
      codon optimized for expression in S. cerevisiae

<400> SEQUENCE: 23
atgagccagt ctaaagaaaa gtccaacgtt attaccaccg tcttgtctga agaattgcca       60
gttaagtact ccgaagaaat ctccgattac gtttaccatg atcaacattg gtggaagtac      120
aaccacttca gaaaattgca ttggtacatc ttcgttctga ctttgacttc taccaacaat      180
ggttacgatg gctctatgtt gaacggtcta caatctttgt ctacttggaa agatgctatg      240
ggtaatcctg aaggttacat ttttgggtgct ttggctaatg gtactatttt cggtggtgtt     300
ttggctgttg ctttttgcttc ttgggcttgt gatagatttg gtagaaagtt gactacctgc     360
ttcggttcta tcgttactgt tattggtgct atattgcaag gtgcctctac taattacgca     420
ttctttttcg tttcccgtat ggttattggt tttggtttcg gtctagcttc tgttgcttct     480
ccaactttga ttgctgaatt gtcttttccca acttacagac aacttgtac tgccttgtac      540
aatgtttttt ggtacttggg tgctgttatt gctgcatggg ttacttatgg tactagaact     600
atcgtttctg cctactcttg gagaaattcca tcttacttgc aaggtttgtt gccattggtt    660
caagtttgtt tggtttggtg ggttccgaaa tctccaagat tcttggtttc taagggtaag    720
attgaaaagg ccagggaatt cttgattaag ttccatactg gtaacgacac ccaagaacaa    780
```

```
gctactagat tggtcgaatt tgagttgaaa gaaattgaag ccgccttgga gatggaaaag      840
attaactcta attctaagta caccgacttc atcaccatca agactttcag aaagagaatc      900
ttcttggttg ctttcactgc ttgtatgact caattgtctg gtaacggttt ggtgtcttac      960
tacttgtcca aggttttgat ctccattggt attaccggtg agaaagaaca attgcaaatc     1020
aacggttgcc tgatgatcta caacttggtt ttgtctttag ctgttgcctt cacctgttac     1080
ttgtttagaa gaaaggccct gttcatcttc tcttgctcat tcatgttgtt gtcctacgtt     1140
atttggacca ttctgtccgc tatcaatcaa cagagaaact tcgaacaaaa aggtctaggt     1200
caaggtgtct tggctatgat ttttatctac tacttggcct acaacatcgg tttgaatggt     1260
ttgccatact tgtacgttac cgaaatcttg ccatatactc atagagctaa gggcatcaac     1320
ttgtattcct tggttattaa catcaccctg atctataacg gtttcgttaa cgctattgct     1380
atggatgcta tttcctggaa gtactacatc gtttactgct gcattattgc cgttgaattg     1440
gttgttgtta tcttcaccta cgttgaaact ttcggttaca ccttggaaga agttgctaga     1500 gttttttgaag gtactgattc tttggccatg gacattaact tgaacggtac agtttccaac     1560
gaaaagatcg atatcgttca ctctgaaaga ggttcctctg cttaa                     1605
```

<210> SEQ ID NO 24
<211> LENGTH: 1692
<212> TYPE: DNA
<213> ORGANISM: Artificial Sequence
<220> FEATURE:
<223> OTHER INFORMATION: sequence of H0 Metschnikowia species QUP2

<400> SEQUENCE: 24

```
atgggctttc gcaacttaaa gcgcaggctc tcaaatgttg gcgactccat gtcagtgcac       60
tctgtgaaag aggaggaaga cttctcccgc gtggaaatcc cggatgaaat ctacaactat      120
aagatcgtcc ttgtggcttt aacagcggcg tcggctgcca tcatcatcgg ctacgatgca      180
ggcttcattg gtggcacggt ttcgttgacg gcgttcaaac tggaatttgg cttggacaaa      240
atgtctgcga cggcggcttc tgctatcgaa gccaacgttg tttccgtgtt ccaggccggc      300
gcctactttg ggtgtctttt cttctatccg attggcgaga tttggggccg taaaatcggt      360
cttcttcttt ccggctttct tttgacgttt ggtgctgcta tttctttgat ttcgaactcg      420
tctcgtggcc ttggtgccat atatgctgga agagtactaa caggttttgg gattggcgga      480
tgtctgagtt tggccccaat ctacgtttct gaaatcgcgc ctgcagcaat cagaggcaag      540
cttgtgggct gctgggaagt gtcatggcag gtgggcggca ttgttggcta ctggatcaat      600
tacggagtct tgcagactct tccgattagc tcacaacaat ggatcatccc gtttgctgta      660
caattgatcc catcggggct tttctgggggc ctttgtcttt tgattccaga gctgccacgt      720
tttcttgtat cgaagggaaa gatcgataag gcgcgcaaaa acttagcgta cttgcgtgga      780
cttagcgagg accaccccta ttctgttttt gagttggaga acattagtaa ggccattgaa      840
gagaacttcg agcaaacagg aagggggtttt ttcgacccat tgaaagcttt gtttttcagc      900
aaaaaaatgc tttaccgcct tctcttgtcc acgtcaatgt tcatgatgca gaatggctat      960
ggaatcaatg ctgtgacata ctactcgccc acgatcttca aatccttagg cgttcagggc     1020
tcaaacgccg gtttgctctc aacaggaatt ttcggtcttc ttaaaggtgc cgcttcggtg     1080
ttctgggtct ttttccttggt tgacacattc ggccgccggt tttgtctttg ctacctctct     1140
ctcccctgct cgatctgcat gtggtatatt ggcgcataca tcaagattgc caaccccttca     1200 gcgaagcttg ctgcaggaga cacagccacc accccagcag gaactgcagc gaaagcgatg     1260
```

```
ctttacatat ggacgattt  ctacggcatt  acgtggaatg  gtacgacctg  ggtgatctgc   1320
gcggagattt  tcccccagtc ggtgagaaca  gccgcgcagg  ccgtcaacgc  ttcttctaat   1380
tggttctggg  ctttcatgat  cggccacttc  actggccagg  cgctcgagaa  tattgggtac   1440
ggatactact  tcttgtttgc  ggcgtgctct  gcaatcttcc  ctgtggtagt  ctggtttgtg   1500
taccccgaaa  caagggtgt   gccttggag   gccgtggagt  atttgttcga  ggtgcgtcct   1560
tggaaagcgc  actcatatgc  tttggagaag  taccagattg  agtacaacga  gggtgaattc   1620
caccaacata  agcccgaagt  actcttacaa  gggtctgaaa  actcggacac  gagcgagaaa   1680
agcctcgcct  ga                                                          1692
```

<210> SEQ ID NO 25
<211> LENGTH: 2049
<212> TYPE: DNA
<213> ORGANISM: Artificial Sequence
<220> FEATURE:
<223> OTHER INFORMATION: sequence of H0 Metschnikowia species QUP2 codon optimized for expression in S. cerevisiae

<400> SEQUENCE: 25

```
atgggtttca  gaaacttgaa  gagaagattg  tctaacgttg  gtgactccat  gtctgttcac     60
tctgttaagg  aagaagaaga  cttctccaga  gttgaaatcc  cagatgaaat  ctacaactac    120
aagatcgtct  tggttgcttt  gactgctgct  tctgctgcta  tcatcatcgg  ttacgatgct    180
ggtttcattg  gtggtactgt  ttcttttgact gctttcaagt  ctgaattcgg  tttggacaag    240
atgtctgcta  ctgctgcttc  tgctatcgaa  atgggtttca  gaaacttgaa  gaggcgtttg    300
tctaatgttg  gtgattccat  gtctgttcac  tccgtcaaag  aagaagagga  tttctccaga    360
gttgaaatcc  cagacgaaat  ctacaactac  aagatcgttt  tggttgcttt  gactgctgct    420
tctgctgcta  ttatcattgg  ttatgatgct  ggtttcatcg  gtggtactgt  ttcttttgaca    480 gctttcaagt  ctgaattcgg  tttggataag  atgtctgcta  cagctgcttc  agctattgaa    540
gctaatgttg  tctctgttt   tcaagctggt  gcttactttg  gttgcctgtt  ttttaccca    600 attggtgaaa  tttggggtcg  taagattggt  ttgttgtgt   ctggtttctt  gttgactttt    660
ggtgctgcca  tttccttgat  ctctaattct  tctagaggtt  tgggtgctat  ctatgctggt    720
agagttttga  ctggtttagg  tattggtggt  tgttcttctt  tagctcccat  ctacgttagt    780
gaaattgctc  cagctgcaat  tagaggtaag  ttagttggtt  gttgggaagt  ttcttggcaa    840
gttggtggta  tcgttggtta  ttggattaac  tatggtgtct  tgcaaaccct  gccaatctct    900
tctcaacaat  ggattattcc  attcgccgtt  caattgattc  catctggttt  gttttggggt    960
ttgtgcttgt  tgattccaga  atctccaaga  ttccttggtg  tccaaaggtaa gattgataag   1020 gccagaaaga  acttggctta  cttgagaggt  ttgtctgaag  atcatccata  ctccgttttt   1080
gagttggaga  catttccaa   ggccatcgaa  gaaactttg   aacaaacagg  tagaggtttc   1140
ttcgacccat  tgaaggcttt  gttttcagc   aagaaaatgc  tgtacaggct  gctgttgtct   1200
acttctatgt  ttatgatgca  aaacggctac  ggtattaacg  ctgttactta  ttactctccc   1260
accatcttta  gtccttgggg  tgttcaaggt  tctaatgccg  gtttgttatc  tactggtatt   1320
ttcggtttgt  tgaaaggtgc  cgcttctgtt  ttttgggttt  tcttcttggt  tgataccttc   1380
ggtagaagat  tctgtttgtg  ctatttgtct  ttgccatgct  ctatctgcat  gtggtatatt   1440
ggtgcctaca  ttaagattgc  taacccatct  gctaaattgg  ctgctggtga  tactgctact   1500
actccagctg  gtactgctgc  taaagctatg  ttgtatattt  ggaccatctt  ctacggtatc   1560
```

```
acttggaatg gtactacctg ggttatttgc gctgaaattt ttccacaatc tgttagaaca    1620
gctgctcaag ctgttaatgc ttcttctaat tggttttggg ccttcatgat tggtcatttt    1680
actggtcaag cttttggaaaa cattggttac ggttactact ttttgttcgc tgcttgttcc    1740 gctatttttcc cagttgtagt ttggttcgtt tacccagaaa caaaaggtgt tccattggaa    1800
gctgttgaat acttgtttga agttagacca tggaaggctc attcttacgc tttagaaaag    1860
taccagatcg agtacaacga aggtgaattc catcaacata agccagaagt tttgttgcag    1920
ggttctgaaa actctgatac ctctgaaaag tctttggcct gaaacgaagg tgaattccac    1980
caacataagc cagaagtttt gttgcaaggt tctgaaaact ctgacacttc tgaaaagtct    2040
ttggcttaa                                                            2049
```

<210> SEQ ID NO 26
<211> LENGTH: 1887
<212> TYPE: DNA
<213> ORGANISM: Artificial Sequence
<220> FEATURE:
<223> OTHER INFORMATION: sequence of H0 Metschnikowia species APS1/HGT19

<400> SEQUENCE: 26

```
atgtcagaaa agcctgttgt gtcgcacagc atcgacacga cgctgtctac gtcatcgaaa      60
caagtctatg acggtaactc gcttcttaag accctgaatg agcgcgatgg cgaacgcggc     120
aatatcttgt cgcagtacac tgaggaacag gccatgcaaa tgggccgcaa ctatgcgttg     180
aagcacaatt tagatgcgac actctttgga aaggcggccg cggtcgcaag aaacccatac     240
gagttcaatt cgatgagttt tttgaccgaa gaggaaaaag tcgcgcttaa cacggagcag     300
accaagaaat ggcacatccc aagaaagttg gtggaggtga ttgcattggg gtccatggcc     360
gctgcggtgc agggtatgga tgagtcggtg gtgaatggtg caacgctttt ctaccccacg     420
gcaatgggta tcacagatat caagaatgcc gatttgattg aaggtttgat caacggtgcg     480
ccctatcttt gctgcgccat catgtgctgg acatctgatt actggaacag gaagttgggc     540
cgtaagtgga ccatttttctg gacatgtgcc atttctgcaa tcacatgtat ctggcaaggt     600
ctcgtcaatt tgaaatggta ccatttgttc attgcgcgtt tctgcttggg tttcggtatc     660
ggtgtcaagt ctgccaccgt gcctgcgtat gctgccgaaa ccaccccggc caaaatcaga     720
ggctcgttgg tcatgctttg gcagttcttc accgctgtcg gaatcatgct tggttacgtg     780
gcgtctttgg cattctatta cattggtgac aatggcattt ctggcggctt gaactggaga     840
ttgatgctag gatctgcatg tcttccagct atcgttgtgt tagtccaagt tccgtttgtt     900
ccagaatccc ctcgttggct catgggtaag gaaagacacg ctgaagcata tgattcgctc     960
cggcaattgc ggttcagtga aatcgaggcg gcccgtgact gtttctacca gtacgtgttg    1020
ttgaaagagg agggctctta tggaacgcag ccattcttca gcagaatcaa ggagatgttc    1080
accgtgagaa gaaacagaaa tggtgcattg ggcgcgtgga tcgtcatgtt catgcagcag    1140
ttctgtggaa tcaacgtcat tgcttactac tcgtcgtcga tcttcgtgga gtcgaatctt    1200
tctgagatca aggccatgtt ggcgtcttgg gggttcggta tgatcaattt cttgtttgca    1260
attccagcgt tctacaccat tgacacgttt ggccgacgca acttgttgct cactactttc    1320
cctcttatgg cggtattctt actcatggcc ggattcgggt tctggatccc gttcgagaca    1380
aacccacacg gccgttttgc ggtgatcact attggtatct atttgtttgc atgtgtctac    1440
tctgcgggcg agggaccagt tcccttcaca tactctgccg aagcattccc gttgtatatc    1500
cgtgacttgg gtatgggctt tgccacggcc acgtgttggt tcttcaactt cattttggca    1560
```

```
tttcctggc ctagaatgaa gaatgcattc aagcctcaag gtgcctttgg ctggtatgcc      1620
gcctggaaca ttgttggctt cttcttagtg ttatggttct tgcccgagac aaagggcttg      1680
acgttggagg aattggacga agtgtttgat gtgcctttga gaaaacacgc gcactaccgt      1740
accaaagaat tagtatacaa cttgcgcaaa tacttcttga ggcagaaccc taagccattg      1800
ccgccacttt atgcacacca agaatggct gttaccaacc cagaatggtt ggaaaagacc      1860
gaggtcacgc acgaggagaa tatctag                                          1887

<210> SEQ ID NO 27
<211> LENGTH: 1887
<212> TYPE: DNA
<213> ORGANISM: Artificial Sequence
<220> FEATURE:
<223> OTHER INFORMATION: sequence of  H0 Metschnikowia species APS1/
      HGT19 codon optimized for expression in S. cerevisiae

<400> SEQUENCE: 27
atgtctgaaa agccagttgt ttctcactct atcgacacca cctcttctac ctcttctaag       60
caagtctacg acggtaactc tttgttgaag acctctaacg aaagagacgg tgaaagaggt      120
aacatcttgt ctcaatacac tgaagaacaa gcaatgcaaa tgggtagaaa ctacgctttg      180
aagcacaact tggacgctac cttgttcggt aaggctgctg ctgtcgctag aaacccatac      240
gagttcaact ctatgtcttt cttgaccgaa gaagaaaagg tcgctttgaa caccgaacaa      300
accaagaagt ggcacatccc aagaaagttg gttgaagtta ttgctttggg ttctatggct      360
gctgctgttc aaggtatgga cgaatctgtt gttaacggtg ctaccttgtt ctacccaacc      420
gctatgggta tcaccgacat caagaacgct gacttgattg aaggtttgat taacggtgcc      480
ccatacttgt gttgtgctat tatgtgttgg acctctgact actggaacag aaagttgggt      540
agaaagtgga ccattttctg gacctgtgct atttctgcta tcacctgtat ctggcaaggt      600
ttggtcaact gaagtggta tcacttgttc attgctagat ctgtctttggg tttcggtatc      660 ggtgtcaagt ctgctaccgt tccagcctac gctgctgaaa ccaccccagc caagattaga      720
ggttctttgg ttatgttgtg gcaattcttc accgctgtcg gtattatgtt gggttacgtt      780 gcttcttttgg ctttctacta cattggtgac aacggtattt ctggtggttt gaactggaga      840 tgatgttgg gttctgcttg tttgccagcc atcgttgttt tggtccaagt tccattcgtt      900
ccagaatctc caagatggtt gatgggtaag gaaagacacg ctgaagccta cgactctttg      960
agacaattga gattctctga aatcgaagcc gctagagact gtttctacca atacgttttg     1020
ttgaaggaag aaggttctta cggtactcaa ccattcttct ctagaatcaa ggaaatgttc     1080
accgttagaa gaaacagaaa cggtgctttg ggtgcttgga ttgttatgtt tatgcaacaa     1140
ttctgtggta tcaacgtcat tgcttactac tcttcttcta tcttcgttga atctaacttg     1200
tctgaaatca aggctatgtt ggcttcttgg ggtttcggta tgattaactt cttgttcgct     1260
attccagcct tctacaccat tgacaccttc ggtagaagaa acttgttgtt gactactttc     1320
ccattgatgg ctgttttctt gttgatggct ggtttcggtt ctggattcc attcgaaacc     1380 aacccacacg gtagattggc tgttatcact attggtatct acttgttcgc ttgtgtctac     1440
tctgctggtg aaggtccagt tccattcacc tactctgctg aagccttccc attgtacatc     1500
agagacttgg gtatgggttt cgctaccgct acctgttggt tcttcaactt cattttggct     1560
ttctcttggc caagaatgaa gaacgctttc aagcctcaag gtgctttcgg ttggtacgct     1620
gcttggaaca ttgttggttt cttcttggtt ttgtggttct tgccagaaac taagggtttg     1680
```

```
actttggaag aattggacga agttttcgac gttccattga gaaagcacgc tcactacaga    1740
actaaggaat tggtttacaa cttgagaaag tacttcttga dacaaaaccc aaagccattg    1800
ccaccattgt acgctcacca agaatggct gttaccaacc cagaatggtt ggaaaagacc     1860
gaagtcaccc acgaagaaaa catctaa                                        1887
```

<210> SEQ ID NO 28
<211> LENGTH: 49
<212> TYPE: DNA
<213> ORGANISM: Artificial Sequence
<220> FEATURE:
<223> OTHER INFORMATION: Primer Y10

<400> SEQUENCE: 28

```
gaaaaaactg gtaccgttta atcagtactg acaataaaaa gattcttgt               49
```

<210> SEQ ID NO 29
<211> LENGTH: 49
<212> TYPE: DNA
<213> ORGANISM: Artificial Sequence
<220> FEATURE:
<223> OTHER INFORMATION: Primer Y10R

<400> SEQUENCE: 29

```
taatttctct tcgtatccca tggttgttta tgttcggatg tgatgtgag                49
```

<210> SEQ ID NO 30
<211> LENGTH: 60
<212> TYPE: DNA
<213> ORGANISM: Artificial Sequence
<220> FEATURE:
<223> OTHER INFORMATION: Primer Y15

<400> SEQUENCE: 30

```
acgccgccat ccagtgtcga aaacgagctt tgtcttgtaa agagtcttcg gtcattttta    60
```

<210> SEQ ID NO 31
<211> LENGTH: 60
<212> TYPE: DNA
<213> ORGANISM: Artificial Sequence
<220> FEATURE:
<223> OTHER INFORMATION: Primer Y15R

<400> SEQUENCE: 31

```
gcggccgcat aggccactag tggatctgat caatacatac aagcatctca caatcacaag    60
```

<210> SEQ ID NO 32
<211> LENGTH: 60
<212> TYPE: DNA
<213> ORGANISM: Artificial Sequence
<220> FEATURE:
<223> OTHER INFORMATION: Primer Y33

<400> SEQUENCE: 32

```
tttttcaccc acaacaaata atatcaaaag atgggttacg aggaaaagct tgtagcgccc    60
```

<210> SEQ ID NO 33
<211> LENGTH: 60
<212> TYPE: DNA
<213> ORGANISM: Artificial Sequence
<220> FEATURE:
<223> OTHER INFORMATION: Primer Y33R

<400> SEQUENCE: 33

```
acgagaacac ccagctaaac gcggtgcgcg ttagaccgtg cccgtcttct cgtctgaaga    60
```

```
<210> SEQ ID NO 34
<211> LENGTH: 66
<212> TYPE: DNA
<213> ORGANISM: Artificial Sequence
<220> FEATURE:
<223> OTHER INFORMATION: Primer Y41

<400> SEQUENCE: 34
cagagcagat tgtactgaga gtgcaccagg cgcgccccat ccagtgtcga accatcatta      60
aaagat                                                                66

<210> SEQ ID NO 35
<211> LENGTH: 68
<212> TYPE: DNA
<213> ORGANISM: Artificial Sequence
<220> FEATURE:
<223> OTHER INFORMATION: Primer Y41R

<400> SEQUENCE: 35
ctccttacgc atctgtgcgg tatttcacac cgcactagac aatacataca agcatctcac      60
aatcacaa                                                              68

<210> SEQ ID NO 36
<211> LENGTH: 38
<212> TYPE: DNA
<213> ORGANISM: Artificial Sequence
<220> FEATURE:
<223> OTHER INFORMATION: Primer Y53

<400> SEQUENCE: 36
tcagtactga caataaaaag attcttgttt tcaagaac                              38

<210> SEQ ID NO 37
<211> LENGTH: 28
<212> TYPE: DNA
<213> ORGANISM: Artificial Sequence
<220> FEATURE:
<223> OTHER INFORMATION: Primer Y53R

<400> SEQUENCE: 37
ctcacatcac atccgaacat aaacaacc                                         28

<210> SEQ ID NO 38
<211> LENGTH: 22
<212> TYPE: DNA
<213> ORGANISM: Artificial Sequence
<220> FEATURE:
<223> OTHER INFORMATION: Primer Y83

<400> SEQUENCE: 38
tatcccgtca cttccacatt cg                                               22

<210> SEQ ID NO 39
<211> LENGTH: 32
<212> TYPE: DNA
<213> ORGANISM: Artificial Sequence
<220> FEATURE:
<223> OTHER INFORMATION: Primer Y83R

<400> SEQUENCE: 39
tattgatata gtgtttaagc gaatgacaga ag                                    32
```

-continued

<210> SEQ ID NO 40
<211> LENGTH: 62
<212> TYPE: DNA
<213> ORGANISM: Artificial Sequence
<220> FEATURE:
<223> OTHER INFORMATION: Primer Y96i

<400> SEQUENCE: 40
atagaaagca aatagttata taattttca tggacgtagg tctagagatc tgtttagctt      60
gc                                                                   62

<210> SEQ ID NO 41
<211> LENGTH: 66
<212> TYPE: DNA
<213> ORGANISM: Artificial Sequence
<220> FEATURE:
<223> OTHER INFORMATION: Primer Y95Ri

<400> SEQUENCE: 41
aatgcaaaag cggctcctaa acagaaattc ttcagtcaat acatacaagc atctcacaat      60
cacaag                                                               66

<210> SEQ ID NO 42
<211> LENGTH: 58
<212> TYPE: DNA
<213> ORGANISM: Artificial Sequence
<220> FEATURE:
<223> OTHER INFORMATION: Primer Y93Ri

<400> SEQUENCE: 42
tcgtctatat caaaactgca tgtttctcta cgtctaatta agggttctcg agagctcg       58

<210> SEQ ID NO 43
<211> LENGTH: 56
<212> TYPE: DNA
<213> ORGANISM: Artificial Sequence
<220> FEATURE:
<223> OTHER INFORMATION: Primer Y91i

<400> SEQUENCE: 43
acttcaatag acttcaatag aaagcaaata gttatatgcc ctgaggatgt atctgg          56

<210> SEQ ID NO 44
<211> LENGTH: 628
<212> TYPE: PRT
<213> ORGANISM: Artificial Sequence
<220> FEATURE:
<223> OTHER INFORMATION: ubiquitin-deficient H0 Metschnikowia species
      Aps1p/Hgt19 codon optimized for expression in S. cerevisiae (with
      K4R; K20R; K30R and K93R mutations)

<400> SEQUENCE: 44

Met Ser Glu Arg Pro Val Val Ser His Ser Ile Asp Thr Thr Ser Ser
1               5                   10                  15

Thr Ser Ser Arg Gln Val Tyr Asp Gly Asn Ser Leu Leu Arg Thr Ser
            20                  25                  30

Asn Glu Arg Asp Gly Glu Arg Gly Asn Ile Leu Ser Gln Tyr Thr Glu
        35                  40                  45

Glu Gln Ala Met Gln Met Gly Arg Asn Tyr Ala Leu Lys His Asn Leu
    50                  55                  60

Asp Ala Thr Leu Phe Gly Lys Ala Ala Ala Val Ala Arg Asn Pro Tyr
65                  70                  75                  80

-continued

```
Glu Phe Asn Ser Met Ser Phe Leu Thr Glu Glu Arg Val Ala Leu
             85              90              95
Asn Thr Glu Gln Thr Lys Lys Trp His Ile Pro Arg Lys Leu Val Glu
            100             105             110
Val Ile Ala Leu Gly Ser Met Ala Ala Val Gln Gly Met Asp Glu
            115             120             125
Ser Val Val Asn Gly Ala Thr Leu Phe Tyr Pro Thr Ala Met Gly Ile
            130             135             140
Thr Asp Ile Lys Asn Ala Asp Leu Ile Glu Gly Leu Ile Asn Gly Ala
145             150             155             160
Pro Tyr Leu Cys Cys Ala Ile Met Cys Trp Thr Ser Asp Tyr Trp Asn
            165             170             175
Arg Lys Leu Gly Arg Lys Trp Thr Ile Phe Trp Thr Cys Ala Ile Ser
            180             185             190
Ala Ile Thr Cys Ile Trp Gln Gly Leu Val Asn Leu Lys Trp Tyr His
            195             200             205
Leu Phe Ile Ala Arg Phe Cys Leu Gly Phe Gly Ile Gly Val Lys Ser
            210             215             220
Ala Thr Val Pro Ala Tyr Ala Ala Glu Thr Thr Pro Ala Lys Ile Arg
225             230             235             240
Gly Ser Leu Val Met Leu Trp Gln Phe Phe Thr Ala Val Gly Ile Met
            245             250             255
Leu Gly Tyr Val Ala Ser Leu Ala Phe Tyr Ile Gly Asp Asn Gly
            260             265             270
Ile Ser Gly Gly Leu Asn Trp Arg Leu Met Leu Gly Ser Ala Cys Leu
            275             280             285
Pro Ala Ile Val Val Leu Val Gln Val Pro Phe Val Pro Glu Ser Pro
            290             295             300
Arg Trp Leu Met Gly Lys Glu Arg His Ala Glu Ala Tyr Asp Ser Leu
305             310             315             320
Arg Gln Leu Arg Phe Ser Glu Ile Glu Ala Ala Arg Asp Cys Phe Tyr
            325             330             335
Gln Tyr Val Leu Leu Lys Glu Glu Gly Ser Tyr Gly Thr Gln Pro Phe
            340             345             350
Phe Ser Arg Ile Lys Glu Met Phe Thr Val Arg Arg Asn Arg Asn Gly
            355             360             365
Ala Leu Gly Ala Trp Ile Val Met Phe Met Gln Gln Phe Cys Gly Ile
            370             375             380
Asn Val Ile Ala Tyr Tyr Ser Ser Ile Phe Val Glu Ser Asn Leu
385             390             395             400
Ser Glu Ile Lys Ala Met Leu Ala Ser Trp Gly Phe Gly Met Ile Asn
            405             410             415
Phe Leu Phe Ala Ile Pro Ala Tyr Thr Ile Asp Thr Phe Gly Arg
            420             425             430
Arg Asn Leu Leu Leu Thr Thr Phe Pro Leu Met Ala Val Phe Leu Leu
            435             440             445
Met Ala Gly Phe Gly Phe Trp Ile Pro Phe Glu Thr Asn Pro His Gly
            450             455             460
Arg Leu Ala Val Ile Thr Ile Gly Ile Tyr Leu Phe Ala Cys Val Tyr
465             470             475             480
Ser Ala Gly Glu Gly Pro Val Pro Phe Thr Tyr Ser Ala Glu Ala Phe
            485             490             495
```

```
Pro Leu Tyr Ile Arg Asp Leu Gly Met Gly Phe Ala Thr Ala Thr Cys
            500                 505                 510

Trp Phe Phe Asn Phe Ile Leu Ala Phe Ser Trp Pro Arg Met Lys Asn
            515                 520                 525

Ala Phe Lys Pro Gln Gly Ala Phe Gly Trp Tyr Ala Ala Trp Asn Ile
            530                 535                 540

Val Gly Phe Phe Leu Val Leu Trp Phe Leu Pro Glu Thr Lys Gly Leu
545                 550                 555                 560

Thr Leu Glu Glu Leu Asp Glu Val Phe Asp Val Pro Leu Arg Lys His
                565                 570                 575

Ala His Tyr Arg Thr Lys Glu Leu Val Tyr Asn Leu Arg Lys Tyr Phe
            580                 585                 590

Leu Arg Gln Asn Pro Lys Pro Leu Pro Pro Leu Tyr Ala His Gln Arg
            595                 600                 605

Met Ala Val Thr Asn Pro Glu Trp Leu Glu Lys Thr Glu Val Thr His
            610                 615                 620

Glu Glu Asn Ile
625

<210> SEQ ID NO 45
<211> LENGTH: 548
<212> TYPE: PRT
<213> ORGANISM: Artificial Sequence
<220> FEATURE:
<223> OTHER INFORMATION: ubiquitin-deficient H0 Metschnikowia species
      Hxt5p (with K7R; K10R, K29R; K43R and K58R mutations)

<400> SEQUENCE: 45

Met Ser Ile Phe Glu Gly Arg Asp Gly Arg Gly Val Ser Ser Thr Glu
1               5                   10                  15

Ser Leu Ser Asn Asp Val Arg Tyr Asp Asn Met Glu Arg Val Asp Gln
            20                  25                  30

Asp Val Leu Arg His Asn Phe Asn Phe Asp Arg Glu Phe Glu Glu Leu
            35                  40                  45

Glu Ile Glu Ala Ala Gln Val Asn Asp Arg Pro Ser Phe Val Asp Arg
50                  55                  60

Ile Leu Ser Leu Glu Tyr Lys Leu His Phe Glu Asn Lys Asn His Met
65                  70                  75                  80

Val Trp Leu Leu Gly Ala Phe Ala Ala Ala Gly Leu Leu Ser Gly
            85                  90                  95

Leu Asp Gln Ser Ile Ile Ser Gly Ala Ser Ile Gly Met Asn Lys Ala
            100                 105                 110

Leu Asn Leu Thr Glu Arg Glu Ala Ser Leu Val Ser Ser Leu Met Pro
            115                 120                 125

Leu Gly Ala Met Ala Gly Ser Met Ile Met Thr Pro Leu Asn Glu Trp
            130                 135                 140

Phe Gly Arg Lys Ser Ser Leu Ile Ile Ser Cys Ile Trp Tyr Thr Ile
145                 150                 155                 160

Gly Ser Ala Leu Cys Ala Gly Ala Arg Asp His His Met Met Tyr Ala
            165                 170                 175

Gly Arg Phe Ile Leu Gly Val Gly Val Gly Ile Glu Gly Gly Cys Val
            180                 185                 190

Gly Ile Tyr Ile Ser Glu Ser Val Pro Ala Asn Val Arg Gly Ser Ile
            195                 200                 205

Val Ser Met Tyr Gln Phe Asn Ile Ala Leu Gly Glu Val Leu Gly Tyr
            210                 215                 220
```

```
Ala Val Ala Ala Ile Phe Tyr Thr Val His Gly Gly Trp Arg Phe Met
225                 230                 235                 240

Val Gly Ser Ser Leu Val Phe Ser Thr Ile Leu Phe Ala Gly Leu Phe
            245                 250                 255

Phe Leu Pro Glu Ser Pro Arg Trp Leu Val His Lys Gly Arg Asn Gly
        260                 265                 270

Met Ala Tyr Asp Val Trp Lys Arg Leu Arg Asp Ile Asn Asp Glu Ser
    275                 280                 285

Ala Lys Leu Glu Phe Leu Glu Met Arg Gln Ala Ala Tyr Gln Glu Arg
290                 295                 300

Glu Arg Arg Ser Gln Glu Ser Leu Phe Ser Ser Trp Gly Glu Leu Phe
305                 310                 315                 320

Thr Ile Ala Arg Asn Arg Arg Ala Leu Thr Tyr Ser Val Ile Met Ile
                325                 330                 335

Thr Leu Gly Gln Leu Thr Gly Val Asn Ala Val Met Tyr Tyr Met Ser
            340                 345                 350

Thr Leu Met Gly Ala Ile Gly Phe Asn Glu Lys Asp Ser Val Phe Met
        355                 360                 365

Ser Leu Val Gly Gly Ser Leu Leu Ile Gly Thr Ile Pro Ala Ile
370                 375                 380

Leu Trp Met Asp Arg Phe Gly Arg Arg Val Trp Gly Tyr Asn Leu Val
385                 390                 395                 400

Gly Phe Phe Val Gly Leu Val Leu Val Gly Val Gly Tyr Arg Phe Asn
                405                 410                 415

Pro Val Thr Gln Lys Ala Ala Ser Glu Gly Val Tyr Leu Thr Gly Leu
            420                 425                 430

Ile Val Tyr Phe Leu Phe Phe Gly Ser Tyr Ser Thr Leu Thr Trp Val
        435                 440                 445

Ile Pro Ser Glu Ser Phe Asp Leu Arg Thr Arg Ser Leu Gly Met Thr
450                 455                 460

Ile Cys Ser Thr Phe Leu Tyr Leu Trp Ser Phe Thr Val Thr Tyr Asn
465                 470                 475                 480

Phe Thr Lys Met Ser Ala Ala Phe Thr Tyr Thr Gly Leu Thr Leu Gly
                485                 490                 495

Phe Tyr Gly Gly Ile Ala Phe Leu Gly Leu Ile Tyr Gln Val Cys Phe
            500                 505                 510

Met Pro Glu Thr Lys Asp Lys Thr Leu Glu Glu Ile Asp Asp Ile Phe
        515                 520                 525

Asn Arg Ser Ala Phe Ser Ile Ala Arg Glu Asn Ile Ser Asn Leu Lys
530                 535                 540

Lys Gly Ile Trp
545

<210> SEQ ID NO 46
<211> LENGTH: 548
<212> TYPE: PRT
<213> ORGANISM: Artificial Sequence
<220> FEATURE:
<223> OTHER INFORMATION: H0 Metschnikowia species Gxf2p/Gal2p (with
      K23R, K26R, K35R, K542R and K546R mutations)

<400> SEQUENCE: 46

Met Ser Ala Glu Gln Glu Gln Gln Val Ser Gly Thr Ser Ala Thr Ile
1               5                   10                  15

Asp Gly Leu Ala Ser Leu Arg Gln Glu Arg Thr Ala Glu Glu Asp
            20                  25                  30
```

```
Ala Phe Arg Pro Lys Pro Ala Thr Ala Tyr Phe Phe Ile Ser Phe Leu
            35                  40                  45

Cys Gly Leu Val Ala Phe Gly Gly Tyr Val Phe Gly Phe Asp Thr Gly
 50                  55                  60

Thr Ile Ser Gly Phe Val Asn Met Asp Asp Tyr Leu Met Arg Phe Gly
 65                  70                  75                  80

Gln Gln His Ala Asp Gly Thr Tyr Tyr Leu Ser Asn Val Arg Thr Gly
                 85                  90                  95

Leu Ile Val Ser Ile Phe Asn Ile Gly Cys Ala Val Gly Gly Leu Ala
                100                 105                 110

Leu Ser Lys Val Gly Asp Ile Trp Gly Arg Arg Ile Gly Ile Met Val
            115                 120                 125

Ala Met Ile Ile Tyr Met Val Gly Ile Ile Gln Ile Ala Ser Gln
130                 135                 140

Asp Lys Trp Tyr Gln Tyr Phe Ile Gly Arg Leu Ile Thr Gly Leu Gly
145                 150                 155                 160

Val Gly Thr Thr Ser Val Leu Ser Pro Leu Phe Ile Ser Glu Ser Ala
                165                 170                 175

Pro Lys His Leu Arg Gly Thr Leu Val Cys Cys Phe Gln Leu Met Val
            180                 185                 190

Thr Leu Gly Ile Phe Leu Gly Tyr Cys Thr Thr Tyr Gly Thr Lys Asn
            195                 200                 205

Tyr Thr Asp Ser Arg Gln Trp Arg Ile Pro Leu Gly Leu Cys Phe Ala
            210                 215                 220

Trp Ala Leu Leu Leu Ile Ser Gly Met Val Phe Met Pro Glu Ser Pro
225                 230                 235                 240

Arg Phe Leu Ile Glu Arg Gln Arg Phe Asp Glu Ala Lys Ala Ser Val
                245                 250                 255

Ala Lys Ser Asn Gln Val Ser Thr Glu Asp Pro Ala Val Tyr Thr Glu
            260                 265                 270

Val Glu Leu Ile Gln Ala Gly Ile Asp Arg Glu Ala Leu Ala Gly Ser
            275                 280                 285

Ala Gly Trp Lys Glu Leu Ile Thr Gly Lys Pro Lys Met Leu Gln Arg
            290                 295                 300

Val Ile Leu Gly Met Met Leu Gln Ser Ile Gln Gln Leu Thr Gly Asn
305                 310                 315                 320

Asn Tyr Phe Phe Tyr Tyr Gly Thr Thr Ile Phe Lys Ala Val Gly Met
                325                 330                 335

Ser Asp Ser Phe Gln Thr Ser Ile Val Leu Gly Ile Val Asn Phe Ala
            340                 345                 350

Ser Thr Phe Val Gly Ile Trp Ala Ile Glu Arg Met Gly Arg Arg Ser
            355                 360                 365

Cys Leu Leu Val Gly Ser Ala Cys Met Ser Val Cys Phe Leu Ile Tyr
            370                 375                 380

Ser Ile Leu Gly Ser Val Asn Leu Tyr Ile Asp Gly Tyr Glu Asn Thr
385                 390                 395                 400

Pro Ser Asn Thr Arg Lys Pro Thr Gly Asn Ala Met Ile Phe Ile Thr
                405                 410                 415

Cys Leu Phe Ile Phe Phe Phe Ala Ser Thr Trp Ala Gly Gly Val Tyr
            420                 425                 430

Ser Ile Val Ser Glu Thr Tyr Pro Leu Arg Ile Arg Ser Lys Gly Met
            435                 440                 445
```

```
Ala Val Ala Thr Ala Ala Asn Trp Met Trp Gly Phe Leu Ile Ser Phe
    450                 455                 460

Phe Thr Pro Phe Ile Thr Ser Ala Ile His Phe Tyr Tyr Gly Phe Val
465                 470                 475                 480

Phe Thr Gly Cys Leu Ile Phe Ser Phe Tyr Val Phe Phe Val
                485                 490                 495

Arg Glu Thr Lys Gly Leu Ser Leu Glu Glu Val Asp Glu Leu Tyr Ala
                500                 505                 510

Thr Asp Leu Pro Pro Trp Lys Thr Ala Gly Trp Thr Pro Pro Ser Ala
                515                 520                 525

Glu Asp Met Ala His Thr Thr Gly Phe Ala Glu Ala Ala Arg Pro Thr
530                 535                 540

Asn Arg His Val
545

<210> SEQ ID NO 47
<211> LENGTH: 544
<212> TYPE: PRT
<213> ORGANISM: Artificial Sequence
<220> FEATURE:
<223> OTHER INFORMATION: ubiquitin-deficient H0 Metschnikowia species
      Gxf1p (with K9R and K24R mutations)

<400> SEQUENCE: 47

Met Ser Gln Asp Glu Leu His Thr Arg Ser Gly Val Glu Thr Pro Ile
1               5                   10                  15

Asn Asp Ser Leu Leu Glu Glu Arg His Asp Val Thr Pro Leu Ala Ala
                20                  25                  30

Leu Pro Glu Lys Ser Phe Lys Asp Tyr Ile Ser Ile Ser Ile Phe Cys
            35                  40                  45

Leu Phe Val Ala Phe Gly Gly Phe Val Phe Gly Phe Asp Thr Gly Thr
50                  55                  60

Ile Ser Gly Phe Val Asn Met Ser Asp Phe Lys Thr Arg Phe Gly Glu
65                  70                  75                  80

Met Asn Ala Gln Gly Glu Tyr Tyr Leu Ser Asn Val Arg Thr Gly Leu
                85                  90                  95

Met Val Ser Ile Phe Asn Val Gly Cys Ala Val Gly Gly Ile Phe Leu
            100                 105                 110

Cys Lys Ile Ala Asp Val Tyr Gly Arg Arg Ile Gly Leu Met Phe Ser
        115                 120                 125

Met Val Val Tyr Val Val Gly Ile Ile Gln Ile Ala Ser Thr Thr
130                 135                 140

Lys Trp Tyr Gln Tyr Phe Ile Gly Arg Leu Ile Ala Gly Leu Ala Val
145                 150                 155                 160

Gly Thr Val Ser Val Ile Ser Pro Leu Phe Ile Ser Glu Val Ala Pro
                165                 170                 175

Lys Gln Leu Arg Gly Thr Leu Val Cys Cys Phe Gln Leu Cys Ile Thr
            180                 185                 190

Leu Gly Ile Phe Leu Gly Tyr Cys Thr Thr Tyr Gly Thr Lys Thr Tyr
        195                 200                 205

Thr Asp Ser Arg Gln Trp Arg Ile Pro Leu Gly Ile Cys Phe Ala Trp
    210                 215                 220

Ala Leu Phe Leu Val Ala Gly Met Leu Asn Met Pro Glu Ser Pro Arg
225                 230                 235                 240
```

Tyr Leu Val Glu Lys Ser Arg Ile Asp Asp Ala Arg Lys Ser Ile Ala
                245                 250                 255

Arg Ser Asn Lys Val Ser Glu Glu Asp Pro Ala Val Tyr Thr Glu Val
            260                 265                 270

Gln Leu Ile Gln Ala Gly Ile Asp Arg Glu Ala Leu Ala Gly Ser Ala
        275                 280                 285

Thr Trp Met Glu Leu Val Thr Gly Lys Pro Lys Ile Phe Arg Arg Val
    290                 295                 300

Ile Met Gly Val Met Leu Gln Ser Leu Gln Gln Leu Thr Gly Asp Asn
305                 310                 315                 320

Tyr Phe Phe Tyr Tyr Gly Thr Thr Ile Phe Lys Ala Val Gly Leu Gln
                325                 330                 335

Asp Ser Phe Gln Thr Ser Ile Ile Leu Gly Ile Val Asn Phe Ala Ser
            340                 345                 350

Thr Phe Val Gly Ile Tyr Ala Ile Glu Arg Met Gly Arg Arg Leu Cys
        355                 360                 365

Leu Leu Thr Gly Ser Ala Cys Met Phe Val Cys Phe Ile Ile Tyr Ser
    370                 375                 380

Leu Ile Gly Thr Gln His Leu Tyr Lys Asn Gly Phe Ser Asn Glu Pro
385                 390                 395                 400

Ser Asn Thr Tyr Lys Pro Ser Gly Asn Ala Met Ile Phe Ile Thr Cys
                405                 410                 415

Leu Tyr Ile Phe Phe Phe Ala Ser Thr Trp Ala Gly Gly Val Tyr Cys
            420                 425                 430

Ile Val Ser Glu Ser Tyr Pro Leu Arg Ile Arg Ser Lys Ala Met Ser
        435                 440                 445

Val Ala Thr Ala Ala Asn Trp Met Trp Gly Phe Leu Ile Ser Phe Phe
    450                 455                 460

Thr Pro Phe Ile Thr Ser Ala Ile His Phe Tyr Tyr Gly Phe Val Phe
465                 470                 475                 480

Thr Gly Cys Leu Ala Phe Ser Phe Phe Tyr Val Tyr Phe Val Val
                485                 490                 495

Glu Thr Lys Gly Leu Ser Leu Glu Glu Val Asp Ile Leu Tyr Ala Ser
            500                 505                 510

Gly Thr Leu Pro Trp Lys Ser Ser Gly Trp Val Pro Pro Thr Ala Asp
        515                 520                 525

Glu Met Ala His Asn Ala Phe Asp Asn Lys Pro Thr Asp Glu Gln Val
    530                 535                 540

<210> SEQ ID NO 48
<211> LENGTH: 543
<212> TYPE: PRT
<213> ORGANISM: Artificial Sequence
<220> FEATURE:
<223> OTHER INFORMATION: ubiquitin-deficient H0 Metschnikowia species
      Xyt1p (with K6R and S75L mutations)

<400> SEQUENCE: 48

Met Gly Tyr Glu Glu Arg Leu Val Ala Pro Ala Leu Lys Phe Lys Asn
1               5                   10                  15

Phe Leu Asp Lys Thr Pro Asn Ile His Asn Val Tyr Val Ile Ala Ala
            20                  25                  30

Ile Ser Cys Thr Ser Gly Met Met Phe Gly Phe Asp Ile Ser Ser Met
        35                  40                  45

Ser Val Phe Val Asp Gln Gln Pro Tyr Leu Lys Met Phe Asp Asn Pro
    50                  55                  60

-continued

Ser Ser Val Ile Gln Gly Phe Ile Thr Ala Leu Met Ser Leu Gly Ser
 65                  70                  75                  80

Phe Phe Gly Ser Leu Thr Ser Thr Phe Ile Ser Glu Pro Phe Gly Arg
                 85                  90                  95

Arg Ala Ser Leu Phe Ile Cys Gly Ile Leu Trp Val Ile Gly Ala Ala
                100                 105                 110

Val Gln Ser Ser Ser Gln Asn Arg Ala Gln Leu Ile Cys Gly Arg Ile
                115                 120                 125

Ile Ala Gly Trp Gly Ile Gly Phe Gly Ser Ser Val Ala Pro Val Tyr
                130                 135                 140

Gly Ser Glu Met Ala Pro Arg Lys Ile Arg Gly Thr Ile Gly Gly Ile
145                 150                 155                 160

Phe Gln Phe Ser Val Thr Val Gly Ile Phe Ile Met Phe Leu Ile Gly
                165                 170                 175

Tyr Gly Cys Ser Phe Ile Gln Gly Lys Ala Ser Phe Arg Ile Pro Trp
                180                 185                 190

Gly Val Gln Met Val Pro Gly Leu Ile Leu Ile Gly Leu Phe Phe
                195                 200                 205

Ile Pro Glu Ser Pro Arg Trp Leu Ala Lys Gln Gly Tyr Trp Glu Asp
210                 215                 220

Ala Glu Ile Ile Val Ala Asn Val Gln Ala Lys Gly Asn Arg Asn Asp
225                 230                 235                 240

Ala Asn Val Gln Ile Glu Met Ser Glu Ile Lys Asp Gln Leu Met Leu
                245                 250                 255

Asp Glu His Leu Lys Glu Phe Thr Tyr Ala Asp Leu Phe Thr Lys Lys
                260                 265                 270

Tyr Arg Gln Arg Thr Ile Thr Ala Ile Phe Ala Gln Ile Trp Gln Gln
                275                 280                 285

Leu Thr Gly Met Asn Val Met Met Tyr Tyr Ile Val Tyr Ile Phe Gln
                290                 295                 300

Met Ala Gly Tyr Ser Gly Asn Thr Asn Leu Val Pro Ser Leu Ile Gln
305                 310                 315                 320

Tyr Ile Ile Asn Met Ala Val Thr Val Pro Ala Leu Phe Cys Leu Asp
                325                 330                 335

Leu Leu Gly Arg Arg Thr Ile Leu Leu Ala Gly Ala Ala Phe Met Met
                340                 345                 350

Ala Trp Gln Phe Gly Val Ala Gly Ile Leu Ala Thr Tyr Ser Glu Pro
                355                 360                 365

Ala Tyr Ile Ser Asp Thr Val Arg Ile Thr Ile Pro Asp Asp His Lys
                370                 375                 380

Ser Ala Ala Lys Gly Val Ile Ala Cys Cys Tyr Leu Phe Val Cys Ser
385                 390                 395                 400

Phe Ala Phe Ser Trp Gly Val Gly Ile Trp Val Tyr Cys Ser Glu Val
                405                 410                 415

Trp Gly Asp Ser Gln Ser Arg Gln Arg Gly Ala Ala Leu Ala Thr Ser
                420                 425                 430

Ala Asn Trp Ile Phe Asn Phe Ala Ile Ala Met Phe Thr Pro Ser Ser
                435                 440                 445

Phe Lys Asn Ile Thr Trp Lys Thr Tyr Ile Ile Tyr Ala Thr Phe Cys
                450                 455                 460

Ala Cys Met Phe Ile His Val Phe Phe Phe Pro Glu Thr Lys Gly
465                 470                 475                 480

```
Lys Arg Leu Glu Glu Ile Gly Gln Leu Trp Asp Glu Gly Val Pro Ala
                485                 490                 495

Trp Arg Ser Ala Lys Trp Gln Pro Thr Val Pro Leu Ala Ser Asp Ala
        500                 505                 510

Glu Leu Ala His Lys Met Asp Val Ala His Ala Glu His Ala Asp Leu
    515                 520                 525

Leu Ala Thr His Ser Pro Ser Ser Asp Glu Lys Thr Gly Thr Val
530                 535                 540

<210> SEQ ID NO 49
<211> LENGTH: 1887
<212> TYPE: DNA
<213> ORGANISM: Artificial Sequence
<220> FEATURE:
<223> OTHER INFORMATION: ubiquitin-deficient H0 Metschnikowia species
      APS1/HGT19 (with K4R; K20R; K30R and K93R mutations)

<400> SEQUENCE: 49
atgtctgaaa gaccagttgt ttctcactct atcgacacca cctcttctac ctcttctaga      60
caagtctacg acggtaactc tttgttgagg acctctaacg aaagagacgg tgaaagaggt     120
aacatcttgt ctcaatacac tgaagaacaa gcaatgcaaa tgggtagaaa ctacgctttg     180
aagcacaact tggacgctac cttgttcggt aaggctgctg ctgtcgctag aaacccatac     240
gagttcaact ctatgtcttt cttgaccgaa gaagaaagag tcgctttgaa caccgaacaa     300
accaagaagt ggcacatccc aagaaagttg gttgaagtta ttgctttggg ttctatggct     360
gctgctgttc aaggtatgga cgaatctgtt gttaacggtg ctaccttgtt ctacccaacc     420
gctatgggta tcaccgacat caagaacgct gacttgattg aaggtttgat taacggtgcc     480
ccatacttgt gttgtgctat tatgtgttgg acctctgact actggaacag aaagtttggt     540
agaaagtgga ccattttctg gacctgtgct atttctgcta tcacctgtat ctggcaaggt     600
ttggtcaact tgaagtggta tcacttgttc attgctagat ctgtttgggt ttcggtatc      660 ggtgtcaagt ctgctaccgt tccagcctac gctgctgaaa ccaccccagc caagattaga     720
ggttctttgg ttatgttgtg gcaattcttc accgctgtcg gtattatgtt gggttacgtt     780
gcttctttgc ttttctacta cattggtgac aacggtattt ctggtggttt gaactggaga     840 tgatgttgg gttctgcttg tttgccagcc atcgttgttt tggtccaagt tccattcgtt     900
ccagaatctc caagatggtt gatgggtaag gaaagacacg ctgaagccta cgactctttg     960
agacaattga gattctctga atcgaagcc gctagagact gtttctacca atacgttttg    1020
ttgaaggaag aaggttctta cggtactcaa ccattcttct ctagaatcaa ggaaatgttc    1080
accgttagaa gaaacagaaa cggtgctttg ggtgctggga ttgttatgtt tatgcaacaa    1140
ttctgtggta tcaacgtcat tgcttactac tcttcttcta tcttcgttga atctaacttg    1200
tctgaaatca aggctatgtt ggcttcttgg ggtttcggta tgattaactt cttgttcgct    1260
attccagcct tctacaccat tgacaccttc ggtagaagaa acttgttgtt gactactttc    1320
ccattgatgg ctgttttctt gttgatggct ggtttcggtt ctggattcc attcgaaacc    1380 aacccacacg gtagattggc tgttatcact attggtatct acttgttcgc ttgtgtctac    1440
tctgctggtg aaggtccagt tccattcacc tactctgctg aagccttccc attgtacatc    1500
agagacttgg gtatgggttt cgctaccgct acctgttggt tcttcaactt cattttggct    1560
ttctcttggc aagaatgaa gaacgctttc aagcctcaag gtgctttcgg ttggtacgct    1620
gcttggaaca ttgttggttt cttcttggtt ttgtggttct gccagaaaac taagggtttg    1680
```

```
actttggaag aattggacga agttttcgac gttccattga gaaagcacgc tcactacaga    1740
actaaggaat tggtttacaa cttgagaaag tacttcttga dacaaaaccc aaagccattg    1800
ccaccattgt acgctcacca aagaatggct gttaccaacc cagaatggtt ggaaaagacc    1860
gaagtcaccc acgaagaaaa catctaa                                       1887
```

<210> SEQ ID NO 50
<211> LENGTH: 1647
<212> TYPE: DNA
<213> ORGANISM: Artificial Sequence
<220> FEATURE:
<223> OTHER INFORMATION: ubiquitin-deficient H0 Metschnikowia species HXT5 (with K7R; K10R, K29R; K43R and K58R mutations)

<400> SEQUENCE: 50

```
atgtccattt tcgaaggtag ggatggtaga ggtgtttcct ctactgaatc cttgtctaac     60
gatgttagat acgacaacat ggaaagagtt gaccaagatg ttttgaggca caatttcaac    120
ttcgacagag agttcgaaga attggaaatt gaagctgccc aagttaacga tagaccatct    180
ttcgttgata ggatcttgtc tttggagtac aagttgcact tcgaaaacaa gaatcacatg    240
gtttggttgt tgggtgcttt tgctgctgct gcaggtttgt tgtctggttt ggatcaatct    300
attatttccg gtgcctctat cggtatgaac aaggctttga atttgaccga agagaagcc    360 tctttggtca gttctttgat gccattgggt gctatggctg ttctatgat tatgactcca    420 ttgaatgaat ggttcggccg taaatcctcc ttgattattt cttgtatttg gtacaccatc    480
ggttctgctt tgtgtgctgg tgctagagat catcacatga gtatgctgg tagattcatc    540 ttaggtgttg gtgttggtat tgaaggtggt tgcgttggta tctacatttc tgaatctgtt    600
ccagccaatg tcagaggttc tatcgttttct atgtaccagt tcaacattgc cttgggtgaa    660
gttttgggtt atgctgttgc tgctatttc tacactgttc atggtggttg gaggtttatg    720
gttggttctt ctttggtttt ctccaccatt ttgtttgccg gcttgttttt tttgccagaa    780
tctccaagat ggttggtcca taagggtaga aatggtatgg cttacgatgt ttggaagaga    840
ttgagagata tcaacgatga atccgccaag ttgaattct tggaaatgag acaagctgcc    900
taccaagaaa gagaaagaag atctcaagag tccttgtttt cttcatgggg tgagttgttt    960
accattgcta gaaatagaag ggctttgacc tactccgtta ttatgattac tttgggtcag   1020
ttgactggtg ttaacgctgt tatgtattac atgtctactt tgatgggtgc catcggtttt   1080
aacgaaaagg attctgtttt catgtccttg gttggtggtg ttctttgtt gattggtact   1140 attccagcta tcttgtggat ggatagattc ggtagaagag tttgggggtta caatttggtt   1200 ggttttttcg tcggtttggt attggtcggt gttggttata gattcaaccc agttactcaa   1260
aaggctgctt ctgaaggtgt ttatttgact ggtttgatcg tctacttctt gttcttcggt   1320
tcttactcta cattgaccctg ggttattcca tccgaatctt tcgatttgag aaccagatct   1380
ttgggtatga ccatttgctc tacttttcttg tacttgtgt ctttcactgt cacttacaac   1440
ttcactaaga tgtctgctgc tttcacttac acaggtttga ctttgggttt ttacggtggt   1500 attgcttttct tgggtttgat ctaccaagtt tgctttatgc cagaaactaa ggacaagacc   1560
ttggaagaaa tcgatgacat cttttaacaga tccgctttct ctattgccag ggaaaacatt   1620
agcaacttga agaaaggtat ctggtaa                                       1647
```

<210> SEQ ID NO 51
<211> LENGTH: 1647
<212> TYPE: DNA

<213> ORGANISM: Artificial Sequence
<220> FEATURE:
<223> OTHER INFORMATION: ubiquitin-deficient H0 Metschnikowia species
      GXF2/GAL2 (with K23R, K26R, K35R, K542R and K546R mutations)

<400> SEQUENCE: 51

```
atgtccgctg aacaagaaca acaagtttct ggtacttctg ccactattga tggtttggct      60
tctttgaggc aagaaaggac tgctgaagaa gaagatgctt ttaggccaaa accagctact     120
gcctacttct tcatttcttt cttgtgtggt ttggttgctc tcggtggtta cgttttggt      180
tttgataccg gtactatctc cggtttcgtt aacatggatg attacttgat gagattcggt     240
caacaacatg ctgatggtac ttactacttg tccaatgtta gaaccggttt gatcgtcagt     300
attttcaaca ttggttgtgc tgttggtggt ttggcattgt ctaaagttgg tgatatttgg     360
ggtagaagaa tcggtattat ggttgccatg atcatctaca tggttggtat cattattcaa     420
atcgcctccc aagacaagtg gtatcaatac tttattggta gattgatcac cggtttgggt     480
gttggtacta cttctgtttt gtctccttg ttcatttccg aatccgctcc aaaacatttg     540
agaggtactt tggtttgctg cttccaattg atggtaacct gggtatttt cttgggttac     600
tgtactactt acggtactaa gaactacacc gattctagac aatggagaat tccattgggt     660
ttgtgttttg cttgggcctt gttgttgatt tctggtatgg tttttatgcc agaatcccca     720
agattcttga tcgaaagaca aagattcgat gaagctaagg cttctgttgc caagtctaat     780
caagtttcta ctgaagatcc agccgtttac actgaagttg aattgattca gccggtatt      840
gatagagaag ctttggctgg ttctgctggt tggaaagaat tgattactgg taagccaaag     900
atgttgcaaa gagtcatttt gggtatgatg ttacaatcca tccaacaatt gaccggtaac     960
aattacttct ctactacgg tacaaccatc ttcaaagctg ttggtatgtc cgattctttt    1020
caaacctcta gtcttggg tatcgttaac ttcgcttcta cctttgttgg tatttgggcc     1080
attgaaagaa tgggtagaag atcttgtttg ttggttggtt cagcttgtat gtctgtttgc    1140
ttcttgatct actctatctt gggttcagtc aacttgtaca tcgatggtta cgaaaacact    1200
ccatctaaca ctagaaagcc aactggtaac gccatgattt tcattacctg tttgttcatc    1260
ttttctctg cctctacttg ggctggtggt gtttattcta tagtttctga aacctaccca    1320
ttgagaatca gatctaaagg tatggctgtt gctactgctg ctaattggat gtggggtttt    1380
ttgatctctt tctttacccc attcatcacc tccgctattc attttttacta cggttttgtt    1440
ttcaccggtt gcttgatctt ctcattcttt tacgtattct tttttcgtccg tgaaactaag    1500
ggtttgtcct ggaagaagt tgacgaatta tacgctactg atttgccacc atggaaaact    1560
gcaggttgga ctccaccatc agctgaagat atggctcata caactggttt tgctgaagct    1620
gctaggccta caaacagaca cgtttga                                         1647
```

<210> SEQ ID NO 52
<211> LENGTH: 1635
<212> TYPE: DNA
<213> ORGANISM: Artificial Sequence
<220> FEATURE:
<223> OTHER INFORMATION: ubiquitin-deficient H0 Metschnikowia species
      GXF1 (with K9R and K24R mutations)

<400> SEQUENCE: 52

```
atgtctcaag atgaattgca caccagatct ggtgttgaaa ctccaatcaa cgactccttg      60
ttggaagaaa gacatgatgt tactccattg gctgctttgc cagaaaaatc tttcaaggac    120
tacatctcca tctccatttt ctgtttgttt gttgctttcg gtggtttcgt tttcggtttt    180
```

```
gatactggta ctatttccgg tttcgttaac atgtctgatt caagactag gttcggtgaa      240 atgaatgctc agggtgaata ttacttgtcc aacgttagaa ctggcctgat ggtttctatt     300
ttcaatgttg gttgtgctgt cggtggtatt ttcttgtgta aaattgctga tgtctacggt     360
agaaggatcg gtttgatgtt ttctatggtt gtctacgttg tcggtatcat tattcaaatt     420
gcttctacca ccaagtggta tcagtacttc attggtagat tgattgctgg tttggctgtt     480
ggtactgttt ctgttatttc ccctttgttc atttccgaag ttgctccaaa acaattgaga     540
ggtactttgg tttgctgttt ccaattgtgt attaccttgg gtatcttctt gggttactgt     600
actacttacg gtactaagac ttacaccgat tctagacaat ggcgtattcc attgggtatt     660
tgttttgctt gggctttgtt tttggttgcc ggtatgttga atatgccaga atctccaaga     720
tacttggtcg aaaagtccag aattgatgat gccagaaagt ccattgctag gtctaacaaa     780
gtttccgaag aagatccagc tgtttacacc gaagttcaat tgattcaagc cggtattgat     840
agagaagctt tggctggttc tgctacttgg atggaattgg ttactggtaa gcctaagatc     900
tttagaagag ttatcatggg tgtcatgttg caatccttgc aacaattgac tggtgacaac     960 tacttttttct actacggtac aaccattttc aaggctgtcg gtttacaaga ttcttttccaa    1020 acctccatca ttttgggtat cgttaacttc gcttctacct tcgttggtat ctacgctatt     1080
gaaagaatgg gtagaagatt gtgtttgttg acaggttctg cttgtatgtt cgtttgcttc     1140
atcatctact cattgatcgg tactcagcac ttgtacaaaa acggttttttc taacgaaccc    1200 tccaacactt acaaaccatc tggtaatgcc atgatcttca ttacctgcct gtacattttc    1260 ttttttcgctt caacttgggc tggtggtgtt tactgtatag tttctgaatc ttacccactg    1320
aggatcagat ctaaagctat gtctgttgct actgctgcaa attggatgtg gggttttttg    1380
atttctttct ttaccccatt catcacctcc gctatccatt tttactatgg ttttgttttc     1440
accggttgct tggctttctc tttcttttac gtttacttct tcgtcgtcga gactaagggt     1500
ttgtctttgg aagaggttga tatcttgtat gcctctggta ctttgccatg gaaatcttca     1560
ggttgggttc caccaactgc tgacgaaatg gctcataatg cttttgataa caaaccaacc     1620
gatgaacagg tttaa                                                     1635

<210> SEQ ID NO 53
<211> LENGTH: 1632
<212> TYPE: DNA
<213> ORGANISM: Artificial Sequence
<220> FEATURE:
<223> OTHER INFORMATION: ubiquitin-deficient H0 Metschnikowia species
      XYT1 (with K6R and S75L mutations)

<400> SEQUENCE: 53
atgggatacg aagagagatt agtggccccc gctttgaaat ttaagaactt tttggataag      60
accccaaata tacataacgt ttacgtaatt gcggcgatct cgtgtacctc aggtatgatg     120
ttcggtttcg atatatcgtc gatgtccgtg ttcgtggacc aacagccgta tttaaaaatg     180
tttgataacc ctagcagcgt gatacaaggg tttataactg cgttgatgtc tttggggagc     240 ttttcggat cgctaacgtc cacttttatt tcagaacctt tggtagacg tgcctctttg      300 ttcatatgcg ggatcctttg ggtaattggg gcggcagttc aaagttcttc tcagaaccgt     360
gcgcagctta tttgtggccg aattattgca gggtggggca tcggattcgg ttctagcgtt     420
gcgccggtat acggttcaga atggccccca cgcaaaatta gaggaacaat cggaggtatt     480 tttcaattttt ctgtcacggt cggaatattc ataatgttcc tgattggcta cggctgctca     540
```

```
tttatacaag gcaaggccag ttttagaatt ccgtggggag ttcaaatggt accaggtctc    600
attctgttga tcggactatt cttcattcct gaatccccaa gatggttagc caaacaaggc    660
tactgggaag acgctgagat catcgtagca aacgttcaag ctaagggtaa caggaacgat    720
gctaatgtgc aaattgaaat gtccgagata aaagatcagt taatgcttga cgagcattta    780
aaggagttta cttatgccga tttgtttacc aaaaaatacc ggcaaaggac gataacagct    840
atatttgccc aaatatggca acagctgaca ggtatgaatg tcatgatgta ctacatcgta    900
tatatatttc aaatggcagg ttattcaggt aatactaatt tagttccttc actcattcag    960
tatattataa atatgctgt tacggtcccc gcattgttct gtcttgatct gcttggcagg    1020
aggacaattt tattagctgg cgccgctttt atgatggcct ggcaatttgg tgttgctggc   1080
attttagcta cttattcaga gccagcctat atttcagata ccgtgagaat tacaattcca   1140
gatgaccata aaagtgccgc taagggtgtc atcgcttgct gctatttgtt tgtttgttcc   1200
ttcgcctttt cctggggtgt aggtatctgg gtttattgtt cagaagtgtg gggtgatagt   1260
caatccagac aaagaggtgc tgcattggca acttctgcta attggatctt caatttcgca   1320
attgcaatgt ttacaccttc ttctttcaaa aatatcactt ggaagactta tatcatttat   1380
gctacatttt gtgcttgtat gttcattcat gttttttttt ttttccctga acaaagggt    1440 aagagactag aagaaattgg acagctatgg gatgaaggtg tcccagcatg gagatctgca   1500
aaatggcaac ccactgtccc actagcaagt gacgctgaat tagctcacaa aatggatgtt   1560
gcacacgctg aacacgcaga cttattggca acccattctc caagtagtga cgaaaaaact   1620
ggtaccgttt aa                                                       1632

<210> SEQ ID NO 54
<211> LENGTH: 544
<212> TYPE: PRT
<213> ORGANISM: Artificial Sequence
<220> FEATURE:
<223> OTHER INFORMATION: ubiquitin-deficient H0 Metschnikowia species
      Gxf1p (with K9R; K24R, K538R mutations)

<400> SEQUENCE: 54

Met Ser Gln Asp Glu Leu His Thr Arg Ser Gly Val Glu Thr Pro Ile
1               5                   10                  15

Asn Asp Ser Leu Leu Glu Glu Arg His Asp Val Thr Pro Leu Ala Ala
            20                  25                  30

Leu Pro Glu Lys Ser Phe Lys Asp Tyr Ile Ser Ile Ser Ile Phe Cys
        35                  40                  45

Leu Phe Val Ala Phe Gly Gly Phe Val Phe Gly Phe Asp Thr Gly Thr
    50                  55                  60

Ile Ser Gly Phe Val Asn Met Ser Asp Phe Lys Thr Arg Phe Gly Glu
65                  70                  75                  80

Met Asn Ala Gln Gly Glu Tyr Tyr Leu Ser Asn Val Arg Thr Gly Leu
                85                  90                  95

Met Val Ser Ile Phe Asn Val Gly Cys Ala Val Gly Gly Ile Phe Leu
            100                 105                 110

Cys Lys Ile Ala Asp Val Tyr Gly Arg Arg Ile Gly Leu Met Phe Ser
        115                 120                 125

Met Val Val Tyr Val Val Gly Ile Ile Ile Gln Ile Ala Ser Thr Thr
    130                 135                 140

Lys Trp Tyr Gln Tyr Phe Ile Gly Arg Leu Ile Ala Gly Leu Ala Val
145                 150                 155                 160
```

Gly Thr Val Ser Val Ile Ser Pro Leu Phe Ile Ser Glu Val Ala Pro
            165                 170                 175

Lys Gln Leu Arg Gly Thr Leu Val Cys Cys Phe Gln Leu Cys Ile Thr
        180                 185                 190

Leu Gly Ile Phe Leu Gly Tyr Cys Thr Thr Tyr Gly Thr Lys Thr Tyr
        195                 200                 205

Thr Asp Ser Arg Gln Trp Arg Ile Pro Leu Gly Ile Cys Phe Ala Trp
        210                 215                 220

Ala Leu Phe Leu Val Ala Gly Met Leu Asn Met Pro Glu Ser Pro Arg
225                 230                 235                 240

Tyr Leu Val Glu Lys Ser Arg Ile Asp Asp Ala Arg Lys Ser Ile Ala
            245                 250                 255

Arg Ser Asn Lys Val Ser Glu Glu Asp Pro Ala Val Tyr Thr Glu Val
            260                 265                 270

Gln Leu Ile Gln Ala Gly Ile Asp Arg Glu Ala Leu Ala Gly Ser Ala
        275                 280                 285

Thr Trp Met Glu Leu Val Thr Gly Lys Pro Lys Ile Phe Arg Arg Val
        290                 295                 300

Ile Met Gly Val Met Leu Gln Ser Leu Gln Gln Leu Thr Gly Asp Asn
305                 310                 315                 320

Tyr Phe Phe Tyr Tyr Gly Thr Thr Ile Phe Lys Ala Val Gly Leu Gln
            325                 330                 335

Asp Ser Phe Gln Thr Ser Ile Ile Leu Gly Ile Val Asn Phe Ala Ser
            340                 345                 350

Thr Phe Val Gly Ile Tyr Ala Ile Glu Arg Met Gly Arg Arg Leu Cys
        355                 360                 365

Leu Leu Thr Gly Ser Ala Cys Met Phe Val Cys Phe Ile Ile Tyr Ser
        370                 375                 380

Leu Ile Gly Thr Gln His Leu Tyr Lys Asn Gly Phe Ser Asn Glu Pro
385                 390                 395                 400

Ser Asn Thr Tyr Lys Pro Ser Gly Asn Ala Met Ile Phe Ile Thr Cys
            405                 410                 415

Leu Tyr Ile Phe Phe Phe Ala Ser Thr Trp Ala Gly Gly Val Tyr Cys
            420                 425                 430

Ile Val Ser Glu Ser Tyr Pro Leu Arg Ile Arg Ser Lys Ala Met Ser
        435                 440                 445

Val Ala Thr Ala Ala Asn Trp Met Trp Gly Phe Leu Ile Ser Phe Phe
450                 455                 460

Thr Pro Phe Ile Thr Ser Ala Ile His Phe Tyr Tyr Gly Phe Val Phe
465                 470                 475                 480

Thr Gly Cys Leu Ala Phe Ser Phe Phe Tyr Val Tyr Phe Phe Val Val
            485                 490                 495

Glu Thr Lys Gly Leu Ser Leu Glu Glu Val Asp Ile Leu Tyr Ala Ser
        500                 505                 510

Gly Thr Leu Pro Trp Lys Ser Ser Gly Trp Val Pro Pro Thr Ala Asp
        515                 520                 525

Glu Met Ala His Asn Ala Phe Asp Asn Arg Pro Thr Asp Glu Gln Val
        530                 535                 540

<210> SEQ ID NO 55
<211> LENGTH: 543
<212> TYPE: PRT
<213> ORGANISM: Artificial Sequence
<220> FEATURE:
<223> OTHER INFORMATION: ubiquitin-deficient H0 Metschnikowia species
Xyt1p (with K6R, S75L, K517R, K539R mutations)

<400> SEQUENCE: 55

```
Met Gly Tyr Glu Glu Arg Leu Val Ala Pro Ala Leu Lys Phe Lys Asn
1               5                   10                  15

Phe Leu Asp Lys Thr Pro Asn Ile His Asn Val Tyr Val Ile Ala Ala
            20                  25                  30

Ile Ser Cys Thr Ser Gly Met Phe Gly Phe Asp Ile Ser Ser Met
        35                  40                  45

Ser Val Phe Val Asp Gln Gln Pro Tyr Leu Lys Met Phe Asp Asn Pro
50                  55                  60

Ser Ser Val Ile Gln Gly Phe Ile Thr Ala Leu Met Ser Leu Gly Ser
65                  70                  75                  80

Phe Phe Gly Ser Leu Thr Ser Thr Phe Ile Ser Glu Pro Phe Gly Arg
                85                  90                  95

Arg Ala Ser Leu Phe Ile Cys Gly Ile Leu Trp Val Ile Gly Ala Ala
            100                 105                 110

Val Gln Ser Ser Gln Asn Arg Ala Gln Leu Ile Cys Gly Arg Ile
    115                 120                 125

Ile Ala Gly Trp Gly Ile Gly Phe Gly Ser Ser Val Ala Pro Val Tyr
    130                 135                 140

Gly Ser Glu Met Ala Pro Arg Lys Ile Arg Gly Thr Ile Gly Gly Ile
145                 150                 155                 160

Phe Gln Phe Ser Val Thr Val Gly Ile Phe Ile Met Phe Leu Ile Gly
                165                 170                 175

Tyr Gly Cys Ser Phe Ile Gln Gly Lys Ala Ser Phe Arg Ile Pro Trp
            180                 185                 190

Gly Val Gln Met Val Pro Gly Leu Ile Leu Leu Ile Gly Leu Phe Phe
    195                 200                 205

Ile Pro Glu Ser Pro Arg Trp Leu Ala Lys Gln Gly Tyr Trp Glu Asp
    210                 215                 220

Ala Glu Ile Ile Val Ala Asn Val Gln Ala Lys Gly Asn Arg Asn Asp
225                 230                 235                 240

Ala Asn Val Gln Ile Glu Met Ser Glu Ile Lys Asp Gln Leu Met Leu
                245                 250                 255

Asp Glu His Leu Lys Glu Phe Thr Tyr Ala Asp Leu Phe Thr Lys Lys
            260                 265                 270

Tyr Arg Gln Arg Thr Ile Thr Ala Ile Phe Ala Gln Ile Trp Gln Gln
    275                 280                 285

Leu Thr Gly Met Asn Val Met Met Tyr Tyr Ile Val Tyr Ile Phe Gln
    290                 295                 300

Met Ala Gly Tyr Ser Gly Asn Thr Asn Leu Val Pro Ser Leu Ile Gln
305                 310                 315                 320

Tyr Ile Ile Asn Met Ala Val Thr Val Pro Ala Leu Phe Cys Leu Asp
                325                 330                 335

Leu Leu Gly Arg Arg Thr Ile Leu Leu Ala Gly Ala Ala Phe Met Met
            340                 345                 350

Ala Trp Gln Phe Gly Val Ala Gly Ile Leu Ala Thr Tyr Ser Glu Pro
    355                 360                 365

Ala Tyr Ile Ser Asp Thr Val Arg Ile Thr Ile Pro Asp Asp His Lys
    370                 375                 380
```

```
Ser Ala Ala Lys Gly Val Ile Ala Cys Cys Tyr Leu Phe Val Cys Ser
385                 390                 395                 400

Phe Ala Phe Ser Trp Gly Val Gly Ile Trp Val Tyr Cys Ser Glu Val
            405                 410                 415

Trp Gly Asp Ser Gln Ser Arg Gln Arg Gly Ala Ala Leu Ala Thr Ser
            420                 425                 430

Ala Asn Trp Ile Phe Asn Phe Ala Ile Ala Met Phe Thr Pro Ser Ser
            435                 440                 445

Phe Lys Asn Ile Thr Trp Lys Thr Tyr Ile Ile Tyr Ala Thr Phe Cys
        450                 455                 460

Ala Cys Met Phe Ile His Val Phe Phe Phe Pro Glu Thr Lys Gly
465             470                 475                 480

Lys Arg Leu Glu Glu Ile Gly Gln Leu Trp Asp Glu Gly Val Pro Ala
            485                 490                 495

Trp Arg Ser Ala Lys Trp Gln Pro Thr Val Pro Leu Ala Ser Asp Ala
            500                 505                 510

Glu Leu Ala His Arg Met Asp Val Ala His Ala Glu His Ala Asp Leu
            515                 520                 525

Leu Ala Thr His Ser Pro Ser Ser Asp Glu Arg Thr Gly Thr Val
530                 535                 540
```

<210> SEQ ID NO 56
<211> LENGTH: 1635
<212> TYPE: DNA
<213> ORGANISM: Artificial Sequence
<220> FEATURE:
<223> OTHER INFORMATION: ubiquitin-deficient H0 Metschnikowia species
      GXF1 (with K9R; K24R, K538R mutations)

<400> SEQUENCE: 56

```
atgtctcaag atgaattgca caccagatct ggtgttgaaa ctccaatcaa cgactccttg      60
ttggaagaaa gacatgatgt tactccattg gctgctttgc cagaaaaatc tttcaaggac     120
tacatctcca tctccatttt ctgtttgttt gttgctttcg gtggtttcgt tttcggtttt     180
gatactggta ctatttccgg tttcgttaac atgtctgatt tcaagactag gttcggtgaa     240
atgaatgctc agggtgaata ttacttgtcc aacgttagaa ctggcctgat ggtttctatt     300
ttcaatgttg ttgtgctgt cggtggtatt ttcttgtgta aaattgctga tgtctacggt     360
agaaggatcg gtttgatgtt ttctatggtt gtctacgttg tcggtatcat tattcaaatt     420
gcttctacca ccaagtggta tcagtacttc attggtagat tgattgctgg tttggctgtt     480
ggtactgttt ctgttatttc ccctttgttc atttccgaag ttgctccaaa acaattgaga     540
ggtactttgg tttgctgttt ccaattgtgt attaccttgg gtatcttctt gggttactgt     600
actacttacg gtactaagac ttacaccgat tctagacaat ggcgtattcc attgggtatt     660
tgttttgctt gggctttgtt tttggttgcc ggtatgttga atatgccaga atctccaaga     720
tacttggtcg aaaagtccag aattgatgat gccagaaagt ccattgctag gtctaacaaa     780
gtttccgaag aagatccagc tgtttacacc gaagttcaat tgattcaagc cggtattgat     840
agagaagctt ggctggttc tgctacttgg atggaattgg ttactggtaa gcctaagatc     900
tttagaagag ttatcatggg tgtcatgttg caatccttgc aacaattgac tggtgacaac     960
tactttttct actacggtac aaccatttc aaggctgtcg gtttacaaga ttcttccaa    1020 acctccatca ttttgggtat cgttaacttc gcttctacct tcgttggtat ctacgctatt    1080
gaaagaatgg gtagaagatt gtgtttgttg acaggttctg cttgtatgtt cgtttgcttc    1140
```

```
atcatctact cattgatcgg tactcagcac ttgtacaaaa acggttttc taacgaaccc    1200 tccaacactt acaaaccatc tggtaatgcc atgatcttca ttacctgcct gtacattttc    1260
tttttcgctt caacttgggc tggtggtgtt tactgtatag tttctgaatc ttacccactg    1320
aggatcagat ctaaagctat gtctgttgct actgctgcaa attggatgtg ggtttttg     1380 atttctttct ttaccccatt catcacctcc gctatccatt tttactatgg ttttgttttc    1440
accggttgct tggctttctc tttctttac gtttacttct tcgtcgtcga gactaagggt    1500
ttgtctttgg aagaggttga tatcttgtat gcctctggta ctttgccatg gaaatcttca    1560
ggttgggttc caccaactgc tgacgaaatg gctcataatg cttttgataa cagaccaacc    1620
gatgaacagg tttaa                                                     1635

<210> SEQ ID NO 57
<211> LENGTH: 1632
<212> TYPE: DNA
<213> ORGANISM: Artificial Sequence
<220> FEATURE:
<223> OTHER INFORMATION: ubiquitin-deficient H0 Metschnikowia species
      XYT1 (with K6R, S75L, K517R, K539R mutations)

<400> SEQUENCE: 57
atgggatacg aagagagatt agtggcccc gctttgaaat ttaagaactt tttggataag      60
accccaaata tacataacgt ttacgtaatt gcggcgatct cgtgtacctc aggtatgatg    120
ttcggtttcg atatatcgtc gatgtccgtg ttcgtggacc aacagccgta tttaaaaatg    180
tttgataacc ctagcagcgt gatacaaggg tttataactg cgttgatgtc tttggggagc    240 ttttcggat cgctaacgtc cacttttatt tcagaacctt ttggtagacg tgcctctttg    300
ttcatatgcg ggatcctttg ggtaattggg cggcagttc aaagttcttc tcagaaccgt    360
gcgcagctta tttgtggccg aattattgca gggtggggca tcggattcgg ttctagcgtt    420
gcgccggtat acggttcaga atggcccca cgcaaaatta aggaacaat cggaggtatt     480 tttcaatttt ctgtcacggt cggaatattc ataatgttcc tgattggcta cggctgctca    540
tttatacaag gcaaggccag ttttagaatt ccgtggggag ttcaaatggt accaggtctc    600
attctgttga tcggactatt cttcattcct gaatccccaa gatggttagc caaacaaggc    660
tactgggaag acgctgagat catcgtagca aacgttcaag ctaagggtaa caggaacgat    720
gctaatgtgc aaattgaaat gtccgagata aaagatcagt taatgcttga cgagcattta    780
aaggagttta cttatgccga tttgtttacc aaaaaatacc ggcaaaggac gataacagct    840
atatttgccc aaatatggca acagctgaca ggtatgaatg tcatgatgta ctacatcgta    900
tatatatttc aaatgcagg ttattcaggt aatactaatt tagttccttc actcattcag    960
tatattataa atatggctgt tacggtcccc gcattgttct gtcttgatct gcttggcagg    1020
aggacaattt tattagctgg cgccgcttt atgatggcct ggcaatttgg tgttgctggc    1080
attttagcta cttattcaga gccagcctat atttcagata ccgtgagaat tacaattcca    1140
gatgaccata aaagtgccgc taagggtgtc atcgcttgct gctatttgtt tgtttgttcc    1200 ttcgccttt cctggggtgt aggtatctgg gttattgtt cagaagtgtg gggtgatagt      1260
caatccagac aaagaggtgc tgcattggca acttctgcta attggatctt caatttcgca    1320
attgcaatgt ttacaccttc ttctttcaaa aatatcactt ggaagactta tatcatttat    1380
gctacatttt gtgcttgtat gttcattcat gtttttttt ttttccctga acaaagggt     1440 aagagactag aagaaattgg acagctatgg gatgaaggtg tcccagcatg gagatctgca    1500
```

```
aaatggcaac ccactgtccc actagcaagt gacgctgaat tagctcacag aatggatgtt      1560
gcacacgctg aacacgcaga cttattggca acccattctc caagtagtga cgaaagaact      1620
ggtaccgttt aa                                                          1632
```

<210> SEQ ID NO 58
<211> LENGTH: 548
<212> TYPE: PRT
<213> ORGANISM: Artificial Sequence
<220> FEATURE:
<223> OTHER INFORMATION: ubiquitin-deficient H0 Metschnikowia species
      Gxf2p/Gal2p (with K23R, K26R, and K35R, mutations)

<400> SEQUENCE: 58

```
Met Ser Ala Glu Gln Glu Gln Gln Val Ser Gly Thr Ser Ala Thr Ile
1               5                   10                  15

Asp Gly Leu Ala Ser Leu Arg Gln Glu Arg Thr Ala Glu Glu Glu Asp
            20                  25                  30

Ala Phe Arg Pro Lys Pro Ala Thr Ala Tyr Phe Phe Ile Ser Phe Leu
        35                  40                  45

Cys Gly Leu Val Ala Phe Gly Gly Tyr Val Phe Gly Phe Asp Thr Gly
    50                  55                  60

Thr Ile Ser Gly Phe Val Asn Met Asp Asp Tyr Leu Met Arg Phe Gly
65                  70                  75                  80

Gln Gln His Ala Asp Gly Thr Tyr Tyr Leu Ser Asn Val Arg Thr Gly
                85                  90                  95

Leu Ile Val Ser Ile Phe Asn Ile Gly Cys Ala Val Gly Gly Leu Ala
            100                 105                 110

Leu Ser Lys Val Gly Asp Ile Trp Gly Arg Arg Ile Gly Ile Met Val
        115                 120                 125

Ala Met Ile Ile Tyr Met Val Gly Ile Ile Gln Ile Ala Ser Gln
    130                 135                 140

Asp Lys Trp Tyr Gln Tyr Phe Ile Gly Arg Leu Ile Thr Gly Leu Gly
145                 150                 155                 160

Val Gly Thr Thr Ser Val Leu Ser Pro Leu Phe Ile Ser Glu Ser Ala
                165                 170                 175

Pro Lys His Leu Arg Gly Thr Leu Val Cys Cys Phe Gln Leu Met Val
            180                 185                 190

Thr Leu Gly Ile Phe Leu Gly Tyr Cys Thr Thr Tyr Gly Thr Lys Asn
        195                 200                 205

Tyr Thr Asp Ser Arg Gln Trp Arg Ile Pro Leu Gly Leu Cys Phe Ala
    210                 215                 220

Trp Ala Leu Leu Leu Ile Ser Gly Met Val Phe Met Pro Glu Ser Pro
225                 230                 235                 240

Arg Phe Leu Ile Glu Arg Gln Arg Phe Asp Glu Ala Lys Ala Ser Val
                245                 250                 255

Ala Lys Ser Asn Gln Val Ser Thr Glu Asp Pro Ala Val Tyr Thr Glu
            260                 265                 270

Val Glu Leu Ile Gln Ala Gly Ile Asp Arg Glu Ala Leu Ala Gly Ser
        275                 280                 285

Ala Gly Trp Lys Glu Leu Ile Thr Gly Lys Pro Lys Met Leu Gln Arg
    290                 295                 300

Val Ile Leu Gly Met Met Leu Gln Ser Ile Gln Gln Leu Thr Gly Asn
305                 310                 315                 320

Asn Tyr Phe Phe Tyr Tyr Gly Thr Thr Ile Phe Lys Ala Val Gly Met
                325                 330                 335
```

Ser Asp Ser Phe Gln Thr Ser Ile Val Leu Gly Ile Val Asn Phe Ala
            340                 345                 350

Ser Thr Phe Val Gly Ile Trp Ala Ile Glu Arg Met Gly Arg Arg Ser
        355                 360                 365

Cys Leu Leu Val Gly Ser Ala Cys Met Ser Val Cys Phe Leu Ile Tyr
    370                 375                 380

Ser Ile Leu Gly Ser Val Asn Leu Tyr Ile Asp Gly Tyr Glu Asn Thr
385                 390                 395                 400

Pro Ser Asn Thr Arg Lys Pro Thr Gly Asn Ala Met Ile Phe Ile Thr
                405                 410                 415

Cys Leu Phe Ile Phe Phe Phe Ala Ser Thr Trp Ala Gly Gly Val Tyr
            420                 425                 430

Ser Ile Val Ser Glu Thr Tyr Pro Leu Arg Ile Arg Ser Lys Gly Met
            435                 440                 445

Ala Val Ala Thr Ala Ala Asn Trp Met Trp Gly Phe Leu Ile Ser Phe
        450                 455                 460

Phe Thr Pro Phe Ile Thr Ser Ala Ile His Phe Tyr Tyr Gly Phe Val
465                 470                 475                 480

Phe Thr Gly Cys Leu Ile Phe Ser Phe Tyr Val Phe Phe Phe Val
                485                 490                 495

Arg Glu Thr Lys Gly Leu Ser Leu Glu Glu Val Asp Glu Leu Tyr Ala
            500                 505                 510

Thr Asp Leu Pro Pro Trp Lys Thr Ala Gly Trp Thr Pro Pro Ser Ala
        515                 520                 525

Glu Asp Met Ala His Thr Thr Gly Phe Ala Glu Ala Ala Lys Pro Thr
    530                 535                 540

Asn Lys His Val
545

<210> SEQ ID NO 59
<211> LENGTH: 1647
<212> TYPE: DNA
<213> ORGANISM: Artificial Sequence
<220> FEATURE:
<223> OTHER INFORMATION: ubiquitin-deficient H0 Metschnikowia species
      Gxf2p/Gal2p (with K23R, K26R, and K35R, mutations)

<400> SEQUENCE: 59
atgtccgctg aacaagaaca acaagtttct ggtacttctg ccactattga tggttttggct      60 tctttgaggc aagaaaggac tgctgaagaa gaagatgctt taggccaaa accagctact      120 gcctacttct tcatttcttt cttgtgtggt ttggttgctt cggtggtta cgttttggt      180 tttgataccg gtactatctc cggtttcgtt aacatggatg attacttgat gagattcggt      240
caacaacatg ctgatggtac ttactacttg tccaatgtta gaaccggttt gatcgtcagt      300
attttcaaca ttggttgtgc tgttggtggt ttggcattgt ctaaagttgg tgatatttgg      360
ggtagaagaa tcggtattat ggttgccatg atcatctaca tggttggtat cattattcaa      420
atcgcctccc aagacaagtg gtatcaatac tttattggta gattgatcac cggtttgggt      480
gttggtacta cttctgtttt gtctcctttg ttcatttccg aatccgctcc aaaacatttg      540
agaggtactt tggtttgctg cttccaattg atggtaacct tgggtatttt cttgggttac      600
tgtactactt acggtactaa gaactacacc gattctagac aatggagaat tccattgggt      660
ttgtgttttg cttgggcctt gttgttgatt tctggtatgg tttttatgcc agaatccca      720 agattcttga tcgaaagaca aagattcgat gaagctaagg cttctgttgc caagtctaat      780

-continued

```
caagtttcta ctgaagatcc agccgtttac actgaagttg aattgattca agccggtatt      840
gatagagaag ctttggctgg ttctgctggt tggaaagaat tgattactgg taagccaaag      900
atgttgcaaa gagtcattt gggtatgatg ttacaatcca tccaacaatt gaccggtaac       960
aattacttct tctactacgg tacaaccatc ttcaaagctg ttggtatgtc cgattctttt     1020
caaacctcta tagtcttggg tatcgttaac ttcgcttcta cctttgttgg tatttgggcc     1080
attgaaagaa tgggtagaag atcttgtttg ttggttggtt cagcttgtat gtctgtttgc     1140
ttcttgatct actctatctt gggttcagtc aacttgtaca tcgatggtta cgaaaacact     1200
ccatctaaca ctagaaagcc aactggtaac gccatgattt tcattacctg tttgttcatc     1260
tttttcttcg cctctacttg ggctggtggt gtttattcta tagtttctga aacctaccca     1320
ttgagaatca gatctaaagg tatggctgtt gctactgctg ctaattggat gtggggtttt     1380
ttgatctctt tctttacccc attcatcacc tccgctattc attttacta cggttttgtt      1440 ttcaccggtt gcttgatctt ctcattcttt tacgtattct ttttcgtccg tgaaactaag     1500
ggtttgtcct tggaagaagt tgacgaatta tacgctactg atttgccacc atggaaaact     1560
gcaggttgga ctccaccatc agctgaagat atggctcata caactggttt tgctgaagct     1620
gctaagccta caaacaaaca cgtttga                                         1647
```